US010919929B2

(12) United States Patent
Arora et al.

(10) Patent No.: US 10,919,929 B2
(45) Date of Patent: Feb. 16, 2021

(54) GLUCOCORTICOID INHIBITORS FOR TREATMENT OF PROSTATE CANCER

(71) Applicant: Sloan-Kettering Institute for Cancer Research, New York, NY (US)

(72) Inventors: Vivek Arora, New York, NY (US); Charles L. Sawyers, New York, NY (US); Michael J. Evans, New York, NY (US); Darren R. Veach, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 15/103,283

(22) PCT Filed: Dec. 11, 2014

(86) PCT No.: PCT/US2014/069854

§ 371 (c)(1),
(2) Date: Jun. 9, 2016

(87) PCT Pub. No.: WO2015/089338

PCT Pub. Date: Jun. 18, 2015

(65) Prior Publication Data

US 2016/0289261 A1 Oct. 6, 2016

Related U.S. Application Data

(60) Provisional application No. 61/914,917, filed on Dec. 11, 2013.

(51) Int. Cl.

| | |
|---|---|
| ***C07J 17/00*** | (2006.01) |
| ***A61K 31/575*** | (2006.01) |
| ***A61K 31/58*** | (2006.01) |
| ***A61K 31/416*** | (2006.01) |
| ***A61K 31/573*** | (2006.01) |
| ***A61K 31/7105*** | (2006.01) |
| ***A61K 31/4439*** | (2006.01) |
| ***A61K 31/4166*** | (2006.01) |
| ***A61K 31/5375*** | (2006.01) |
| ***A61K 31/713*** | (2006.01) |
| ***G01N 33/74*** | (2006.01) |
| ***A61K 45/06*** | (2006.01) |
| ***C07J 9/00*** | (2006.01) |
| ***C07J 43/00*** | (2006.01) |

(52) U.S. Cl.

CPC ............. *C07J 17/00* (2013.01); *A61K 31/416* (2013.01); *A61K 31/4166* (2013.01); *A61K 31/4439* (2013.01); *A61K 31/5375* (2013.01); *A61K 31/573* (2013.01); *A61K 31/575* (2013.01); *A61K 31/58* (2013.01); *A61K 31/713* (2013.01); *A61K 31/7105* (2013.01); *A61K 45/06* (2013.01); *C07J 9/00* (2013.01); *C07J 43/003* (2013.01); *G01N 33/743* (2013.01)

(58) Field of Classification Search

CPC ............ A61K 2300/00; A61K 31/4166; A61K 31/573; A61K 31/416; A61K 31/4439; A61K 31/5375; A61K 31/575; A61K 31/58; A61K 31/7105; A61K 31/713; A61K 45/06; C07J 17/00; C07J 43/003; C07J 9/00; G01N 33/743; A61P 35/00

USPC .......................................................... 514/171

See application file for complete search history.

(56) References Cited

U.S. PATENT DOCUMENTS

| | | | | |
|---|---|---|---|---|
| 8,648,105 B2 * | 2/2014 | Jung | C07D 233/86 514/389 |
| 8,658,128 B2 * | 2/2014 | Altschul | A61K 31/00 424/1.11 |
| 9,114,147 B2 * | 8/2015 | Altschul | A61K 31/00 |
| 9,289,436 B2 * | 3/2016 | Szmulewitz | A61K 31/4166 |

(Continued)

FOREIGN PATENT DOCUMENTS

| | | | |
|---|---|---|---|
| FR | 2522328 | A1 | 9/1983 |
| WO | WO-2013/126581 | A1 | 8/2013 |

OTHER PUBLICATIONS

Taplin et al. (AN 2008:630761 HCAPLUS, DN 149:95104 abstract of BJU international (2008), 101(9), 1084-1089).*
Bachmann et al. (Neuropsychopharmacology (2003) 28, 1056-1067).*
Ligr et al. J Urol. Sep. 2012; 188(3):981-8).*
Sausville et al. (Cancer Research, 2006, vol. 66, pp. 3351-3354).*
Johnson et al. (British J. of Cancer, 2001, 84(10):1424-1431).*
International Search Report for PCT/US2014/69854, 5 pages (dated Jul. 24, 2015).

(Continued)

*Primary Examiner* — Sabiha N Qazi
(74) *Attorney, Agent, or Firm* — Choate, Hall & Stewart LLP; Brenda Herschbach Jarrell; Michael A. Shinall

(57) ABSTRACT

The present invention encompasses the recognition that reproducible and detectable changes in the level and or activity of Glucocorticoid Receptor (GR) are associated with incidence and/or risk of Castration Resistant Prostate Cancer (CRPC) and/or doubly resistant prostate cancer, specifically in individuals having prostate cancer and on antiandrogen therapy, and provides for the use of GR inhibitors to treat and/or reduce risk of CRPC and/or doubly resistant prostate cancer. In some embodiments, GR inhibitors also have Androgen Receptor (AR) inhibitory activity or are administered in conjunction with AR inhibitors. The present invention also provides technologies for identification and/or characterization of agents to treat and/or reduce risk of CRPC and/or doubly resistant prostate cancer; in some embodiments such agents alter level and/or activity of a GR. In some embodiments, provided agents show effects on a GR's activity of regulating transcription of one or more target genes. The present invention also provides systems for using such agents, for example to treat and/or reduce risk of CRPC and/or doubly resistant prostate cancer.

7 Claims, 45 Drawing Sheets

Specification includes a Sequence Listing.

(56) References Cited

U.S. PATENT DOCUMENTS

| | | | | |
|---|---|---|---|---|
| 9,314,473 | B2 * | 4/2016 | Altschul | A61N 5/1001 |
| 2012/0022121 | A1 * | 1/2012 | Dalton | C07D 209/04 514/367 |
| 2013/0029953 | A1 | 1/2013 | Nickisch et al. | |
| 2015/0010503 | A1 * | 1/2015 | Szmulewitz | A61K 31/4166 424/85.4 |
| 2016/0151388 | A1 * | 6/2016 | Szmulewitz | A61K 31/4166 424/649 |

OTHER PUBLICATIONS

Written Opinon for PCT/US2014/69854, 10 pages (dated Jul. 24, 2015).

Chen, H. et al., 3D-QSAR and Docking Study of the Binding Mode of Steroids to Progesterone Receptor in Active Site, QSAR Comb. Sci., 22:604-613 (2003).

Richards, S. et al., Synthesis and activity of novel bile-acid conjugated glucocorticoid receptor antagonists, Bioorganic & Medicinal Chemistry Letters, 16:6086-6090 (2006).

Taplin, M. et al., A phase II study of mifepristone (RU-486) in castration-resistant prostate cancer, with a correlative assesment of androgen-related hormones, BJU International, 101:1084-1089 (2008).

* cited by examiner

| | | | | | | |
|---|---|---|---|---|---|---|
| 25% Percentile | 0.7 | 1.6 | 12.0 | 0.6 | 0.8 | 0.5 |
| Median | 1.0 | 1.8 | 26.9 | 1.0 | 1.0 | 1.0 |
| 75% Percentile | 1.5 | 3.1 | 51.5 | 1.5 | 1.1 | 1.4 |

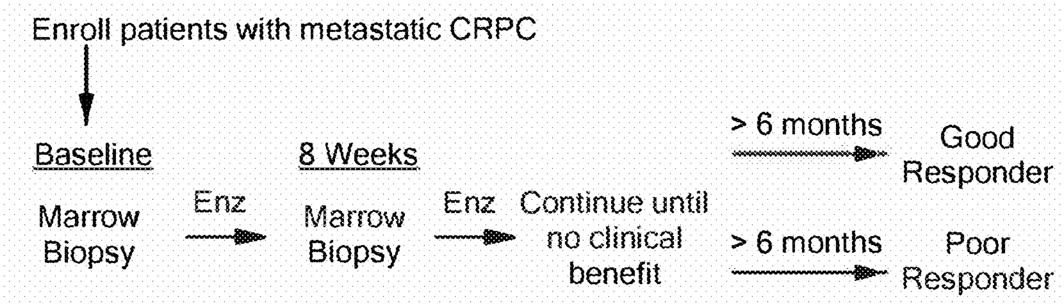
FIG. 5A
FIG. 5B
| PSA Decline | Good | Poor |
|---|---|---|
| More than 50% | 11 | 1 |
| Less than 50% | 2 | 13 |
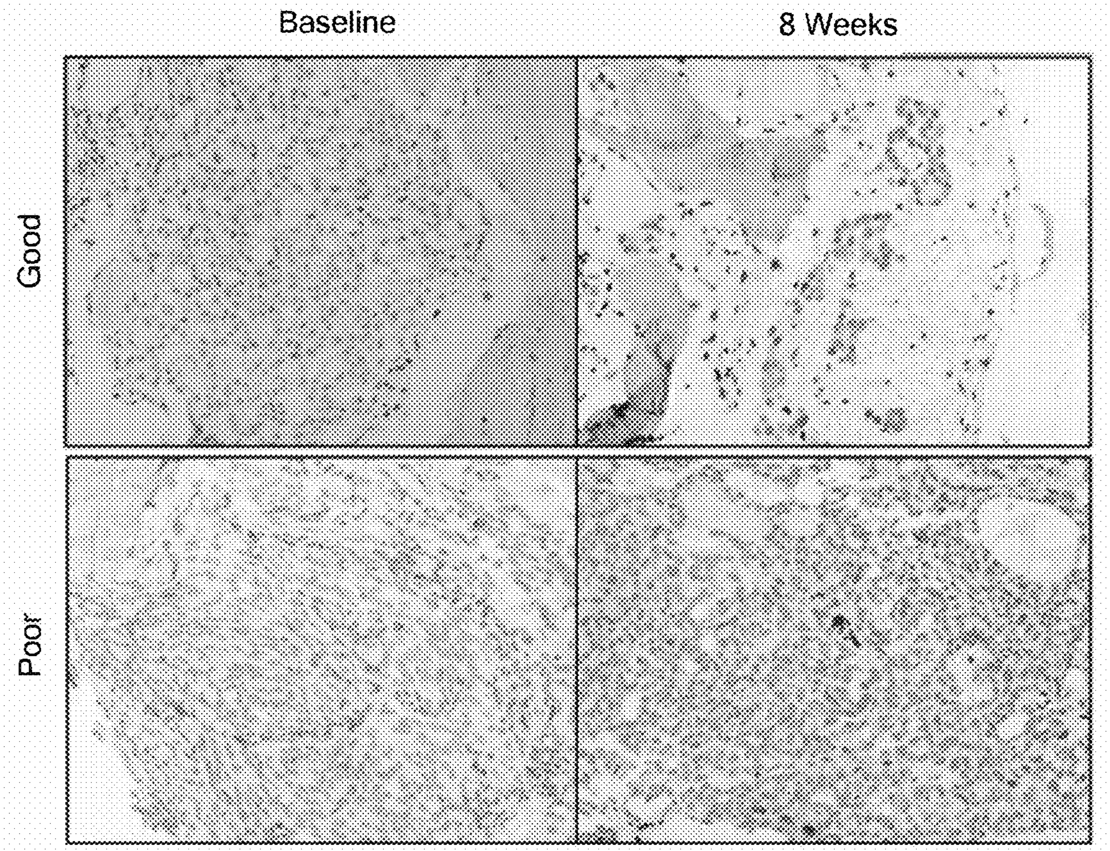
FIG. 5C FIG. 11E
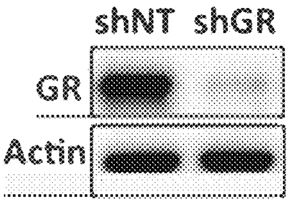
FIG. 11F
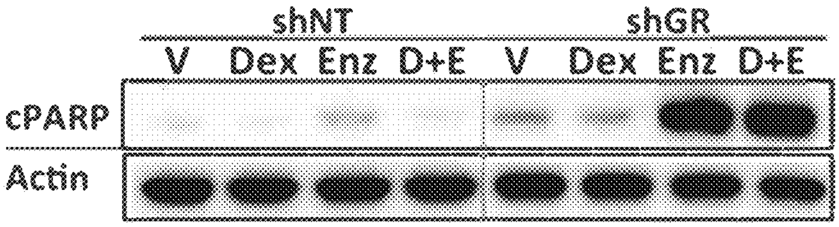
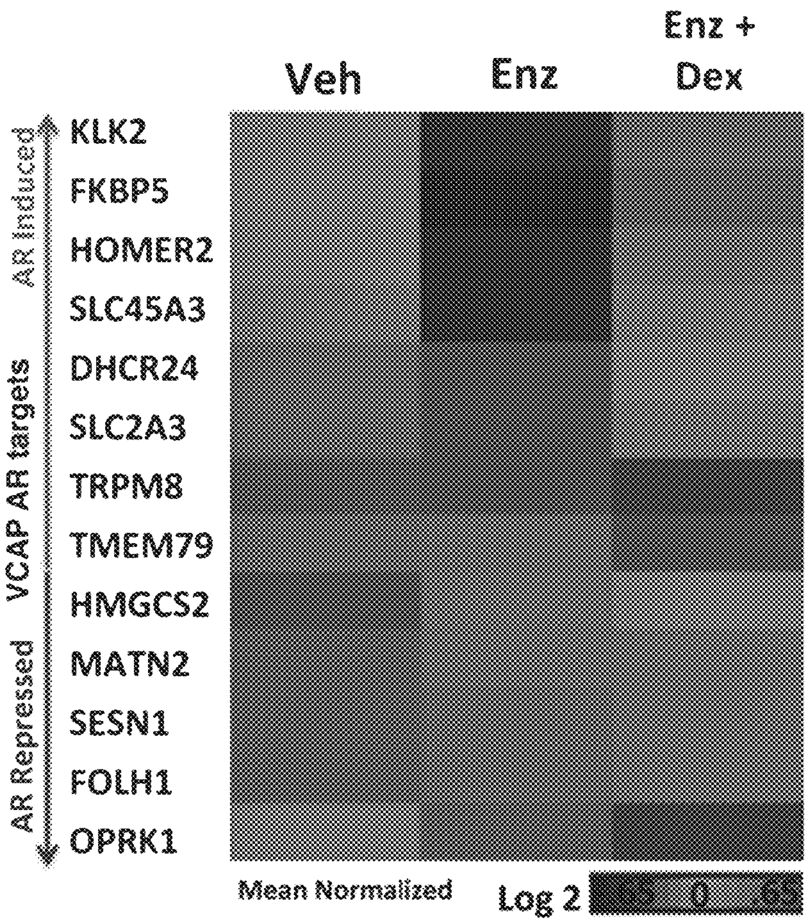
FIG. 11G FIG. 12A
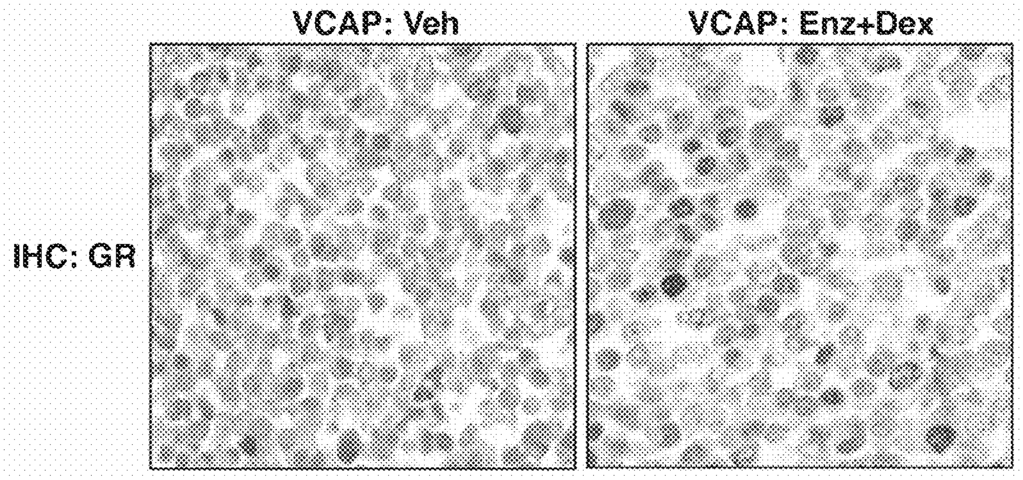
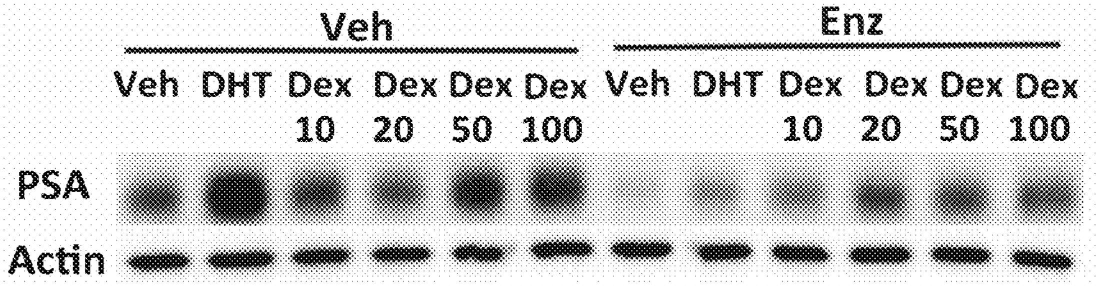
FIG. 12B Luciferase Reporter Assay in CSS Media Utilizing Retroviral Probasin-AR Luciferase Reporter

Summary of 10-ns MD Simulations

| RU486 Series | | | | | | ORG34517 Series | | |
|---|---|---|---|---|---|---|---|---|
| Name | Sub. Struct. | H12 Shift(Å) | Name | Sub. Struct. | H12 Shift(Å) | Name | Sub. Struct. | H12 Shift(Å) |
| RU486 | None | *2.40* | | | | ORG34517 | None | 1.64 |
| L1 ABR147 |  | 2.08 | L6 |  | 2.81 | R1 |  | 1.53 |
| L2 |  | 2.65 | L7 |  | 2.99 | R2 ABR167 |  | 3.42 |
| L3 ABR157 |  | 3.84 (?) | L8 |  | 5.46 | R3 |  | 2.46 |
| L4 ABR156 |  | 2.27 | L9 ABR173 |  | 3.61 | R4 |  | 2.31 |
| L5 |  | 3.75 (?) | L10 ABR173 – ether + CH2 | | 1.73 | R5 |  | 3.25 |

GLUCOCORTICOID INHIBITORS FOR TREATMENT OF PROSTATE CANCER

GOVERNMENT SUPPORT

This invention was made with government support under grant numbers: CA155169 awarded by National Institutes of Health and W81:XWH-1 1-1-0274 awarded by the Army Medical Research and Materiel Command. The government has certain rights in the invention.

SEQUENCE LISTING

The instant application contains a Sequence Listing which has been submitted electronically in ASCII format and is hereby incorporated by reference in its entirety. The ASCII copy, created on Apr. 21, 2015, is named 2003080 1127 Sequence Listing.TXT and is 170 megabytes in size.

BACKGROUND

According to American Cancer Society statistics released in 2013, almost 50% of American men, and more than 30% of American women, will develop cancer in their lifetime (see Cancer Facts & FIGS. 2013 from American Cancer Society Inc.,). Although remarkable progress has been made in understanding the biological basis of and in treating cancer, cancer remains second only to cardiac disease as the main cause of death in the United States.

Prostate cancer is the most common form of cancer in males. It typically afflicts aging males, but it can afflict males of all ages. A significant number of males die from prostate cancer every year, and it is the second leading cause of cancer deaths in men.

SUMMARY

The present invention encompasses the recognition that reproducible and detectable changes in the level and/or activity of Glucocorticoid Receptor (GR) are associated with incidence and/or risk of Castration Resistant Prostate Cancer (CRPC) and/or doubly resistant prostate cancer, particularly in individuals having prostate cancer and on antiandrogen therapy, and provides for the use of GR inhibitors to treat and/or reduce risk of CRPC and/or doubly resistant prostate cancer. In some embodiments, GR inhibitors useful in accordance with the present invention also have Androgen Receptor (AR) inhibitory activity and/or are administered in conjunction with AR inhibitors. The present invention also provides technologies for identification and/or characterization of agents to treat and/or reduce risk of CRPC and/or doubly resistant prostate cancer; in some embodiments such agents alter level and/or activity of a GR. In some embodiments, provided agents show effects on a GR's activity of regulating transcription of one or more target genes. The present invention also provides systems for using such agents, for example to treat and/or reduce risk of CRPC and/or doubly resistant prostate cancer.

In certain embodiments, the present disclosure provides methods for treating or reducing the risk of castration resistant prostate cancer comprising administering to a subject suffering from or susceptible to castration resistant prostate cancer a GR inhibitor. In some embodiments, the subject suffering from or susceptible to castration resistant prostate cancer is a subject who has received castration therapy.

In some embodiments, the present disclosure provides methods for treating or reducing the risk of doubly resistant prostate cancer comprising administering to a subject suffering from or susceptible to doubly resistant prostate cancer a GR inhibitor. In some embodiments, the subject suffering from or susceptible to doubly resistant prostate cancer is a subject who has received both castration therapy and Androgen Receptor inhibitor therapy.

In certain embodiments, the present disclosure provides methods for treating or reducing the risk of castration resistant prostate cancer comprising administering to a subject suffering from or susceptible to castration resistant prostate cancer a combination of a Glucocorticoid Receptor inhibitor and an Androgen Receptor inhibitor. In some embodiments, the subject suffering from or susceptible to castration resistant prostate cancer is a subject who has received castration therapy.

In certain embodiments, the present disclosure provides methods for treating or reducing the risk of doubly resistant prostate cancer comprising administering to a subject suffering from or susceptible to doubly resistant prostate cancer a combination of a Glucocorticoid Receptor inhibitor and an Androgen Receptor inhibitor. In some embodiments, the subject suffering from or susceptible to doubly resistant prostate cancer is a subject who has received both castration therapy and Androgen Receptor inhibitor therapy.

In some embodiments, according to the methods presented herein, castration therapy comprises physical castration. In some embodiments, castration therapy comprises chemical castration. In some embodiments, Androgen Receptor inhibitor therapy comprises treatment with ARN-509 and/or enzalutamide.

In some embodiments, according to the methods presented herein, the step of administering comprises administering to a subject whose Androgen Receptor is inhibited. In some embodiments, the Glucocorticoid Receptor inhibitor does not significantly activate Androgen Receptor levels and/or activity. In some embodiments, the Glucocorticoid Receptor inhibitor is an Androgen Receptor inhibitor. In some embodiments, the Glucocorticoid Receptor inhibitor is not an Androgen Receptor inhibitor.

In some embodiments, according to the methods presented herein, the Glucocorticoid Receptor inhibitor inhibits Glucocorticoid Receptor transcriptional activation activity. In some embodiments, the Glucocorticoid Receptor inhibitor is characterized in that a Glucocorticoid Receptor mRNA level is lower in a relevant Glucocorticoid Receptor expression system when the inhibitor is present as compared with a reference level observed under otherwise comparable conditions when it is absent. In some embodiments, the Glucocorticoid Receptor inhibitor is characterized in that a Glucocorticoid Receptor protein level is lower in a relevant Glucocorticoid Receptor expression system when the inhibitor is present as compared with a reference level observed under otherwise comparable conditions when it is absent. In some embodiments, the Glucocorticoid Receptor inhibitor is or comprises an siRNA agent that targets the Glucocorticoid Receptor. In some embodiments, the Glucocorticoid Receptor inhibitor is or comprises a short hairpin RNA (shRNA) that targets the Glucocorticoid Receptor. In some embodiments, the Glucocorticoid Receptor inhibitor is or comprises an antibody that specifically binds to the Glucocorticoid Receptor. In some embodiments, the Glucocorticoid Receptor inhibitor is or comprises a small molecule characterized in that, when the small molecule is contacted with a system expressing or capable of expressing Glucocorticoid Receptor, level and/or activity of Glucocorticoid Receptor in the system is reduced when the small molecule is present as compared with a reference level or activity observed under otherwise comparable conditions when it is absent. In some embodiments, the Glucocorticoid Receptor inhibitor is selected from the group consisting of RU-486 and ORG 34517. In some embodiments, the Glucocorticoid Receptor inhibitor is selected from the group consisting of analogs of RU-486. In some embodiments, the Glucocorticoid Receptor inhibitor is selected from the group consisting of analogs of ORG 34517. In some embodiments, the Glucocorticoid Receptor inhibitor is selected from the group consisting of

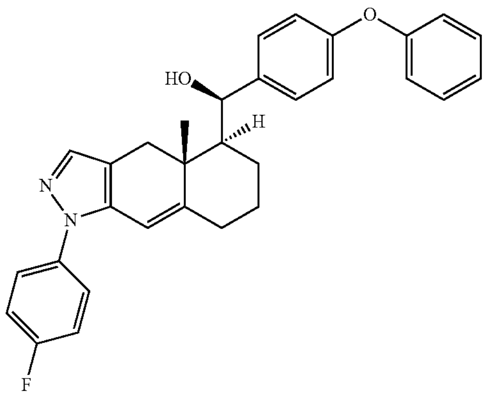

and

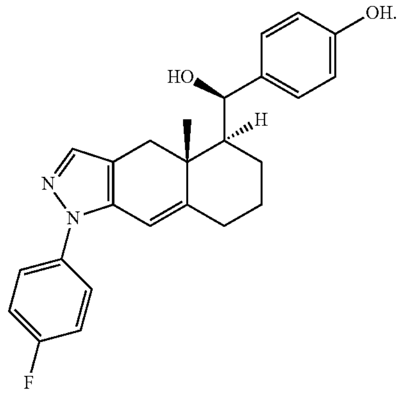

In some embodiments, according to the methods presented herein, the Androgen Receptor inhibitor inhibits Androgen Receptor transcriptional activation activity. In some embodiments, the Androgen Receptor inhibitor is characterized in that an Androgen Receptor mRNA level is lower in a relevant Androgen Receptor expression system when the inhibitor is present as compared with a reference level observed under otherwise comparable conditions when it is absent. In some embodiments, the Androgen Receptor inhibitor is characterized in that an Androgen Receptor protein level is lower in a relevant Androgen Receptor expression system when the inhibitor is present as compared with a reference level observed under otherwise comparable conditions when it is absent. In some embodiments, the Androgen Receptor inhibitor is or comprises an siRNA agent that targets the Androgen Receptor. In some embodiments, the Androgen Receptor inhibitor is or comprises a short hairpin RNA (shRNA) that targets the Androgen Receptor. In some embodiments, the Androgen Receptor inhibitor is or comprises an antibody that specifically binds to the Androgen Receptor. In some embodiments, the Androgen Receptor inhibitor is or comprises a small molecule characterized in that, when the small molecule is contacted with a system expressing or capable of expressing Androgen Receptor, level and/or activity of Androgen Receptor in the system is reduced when the small molecule is present as compared with a reference level or activity observed under otherwise comparable conditions when it is absent. In some embodiments, the Androgen Receptor inhibitor is selected from the group consisting of 3,3'-diindolylmethane (DIM), abiraterone acetate, ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, and/or turosteride.

In some embodiments, the present disclosure provides methods for identifying or characterizing agents for the treatment of castration resistant prostate cancer and/or doubly resistant prostate cancer comprising contacting a system in which Glucocorticoid Receptor and Androgen Receptor are present and active with at least one test agent, determining a level or activity of Glucocorticoid Receptor in the system when the agent is present as compared with a Glucocorticoid Receptor reference level or activity observed under otherwise comparable conditions when it is absent, determining a level or activity of Androgen Receptor in the system when the agent is present as compared with an Androgen Receptor reference level or activity observed under otherwise comparable conditions when it is absent, and classifying the at least one test agent as a treatment of castration resistant prostate cancer and/or doubly resistant prostate cancer if the level or activity of Glucocorticoid Receptor is significantly reduced when the test agent is present as compared with the Glucocorticoid Receptor reference level or activity and the Androgen Receptor is not significantly increased when the test agent is present as compared with the Androgen Receptor reference level or activity. In some embodiments, the test agent is classified as a treatment of castration resistant prostate cancer and/or doubly resistant prostate cancer if the level or activity of Androgen Receptor is significantly reduced when the test agent is present as compared with the Androgen Receptor reference level or activity. In some embodiments, the level or activity of Glucocorticoid Receptor comprises a Glucocorticoid Receptor mRNA level. In some embodiments, the level or activity of Androgen Receptor comprises a Androgen Receptor mRNA level. In some embodiments, the level or activity of Glucocorticoid Receptor comprises a Glucocorticoid Receptor protein level. In some embodiments, the level or activity of Androgen Receptor comprises a Androgen Receptor protein level. In some embodiments, a significant reduction in the level or activity of Glucocorticoid Receptor comprises a greater than 50% reduction of Glucocorticoid Receptor activity. In some embodiments, a significant reduction in the level or activity of Glucocorticoid Receptor comprises a greater than 50% reduction of Glucocorticoid Receptor levels. In some embodiments, a significant reduction in the level or activity of Androgen Receptor comprises a greater than 50% reduction of Androgen Receptor activity. In some embodiments, a significant reduction in the level or activity of Androgen Receptor comprises a greater than 50% reduction of Androgen Receptor levels. In some embodiments, the test agent is or comprises an siRNA. In some embodiments, the test agent is or comprises a short hairpin RNA (shRNA). In some embodiments, the test agent is or comprises a polypeptide. In some embodiments, the test agent is or comprises an antibody. In some embodiments, the test agent is or comprises a small molecule. In some embodiments, the at least one test agent is or comprises a set of test agents that show significant structural similarity and discrete structural differences such that the step of determining, when performed for the set of test agents, establishes a structure-function relationship between one or more structural elements present within the set of test agents and Glucocorticoid Receptor inhibitory activity.

In some embodiments, the present disclosure provides compounds of formula I':

I'

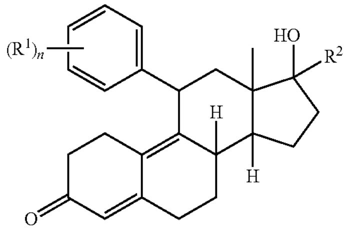

or a pharmaceutically acceptable salt thereof, wherein each $R^1$ is independently selected from halogen, optionally substituted $C_{1-6}$aliphatic, $NO_2$, —CN, —OR, —SR, —$N(R)_2$, —$C(R)_3$, —C(O)R, —C(O)OR, —S(O)R, —$S(O)_2R$, —$C(O)N(R)_2$, $SO_2N(R)_2$, OC(O)R, —N(R)C(O)R, —N(R)C(O)OR, —$N(R)SO_2R$, and $OC(O)N(R)_2$; or two $R^1$ groups on adjacent atoms are taken together with their intervening atoms to form an optionally substituted fused 5- to 7-membered ring having 0-3 heteroatoms selected from oxygen, nitrogen, or sulfur; and $R^2$ is optionally substituted unsaturated $C_{2-6}$aliphatic; and each R is independently hydrogen or an optionally substituted group selected from $C_{1-6}$ aliphatic, phenyl, 3- to 8-membered saturated or partially unsaturated carbocyclyl ring, 3- to 8-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur; 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered saturated or partially unsaturated bicyclic heteroaryl having 1-4 heteroatoms selected from oxygen, nitrogen, or sulfur, or 8- to 10-membered bicyclic aryl; and n is from 0-4.

BRIEF DESCRIPTION OF THE DRAWING

FIGS. 5A-5E demonstrate GR induction in disseminated tumor cells is associated with poor clinical response to enzalutamide and persistence of PSA. A. Schematic of sample acquisition timeline and response groups. B. Number of good or poor responders who achieved PSA decline greater than 50%. C. Examples of GR IHC images from matched samples at baseline and 8 weeks. D. Percent GR positive epithelial cells in all tissue available at 0 and 8 weeks or E. matched samples obtained from the same patient at 0 and 8 weeks+/−s.e.m. Comparisons are by Mann-Whitney test.

FIGS. 11A-11H demonstrate that GR activity is sufficient to confer enzalutamide resistance in VCaP. FOR ALL PANELS: VCaP cells do not tolerate charcoal stripped media and were cultured in standard culture conditions (fetal bovine serum with endogenous hormones). Enz=10 micromolar, Dex=100 nM, CMP 15=1 micromolar. A. Western blot analysis of prostate cancer cell lines. B, C and D. Cell viability assessed by CellTiter-Glo (Promega) assay and normalized to day 1 value after indicated treatments+/−s.e.m. E. Confirmation of GR knock-down by western blot after infection with GR targeting shRNA. F. Apoptosis as assessed by cPARP western blot after 3 days of indicated treatment. G. A suite of AR targets relevant to VCaP was defined (see methods) and normalized expression of each gene after 24 hours of indicated drug treatments is depicted by heat map and ranked by degree of induction with Dex. H. Expression of the top two genes from B. (KLK2 and FKBP5) after 24 hours of indicated treatments+/−s.e.m.

FIGS. 12A-12C show GR expression and activity in VCaP. A. GR IHC of VCAP of cells in standard media treated with vehicle or Dex 100 nM+Enz 10 micromolar for 30 minutes prior to fixation. B. KLK3(PSA) western blots of VCaP lysates generated from cells in standard media treated with indicated drugs for 3 days. DHT=0.1 nM, Dex concentrations are indicated (nM), Enz=10 micromolar. C. Expression analysis using RT-qPCR of VCaP infected with a non-targeting or GR-targeting hairpin. Cells were treated in standard media as indicated for 24 hours prior to harvest. Dex=100 nM, Enz=10 micro-molar.+/−s.e.m.

DEFINITIONS

Figure 1B:
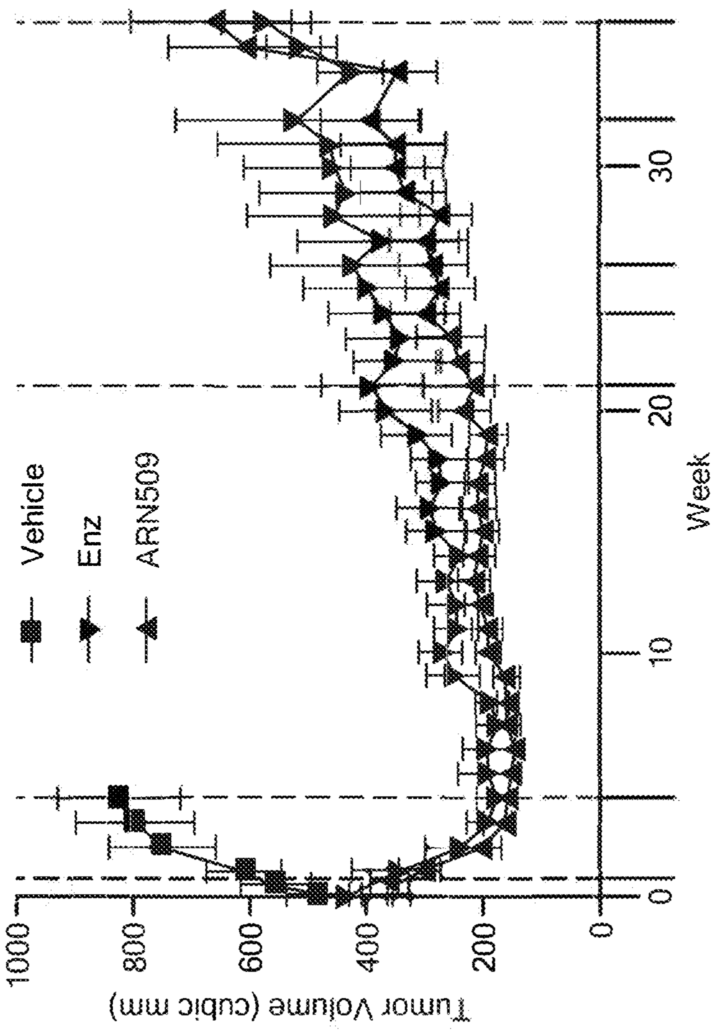
FIGS. 1A-1E demonstrate that GR mRNA and protein is expressed in resistant tissues. A. Most differentially expressed genes in a pilot cohort of LnCaP/AR xenograft tumors with acquired resistance to ARN-509 (n=6) or RD162 (n=9) compared to control (n=3) determined by microarray (Affymetrix Ex1.0). Mice with resistant tissues were continued on drug treatment through time of harvest. In vitro androgen-induced or -repressed genes are annotated. B. Mean tumor volumes+/−s.e.m of LnCaP/AR xenografts in validation cohort. Days tumors were harvested are annotated on x-axis (long hash mark). C. RT-qPCR analysis of GR and AR mRNA expression in a validation cohort of LnCaP/AR xenograft tumors from mice treated with vehicle (control, n=10), 4 days of anti-androgen (n=8), or with acquired resistance to 10 mg/kg enzalutamide (n=8) or 10 mg/kg ARN-509 (n=8). D. Western blot analysis of GR and AR protein expression in a subset of tissues also analyzed in B. Control (n=6), 4 day (n=5), Resistant (n=13). Resistant samples were loaded for protein analysis from highest to lowest GR levels based on corresponding mRNA analysis. E. Intracellular GR flow cytometric analysis of LnCaP/AR, CS1, and LREX', cells passaged in vitro, under standard passage conditions (see methods).

Agent: The term "agent" as used herein may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, siRNAs, shRNAs, DNA/RNA hybrids, antisense oligonucleotides, ribozymes, peptides, peptide mimetics, small molecules, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Androgen: The term "androgen" is used herein to refer to an agent that has androgenic activity. Androgenic activity may be determined or characterized in any of a variety of ways, including in any of a variety of biological activity assays (e.g., in vitro or in vivo assays, for example utilizing animals and/or animal tissues) in which the agent is observed to have one or more activities similar or comparable to that of a known (i.e., reference) androgen assessed under comparable conditions (whether simultaneously or otherwise). In some embodiments, androgenic activity is or comprises transcriptional regulation (e.g., activation) of an androgen-responsive target gene. In some embodiments, androgenic activity is or comprises binding to an androgen receptor. In some embodiments, androgenic activity is or comprises stimulation of prostate growth in rodents. Exemplary known androgens include, for example, androstanedione, androstenediol, androstenedione, androsterone, dehydroepiandrosterone, dihydrotestosterone (DHT), and testosterone.

Antiandrogen: As used herein, the term "antiandrogen" is used herein to refer to an agent that inhibits androgenic activity In some embodiments, inhibiting androgenic activity is or comprises inhibiting biological activity of an AR. In some embodiments, inhibiting androgenic activity is or comprises competing with one or more androgens for binding to an AR. Exemplary known antiandrogens include, for example, 3,3'-diindolylmethane (DIM), bexlosteride, bicalutamide, dutasteride, epristeride, finasteride, flutamide, izonsteride, ketoconazole, N-butylbenzene-sulfonamide, nilutamide, megestrol, steroidal antiandrogens, and/or turosteride. In some embodiments, antiandrogens comprise second generation antiandrogens. Exemplary second generation antiandrogens include but are not limited to ARN-509 and enzalutamide.

Animal: As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: $CH_1$, $CH_2$, and the carboxy-terminal $CH_3$ (located at the base of the Y's stem). A short region, known as the "switch", connects the heavy chain variable and constant regions. The "hinge" connects $CH_2$ and $CH_3$ domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $CH_2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain (κ and λ) classes, several heavy chain (e.g., μ, γ, α, ε, δ) classes, and certain heavy chain subclasses (α1, α2, γ1, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is polyclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc) antibodies, Small Modular ImmunoPharmaceuticals ("SMIPs™"), single chain antibodies, cameloid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc].

Antibody fragment: As used herein, an "antibody fragment" includes a portion of an intact antibody, such as, for example, the antigen-binding or variable region of an antibody. Examples of antibody fragments include Fab, Fab', $F(ab')_2$, and Fv fragments; triabodies; tetrabodies; linear antibodies; single-chain antibody molecules; and CDR-containing moieties included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc.

Approximately: As used herein, the term "approximately" and "about" is intended to encompass normal statistical variation as would be understood by those of ordinary skill in the art as appropriate to the relevant context. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Carrier: As used herein, the term "carrier" refers to a pharmaceutically acceptable (e.g., safe and non-toxic for administration to a human) carrier substance useful for preparation of a pharmaceutical formulation. In many embodiments, a carrier is biologically substantially inert, e.g., so that activity of a biologically active substance is not materially altered in its presence as compared with in its absence. In some embodiments, a carrier is a diluent.

Comparable: The term "comparable" as used herein refers to a system, set of conditions, effects, or results that is/are sufficiently similar to a test system, set of conditions, effects, or results, to permit scientifically legitimate comparison. Those of ordinary skill in the art will appreciate and understand which systems, sets of conditions, effect, or results are sufficiently similar to be "comparable" to any particular test system, set of conditions, effects, or results as described herein.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Designed: As used herein, the term "designed" refers to an agent (i) whose structure is or was selected by the hand of man; (ii) that is produced by a process requiring the hand of man; and/or (iii) that is distinct from natural substances and other known agents.

Docking: As used herein, the term "docking" refers to orienting, rotating, translating a chemical entity in the binding pocket, domain, molecule or molecular complex or portion thereof based on distance geometry or energy. Docking may be performed by distance geometry methods that find sets of atoms of a chemical entity that match sets of sphere centers of the binding pocket, domain, molecule or molecular complex or portion thereof. See Meng et al. J. Comp. Chem. 4: 505-524 (1992). Sphere centers are generated by providing an extra radius of given length from the atoms (excluding hydrogen atoms) in the binding pocket, domain, molecule or molecular complex or portion thereof. Real-time interaction energy calculations, energy minimizations or rigid-body minimizations (Gschwend et al., J. Mol. Recognition 9:175-186 (1996)) can be performed while orienting the chemical entity to facilitate docking. For example, interactive docking experiments can be designed to follow the path of least resistance. If the user in an interactive docking experiment makes a move to increase the energy, the system will resist that move. However, if that user makes a move to decrease energy, the system will favor that move by increased responsiveness. (Cohen et al., J. Med. Chem. 33:889-894 (1990)). Docking can also be performed by combining a Monte Carlo search technique with rapid energy evaluation using molecular affinity potentials. See Goodsell and Olson, Proteins: Structure, Function and Genetics 8:195-202 (1990). Software programs that carry out docking functions include but are not limited to MATCHMOL (Cory et al., J. Mol. Graphics 2: 39 (1984); MOLFIT (Redington, Comput. Chem. 16: 217 (1992)) and DOCK (Meng et al., supra).

Dosage form: As used herein, the terms "dosage form" and "unit dosage form" refer to a physically discrete unit of a therapeutic composition for administration to a subject to be treated. Each unit dosage form contains a predetermined quantity of active agent calculated to produce a desired therapeutic effect when administered in accordance with a dosing regimen. It will be understood, however, that a total dosage of the active agent may be decided by an attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated from one another by a time period of the same length; in some embodiments, a dosing regimen comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 3535%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the whole.

Improve, increase, or reduce: As used herein, the terms "improve," "increase" or "reduce," or grammatical equivalents, indicate a change in a value relative to a comparable baseline or reference measurement. In some embodiments, a comparable baseline or reference measurement is a measurement taken in the same system (e.g., of the same individual) prior to initiation of an event of interest (e.g., of therapy). In some embodiments, a comparable baseline or reference measurement is one taken in a different system (e.g., a different individual or cell) under otherwise identical conditions (e.g., in a normal cell or individual as compared with one suffering from or susceptible to a particular disease, disorder or condition, for example due to presence of a particular genetic mutation).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Inhibitor: The term "inhibitor" is used to refer to an entity whose presence in a system in which an activity of interest is observed correlates with a decrease in level and/or nature of that activity as compared with that observed under otherwise comparable conditions when the inhibitor is absent. In some embodiments, an inhibitor interacts directly with a target entity whose activity is of interest. In some embodiments, an inhibitor interacts indirectly (i.e., directly with an intermediate agent that interacts with the target entity) with a target entity whose activity is of interest. In some embodiments, an inhibitor affects level of a target entity of interest; alternatively or additionally, in some embodiments, an inhibitor affects activity of a target entity of interest without affecting level of the target entity. In some embodiments, an inhibitor affects both level and activity of a target entity of interest, so that an observed difference in activity is not entirely explained by or commensurate with an observed difference in level.

Isolated: As used herein, the term "isolated" is used to refer to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Nucleic Acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" may be used to refer to the multiple polypeptides that are physically associated and function together as the discrete unit. In some embodiments, proteins may include moieties other than amino acids (e.g., may be glycoproteins, proteoglycans, etc.) and/or may be otherwise processed or modified. Those of ordinary skill in the art will appreciate that in some embodiments the term "protein" may refer to a complete polypeptide chain as produced by a cell (e.g., with or without a signal sequence), and/or to a form that is active within a cell (e.g., a truncated or complexed form). In some embodiments where a protein is comprised of multiple polypeptide chains, such chains may be covalently associated with one another, for example by one or more disulfide bonds, or may be associated by other means.

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Risk: As will be understood from context, a "risk" of a disease, disorder or condition is a degree of likelihood that a particular individual will develop the disease, disorder, or condition. In some embodiments, risk is expressed as a percentage. In some embodiments, risk is from 0, 1, 2, 3, 4, 5, 6, 7, 8, 9, 10 up to 100%. In some embodiments risk is expressed as a risk relative to a risk associated with a reference sample or group of reference samples. In some embodiments, a reference sample or group of reference samples have a known risk of a disease, disorder, or condition. In some embodiments a reference sample or group of reference samples are from individuals comparable to a particular individual. In some embodiments, relative risk is 0, 1, 2, 3, 4, 5, 6, 7, 8, 9, 10 or more.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or bronchioalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Small molecule: As used herein, the term "small molecule" means a low molecular weight organic compound that may serve as an enzyme substrate or regulator of biological processes. In general, a "small molecule" is a molecule that is less than about 5 kilodaltons (kD) in size. In some embodiments, provided nanoparticles further include one or more small molecules. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, one or more small molecules are encapsulated within the nanoparticle. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc. In some embodiments, a small molecule is a therapeutic. In some embodiments, a small molecule is an adjuvant. In some embodiments, a small molecule is a drug.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with and/or displays one or more symptoms of the disease, disorder, and/or condition.

Therapeutic agent: As used herein, the phrase "therapeutic agent" refers to any agent that has a therapeutic effect and/or elicits a desired biological and/or pharmacological effect, when administered to a subject. In some embodiments, an agent is considered to be a therapeutic agent if its administration to a relevant population is statistically correlated with a desired or beneficial therapeutic outcome in the population, whether or not a particular subject to whom the agent is administered experiences the desired or beneficial therapeutic outcome.

Therapeutically effective amount: As used herein, the term "therapeutically effective amount" refers to an amount of an agent which confers a therapeutic effect on a treated subject, at a reasonable benefit/risk ratio applicable to any medical treatment. A therapeutic effect may be objective (i.e., measurable by some test or marker) or subjective (i.e., subject gives an indication of or feels an effect). In particular, a "therapeutically effective amount" refers to an amount of a therapeutic agent effective to treat, ameliorate, or prevent a desired disease or condition, or to exhibit a detectable therapeutic or preventative effect, such as by ameliorating symptoms associated with a disease, preventing or delaying onset of a disease, and/or also lessening severity or frequency of symptoms of a disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other agents. Also, a specific therapeutically effective amount (and/or unit dose) for any particular patient may depend upon a variety of factors including what disorder is being treated; disorder severity; activity of specific agents employed; specific composition employed; age, body weight, general health, and diet of a patient; time of administration, route of administration; treatment duration; and like factors as is well known in the medical arts.

Therapeutic regimen: A "therapeutic regimen", as that term is used herein, refers to a dosing regimen whose administration across a relevant population is correlated with a desired or beneficial therapeutic outcome.

Treatment: As used herein, the term "treatment" (also "treat" or "treating") refers to any administration of a substance that partially or completely alleviates, ameliorates, relives, inhibits, delays onset of, reduces severity of, and/or reduces frequency, incidence or severity of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Vector: As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocyclyl" or "cycloalkyl") refers to a monocyclic C3-C7 hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in this context in reference to a ring atom, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^o$; $-(CH_2)_{0-4}OR^o$; $-O(CH_2)_{0-4}R^o$, $-O-(CH_2)_{0-4}C(O)OR^o$; $-(CH_2)_{0-4}CH(OR^{o)}{}_2$; $-(CH_2)_{0-4}SR^o$; $-(CH_2)_{0-4}Ph$, which may be substituted with $R^o$; $-(CH_2)_{0-4}O(CH_2)_{0-1}Ph$ which may be substituted with $R^o$; $-CH{=}CHPh$, which may be substituted with $R^o$; $-(CH_2)_{0-4}O(CH_2)_{0-1}$-pyridyl which may be substituted with $R^o$; $NO_2$; $-CN$; $-N_3$; $-(CH_2)_{0-4}N(R^o)_2$; $-(CH_2)_{0-4}N(R^o)C(O)R^o$; $-N(R^o)C(S)R^o$; $-(CH_2)_{0-4}N(R^o)C(O)NR^o{}_2$; $-N(R^o)C(S)NR^o{}_2$; $-(CH_2)_{0-4}N(R^o)C(O)OR^o$; $-N(R^o)N(R^o)C(O)R^o$; $-N(R^oN(R^o)C(O)NR^o{}_2$; $-N(R^oN(R^o)C(O)OR^o$; $-(CH_2)_{0-4}C(O)R^o$; $-C(S)R^o$; $-(CH_2)_{0-4}C(O)OR^o$; $-(CH_2)_{0-4}C(O)SR^o$; $-(CH_2)_{0-4}C(O)OSiR^o{}_3$; $-(CH_2)_{0-4}OC(O)R^o$; $-OC(O)(CH_2)_{0-4}SR-$, $SC(S)SR^o$; $-(CH_2)_{0-4}SC(O)R^o$; $-(CH_2)_{0-4}C(O)NR^o{}_2$; $-C(S)NR^o{}_2$; $-C(S)SR^o$; $-SC(S)SR^o$, $-(CH_2)_{0-4}OC(O)NR^o{}_2$; $-C(O)N(OR^o)R^o$; $-C(O)C(O)R^o$; $-C(O)CH_2C(O)R^o$; $-C(NOR^o)R^o$; $-(CH_2)_{0-4}SSR^o$; $-(CH_2)_{0-4}S(O)_2R^o$; $-(CH_2)_{0-4}S(O)_2OR^o$; $-(CH_2)_{0-4}OS(O)_2R^o$; $-S(O)_2NR^o{}_2$; $-(CH_2)_{0-4}S(O)R^o$; $-N(R^o)S(O)_2NR^o{}_2$; $-N(R^o)S(O)_2R^o$; $-N(OR^o)R^o$; $-C(NH)NR^o{}_2$; $-P(O)_2R^o$; $-P(O)R^o{}_2$; $-OP(O)R^o{}_2$; $-OP(O)(OR^{o)}{}_2$; $SiR^o{}_3$; $-(C_{1-4}$ straight or branched)alkylene)O$-N(R^o)_2$; or $-(C_{1-4}$ straight or branched)alkylene)C(O)O$-N(R^o)_2$, wherein each $R^o$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, $-(CH_2)_{0-2}R^\bullet$, -(halo$R^\bullet$), $-(CH_2)_{0-2}OH$, $-(CH_2)_{0-2}OR^\bullet$, $-(CH_2)_{0-2}CH(OR^\bullet)_2$; $-O$(halo$R^\bullet$), $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet{}_2$, $NO_2$, $-SiR^\bullet{}_3$, $-OSiR^\bullet{}_3$, $-C(O)SR^\bullet$, $-(C_{1-4}$ straight or branched alkylene)C(O)O$R^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include $=O$ and $=S$.

Suitable divalent substituents on a saturated carbon atom of an "optionally substituted" group include the following: $=O$, $=S$, $=NNR^*{}_2$, $=NNHC(O)R^*$, $=NNHC(O)OR^*$, $=NNHS(O)_2R^*$, $=NR^*$, $=NOR^*$, $-O(C(R^*{}_2))_{2-3}O-$, or $-S(C(R^*{}_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(halo$R^\bullet$), $-OH$, $-OR^\bullet$, $-O$(halo$R^\bullet$), $-CN$, $-C(O)OH$, $-C(O)OR^\bullet$, $-NH_2$, $-NHR^\bullet$, $-NR^\bullet{}_2$, or $-NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}$ Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

DETAILED DESCRIPTION OF CERTAIN EMBODIMENTS

Prostate Cancer

Prostate cancer is the second most common cause of cancer death in men in the United States, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites.

Castration Therapy

Prostate cancer cells are known to depend on androgen receptor (AR) for their proliferation and survival. As such, prostate cancer patients are physically castrated or chemically castrated by treatment with agents that block production of testosterone (e.g. GnRH agonists), alone or in combination with antiandrogens, which antagonize effects of any residual testosterone. This approach is effective as evidenced by a drop in PSA and regression of any visible tumor.

Anti-androgens are useful for the treatment of prostate cancer during its early stages. However, prostate cancer often advances to a hormone-refractory state in which the disease progresses despite continued androgen ablation or anti-androgen therapy. Antiandrogens include but are not limited to flutamide, nilutamide, bicalutamide, and/or megestrol.

Castration Resistant Prostate Cancer

This hormone-refractory state to which most patients eventually progresses in the presence of continued androgen ablation or anti-androgen therapy is known as "castration resistant" prostate cancer (CRPC).

CRPC is associated with an overexpression of AR. Compelling data demonstrates that AR is expressed in most prostate cancer cells and overexpression of AR is necessary and sufficient for androgen-independent growth of prostate cancer cells. Failure in hormonal therapy, resulting from development of androgen-independent growth, is an obstacle for successful management of advanced prostate cancer.

Advances in Prostate Cancer Treatment

Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

Recently, more effective second generation antiandrogens have been developed. These include but are not limited to ARN-509 and enzalutamide, which are thought to function both by inhibiting AR nuclear translocation and DNA binding.

Doubly Resistant Prostate Cancer

Recently approved therapies that target androgen receptor (AR) signaling such as abiraterone and enzalutamide have transformed clinical management of CRPC. Despite these successes, sustained response with these agents is limited by acquired resistance which typically develops within ~6-12 months. Doubly resistant prostate cancer is characterized in that tumor cells have become castration resistant and overexpress AR, a hallmark of CRPC. However, cells remain resistant when treated with second generation antiandrogens.

In some embodiments doubly resistant prostate cancer cells are characterized by a lack of effectiveness of second generation antiandrogens in inhibiting tumor growth. In some embodiments doubly resistant prostate cancer cells are characterized in that tumor volume increases by 1, 2, 3, 4, 5, 6, 7, 8, 9, 10, 15, 20, 25, 30, 35, 40, 45, 50, 55, 60, 65, 70, 75, 80, 85, 90, 95, 100% or more in the presence of second generation antiandrogens relative to a historical level.

In some embodiments, doubly resistant prostate cancer cells are characterized in that tumor volume increases after 1, 2, 3, 4, 5, 6, or 7 days or 1, 2, 3, 4, 5, 6, 7, 8, 9, 10, 15, 20, 25, 30, 35, 40, 45, 50 weeks of Androgen Receptor inhibitor therapy.

In some embodiments, Androgen Receptor inhibitor therapy comprises treatment with 0.001, 0.01, 0.1, 1, 2, 3, 4, 5, 6, 7, 8, 9, 10, 5, 20, 25, 30, 35, 40, 45, 50, 55, 60, 65, 70, 75, 80, 85, 90, 95, 100, 1000, 10,000, 100,000 mg/kg ARN-509 or enzalutamide administered 1, 2, 3, 4, or 5 times daily, once every other day, once every 2, 3, 4, 5 or 6 days, or once a week. In some embodiments, treatment with second generation antiandrogens comprises treatment with 10 mg/kg ARN-509 or enzalutamide daily.

Androgen Receptor

The androgen receptor (AR), located on Xql 1-12, is a 110 kD nuclear receptor that, upon activation by androgens, mediates transcription of target genes that modulate growth and differentiation of prostate epithelial cells. Similar to other steroid receptors, unbound AR is mainly located in cytoplasm and associated with a complex of heat shock proteins (HSPs) through interactions with its ligand-binding domain. Upon agonist binding, AR undergoes a series of conformational changes: heat shock proteins dissociate from AR, and transformed AR undergoes dimerization, phosphorylation, and nuclear translocation, which is mediated by its nuclear localization signal. Translocated receptor then binds to androgen response elements (ARE), which are characterized by a six-nucleotide half-site consensus sequence 5'-TGTTCT-3' spaced by three random nucleotides and are located in promoter or enhancer regions of AR gene targets. Recruitment of other transcription co-regulators (including co-activators and co-repressors) and transcriptional machinery further ensures transactivation of AR-regulated gene expression. All of these processes are initiated by ligand-induced conformational changes in the ligand-binding domain.

AR signaling is crucial for development and maintenance of male reproductive organs including prostate glands, as genetic males harboring loss of function AR mutations and mice engineered with AR defects do not develop prostates or prostate cancer. This dependence of prostate cells on AR signaling continues even upon neoplastic transformation.

AR has been purified, characterized, cloned and sequenced from both mouse and human sources. The AR protein contains 920 amino acid residues. Exemplary amino acid and nucleotide sequences from a full-length human AR polypeptide are shown below as SEQ IDs NO: 1 and 2. In some embodiments, an AR polypeptide includes at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids of a AR polypeptide sequence, e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids of the sequence shown in SEQ ID NO: 1 or of a sequence at least 60% (e.g., at least 65%, 70%, 75%, 80%, 85%, 90%, 95%, or 98%) identical to SEQ ID NO: 1. In some embodiments, an AR polypeptide comprises an amino acid sequence that is at least 60% (e.g., at least 65%, 70%, 75%, 80%, 85%, 90%, 95%, or 98%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids of the sequence shown in SEQ ID NO: 1. In some embodiments, an AR polypeptide is a full-length AR polypeptide (e.g., the polypeptide comprises the amino acid sequence of SEQ ID NO: 1).

Glucocorticoid Receptor

In some embodiments, the present invention encompasses the recognition that increased signaling through the glucocorticoid receptor can compensate for inhibition of androgen receptor signaling in castration resistant prostate cancer and doubly resistant prostate cancer. That is, CRPC occurs when cells overexpress AR. When those cells are then treated with second generation antiandrogens, AR target gene expression is inhibited. Doubly resistant prostate cancer develops when expression of a subset of those target genes is restored, indicating that a transcription factor other than AR is responsible for the target gene activation.

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for some of the anti-inflammatory activity of exogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU-486 is an example of a non-selective glucocorticoid receptor antagonist.

Exemplary amino acid and nucleotide sequences from a full-length human GR polypeptide are shown below as SEQ ID NOs: 3-21. In some embodiments, a GR polypeptide includes at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids of a GR polypeptide sequence as set forth in one or more of SEQ ID NOs: 3-21, e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids of the sequence shown in any of SEQ ID NOs: 3-13 or of a sequence at least 60% (e.g., at least 65%, 70%, 75%, 80%, 85%, 90%, 95%, or 98%) identical to one or more of SEQ ID NOs: 3-13. In some embodiments, a GR polypeptide comprises an amino acid sequence that is at least 60% (e.g., at least 65%, 70%, 75%, 80%, 85%, 90%, 95%, or 98%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids of the sequence shown in one or more of SEQ ID NOs: 3-13.

In some embodiments, GR transcription is activated in patients susceptible to or suffering from CRPC or Doubly Resistant Prostate Cancer relative to a reference. In some embodiments, transcription of GR is activated 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, or 10,000 fold or more.

In some embodiments, transcriptional activation of GR is detected by determining a level of GR mRNA transcripts. Methods of detecting and/or quantifying levels of mRNA transcripts are well known in the art and include but are not limited to northern analysis, semi-quantitative reverse transcriptase PCR, quantitative reverse transcriptase PCR, and microarray analysis. These and other basic RNA transcript detection procedures are described in Ausebel et al. (Ausubel F M, Brent R, Kingston R E, Moore D D, Seidman J G, Smith J A, Struhl K (eds). 1998. *Current Protocols in Molecular Biology*. Wiley: New York).

In some embodiments, transcriptional activation of GR is detected by determining a level of GR protein. Methods of detecting and/or quantifying protein levels are well known in the art and include but are not limited to western analysis and mass spectrometry. These and all other basic protein detection procedures are described in Ausebel et al. (Ausubel F M, Brent R, Kingston R E, Moore D D, Seidman J G, Smith J A, Struhl K (eds). 1998. *Current Protocols in Molecular Biology*. Wiley: New York).

In some embodiments, a reference is a sample from an individual without CRPC. In some embodiments, a reference is a sample from an individual without Doubly Resistant Prostate Cancer. In some embodiments, a reference is a sample from an individual without prostate cancer.

Inhibitors (i.e., Inhibitor Agents)

In some embodiments, the present invention encompasses the recognition that inhibition of GR comprises an effective treatment for CRPC and/or doubly resistant prostate cancer.

In some embodiments, an inhibitor for use in accordance with the present invention is or comprises a GR inhibitor. In some embodiments, an inhibitor for use in accordance with the present invention is or comprises a GR and/or an AR inhibitor. In some embodiments, an inhibitor for use in accordance with the present invention is or comprises an AR inhibitor. In some embodiments, an inhibitor for use in accordance with the present invention inhibits SGK1, GR and/or AR level and/or activity. In some embodiments, such level refers to level of SGK1, GR and/or AR mRNA. In some embodiments, such level refers to level of SGK1, GR and/or AR protein. such level refers to level of particular form (e.g., three-dimensional folded form or complex, post-transcriptionally modified form, etc) of SGK1, GR and/or AR protein. In some embodiments, levels comprise levels of a particular form of SGK1, GR and/or AR protein. In some embodiments, a particular form of GR and/or AR protein comprises an active form. In some embodiments, a particular form of SGK1, GR and/or AR protein is or comprises a phosphorylated form. In some embodiments, a particular form of SGK1, GR and/or AR protein is or comprises a glycosylated form. In some embodiments, a particular form of SGK1, GR and/or AR protein is or comprises a sulfylated form. In some embodiments, a particular form of SGK1, GR and/or AR protein is or comprises an enzymatically cleaved form.

In some embodiments, an inhibitor (e.g., an SGK1, GR, and/or AR inhibitor) is an inhibitory agent characterized in that, when the agent is contacted with a system expressing or capable of expressing active target (e.g., active SGK1, GR, and/or AR), level and/or activity of the target in the system is reduced (in the absolute and/or relative to level and/or activity of a reference entity, which reference entity in some embodiments may be or comprise a different form of the same target) in its presence compared with a reference level or activity observed under otherwise comparable conditions when the agent is absent or is present at a lower level.

In some embodiments, detection, assessment, and/or characterization of an inhibitor includes determination of a reference target level or activity (e.g., that observed under otherwise comparable conditions in absence of the inhibitor) is determined. In some embodiments such a reference target level or activity is determined concurrently with an inhibited target level or activity (i.e., a level or activity of the target when the inhibitor is present at a particular level; in some embodiments at more than one levels. In some embodiments, a reference level or activity is determined historically relative to determination of the inhibited level or activity. In some embodiments, a reference level or activity is or comprises that observed in a particular system, or in a comparable system, under comparable conditions lacking the inhibitor. In some embodiments, a reference level or activity is or comprises that observed in a particular system, or a comparable system, under otherwise identical conditions lacking the inhibitor.

In some embodiments, detection, assessment, and/or characterization of an inhibitor includes determination of a control entity level or activity (e.g., a level or activity of a control entity observed when the inhibitor is present). In some embodiments, the control is an entity other than the inhibitor's target. In some embodiments, the control entity is a form of the target different from the relevant inhibited form. In some embodiments, such a control entity level or activity is determined concurrently with an inhibited target level or activity (i.e., a level or activity of the target when the inhibitor is present at a particular level; in some embodiments at more than one levels). In some embodiments, a control entity level or activity is determined historically relative to determination of the inhibited level or activity. In some embodiments, a control entity level or activity is or comprises that observed in a particular system, or in a comparable system, under comparable conditions including presence of the inhibitor. In some embodiments, a control entity level or activity is or comprises that observed in a particular system, or a comparable system, under identical conditions including presence of the inhibitor.

In some embodiments, inhibitor is characterized in that RNA level is lower in a relevant expression system when the inhibitor is present as compared with a reference level observed under otherwise comparable conditions when it is absent. In some embodiments, GR mRNA level is reduced 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference level or to an appropriate control.

In some embodiments, a GR inhibitor is characterized in that GR protein level is lower in a relevant expression system when the inhibitor is present as compared with a reference level observed under otherwise comparable conditions when it is absent. In some embodiments, GR protein level is reduced 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference level or to an appropriate control.

In some embodiments, a GR inhibitor inhibits GR activity. In some embodiments, a GR inhibitor inhibits GR transcriptional activation activity. Any of a variety of assays can be used to assess GR transcriptional activation activity. Techniques well known in the art include direct binding assays and competition assays. In some embodiments, GR activity is assessed by mRNA levels of genes regulated by GR.

Genes regulated by GR include but are not limited to ABHD2, ACTA2, ATAD2, AZGP1, BCL6, C1ORF149, C6ORF85, C7ORF63, C9ORF152, CEBPD, CGNL1, CHKA, CRY2, DBC1, DDIT4, EEF2K, EMP1, ERRFI1, FKBP5, FLJ22795, FOXO3, GADD45B, GHR, HERC5, HOMER2, HSD11B2, KBTBD11, KIAA0040, KLF15, KLF9, KRT80, $LIN_7B$, LOC100130886, LOC100131392, LOC100134006, LOC340970, LOC399939, LOC440040, LOC728431, MEAF6, MT1X, NPC1, NRP1, PGC, PGLYRP2, PHLDA1, PNLIP, PPAP2A, PRKCD, PRR15L, RGS2, RHOB, S100P, $SCNN_1G$, SGK, SGK1, SLC25A18, SPRYD5, SPSB1, STK39, TRIM48, TUBA3C, TUBA3D, TUBA3E, ZBTB16, ZMIZ1, and ZNF812.

In some embodiments, a GR inhibitor is characterized in that level of a particular form of lower in a relevant expression system when the inhibitor is present as compared with a reference level observed under otherwise comparable conditions when it is absent. In some embodiments, level of the relevant GR form is reduced 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference level or to an appropriate control.

In some embodiments a reference GR level or activity is determined. In some embodiments a reference GR level or activity is determined concurrently with the determined GR level or activity. In some embodiments, a reference GR level or activity is or comprises that observed in the system or a comparable system under comparable conditions lacking the GR inhibitor. In some embodiments, a reference GR level or activity comprises the GR level or activity that is observed in the system or a comparable system under otherwise identical conditions lacking the GR inhibitor.

In some embodiments, a reference GR level or activity comprises the GR level or activity that is observed in the system or a comparable system under comparable conditions that includes presence of a positive control agent. In some embodiments, a positive control agent comprises an agent characterized in that level or activity of SGK1 activation is higher in an SGK1 expression system when that system is contacted with the agent than under otherwise identical conditions when the system is not so contacted with the agent.

In some embodiments, a reference GR level or activity comprises the SGK1 activation level or activity that is observed in the system or a comparable system under comparable conditions that include presence of a negative control agent. In some embodiments, a negative control agent comprises an agent characterized in that level or activity of GR is lower in a GR expression system when that system is contacted with the agent than under otherwise identical conditions when the system is not so contacted with the agent.

In some embodiments, a GR inhibitor is characterized in that it reduces tumor volume by 1, 2, 3, 4, 5, 6, 7, 8, 9, 10, 15, 20, 25, 30, 35, 40, 45, 50, 55, 60, 65, 70, 75, 80, 85, 90, 95, 100% or more.

In some embodiments, a GR inhibitor is characterized in that it reduces tumor volume by 1, 2, 3, 4, 5, 6, 7, 8, 9, 10, 15, 20, 25, 30, 35, 40, 45, 50, 55, 60, 65, 70, 75, 80, 85, 90, 95, 100% or more.

In some embodiments, the present invention encompasses the recognition that inhibition of GR in conjunction with inhibition of AR comprises an effective treatment for CRPC and/or doubly resistant prostate cancer.

In some embodiments, inhibitor does not significantly activate AR. In some embodiments, a GR inhibitor is an AR inhibitor. In some embodiments, a GR inhibitor is not an AR inhibitor.

In some embodiments, an AR inhibitor is an inhibitory agent characterized in that, when the agent is contacted with a system expressing or capable of expressing Androgen Receptor, level and/or activity of Androgen Receptor in the system is reduced in its presence compared with a reference level or activity observed under otherwise comparable conditions when the agent is absent or is present at a lower level.

In some embodiments, an AR inhibitor is characterized in that a Androgen Receptor mRNA level is lower in a relevant Androgen Receptor expression system when the inhibitor is present as compared with a reference level observed under otherwise comparable conditions when it is absent. In some embodiments, an Androgen Receptor mRNA level is reduced 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference level.

In some embodiments, an AR inhibitor inhibits AR activity. In some embodiments, an AR inhibitor inhibits AR transcriptional activation activity. Any of a variety of assays can be used to assess AR transcriptional activation activity. Techniques well known in the art include direct binding assays and competition assays. In some embodiments, AR activity is assessed by mRNA levels of genes regulated by AR. Genes regulated by AR include but are not limited to ABHD2, ACTA2, ATAD2, AZGP1, BCL6, C1ORF149, C6ORF85, C7ORF63, C9ORF152, CEBPD, CGNL1, CHKA, CRY2, DBC1, DDIT4, EEF2K, EMP1, ERRFI1, FKBP5, FLJ22795, FOXO3, GADD45B, GHR, HERC5, HOMER2, HSD11B2, KBTBD11, KIAA0040, KLF15, KLF9, KRT80, $LIN_7B$, LOC100130886, LOC100131392, LOC100134006, LOC340970, LOC399939, LOC440040, LOC728431, MEAF6, MT1X, NPC1, NRP1, PGC, PGLYRP2, PHLDA1, PNLIP, PPAP2A, PRKCD, PRR15L, RGS2, RHOB, S100P, $SCNN_1G$, SGK, SGK1, SLC25A18, SPRYD5, SPSB1, STK39, TRIM48, TUBA3C, TUBA3D, TUBA3E, ZBTB16, ZMIZ1, and ZNF812. In some embodiments, a mRNA level of a gene regulated by AR is reduced 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference level.

In some embodiments a reference AR level or activity is determined. In some embodiments a reference AR level or activity is determined concurrently with the determined AR level or activity. In some embodiments, a reference AR level or activity is determined historically relative to the determined AR level or activity. In some embodiments, a reference AR level or activity comprises an AR level or activity that is observed in the system or a comparable system under comparable conditions lacking the AR inhibitor. In some embodiments, a reference AR level or activity comprises the AR level or activity that is observed in the system or a comparable system under otherwise identical conditions lacking the AR inhibitor.

In some embodiments, a reference AR level or activity comprises the AR level or activity that is observed in the system or a comparable system under comparable conditions that includes presence of a positive control agent. In some embodiments, a positive control agent comprises an agent characterized in that level or activity of AR activation is higher in a AR expression system when that system is contacted with the agent than under otherwise identical conditions when the system is not so contacted with the agent.

In some embodiments, a reference AR level or activity comprises the AR activation level or activity that is observed in the system or a comparable system under comparable conditions that include presence of a negative control agent. In some embodiments, a negative control agent comprises an agent characterized in that level or activity of AR is lower in a AR expression system when that system is contacted with the agent than under otherwise identical conditions when the system is not so contacted with the agent.

In some embodiments, an AR inhibitor is characterized in that it reduces tumor volume by 1, 2, 3, 4, 5, 6, 7, 8, 9, 10, 15, 20, 25, 30, 35, 40, 45, 50, 55, 60, 65, 70, 75, 80, 85, 90, 95, 100% or more.

As described herein, GR inhibitors, and AR inhibitors for use in accordance with the present invention are inhibitory agents and can be of any class of chemical compounds, including for example a class of chemical compounds selected from the group consisting of macromolecules (e.g. polypeptides, protein complexes, nucleic acids, lipids, carbohydrates, etc) and small molecules (e.g., amino acids, nucleotides, organic small molecules, inorganic small molecules, etc). Particular examples of protein macromolecules are proteins, protein complexes, and glycoproteins, for example such as antibodies or antibody fragments. Particular examples of nucleic acid macromolecules include DNA, RNA (e.g., siRNA, shRNA), and PNA (peptide nucleic acids). In some embodiments, nucleic acid macromolecules are partially or wholly single stranded; in some embodiments they are partially or wholly double stranded, triple stranded, or more. Particular examples of carbohydrate macromolecules include polysaccharides. Particular examples of lipid macromolecules include esters of fatty acids (e.g. triesters such as triglycerides), phospholipids, eicosanoids (e.g., prostaglandins), etc. Examples of small molecules include peptides, peptidomimetics (e.g., peptoids), amino acids, amino acid analogs, oligonucleotides, nucleotides, nucleotide analogs, terpenes, steroids, vitamins and inorganic compounds e.g., heteroorganic or organometallic compounds.

In some embodiments, an AR inhibitor is or comprises a small molecule.

In some embodiments, Ritor will have a formula weight of less than about 10,000 grams per mole, less than 5,000 grams per mole, less than 1,000 grams per mole, or less than about 500 grams per mole, e.g., between 5,000 to 500 grams per mole.

In some embodiments, a GR inhibitor is selected from the group consisting of RU-486 and analogs thereof. In some embodiments, a GR inhibitor is selected from the group consisting of ORG 34517,

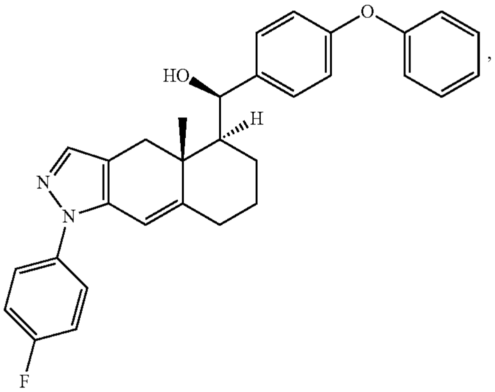

,

-continued

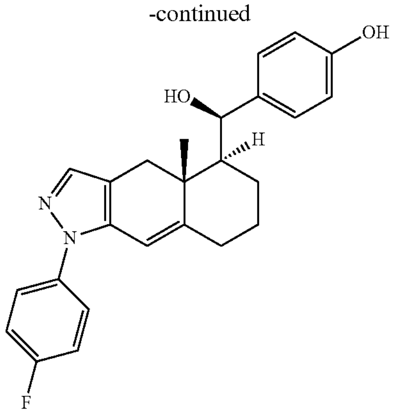

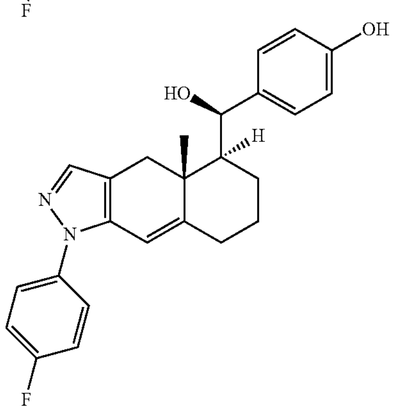

and analogs thereof.

In some embodiments, an AR inhibitor is selected from the group consisting of 3,3'-diindolylmethane (DIM), abiraterone acetate, ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, turosteride, and analogs and combinations thereof.

In some embodiments, an AR inhibitor is selected from the group consisting of ARN-509 and analogs thereof and/or enzalutamide and analogs thereof. In some embodiments, an AR inhibitor is or comprises ARN-509. In some embodiments, an AR inhibitor is or comprises enzalutamide.

In some embodiments, the present invention provides a compound of formula I'

I'

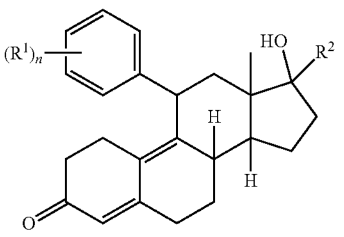

or a pharmaceutically acceptable salt thereof, wherein:

each $R^1$ is independently selected from halogen, optionally substituted $C_{1-6}$aliphatic, $NO_2$, —CN, —OR, —SR, $—N(R)_2$, $—C(R)_3$, —C(O)R, —C(O)OR, —S(O)R, $—S(O)_2R$, $—C(O)N(R)_2$, $SO_2N(R)_2$, OC(O)R, —N(R)C(O)R, —N(R)C(O)OR, $—N(R)SO_2R$, and $OC(O)N(R)_2$; or two $R^1$ groups on adjacent atoms are taken together with their intervening atoms to form an optionally substituted fused 5- to 7-membered ring having 0-3 heteroatoms selected from oxygen, nitrogen, or sulfur;

$R^2$ is optionally substituted unsaturated $C_{2-6}$aliphatic;

each R is independently hydrogen or an optionally substituted group selected from $C_{1-6}$ aliphatic, phenyl, 3- to 8-membered saturated or partially unsaturated carbocyclyl ring, 3- to 8-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur; 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered saturated or partially unsaturated bicyclic heteroaryl having 1-4 heteroatoms selected from oxygen, nitrogen, or sulfur, or 8- to 10-membered bicyclic aryl; and n is from 0-4.

In certain embodiments, n is 1-3. In some embodiments, n is 1. In some embodiments, n is 2. In some embodiments, n is 3. In some embodiments, n is 4.

In some embodiments, each $R^1$ is independently selected from optionally substituted $C_{1-6}$aliphatic, —OR, —SR, or —$N(R)_2$. In some embodiments, each $R^1$ is independently —OR, —SR, or —$N(R)_2$, wherein each R is independently an optionally substituted group selected from $C_{1-6}$alkyl, $C_{3-7}$cycloalkyl, phenyl, 8- to 10-membered bicyclic aryl, 5- to 6-membered heteroaryl having 1-4 heteroatoms selected from oxygen, nitrogen, or sulfur, or 7- to 10-membered saturated or partially unsaturated bicyclic heteroaryl having 1-4 heteroatoms selected from oxygen, nitrogen, or sulfur.

In some embodiments, $R^1$ is —OR, —SR, —$N(R)_2$, —S(O)R, —$S(O)_2R$, or —$C(R)_3$, and R is optionally substituted phenyl.

In some embodiments, $R^1$ is —OR, —SR, —$N(R)_2$, or —$C(R)_3$, and R is an optionally substituted 3- to 8-membered saturated or partially unsaturated carbocyclyl ring.

In some embodiments, $R^1$ is —OR, —SR, —$N(R)_2$, —S(O)R, —$S(O)_2R$, or —$C(R)_3$, and R is an optionally substituted 5-membered heteroaryl having 1 heteroatom selected from oxygen, nitrogen, or sulfur.

In some embodiments, $R^1$ is —OR, —SR, —$N(R)_2$, —S(O)R, —$S(O)_2R$, or —$C(R)_3$, and R is an optionally substituted 6-membered heteroaryl having 1-3 heteroatoms selected from oxygen, nitrogen, or sulfur.

In some embodiments, each $R^1$ is optionally substituted $C_{1-6}$aliphatic. In some embodiments, $R^1$ is $C_1$alkyl-$C_{3-7}$cycloalkyl, $C_1$alkyl-heteroaryl, or $C_1$alkyl-aryl, wherein the aryl groups is selected from phenyl or 8- to 10-membered bicyclic aryl, and the heteroaryl group selected from 5- to 6-membered heteroaryl having 1-4 heteroatoms selected from oxygen, nitrogen, or sulfur, or 7- to 10-membered saturated or partially unsaturated bicyclic heteroaryl having 1-4 heteroatoms selected from oxygen, nitrogen, or sulfur.

In some embodiments, two $R^1$ groups on adjacent atoms are taken together with their intervening atoms to form an optionally substituted fused 5- to 7-membered ring having 0-3 heteroatoms selected from oxygen, nitrogen, or sulfur. In some embodiments, two $R^1$ groups on adjacent atoms are taken together with their intervening atoms to form an optionally substituted fused 5-membered ring having 0-2 heteroatoms selected from oxygen, nitrogen, or sulfur. In some embodiments, two $R^1$ groups on adjacent atoms are taken together with their intervening atoms to form an optionally substituted fused 6-membered ring having 0-2 heteroatoms selected from oxygen, nitrogen, or sulfur.

In some embodiments, $R^2$ is optionally substituted unsaturated $C_{2-4}$aliphatic. In some embodiments, $R^2$ is unsaturated $C_{2-6}$aliphatic. In some embodiments, $R^2$ is unsaturated C2-5aliphatic. In some embodiments, $R^2$ is unsaturated $C_{2-4}$aliphatic. In some embodiments, $R^2$ is unsaturated $C_{2-3}$aliphatic. In some embodiments, $R^2$ is selected from the group consisting of ethyn-1-yl, 1-propyn-1-yl, 1-butyn-1-yl, ethen-1-yl, 1-propen-1-yl, and 1-buten-1-yl.

In some embodiments, R is selected from methyl, ethyl, propyl, isopropyl, butyl, or tert-butyl.

In some embodiments, the present invention provides a compound of formula I:

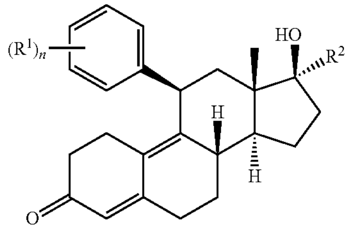

I or a pharmaceutically acceptable salt thereof, wherein each of $R^1$, $R^2$, and n is as defined above and described in classes and subclasses herein.

In some embodiments, the present invention provides a compound of formula II:

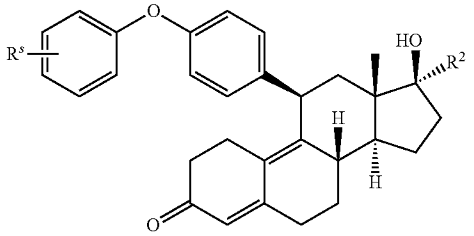

II or a pharmaceutically acceptable salt thereof, wherein $R^2$ is as defined above and described in classes and subclasses herein, both singly and in combination, and $R^s$ when present is a suitable monovalent substituent as defined above and described in classes and subclasses herein, both singly and in combination.

In some embodiments, $R^s$ is selected from —OH, —$NH_2$, —$CH_3$, —Br, —Cl, —F, —I, —SH, —$SOR^o$, —$SO_2R^o$, —O—$C_{1-6}$alkyl, —$N(R^o)_2$, —S—$C_{1-6}$alkyl, and —$C(R^o)_2$—$C_{1-6}$alkyl. In some embodiments, each $R^o$ is independently hydrogen or $C_{1-6}$alkyl.

In some embodiments, the present invention provides a compound of formula II-a:

II-a

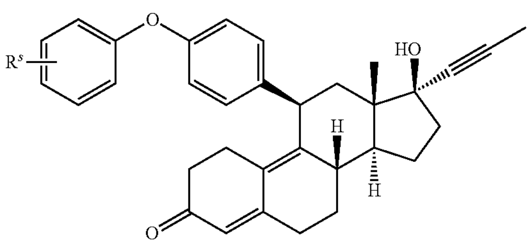

or a pharmaceutically acceptable salt thereof, wherein $R^s$, when present, is a suitable monovalent substituent on a substitutable carbon as defined above and described in classes and subclasses herein, both singly and in combination.

In some embodiments, two $R^1$ groups on adjacent atoms are taken together with their intervening atoms to form an optionally substituted fused 5-membered ring having 0-2 heteroatoms selected from oxygen, nitrogen, or sulfur. In some embodiments, the present invention provides a compound of formula III:

III

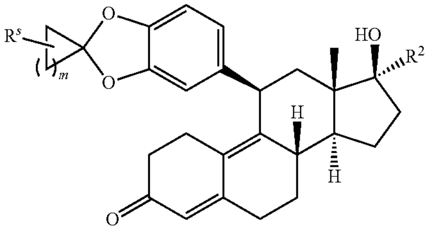

or a pharmaceutically acceptable salt thereof, wherein m is 1-8 and $R^s$, when present, and $R^2$ are as defined above and described in classes and subclasses herein, both singly and in combination. In some embodiments, $R^s$ is selected from $C_{1-6}$alkyl, —OH, —$NH_2$, $CH_3$, halogen, —O-aryl, —$NR^o$-aryl, —S-aryl, —O—$C_{3-7}$cycloalkyl, —$NR^o$—$C_{3-7}$cycloalkyl, —S—$C_{3-7}$cycloalkyl, —$C(R^o)_2$—$C_{3-7}$cycloalkyl, —$OC_{1-6}$alkyl, —$N(R^o)C_{1-6}$alkyl, —S—$C_{1-6}$alkyl, and —$C(R^o)_2$-aryl.

In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8.

In some embodiments, the present invention provides a compound of formula III-a:

III-a

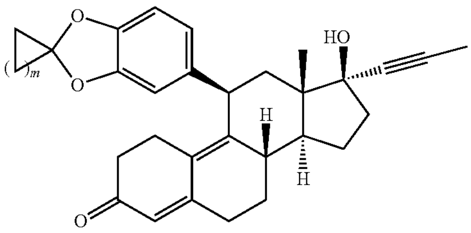

or a pharmaceutically acceptable salt thereof, wherein m is 1-8.

In some embodiments, the present invention provides a compound of formula IV:

IV

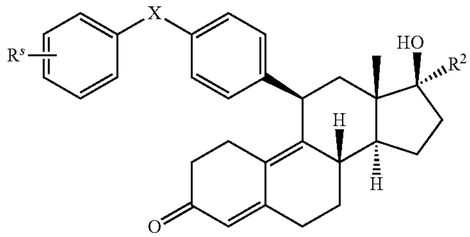

or a pharmaceutically acceptable salt thereof, wherein m is 1-8, X is —O—, —S—, —S(O)—, —$S(O)_2$—, —NR—, or —$C(R^o)_2$—, and $R^s$, when present, $R^2$, and $R^o$ are as defined above and described in classes and subclasses herein, both singly and in combination. In certain embodiments, X is selected from —O—, —S—, —NR—, or —$C(R^o)_2$—.

In some embodiments, the present invention provides a compound of formula V:

V

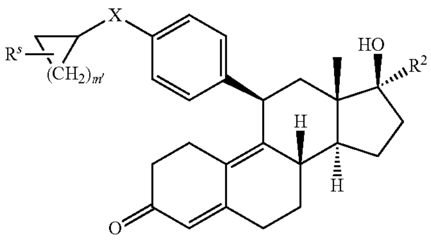

or a pharmaceutically acceptable salt thereof, wherein m' is 1-8, and each of $R^s$, when present, X, and $R^2$ is as defined above and described in classes and subclasses herein, both singly and in combination. In some embodiments, $R^s$ is selected from $C_{1-6}$alkyl, —O-aryl, —$NR^o$-aryl, —S-aryl, —O—$C_{3-7}$cycloalkyl, —$NR^o$—$C_{3-7}$cycloalkyl, —S—$C_{3-7}$ cycloalkyl, —$C(R^o)_2$—$C_{3-7}$cycloalkyl, —$OC_{1-6}$alkyl, —$N(R^o)C_{1-6}$alkyl, —S—$C_{1-6}$alkyl, and —$C(R^o)_2$-aryl. In some embodiments, each $R^o$ is independently hydrogen or $C_{1-6}$alkyl.

In some embodiments, the present invention provides a compound of formula VI:

VI

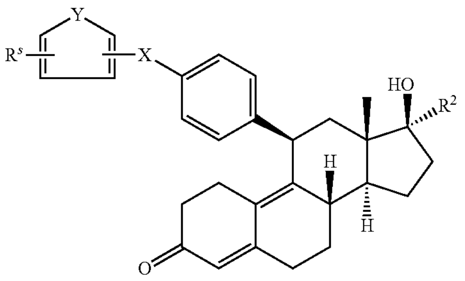

or a pharmaceutically acceptable salt thereof, wherein Y is —O—, —$NR^s$—, —NH—, or —S—, and each of $R^s$, when present, X, and $R^2$ is as defined above and described in classes and subclasses herein, both singly and in combination.

In some embodiments, the present invention provides a compound of formula VII:

VII

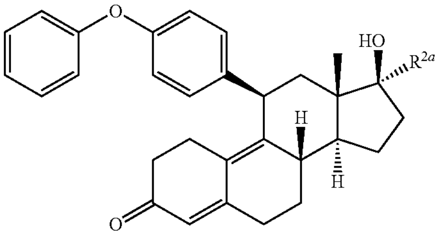

or a pharmaceutically acceptable salt thereof, wherein $R^{2a}$ is unsaturated C2-6aliphatic, acetyl, guanidinyl, or cyano. In some embodiments, $R^{e}$a is selected from the group consisting of ethyn-1-yl, 1-propyn-1-yl, 1-butyn-1-yl, ethen-1-yl, 1-propen-1-yl, and 1-buten-1-yl.

In some embodiments, the present invention provides a compound of formula VIII:

VIII

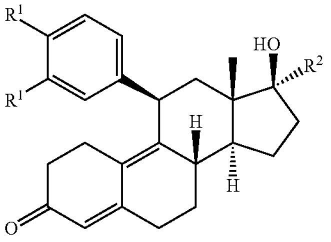

or a pharmaceutically acceptable salt thereof, wherein $R^1$ is —OR or both $R^1$ groups are taken together with their intervening atoms to form an optionally substituted fused 5- to 7-membered ring having 0-3 heteroatoms selected from oxygen, nitrogen, or sulfur, and each of R and $R^2$ is as defined above and described in classes and subclasses herein, both singly and in combination. In some embodiments, the bridge formed by two $R^1$ groups taken together is selected from —$OCH_2O$—, —$OCH_2CH_2O$—, —OC(O)O—, and —$OCOCH_2O$—.

In some embodiments, a provided compound is:

I-1

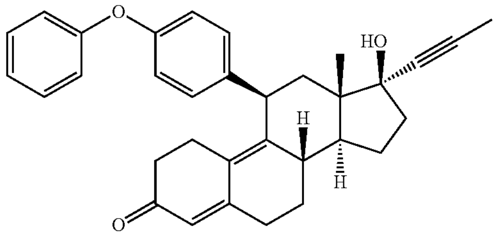

ABR173 or a pharmaceutically acceptable salt thereof.

In some embodiments, a provided compound is:

I-2

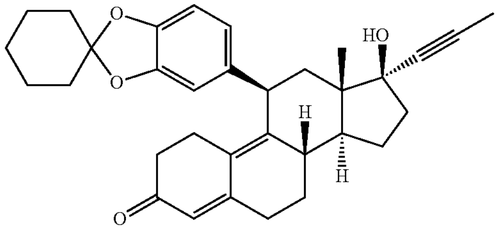

ABR167 or a pharmaceutically acceptable salt thereof.

In certain embodiments a provided compound is selected from the following, or a pharmaceutically acceptable salt thereof:

I-3

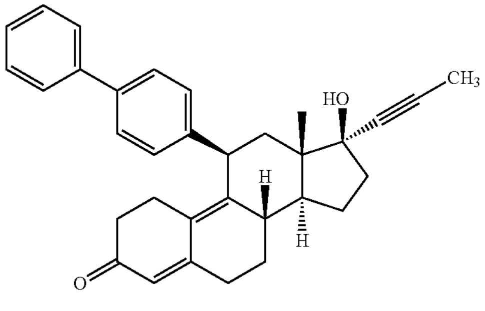

I-4

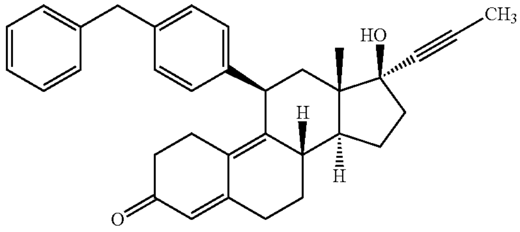

-continued

I-5

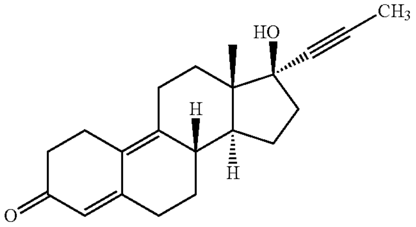

I-6

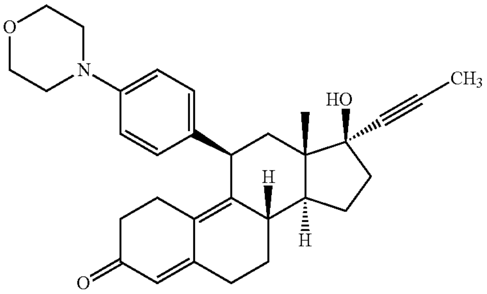

I-7

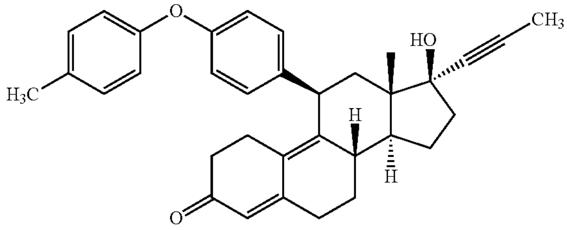

I-8

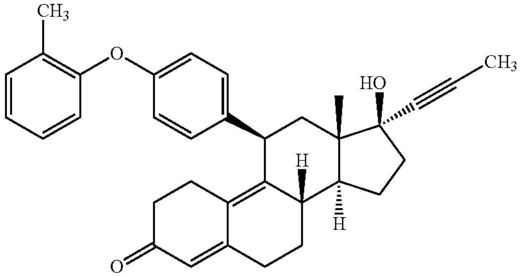

I-9

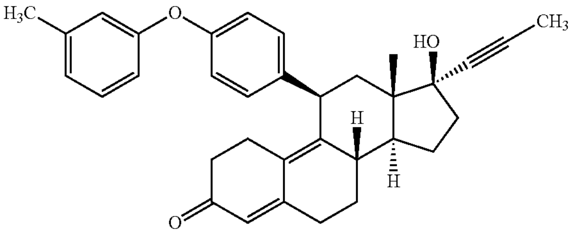

I-10

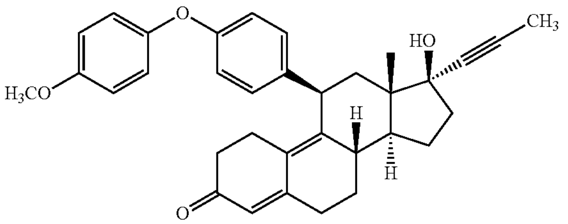

In some embodiments, a provided compound is other than the compounds depicted in FIG. 8.

In certain embodiments, compounds of formula I', I, II, II-a, III, III-a, IV, V, VI, VII, and VIII, and compounds I-1 through I-10, are useful in each of the methods described herein.

Synthesis of Compounds

Compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

In certain embodiments, the present compounds are generally prepared according to Scheme A set forth below:

Scheme A

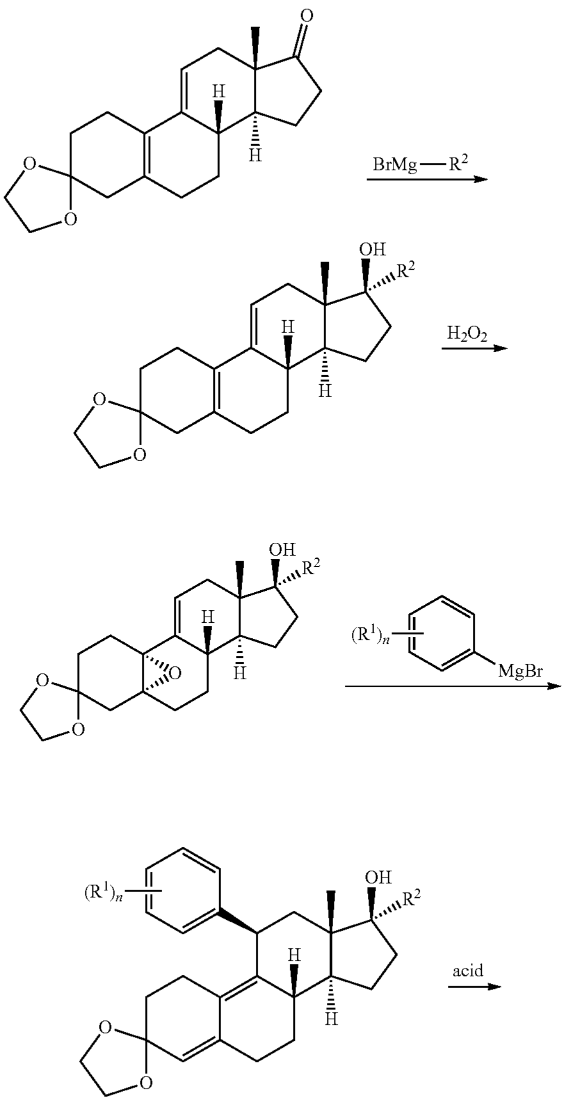

-continued

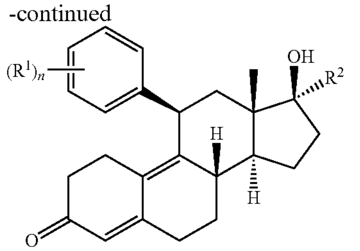

I

Compounds of the invention may also be made according to the methods described by Prat et al., Tet. Lett. 45 (2004), 765-768; Prat et al., Org. Proc. Res. & Dev. (2004), 8, 219-228; Napolitano et al., Gazzetta Chimica Italiana 120 (1990), 323-326; Teutsch et al., Tet. Lett. 22 (1979), 2051-2054; US Patent Publication Nos. 2004224933 and 2004229853 and French Patent Application Publication No. 2,201,287, the entire contents of each of which are hereby incorporated by reference herein.

In some embodiments, "ABR173" and "ABR208" are used interchangeably, and "ABR167" and "ABR240" are also used interchangeably.

Antibodies

In some embodiments, an AR inhibitor for use in accordance with the present invention is or comprises an antibody or antigen-binding fragment thereof. In some embodiments, a GR inhibitor is or comprises an antibody or antigen-biding fragment thereof that binds specifically to a GR polypeptide (e.g., to a reference GR as set forth in one or more of SEQ ID NOs 3-13, or to a polypeptide whose amino acid sequence shows at least 60%, 65%, 70%, 75%, 80%, 85%, 90%, 95%, 96%, 97%, 98%, 99% or more overall sequence identity therewith). In some embodiments, an AR inhibitor is or comprises an antibody or antigen-binding fragment thereof that binds to an AR polypeptide (e.g., to a reference AR as set forth in SEQ ID NO: 1, or to a polypeptide whose amino acid sequence shows at least 60%, 65%, 70%, 75%, 80%, 85%, 90%, 95%, 96%, 97%, 98%, 99% or more overall sequence identity therewith).

An inhibitory agent as described herein may be or comprise an antibody, or fragment thereof, of any appropriate isotype, including, for example: IgG (e.g., IgG1, IgG2, IgG3, IgG4), IgM, IgA1, IgA2, IgD, or IgE. In some embodiments, an antibody, or fragment thereof, is an IgG isotype, e.g., IgG1 or IgG4.

In some embodiments, an inhibitory agent may be or comprise a full-length antibody is full-length. In some embodiments, an inhibitory agent may be or comprise only an antigen-binding fragment (e.g., a Fab, $F(ab)_2$, Fv or single chain Fv fragment) of an antibody (e.g., an may lack or be substantially free of other antibody components),In some embodiments, an inhibitory agent may be or comprise multiple antigen-binding components of an antibody (e.g., as in a diabody or zybody). In some embodiments, an inhibitory agent may include one or more CDRs found in a full-length antibody raised in an organism against the relevant antigen. In some embodiments, an inhibitory agent may include such CDRs in a different polypeptide context than that in which they are found in the organism-raised antibody.

In some embodiments, an inhibitory agent may be or comprise an antibody, or fragment thereof, that is monoclonal, recombinant, chimeric, deimmunized, human, humanized, etc as these terms are understood in the art.

As is known in the art, monoclonal antibodies can be produced by a variety of techniques, including conventional monoclonal antibody methodology, e.g., the standard somatic cell hybridization technique of Kohler and Milstein, Nature 256: 495, 1975. Polyclonal antibodies can be produced by immunization of animal or human subjects. See generally, Harlow, E. and Lane, D. *Antibodies: A Laboratory Manual*, Cold Spring Harbor Laboratory Press, Cold Spring Harbor, N.Y., 1988. Recombinant, chimeric, deimmunized, human, or humanized antibodies can also be produced using standard techniques, as is known in the art. Techniques for engineering and preparing antibodies are described, for example, in U.S. Pat. No. 4,816,567, issued Mar. 28, 1989; U.S. Pat. No. 5,078,998, issued Jan. 7, 1992; U.S. Pat. No. 5,091,513, issued Feb. 25, 1992; U.S. Pat. No. 5,225,539, issued Jul. 6, 1993; U.S. Pat. No. 5,585,089, issued Dec. 17, 1996; U.S. Pat. No. 5,693,761, issued Dec. 2, 1997; U.S. Pat. No. 5,693,762, issued Dec. 2, 1997; U.S. Pat. No. 5,869,619; issued 1991; U.S. Pat. No. 6,180,370, issued Jan. 30, 2001; U.S. Pat. No. 6,548,640, issued Apr. 15, 2003; U.S. Pat. No. 6,881,557, issued Apr. 19, 2005; U.S. Pat. No. 6,982,321, issued Jan. 3, 2006; incorporated herein by reference. Antibodies described herein can be used, e.g., for detection (e.g., diagnostic) assays, and/or for therapeutic applications.

RNAi

In some embodiments, a GR inhibitor or an AR inhibitor for use in accordance with the present invention inhibits via RNA interference. RNA interference refers to sequence-specific inhibition of gene expression and/or reduction in target RNA levels mediated by an at least partly double-stranded RNA, which RNA comprises a portion that is substantially complementary to a target RNA. Typically, at least part of the substantially complementary portion is within the double stranded region of the RNA. In some embodiments, RNAi can occur via selective intracellular degradation of RNA. In some embodiments, RNAi can occur by translational repression. In some embodiments, RNAi agents mediate inhibition of gene expression by causing degradation of target transcripts. In some embodiments, RNAi agents mediate inhibition of gene expression by inhibiting translation of target transcripts. In some embodiments, RNAi agent includes a portion that is substantially complementary to a target RNA. In some embodiments, RNAi agents are at least partly double-stranded. In some embodiments, RNAi agents are single-stranded. In some embodiments, exemplary RNAi agents can include small interfering RNA (siRNA), short hairpin RNA (shRNA), and/or microRNA (miRNA). In some embodiments, an agent that mediates RNAi includes a blunt-ended (i.e., without overhangs) dsRNA that can act as a Dicer substrate. For example, such an RNAi agent may comprise a blunt-ended dsRNA which is >25 base pairs length. RNAi mechanisms and the structure of various RNA molecules known to mediate RNAi, e.g. siRNA, shRNA, miRNA and their precursors, are described, e.g., in Dykxhhorn et al., 2003, Nat. Rev. Mol. Cell. Biol., 4:457; Hannon and Rossi, 2004, Nature, 431:3761; and Meister and Tuschl, 2004, Nature, 431:343; all of which are incorporated herein by reference.

In some embodiments, a GR inhibitor or an AR inhibitor for use in accordance with the present invention an siRNA or an shRNA. In some embodiments, an inhibitory agent is or comprises a siRNA or shRNA that binds specifically to SGK1 RNA (e.g., to a reference SGK1 as set forth in one or more of SEQ ID NOs 26-29, or to an RNA whose nucleic acid sequence shows at least 60%, 65%, 70%, 75%, 80%, 85%, 90%, 95%, 96%, 97%, 98%, 99% or more overall sequence identity therewith). In some embodiments, the siRNA or an shRNA binds to full length SGK1 RNA. In some embodiments, the siRNA or an shRNA binds to a fragment of SGK1 RNA at least 5 (e.g., at least 6, 7, 8, 9, 10, 15, 20, 25, 30, 35, 40 or more nucleotides long). In some embodiments, an inhibitory agent is or comprises a siRNA or shRNA that binds specifically to GR RNA (e.g., or shRNA binds specifically to RNA (e.g., to a reference GR as set forth in one or more of SEQ ID NOs 14-21, or to an RNA whose nucleic acid sequence shows at least 60%, 65%, 70%, 75%, 80%, 85%, 90%, 95%, 96%, 97%, 98%, 99% or more overall sequence identity therewith). In some embodiments, the siRNA or an shRNA binds to full length GR RNA. In some embodiments, the siRNA or an shRNA binds to a fragment of GR RNA at least 5 (e.g., at least 6, 7, 8, 9, 10, 15, 20, 25, 30, 35, 40 or more nucleotides long).). In some embodiments, an inhibitory agent is or comprises a siRNA or shRNA that binds specifically to AR RNA (e.g., to a reference AR as set forth in SEQ ID NO: 2, or to an RNA whose nucleic acid sequence shows at least 60%, 65%, 70%, 75%, 80%, 85%, 90%, 95%, 96%, 97%, 98%, 99% or more overall sequence identity therewith). In some embodiments, the siRNA or an shRNA binds to full length AR RNA. In some embodiments, the siRNA or an shRNA binds to a fragment of AR RNA at least 5 (e.g., at least 6, 7, 8, 9, 10, 15, 20, 25, 30, 35, 40 or more nucleotides long). In some embodiments, an AR inhibitor is or comprise siRNA that targets AR. In some embodiments, a GR inhibitor is or comprise shRNA that targets GR. In some embodiments, an AR inhibitor is or comprise shRNA that targets AR. Inhibitory nucleic acids are well known in the art. For example, siRNA, shRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

RNA interference refers to sequence-specific inhibition of gene expression and/or reduction in target RNA levels mediated by an at least partly double-stranded RNA, which RNA comprises a portion that is substantially complementary to a target RNA. Typically, at least part of the substantially complementary portion is within the double stranded region of the RNA. In some embodiments, RNAi can occur via selective intracellular degradation of RNA. In some embodiments, RNAi can occur by translational repression. In some embodiments, RNAi agents mediate inhibition of gene expression by causing degradation of target transcripts. In some embodiments, RNAi agents mediate inhibition of gene expression by inhibiting translation of target transcripts. Generally, an RNAi agent includes a portion that is substantially complementary to a target RNA. In some embodiments, RNAi agents are at least partly double-stranded. In some embodiments, RNAi agents are single-stranded. In some embodiments, exemplary RNAi agents can include small interfering RNA (siRNA), short hairpin RNA (shRNA), and/or microRNA (miRNA). In some embodiments, an agent that mediates RNAi includes a blunt-ended (i.e., without overhangs) dsRNA that can act as a Dicer substrate. For example, such an RNAi agent may comprise a blunt-ended dsRNA which is >25 base pairs length. RNAi mechanisms and the structure of various RNA molecules known to mediate RNAi, e.g. siRNA, shRNA, miRNA and their precursors, are described, e.g., in Dykxhhorn et al., 2003, Nat. Rev. Mol. Cell. Biol., 4:457; Hannon and Rossi, 2004, Nature, 431:3761; and Meister and Tuschl, 2004, Nature, 431:343; all of which are incorporated herein by reference.

An siRNA, shRNA, or antisense oligonucleotide may inhibit the transcription of a gene or prevent the translation of a gene transcript in a cell. In some embodiments, an inhibitory agent comprises a siRNA or shRNA from 16 to 1000 nucleotides long. In some embodiments, an inhibitory agent comprises an siRNA or, shRNA, from 18 to 100 nucleotides long. In certain embodiments, an inhibitory agent comprises a siRNA or shRNA that is an isolated nucleic acid that targets a nucleotide sequence such as the AR coding sequence (SEQ ID NO: 2), the GR coding sequence (SEQ ID NOs: 14-21), or the SGK1 coding sequence (SEQ ID NOs: 26-29).

In some embodiments, an siRNA, shRNA or antisense oligonucleotide is specifically hybridizable to an mRNA encoding a GR polypeptide whose amino acid sequence shows at least 60% (e.g., at least 65%, 70%, 75%, 80%, 85%, 90%, 95%, or 98%) overall sequence identity with a GR polypeptide of any of SEQ ID NOs 3-13. In certain embodiments, the siRNA, shRNA, or antisense oligonucleotide is an isolated nucleic acid that targets to a nucleotide sequence encoding polypeptide fragments of GR. In some embodiments, an siRNA, shRNA or antisense oligonucleotide is specifically hybridizable to an mRNA encoding an AR polypeptide whose amino acid sequence shows at least 60% (e.g., at least 65%, 70%, 75%, 80%, 85%, 90%, 95%, or 98%) overall sequence identity with an AR polypeptide of SEQ ID NO 1. In certain embodiments, the siRNA, shRNA, or antisense oligonucleotide is an isolated nucleic acid that targets a nucleotide sequence encoding polypeptide fragments of AR.

Expression Systems

In some embodiments, a GR inhibitor or an AR inhibitor for use in accordance with the present invention are characterized in that levels of GR and/or AR are reduced in an expression system when the inhibitor is present as compared with a reference level observed under otherwise comparable conditions when it is absent.

In some embodiments an expression system is or comprises a GR expression system. In some embodiments a GR expression system is or comprises an expression system in which GR is expressed. In some embodiments an expression system is or comprises an AR expression system. In some embodiments an AR expression system is or comprises an expression system in which AR is expressed.

In some embodiments the expression system is or comprises an in vitro expression system. In some embodiments, the expression system is or comprises an in vivo expression system.

In some embodiments an expression system is or comprises cells. In some embodiments, cells comprise prokaryotic cells. In some embodiments, cells comprise eukaryotic cells. In some embodiments, cells are human cells. In some embodiments, cells are mouse cells. In some embodiments, cells are tumor cells. In some embodiments, cells are cells from an individual susceptible to, suffering from, or who has previously had prostate cancer. In some embodiments, cells are cells from an individual susceptible to, suffering from, or who has previously had CRPC. In some embodiments, cells are cells from an individual susceptible to, suffering from, or who has previously had doubly resistant prostate cancer. In some embodiments, cells are prostate cancer cells. In some embodiments, cells are obtained from a living organism. In some embodiments, cells are obtained from cell culture. In some embodiments, cells comprise any cell type capable of expressing GR. In some embodiments, cells comprise any cell type capable of expressing AR. In some embodiments, cells comprise any cell type capable of expressing GR and AR. In some embodiments, cells comprise mouse cell lines. In some embodiments, cells comprise human prostate adenocarcinoma cells. In some embodiments, cells comprise LNCaP/AR cells. In some embodiments, cells comprise CWR22PC cells. In some embodiments, cells comprise CV1 cells. In some embodiments, cells comprise VCaP cells. In some embodiments, cells comprise CS I cells. In some embodiments, cells comprise LREX' cells.

In some embodiments the expression system is or comprises cells in cell culture. Techniques for culturing a wide variety of cell types are well known in the art. See, for example, Current Protocols in Molecular Biology (N.Y., John Wiley & Sons; Davis et al. 1986). In some embodiments, an expression system may comprise cells in cell culture wherein the cells are cultured in cell culture media. In some embodiments, cell culture media utilized in accordance with the present invention is or comprises serum-free cell culture media. In certain embodiments, utilized cell culture media is fully defined synthetic cell culture media. In some embodiments, utilized cell culture media is Roswell Park Memorial Institute medium (RPMI). In certain embodiments, utilized cell culture media is Dulbecco's Modified Eagle Medium (DMEM). In certain embodiments, utilized cell culture media is Iscove's Modified Dulbecco's Medium (IMEM). In certain embodiments, utilized cell culture media is RPMI, Ham's F-12, or Mammary Epithelial Cell Growth Media (MEGM). In some embodiments, utilized cell culture media comprises additional components including Fetal Bovine Serum (FBS), charcoal-stripped, dextran-treated fetal bovine serum (CSS), Bovine Serum (BS), and/or Glutamine or combinations thereof. In some embodiments, utilized cell culture media are supplemented with an antibiotic to prevent contamination. Useful antibiotics in such circumstances include, for example, penicillin, streptomycin, and/or gentamicin and combinations thereof. Those of skill in the art are familiar with parameters relevant to selection of appropriate cell culture media.

In some embodiments the expression system is or comprises tissue. In some embodiments, the tissue is or comprises prostate tissue. In some embodiments, the tissue is or comprises tissue from a tumor. In some embodiments, the tissue is from an individual susceptible to, suffering from, or who has previously had prostate cancer. In some embodiments, the tissue is from an individual susceptible to, suffering from, or who has previously had CRPC. In some embodiments, the tissue is from an individual susceptible to, suffering from, or who has previously had doubly resistant prostate cancer.

In some embodiments the expression system is or comprises an organism. In some embodiments, an organism is an animal. In some embodiments, an organism is an insect. In some embodiments, an organism is a fish. In some embodiments, an organism is a frog. In some embodiments, an organism is a chicken. In some embodiments, an organism is a mouse. In some embodiments, an organism is a rabbit. In some embodiments, an organism is a rat. In some embodiments, an organism is a dog. In some embodiments, an organism is a non-human primate. In some embodiments, an organism is a human.

In some embodiments the expression system is or comprises allogenic cells within a host organism. In some embodiments, allogenic cells comprise any cells described herein. In some embodiments, a host organism comprises any organism described herein. In some embodiments allogenic cells comprise LNCaP/AR cells and a host organism comprises castrated mice.

In some embodiments, an expression system comprises native SGK1, AR and/or GR present in the genome of the cell, tissue, or host organism. In some embodiments, an expression system comprises exogenous SGK1, AR and/or GR DNA for expressing SGK1, AR and/or GR. Polynucleotides (e.g., DNA fragments) encoding an SGK1, AR and/or GR protein for can be generated by any of a variety of procedures. They can be cleaved from larger polynucleotides (e.g., genomic sequences, cDNA, or the like) with appropriate restriction enzymes, which can be selected, for example, on the basis of published sequences of human SGK1, AR and/or GR. mRNA sequences for human SGK1 are shown in SEQ ID NOs: 26-29. The mRNA sequence for human AR is shown in SEQ ID NO: 2. mRNA sequences for human GR are shown in SEQ ID NOs: 14-21. In some embodiments, polynucleotides encoding an SGK1, AR and/or GR protein can be generated by PCR amplification by selecting appropriate primers based on published sequences such as those above. Methods of PCR amplification, including the selection of primers, conditions for amplification, and cloning of the amplified fragments, are known in the art. See, e.g., Innis, M. A. et al., eds. PCR Protocols: a guide to methods and applications, 1990, Academic Press, San Diego, Calif. and Wu et al., eds., Recombinant DNA Methodology, 1989, Academic Press, San Diego, Calif. In some embodiments, polynucleotide fragments encoding an SGK1, AR and/or GR protein can be generated by chemical synthesis. Combinations of the above recombinant or non-recombinant methods, or other conventional methods, can also be employed.

In some embodiments, an expression system comprises exogenous AR and/or GR DNA for expressing AR and/or GR contained within an expression vector. An isolated polynucleotide encoding AR and/or GR protein or a fragment thereof can be cloned into any of a variety of expression vectors, under the control of a variety of regulatory elements, and expressed in a variety of cell types and hosts, described herein.

Various types of vectors are suitable for expression of AR and/or GR polypeptides in an expression system described herein. The term "vector" refers to a nucleic acid molecule capable of transporting another nucleic acid to which it has been linked and can include, for example, a plasmid, cosmid or viral vector. The vector can be capable of autonomous replication or it can integrate into a host DNA. Viral vectors include, e.g., replication defective retroviruses, adenoviruses and adeno-associated viruses. Other types of viral vectors are known in the art.

In some embodiments, an expression vector is or comprises any vector suitable for containing a nucleic acid encoding an AR and/or GR polypeptide in a form suitable for expression of the nucleic acid encoding an AR and/or GR polypeptide in a host cell. In some embodiments, an expression vector includes one or more regulatory sequences operatively linked to the nucleic acid sequence to be expressed. In some embodiments, regulatory sequences are or comprise promoters, enhancers and/or other expression control elements (e.g., polyadenylation signals). In some embodiments, regulatory sequences are or comprise native regulatory sequences. In some embodiments, regulatory sequences are or comprise those which direct constitutive expression of a nucleotide sequence. In some embodiments, regulatory sequences are or comprise tissue-specific regulatory sequences. In some embodiments, regulatory sequences are or comprise inducible sequences. The design of the expression vector can depend on such factors as the choice of the host cell to be transformed, the level of expression of protein desired, and the like.

In some embodiments, a GR or AR expression system comprises recombinant expression vectors designed for expression of and/or GR polypeptides in prokaryotic cells. In some embodiments, a GR or AR expression system comprises recombinant expression vectors designed for expression of SGK1, AR and/or GR polypeptides in eukaryotic cells. For example, polypeptides can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif., 1990. In some embodiments, a GR or AR expression system comprises recombinant expression vectors designed for expression of S AR and/or GR polypeptides in vitro. For example, a recombinant expression vector can be transcribed and translated in vitro using T7 promoter regulatory sequences and T7 polymerase.

Techniques for introducing vector DNA into host cells via conventional transformation or transfection techniques are well known in the art. As used herein, the terms "transformation" and "transfection" are intended to refer to a variety of art-recognized techniques for introducing foreign nucleic acid (e.g., DNA) into a host cell, including, for example, calcium phosphate or calcium chloride co-precipitation, DEAE-dextran-mediated transfection, lipofection, gene gun, or electroporation.

Uses

Test Agents

The present disclosure provides assays for designing, detecting, identifying, and/or characterizing one or more agents to evaluate an effect of the test agent on level or activity of an SGK1, GR and/or AR polypeptide and/or to otherwise assess usefulness as inhibitory agents in accordance with the present invention.

Any agent or collection of agents can be designed, detected, identified, characterized and/or otherwise evaluated as a test agent as described herein. For example, any class of inhibitory agents as described above may be so designed, detected, identified, characterized and/or otherwise evaluated. The test agent can be naturally occurring (e.g., a herb or a nature product), synthetic, or both. Examples of macromolecules are proteins (e.g., antibodies, antibody fragments), protein complexes, and glycoproteins, nucleic acids, e.g., DNA, RNA (e.g., siRNA), and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds.

In certain embodiments, the test agent is an antibody or antibody fragment (e.g., diabody) directed to GR and/or AR polypeptide. The antibody or antibody fragment may be directed to any region of the GR and/or AR polypeptide. The antibody may be polyclonal or monoclonal. The antibody may be of any isotype. The antibody may be derived from any species; however, for use in humans, the antibody is typically of human origin or has been humanized. If the antibody is to be used in other species, the antibody may be adapted to that species. In certain embodiments, the antibody is a humanized monoclonal antibody. In certain specific embodiments, the antibody is a wholly human monoclonal antibody.

In some embodiments, a collection of test agents is provided, and is subjected to one or more assays or assessments as described herein. In some such embodiments, results of such assays or assessments are compared against an appropriate reference so that an inhibitory agent is detected, identified, characterized and/or otherwise evaluated.

In some embodiments one or more test agents is designed by chemical modeling. For example, in some embodiments, one or more crystal structures is provided including a binding cleft into which potential inhibitory agent moieties are docked in silico. Alternatively or additionally, in some embodiments, one or more reference chemical structures is provided of compounds or agents that do or do not bind to the target of interest, and structures of one or more test compounds is/are designed with reference to such reference chemical structures, e.g., by preserving interacting moieties and/or modifying or removing non-interacting moieties. In some embodiments, chemical modeling is performed in silico. In some embodiments, chemical modeling is performed using computers, for example that store reference structures and for example permit overlay or other comparison of test structures therewith. In some embodiments, analogs or derivatives of known compounds or agents are designed as described herein, and are optionally prepared and subjected to one or more assays or assessments so that their activity as an inhibitory agent is detected, identified, characterized and/or otherwise evaluated.

In some embodiments, test agents may be individually subjected to one or more assays or assessments as described herein. In some embodiments, test agents may be pooled together and then subjected to one or more assays or assessments as described herein. Pools so subjected may then be split for further assays or assessments.

In some embodiments, high throughput screening methods are used to screen a chemical or peptide library, or other collection, containing a large number of potential test compounds. Such "chemical libraries" are then screened in one or more assays to identify those library members (particular chemical species or subclasses) that display a desired characteristic activity. Compounds thus identified can serve as conventional "lead compounds" or can themselves be used as potential or actual modulators (e.g., as therapeutics).

A chemical compound library typically includes a collection of diverse chemical compounds, for example, generated by either chemical synthesis or biological synthesis, by combining a number of chemical "building blocks" such as reagents. For example, a linear chemical library such as a polypeptide library may be formed by combining a set of chemical building blocks (amino acids), e.g., in particular specified arrangements or in every possible way for a given compound length (i.e., the number of amino acids in a polypeptide compound). Millions of chemical compounds can be synthesized through such combinatorial mixing of chemical building blocks.

Preparation and screening of libraries of chemical compounds or agents is well known to those of skill in the art. Such libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis or preparation of compound libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., scaffold or framework).

Devices for the preparation of small molecule libraries (e.g., combinatorial libraries) are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous small molecule libraries are commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Test agents can also be obtained from: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) J. Med. Chem. 37:2678-85); spatially addressable parallel solid phase or solution phase libraries; synthetic library methods requiring deconvolution; the 'one-bead one-compound' library method; synthetic library methods using affinity chromatography selection, or any other source, including assemblage of sets of compounds having a structure and/or suspected activity of interest. Biological libraries include libraries of nucleic acids and libraries of proteins. Some nucleic acid libraries provide, for example, functional RNA and DNA molecules such as nucleic acid aptamers or ribozymes. A peptoid library can be made to include structures similar to a peptide library. (See also Lam (1997) Anticancer Drug Des. 12:145). In certain embodiments, one or more test agents is or comprises a nucleic acid molecule, that mediates RNA interference as described herein. A library of proteins may be produced by an expression library or a display library (e.g., a phage display library).

Libraries of test agents may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222: 301-310; Ladner supra.).

Design, Identification, and/or Characterization of GR Inhibitors

In some embodiments, test agents are selected randomly. In some embodiments, the present disclosure provides systems for designing, identifying and/or characterizing test agents. In some embodiments, test agents are designed, identified and/or characterized in vivo. In some embodiments, test agents are designed, identified and/or characterized in vitro. In some embodiments, test agents are designed, identified and/or characterized in silico.

In some embodiments designing, identifying and/or characterizing test agents in silico comprises the steps of: a) providing an image of target protein crystal (e.g., and SGK1, GR, or AR protein crystal) a GR crystal that includes at least one potential interaction site; b) docking in the image at least one moiety that is a potential GR inhibitor structural element; and c) assessing one or more features of a potential moiety-interaction site interaction.

In some embodiments, the one or more features include at least one feature selected from the group consisting of: spatial separation between the moiety and the potential interaction site; energy of the potential moiety-interaction site interaction, and/or combinations thereof.

In some embodiments, a method further comprises a step of providing an image of a potential GR inhibitor comprising the moiety docked with the image of the target GR crystal. In some embodiments, a method further comprises a step of comparing the image with that of an target GR crystal including a bound known modulator, substrate, or product.

Assessing Treatments

In some embodiments, the present invention provides technologies for identifying and/or characterizing potential treatments for CRPC and/or doubly resistant prostate cancer. For example, in accordance with the present invention, useful treatments modulate level and/or activity of GR.

In some embodiments, the invention presented herein comprises methods for identifying and/or characterizing agents for the treatment of castration resistant prostate cancer and/or doubly resistant prostate cancer comprising contacting a system capable of expressing active e.g., in which active s present) with at least one test agent, determining a level or activity of the system when the agent is present as compared with a reference level or activity observed under otherwise comparable conditions when it is absent, and classifying the at least one test agent as a treatment of castration resistant prostate cancer and/or doubly resistant prostate cancer if the level or activity of s significantly reduced when the test agent is present as compared with reference level or activity.

In some embodiments, the invention presented herein comprises methods for identifying and/or characterizing agents for the treatment of castration resistant prostate cancer and/or doubly resistant prostate cancer comprising contacting a system capable of expressing active e.g., in which active GR is present) and also capable of expressing an appropriate reference entity (e.g., in which such a reference entity is present), and determining effect of the assessed agent on GR level or activity relative to that of the reference entity. In some embodiments, agents are identified and/or characterized as GR inhibitors as described herein In which GR and AR are present and active with at least one test agent, determining a level or activity of GR in the system when the agent is present as compared with a GR reference level or activity observed under otherwise comparable conditions when it is absent, determining a level or activity of AR in the system when the agent is present as compared with an AR reference level or activity observed under otherwise comparable conditions when it is absent, classifying the at least one test agent as a treatment of castration resistant prostate cancer and/or doubly resistant prostate cancer if the level or activity of GR is significantly reduced when the test agent is present as compared with the GR reference level or activity and the AR is not significantly increased when the test agent is present as compared with the AR reference level or activity. In some embodiments, the test agent is classified as a treatment of castration resistant prostate cancer and/or doubly resistant prostate cancer if the level or activity of AR is significantly reduced when the test agent is present as compared with the AR reference level or activity.

In some embodiments, the level or activity of GR comprises GR transcriptional activation activity. In some embodiments, the level or activity of GR comprises a GR mRNA level. In some embodiments, the level or activity of GR comprises a GR protein level. In some embodiments, the level or activity of AR comprises AR transcriptional activation activity. In some embodiments, the level or activity of AR comprises a AR mRNA level. In some embodiments, the level or activity of AR comprises a AR protein level. Methods for assaying mRNA and protein levels are described herein.

In some embodiments, a system comprises an expression system as described herein.

In some embodiments, a significant reduction in the level or activity of GR comprises a greater than 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000% or more reduction of GR level or activity. In some embodiments, a significant reduction in the level or activity of GR comprises a greater than 50% reduction of GR level or activity.

In some embodiments, a significant reduction in the level or activity of AR comprises a greater than 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000% or more reduction of AR level or activity. In some embodiments, a significant reduction in the level or activity of AR comprises a greater than 50% reduction of AR level or activity.

In accordance with methods of the present invention, test agents are contacted with a system capable of expressing active and optionally AR) as described herein. Methods of contacting test agents to in vitro and in vivo systems are well known in the art. Methods of contacting test agents to in vitro systems include, but are not limited to, pipetting, mixing, or any other means of transferring a solid or liquid into cell culture or a cell free system. Methods of contacting test agents to in vivo systems include, but are not limited to direct administration to a target tissue, such as heart or muscle (e.g., intramuscular), tumor (intratumorally), nervous system (e.g., direct injection into the brain; intraventricularly; intrathecally). Alternatively or additionally, test agents can be administered by inhalation, parenterally, subcutaneously, intradermally, transdermally, or transmucosally (e.g., orally or nasally). More than one route can be used concurrently, if desired.

In some embodiments a reference GR and/or AR level or activity is determined. In some embodiments a reference GR and/or AR level or activity is determined concurrently with the determined GR and/or AR level or activity. In some embodiments, a reference GR and/or AR level or activity is determined historically relative to the determined GR and/or AR level or activity. In some embodiments, a reference GR and/or AR level or activity comprises a GR and/or AR level or activity that is observed in the system or a comparable system under comparable conditions lacking the test agent. In some embodiments, a reference GR and/or AR level or activity comprises the GR and/or AR level or activity that is observed in the system or a comparable system under otherwise identical conditions lacking the test agent.

In some embodiments, a reference GR and/or AR level or activity comprises the GR and/or AR level or activity that is observed in the system or a comparable system under comparable conditions that includes presence of a positive control agent. In some embodiments, a positive control agent comprises an agent characterized in that level or activity of GR and/or AR activation is higher in a GR and/or AR expression system when that system is contacted with the agent than under otherwise identical conditions when the system is not so contacted with the agent.

In some embodiments, a reference GR and/or AR level or activity comprises the GR and/or AR activation level or activity that is observed in the system or a comparable system under comparable conditions that include presence of a negative control agent. In some embodiments, a negative control agent comprises an SGK1 expression system when that system is contacted with the agent than under otherwise identical conditions when the system is not so contacted with the agent. Current invention provides methods of identifying and/or characterizing agents for treating or reducing incidence or risk for CRPC, comprising the determination of transcription level or activity of one or more targets of GR transcriptional activation contacted to a test agent and identifying the test agent as reducing incidence or risk for CRPC if the transcription level or activities are reduced relative to transcription level or activities in comparable conditions lacking the test agent.

Treatment

The present invention encompasses the recognition that SGK1, GR and/or AR inhibitors described herein, and combinations thereof, can be used as effective treatments for CRPC and doubly resistant prostate cancer. In some embodiments, the invention comprises methods for treating or reducing the risk of castration resistant prostate cancer comprising administering to a subject suffering from or susceptible to castration resistant prostate cancer a GR inhibitor. In some embodiments, the invention comprises methods for treating or reducing the risk of doubly resistant prostate cancer comprising administering to a subject suffering from or susceptible to doubly resistant prostate cancer a GR inhibitor. In some embodiments, the invention comprises methods for treating or reducing the risk of castration resistant prostate cancer comprising administering to a subject suffering from or susceptible to castration resistant prostate cancer an m the group consisting of AR inhibitors, GR inhibitors, and combinations thereof. In some embodiments, the invention comprises methods for treating or reducing the risk of castration resistant prostate cancer comprising administering to a subject suffering from or susceptible to castration resistant prostate cancer a combination of an AR inhibitor and a GR inhibitor, which combination is characterized in that its administration correlates with reduction in level or activity of SGK1 in a prostate cancer patient population. In some embodiments, the invention comprises methods for treating or reducing the risk of doubly resistant prostate cancer comprising administering to a subject suffering from or susceptible to doubly resistant prostate cancer a combination of an m the group consisting of AR inhibitors, GR inhibitors, and combinations thereof. In some embodiments, the invention comprises methods for treating or reducing the risk of doubly resistant prostate cancer comprising administering to a subject suffering from or susceptible to doubly resistant prostate cancer a combination of an AR inhibitor and a GR inhibitor, which combination is characterized in that its administration correlates with reduction in level or activity of SGK1 in a prostate cancer patient population.

In some embodiments, a subject suffering from or susceptible to castration resistant prostate cancer is a subject who has received castration therapy as described herein.

In some embodiments, a subject suffering from or susceptible to doubly resistant prostate cancer is a subject who has received both castration therapy and AR inhibitor therapy, as described herein.

In some embodiments, a subject suffering from or susceptible to CRPC is a subject with statistically significantly elevated levels of GR or of a GR-responsive entity such as SGK1. The present invention provides methods of identifying such subjects, and/or of monitoring the effect of therapy (e.g., of androgen inhibitor therapy), by detecting levels and/or activity of GR or a target thereof. In some embodiments, such monitoring may allow informed decisions to be made about continuing, terminating, and/or modifying therapy.

In some embodiments, methods of identifying subjects and/or of monitoring the effect of therapy in a subject include obtaining a sample from a subject and performing an analysis on the sample. In some embodiments, methods involve taking a plurality of samples over a designated period of time; in some such embodiments, samples are taken at regular intervals during or within the period of time.

Some particular embodiments of example analyses that may be performed on patient samples are set forth, for example, in Example 3.

In accordance with various embodiments of methods of the invention, an inhibitor described herein can be administered to a subject alone, or as a component of a composition or medicament (e.g., in the manufacture of a medicament for the prevention or treatment of CRPC or doubly resistant prostate cancer), as described herein. In some embodiments, a provided inhibitor can be formulated with a physiologically acceptable carrier or excipient to prepare a pharmaceutical composition. In some embodiments, a carrier utilized in such a pharmaceutical compositions, and/or the composition itself, can be sterile. In some embodiments, a pharmaceutical composition is formulated for a specific mode of administration. Methods of formulating compositions are known in the art (see, e.g., Remington's Pharmaceuticals Sciences, $17^{th}$ Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

An inhibitor described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

An inhibitor described herein (or a composition or medicament containing an inhibitor described herein) is administered by any appropriate route. In some embodiments, an inhibitor is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an inhibitor is administered intravenously. In some embodiments, an inhibitor is administered orally. In other embodiments, an inhibitor is administered by direct administration to a target tissue, such as heart or muscle (e.g., intramuscular), tumor (intratumorallly), nervous system (e.g., direct injection into the brain; intraventricularly; intrathecally). Alternatively, an inhibitor (or a composition or medicament containing an inhibitor) can be administered by inhalation, parenterally, intradermally, transdermally, or transmucosally (e.g., orally or nasally). More than one route can be used concurrently, if desired.

In some embodiments, a composition is administered in a therapeutically effective amount and/or according to a dosing regimen that is correlated with a particular desired outcome (e.g., with treating or reducing risk for CRPC and/or doubly resistant prostate cancer).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, an inhibitor is administered at a therapeutically effective amount. As used herein, the term "therapeutically effective amount" is largely determined based on the total amount of the inhibitor contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of CPMC and/or doubly resistant prostate cancer.

In some embodiments, provided compositions, including those provided as pharmaceutical formulations, comprise a liquid carrier such as but not limited to water, saline, phosphate buffered saline, Ringer's solution, dextrose solution, serum-containing solutions, Hank's solution, other aqueous physiologically balanced solutions, oils, esters and glycols.

In some embodiments, a formulation comprising an inhibitor described herein administered as a single dose. In some embodiments, a formulation comprising an inhibitor described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an inhibitor described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an inhibitor described herein is administered at regular intervals indefinitely. In some embodiments, a formulation comprising an inhibitor described herein is administered at regular intervals for a defined period. In some embodiments, a formulation comprising an inhibitor described herein is administered at regular intervals for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

Combination Therapy

In some embodiments, an inhibitor is administered in combination with one or more known therapeutic agents (e.g., anti-androgens) currently used for prostate cancer treatment and CPMC treatment as described herein (Table 1). In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

TABLE 1

Anti-androgen Drugs Currently Used Therapeutically

| Anti-androgen Drug | Description | Recommended Dosage |
|---|---|---|
| Leuprolide | A luteinizing hormone-releasing hormone (LHRH) agonist, which means that it resembles a chemical produced by the hypothalamus (a gland located in the brain) that lowers the level of testosterone in the bloodstream. Also reduces | Available in an injectable form and as an implant. The implant form, used to treat prostate cancer, contains 22.5 mg of leuprolide and is inserted under the skin every three months. This type of slow-release medication is called depot form. A longer-acting implant that lasts 12 months |

TABLE 1-continued

Anti-androgen Drugs Currently Used Therapeutically

| Anti-androgen Drug | Description | Recommended Dosage |
|---|---|---|
| | levels of estrogen in girls and women, and may be used to treat endometriosis or tumors in the uterus. It is presently under investigation as a possible treatment for the paraphilias. | is also available. Injectable leuprolide is injected once a day in a 1-mg dose to treat prostate cancer. Dosage for endometriosis or uterine tumors is 3.75 mg injected into a muscle once a month for three to six months. |
| Goserelin | Also an LHRH agonist, and works in the same way as leuprolide. | Implanted under the skin of the upper abdomen. Dosage for treating cancer of the prostate is one 3.6-mg implant every 28 days or one 10.8-mg implant every 12 weeks. For treating endometriosis, dosage is one 3.6-mg implant every 28 days for six months. |
| Triptorelin | A LHRH agonist, and works in the same way as leuprolide. Not usually given to women. | Given as a long-lasting injection for treatment of prostate cancer or paraphilias. Usual dose for either condition is 3.75 mg, injected into a muscle once a month. |
| Abarelix | Newer drug that works by blocking hormone receptors in the pituitary gland. Recommended for the treatment of prostate cancer in men with advanced disease who refuse surgery, cannot take other hormonal treatments, or are poor candidates for surgery. | Given in 100-mg doses by deep injection into the muscles of the buttocks. It is given on days 1, 15, and 29 of treatment, then every four weeks for a total treatment duration of 12 weeks. |
| Ketoconazole | An antifungal drug available in tablets to be taken by mouth. Its use in treating hirsutism is off-label. | For treatment of hirsutism, 400 mg by mouth once per day. |
| Flutamide | A nonsteroidal antiandrogen medication that blocks the use of androgen by the body. | Available in capsule as well as tablet form. For treatment of prostate cancer, 250 mg by mouth three times a day. For virilization or hyperandrogenism in women, 250 mg by mouth three times a day. It should be used in women, however, only when other treatments have proved ineffective. |
| Nilutamide | Another nonsteroidal antiandrogen drug that works by blocking the body's use of androgens. | To treat prostate cancer, nilutamide is taken in a single 300-mg daily dose by mouth for the first 30 days of therapy, then a single daily dose of 150 mg. |
| Bicalutamide | A nonsteroidal antiandrogen medication that works in the same way as flutamide. | Taken by mouth in a single daily dose of 50 mg to treat prostate cancer. |
| Cyproterone acetate | A steroidal antiandrogen drug that works by lowering testosterone production as well as blocking the body's use of androgens. | Taken by mouth three times a day in 100-mg doses to treat prostate cancer. Dose for treating hyperandrogenism or virilization in women is one 50-mg tablet by mouth each day for the first ten days of the menstrual cycle. Cyproterone acetate given to treat acne is usually given in the form of an oral contraceptive (Diane-35) that combines the drug (2 mg) with ethinyl estradiol (35 mg). Diane-35 is also taken as hormonal therapy by MTF transsexuals. The dose for treating paraphilias is 200-400 mg by injection in depot form every 1-2 weeks, or 50-200 mg by mouth daily. |
| Medroxyprogesterone | A synthetic derivative of progesterone that prevents ovulation and keeps the lining of the uterus from breaking down, thus preventing uterine bleeding. | For the treatment of paraphilias, given as an intramuscular 150-mg injection daily, weekly, or monthly, depending on the patient's serum testosterone levels, or as an oral dose of 100-400 mg daily. As hormonal therapy for MTF transsexuals, 10-40 mg per day. For polycystic ovary syndrome, 10 mg daily for 10 days. |
| Spironolactone | A potassium sparing diuretic that may be given to treat androgen excess in women. | For hyperandrogenism in women, 100-200 mg per day by mouth; for polycystic ovary syndrome, 50-200 mg per day. For the treatment of acne, 200 mg per day. For hormonal therapy for MTF transsexuals, 200-400 mg per day. A topical form of spironolactone is available for the treatment of androgenetic alopecia. |

EXAMPLES

Example 1: Glucocorticoid Receptor Confers Resistance to Anti-Androgens by Bypassing Androgen Receptor Blockade The treatment of advanced prostate cancer has been transformed by novel antiandrogen therapies such as enzalutamide. The present disclosure demonstrates that resistance to such therapies can result from induction of glucocorticoid receptor (GR) expression. That is, the present disclosure demonstrates GR induction as a common feature of drug resistant tumors in a credentialed preclinical model, and furthermore confirms that this finding is also confirmed in patient samples.

As is identified herein, GR substituted for the androgen receptor (AR) to activate a similar but distinguishable set of target genes and was necessary for maintenance of the resistant phenotype. The GR agonist dexamethasone was sufficient to confer enzalutamide resistance whereas a GR antagonist restored sensitivity. Acute AR inhibition resulted in GR upregulation in a subset of prostate cancer cells due to relief of AR-mediated feedback repression of GR expression. The findings presented herein establish a novel mechanism of escape from AR blockade through expansion of cells primed to drive AR target genes via an alternative nuclear receptor upon drug exposure, and furthermore define strategies for pharmacologically countering such escape.

Recently approved drugs that target androgen receptor (AR) signaling such as abiraterone and enzalutamide have rapidly become standard therapies for advanced stage prostate cancer (Scher et al., 2012b) (de Bono et al., 2011). Despite their success, sustained response with these agents is limited by acquired resistance which typically develops within ~6-12 months.

Clinical success of kinase inhibitors in other tumors such as melanoma, lung cancer, leukemia and sarcoma is similarly transient (Sawyers et al., 2002) (Chapman et al., 2011) (Demetri et al., 2002) (Maemondo et al., 2010), resulting in numerous efforts to define mechanisms of acquired resistance. One strategy that has proven particularly useful in elucidating mechanisms of resistance to kinase inhibitors is prolonged treatment of drug-sensitive preclinical models to derive drug-resistant sublines, followed by genome-wide profiling studies to ascertain differences that may play a causal role in conferring drug resistance. A common mechanism that has emerged from these kinase inhibitor studies is reactivation of the signaling pathway targeted by the drug, whether directly (e.g., by mutation of the kinase target) or indirectly (e.g., by bypassing pathway inhibitor blockade through amplification of an alternative kinase) (Glickman and Sawyers, 2012). Both scenarios have been validated in clinical specimens and are guiding efforts to discover next generation inhibitors and to develop rational drug combinations.

Clinically relevant mechanisms of resistance to hormone therapy in prostate cancer have also been elucidated using preclinical models. Hormone therapy, through the use of drugs that lower serum testosterone or competitively block the binding of androgens to AR, has been the mainstay of treatment for metastatic prostate cancer for decades, but is not curative. The late stage of disease, which is refractory to hormone therapy, is termed castration resistant prostate cancer (CRPC). The molecular basis of progression to CRPC in mouse models was previously examined and it was discovered that increased AR expression was the primary mechanism (Chen et al., 2004). This observation was then used to screen for novel anti-androgens that restore AR inhibition in the setting of increased AR levels. These efforts yielded three second-generation anti-androgens: enzalutamide, ARN-509, and RD162 (Tran et al., 2009) (Clegg et al., 2012). Enzalutamide and ARN-509 were further developed for clinical use, culminating in FDA approval of enzalutamide in 2012 based on increased survival (Scher et al., 2012b).

Now with widespread use, resistance to enzalutamide is a major clinical problem. An AR point mutation has recently been identified as one resistance mechanism by derivation of drug-resistant sublines following prolonged exposure to enzalutamide or ARN-509 (Balbas et al., 2013) (Joseph et al., 2013) (Korpal et al., 2013). This AR mutation has also been recovered from patients with resistance to ARN-509 but only in a minority of cases (Joseph et al., 2013). The present invention establishes a novel and potentially more prevalent mechanism of resistance by which tumors bypass AR blockade through upregulation of the glucocorticoid receptor (GR). The present invention furthermore defines novel therapeutic modalities for the treatment of prostate cancer, including for the treatment of CRPC, through administration of inhibitory agents that target GR and/or that target one or more downstream markers responsive to GR. A particular such downstream marker of interest, as established herein, is SGK1. Such GR and/or SGK1 inhibitors may be administered alone, together, and/or in combination with one or more other cancer therapies (e.g., with an AR inhibitor such as an anti-androgen).) is described herein.

Methods

Cell Lines:

LNCaP/AR and VCaP cells were maintained as previously described (Tran et al., 2009). LREX' cells were derived from a single enzalutamide resistant tumor that was harvested, disaggregated with collagenase treatment, and then maintained in RPMI supplemented with 20% FBS and 1 μM enzalutamide. Cells were initially grown on collagen-coated flasks until confluent and then were maintained on standard tissue culture dishes. CS1 were similarly derived from vehicle treated tumors and maintained in standard LNCaP/AR media. LNCaP/AR and LREX' cells were cultured in phenol-red free RPMI with 10% charcoal-stripped FBS prior to drug treatments.

Xenografts:

For all experiments, tumors measurements were obtained weekly using the average of three consecutively obtained volume measurements calculated from three-dimensional calipers measurements. LNCaP/AR xenografts were established in castrate mice as described previously (Tran et al., 2009). Once tumors were established, mice were treated with either enzalutamide, ARN-509, or RD162 (10 mg/kg), or vehicle alone (1% carboxymethyl cellulose, 0.1% Tween-80, 5% DMSO) 5 days a week by oral gavage. 4 day treated mice received ARN-509. Vehicle treated mice were harvested after either 4 or 28 days of treatment. For the validation cohort, 25 tumors were initiated on treatment with intention to continue until resistance, from which 19 resistant tissues were harvested (16 of which had attained a volume greater than at start of treatment.) Xenografts with LNCaP/AR sub-lines were established by injecting two million cells per flank into castrate mice. Mice injected with resistant sub-lines were initiated on treatment with enzalutamide (10 mg/kg) immediately after injection. For xenograft knock-down experiments, cells were infected with virus expressing a control (NT) or GR targeting hairpin, selected with puromycin treatment, and then implanted.

Global Transcriptome Analysis:

RNA extracted from xenograft tumors was analyzed by either Affymetrix HuExl (pilot cohort) or Illumina HT-12 (validation cohort, LREX') microarray. (A technical note: NR3C1 probe in Illumina HT-12 array appears to be non-functional and did not detect GR in any tissue, including LnCaP/AR cells engineered to express high levels.) For LREX' in vitro analysis, cells were plated into steroid depleted media for 48 hours prior to drug treatment. Drug treatments were performed in triplicate with a final concentration of 1 nM DHT, 1 OnM or 100 nM dexamethasone, and/or 10 μM enzalutamide for 8 hours. For VCaP in vitro analysis VCaP cells were maintained in standard media with complete fetal bovine serum and were treated in triplicate for 24 hours with vehicle, 0.1 nM DHT, 100 nM Dex, and/or 10 μM enzalutamide. All expression data was quantile normalized and analyzed with Partek software.

Chromatin Immuno-Precipitation:

LREX' cells were maintained in steroid depleted media for 4 days. The day prior to drug treatment, cells were given fresh media. Material from two 15 cm plates of cells were divided for ChIP. For ChiP-seq, agonist stimulation was carried out for 30 minutes prior to harvest. Fixation and processing for was carried out as described by others (Goldberg et al., 2010). Immunoprecipitation was carried out with Anti-Androgen Receptor Antibody, PG-21 (Millipore) or Glucocorticoid Receptor Antibody #7437 (Cell Signaling). Immunoprecipitated DNA was quantified by picogreen and size was evaluated on a HighSense BioAnalyzer chip. Fragments between 100 and 600 bp were collected using an automated system (Pippin Prep, Sage Science) then end repaired, ligated and amplified for 15 cycles using reagents included in the Truseq DNA Sample Preparation kit from Illumina. Experimental conditions followed strictly the instructions of the manufacturer, with the exception of the adaptors being diluted 1/10 for the input DNA and 1/50 for all other samples. Barcoded libraries were run on a Hiseq 2000 in a 50 bp/50 bp paired end run, using the TruSeq SBS Kit v3 (Illumina). For ChiP-qPCR, ligand treatments were performed for 1 hour and fixation and processing was carried out using a chromatin immunoprecipitation assay kit (Millipore) in accordance with the manufacture's protocol. Immunoprecipitation was carried out with Anti-Androgen Receptor Antibody, PG-21 (Millipore), Glucocorticoid Receptor Antibody #3660 (Cell Signaling), or Normal Rabbit IgG (Millipore: 12-370).

ChIP-Seq Data Analysis:

The sequencing reads (50 bp, paired-end) were aligned to the human genome (hg19, build 37) using the program Bowtie (Langmead et al., 2009). 8,201,777 and 18,876,986 reads from DHT-treated AR ChIP-seq and Dex-treated GR ChIP-seq LREX' samples were aligned to a single genomic location with no more than two mismatches. These aligned reads were analyzed by the software MACS (Zhang et al., 2008) for peak identification with data from ChIP input DNAs as controls. The top 5,217 AR and 15,851 GR peaks were selected based on analysis of false discovery rate and peak intensities. Genes with peaks located from −50 kb of their transcription start sites to +5 kb of their transcription termination sites were defined as AR or GR targets, using the human RefSeq annotation as reference. The MEME software suite (Bailey et al., 2009) was applied to 100-bp sequences around the AR or GR peak summits for finding motifs, with the program MEME for motif discovery and MAST for motif scanning (p value <0.001).

```
Chi P-PCR Primers:
SGK1
F:     CTTCCCACCCACTTGTGCTT,         (SEQ ID NO: 30)

R:     GAAAGGTGCCAGAGGAGACC;         (SEQ ID NO: 31)

FKBP5
F:     CCCCCTATTTTAATCGGAGTAC,       (SEQ ID NO: 32)

R:     TTTTGAAGAGCACAGAACACCCT;      (SEQ ID NO: 33)

KLK3
F:     ATGTTCACATTAGTACACCTTGCC,     (SEQ ID NO: 34)

R:     TCTCAGATCCAGGCTTGCTTACTGTC;   (SEQ ID NO: 35)

NDRG1
F:     ATGGCCCCAGATATGTTCCA,         (SEQ ID NO: 36)

R:     CCCAAGGTCTCAGAGCCAGT;         (SEQ ID NO: 37)

TIPARP
F:     CGTCTGGGGAGTAGGCAAAT,         (SEQ ID NO: 38)

R:     CCCGAGGGAGGATGTGAAAC;         (SEQ ID NO: 39)

NR3C1
F:     ACCAGACTGAATGTGCAAGC,         (SEQ ID NO: 40)

R:     AGGGTTTTTGATGGCACTGA          (SEQ ID NO: 41)
```

GR Expression and GR/AR Knockdown:

shRNA knock-down experiments were carried out by infection of LREX' or VCAP cells with MISSION® TRC2 pLKO.5-puro containing a non-targeting or GR specific hairpin (NT: GGGATAATGGTGATTGAGATGGCTC-GAGCCAT CTCAATCACCATTATCCTTTTT (SEQ ID NO: 42), GR: CCGGCACAGGCTTCAGGTATCTTATC-TCGAG ATAAGATACCTGAAGCCTGTGTTTTTG (SEQ ID NO: 43)). siRNA knock-down experiments were performed Dhamarcon SMARTpool: ON-TARGETplus AR siRNA, L-003400-00-0005 or ON-TARGETplus Non-targeting Pool, D-001810-10-20 according to manufactures protocol with a final concentration of 50 nM siRNA. For GR expression experiments, a stop codon was engineered into the NR3C1 alpha ORF (Origene RC204878) by PCR and then it was sub-cloned in pMItdT (a generous gift from Dr. Yu Chen, MSKCC.) pMItdT-EGFP was introduced into control cells. Infected cells were sorted by tdTomato expression using flow cytometry.

In Vitro Growth Assays:

VCaP: Cells were plated in triplicate and then assayed in triplicate at the time points indicated using CellTiter-Glo (Promega). Viability is plotted normalized to day 1. For knockdown studies, cells were infected and then plated 3 days later for the experiment without prior drug selection. LnCaP/AR and sub-lines: Equivalent numbers of cells were plated and then harvested and counted in triplicate at indicated time points using the Beckman Coulter Vi-Cell XR. Cells were passaged at each time point and identical numbers of cells re-plated. Fold increase in cell numbers were determined for each time interval.

Intracellular Staining and Flow Cytometric Analysis:

Cells were re-suspended in Fixation/Permeabilization working solution (eBioscience; San Diego, Calif., USA) at a concentration of 1-2×$10^6$ cells/ml for 30 minutes at room temperature. The cells were subsequently stained with primary antibodies, Rabbit (DA1E) mAb IgG XP® Isotype Control, androgen receptor (D6F11) XP® Rabbit mAb, or glucocorticoid receptor (D6H2L) XP® Rabbit mAb (Cell Signaling Technology; Danvers, Mass., USA) for 20 minutes at room temperature. The cells were washed twice with Flow Cytometry Staining Buffer (eBioscience; San Diego, Calif., USA), and then stained with secondary antibody, Allophycocyanin-AffiniPure F(ab')$_2$ Fragment Donkey Anti-Rabbit IgG (Jackson ImmunoResearch Laboratories, Inc.; Westgrove, Pa., USA) for 20 minutes at room temperature. Following two more washes, the cells were re-suspended in Flow Cytometry Staining Buffer and analyzed by flow cytometry on a LSRII (BD Biosciences; San Jose, Calif., USA) using FlowJo software (Tree Star, Ashland, Oreg., USA). For GR staining, cells were maintained in their standard media and treated with dexamethasone for 20 minutes prior to harvest to fully expose antigen. For AR staining, cells were cultured in charcoal stripped media without added ligands for 3 days prior to harvest.

RNA Extraction and RT-qPCR Analysis:

RNA was extracted from cell lines using the RNeasy kit (Qiagen). Frozen tumors were lysed with lysing matrix A using the Fast-Prep24 tissue homogenizer system (MP BIOMEDICALS) in Trizol (Invitrogen) followed by clean up with RNeasy (Qiagen). cDNA was generated with the High Capacity cDNA Reverse Transcription Kit (Applied Biosystems.) Data was quantified relative to either beta Actin or GAPDH expression and relative expression was generally plotted. Primers for ACTB (PPH00073E), NDRG1 (PPH02202B), NR3C1 (PPH02652A), and SGK1 (PPH00387E), STK39 (PPH14239B), GRB 10 (PPH05866B), TIPARP (PPH07883A), PMEPA1 (PPH01013B) were purchased from SA Biosciences. Other qPCR primers are as follows: AR (F: CCATCTTGTCGTCAATGTTATGAAGC (SEQ ID NO: 44), R: AGCTTCTGGGTTGTCTCCTCAGTGG (SEQ ID NO: 45)), FKBP5 (F: CAGATCTCCATGTGCCAGAA (SEQ ID NO: 46), R: CTTGCCCATTGCTTTATTGG (SEQ ID NO: 47)), GAPDH (F: TGCACCACCAACTGCTTAGC (SEQ ID NO: 48), R: GGCATGGACTGTGGTCATGAG (SEQ ID NO: 49)) and KLK3 (F: GTCTGCGGCGGTGTTCTG (SEQ ID NO: 50), R: TGCCGACCCAGCAAGATC (SEQ ID NO: 51)).

Protein Extraction and Western Blot Analysis:

Protein was extracted from cell lines using M-PER Reagent (Thermo Scientific). Protein was extracted from frozen tumors with lysing martix A using the Fast-Prep 24 tissue homogenizer system (MP BioMedicals) using 1% SDS, 10 mM EDTA and 50 mM Tris, pH 8.0. Protein was quantified by BCA Protein Assay (Thermo Scientific). The following antibodies were used for western blots: anti-AR PG-21 at 1:5000 (Miilipore 06-680), anti-GR at 1:1000 (BD Transduction Laboratories 611227), β-actin at 1:20,000 (AC-15, Sigma), anti cPARP at 1:1000 (Cell Signaling #9541).

Cell Line, Xenograft and Tissue Microarray IHC:

Cell line pellets or tumor pieces were fixed in 4% PFA prior to paraffin embedding and then were stained for GR at 1:200 with anti-glucocorticoid receptor (D6H2L) XP® Rabbit mAb (Cell Signaling Technology, #12041) using the Ventana BenchMark ULTRA. TMA was stained for GR at 1:200 with anti-glucocorticoid receptor (BD Transduction Laboratories #611227) using the Ventana BenchMark ULTRA.

Drugs:

DHT and Dexamethasone were purchased from Sigma. ARN-509, RD162, and enzalutamide were all synthesized by the organic synthesis core at MSKCC. Compound 15 was a gift from Tom Scanlan (OHSU). All drugs were dissolved in DSMO in 1000X stocks.

Bone Marrow Evaluation:

Patients were treated with enzalutamide 160 mg daily. Bone marrow biopsy and aspirate (~5 mL) were performed before treatment and at week 8. The bone marrow specimens were obtained by transiliac biopsy, and samples were processed according to standard MD Anderson Cancer Center decalcification and fixation procedures. After pathologic evaluation, samples were stored in the MD Anderson Cancer Center Prostate Cancer Tissue Bank. Imaging studies were performed at the time of suspected prostate cancer progression or at the treating physician's discretion, but generally not prior to 12 weeks post-treatment initiation. Therapy was discontinued at the treating physician's discretion in patients exhibiting progression. Retrospective analysis for GR was performed by IHC on 3.5-mm formalin-fixed, paraffin-embedded bone marrow biopsy sections with anti-GR at a dilution of 1:200 (BD Transduction Laboratories #611227). A Dako autostainer and standard 3,3-diaminobenzidine were used. GR expression was assessed in a blinded fashion by two pathologists scoring at least 100 tumor cells per specimen. Plotted are either data from all specimens or only from patients with usable material at baseline and 8 weeks.

AR Target Gene List Derivation:

The 74 AR target gene list utilized for evaluation of AR pathway status in the LnCaP/AR model includes all genes that showed at least a 1.6-fold change (FDR <0.05) when comparing control and 4 day treated xenografts and that were also found to have an AR binding peak by ChIP-seq analysis of LNCaP/AR in vitro (Cai et al, in preparation). The VCaP AR target gene list includes all genes that that showed reciprocal expression change with 24 hour DHT (.1 nM) or enzalutamide (10 μM) of at least 1.4 fold (p<0.05) (Illumina HT-12) and were also found to have an AR binding peak by ChIP-seq analysis of VCaP (Cai et al, in preparation).

AR/GR Signature Analysis and Gene Set Enrichment Analysis:

AR and GR signature genes were defined as all genes showing >1.6 fold (FDR<0.05) expression change with either 1 nM DHT or 100 nM Dex treatment, respectively, of LREX' cells for 8 hours in charcoal stripped media. For GSEA, signature genes induced by either DHT or Dex treatment were used. GR selective genes showed at least 1.1 fold higher expression in Dex treated samples compared to DHT treated samples (FDR <0.05). AR selective genes showed at least a 1.1 fold higher expression in DHT treated samples compared to Dex treated samples (FDR <0.05).

Statistics:

Microarray data analysis and comparisons were performed with Partek Software. All RT-qPCR comparisons are by two-sided t-test. Xenograft volumes and GR IHC of clinical specimens are compared by one-sided Mann-Whitney test. In vitro growth comparisons are by two-sided t-test. GSEA statistical analysis was carried out with publicly available software from the Broad Institute (Cambridge, Mass.: http://www.broadinstitute.org/gsea/index.jsp). In all figures, *=<0.05, =<0.01, *=<0.001, and ****=<0.0001.

Results

GR is Expressed in Antiandrogen-Resistant Tumors

It was previously showed that LNCaP/AR xenograft tumors regress during the first 28 days of treatment with ARN-509 (Clegg et al., 2012), enzalutamide or RD162 (Tran et al., 2009). In a pilot study to explore mechanisms of acquired resistance to these drugs, mice were treated continually and harvested tumors after progression (mean 163 days, Table 2A). Tissue from fourteen resistant tumors obtained from long term antiandrogen treated mice (n=5

ARN-509, n=9 RD162) and from three control tumors from vehicle treated mice were analyzed by expression array. Aggregated data from resistant and control tumors in this pilot cohort were compared to identify expression changes commonly associated with resistance (FIG. 1A). Among the most up-regulated genes in the resistant tumors was the glucocorticoid receptor (GR, gene symbol NR3C1) which shares overlapping target specificity with AR (Mangelsdorf et al., 1995). Of note, several of the most differentially expressed genes were known androgen regulated genes (confirmed by transcriptome analysis of short term DHT treated LnCaP/AR cells, in vitro (Table 2B)), but they were altered in directions that did not reflect restored AR signaling. On the one hand, SGK1 (Serum Glucocorticoid Induced Kinase 1), a known AR and GR-induced target gene, was among the most up-regulated genes, but several other androgen-induced genes (PMEPA1, SNAI2, $KCNN_2$, LONRF1, SPOCK1) were among the most repressed. Conversely, several androgen-repressed genes (UGT2B15, PMP22, $CAMK2N_1$, UGT2B 17) were among the most up-regulated (FIG. 1A). These findings indicated that resistance in this model system is unlikely to be mediated by simple restoration of AR activity and raised the possibility that GR may play a role.

Figure 1A:
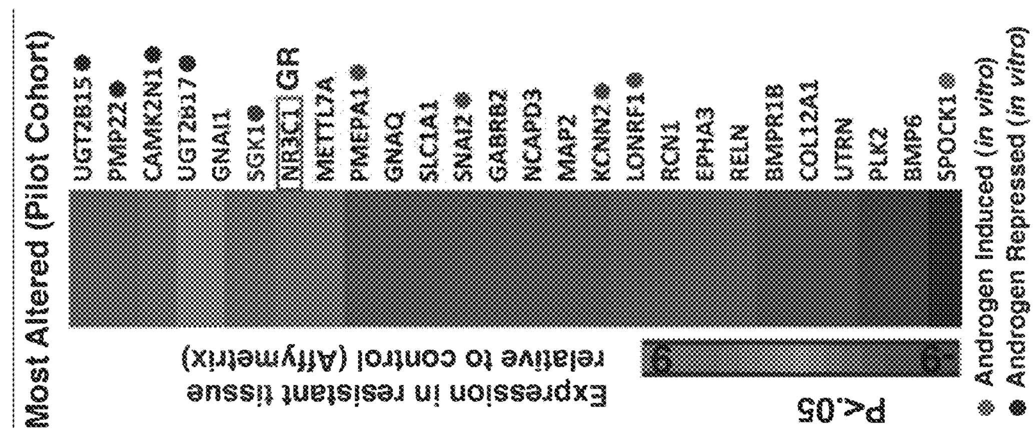
Figure 1C:
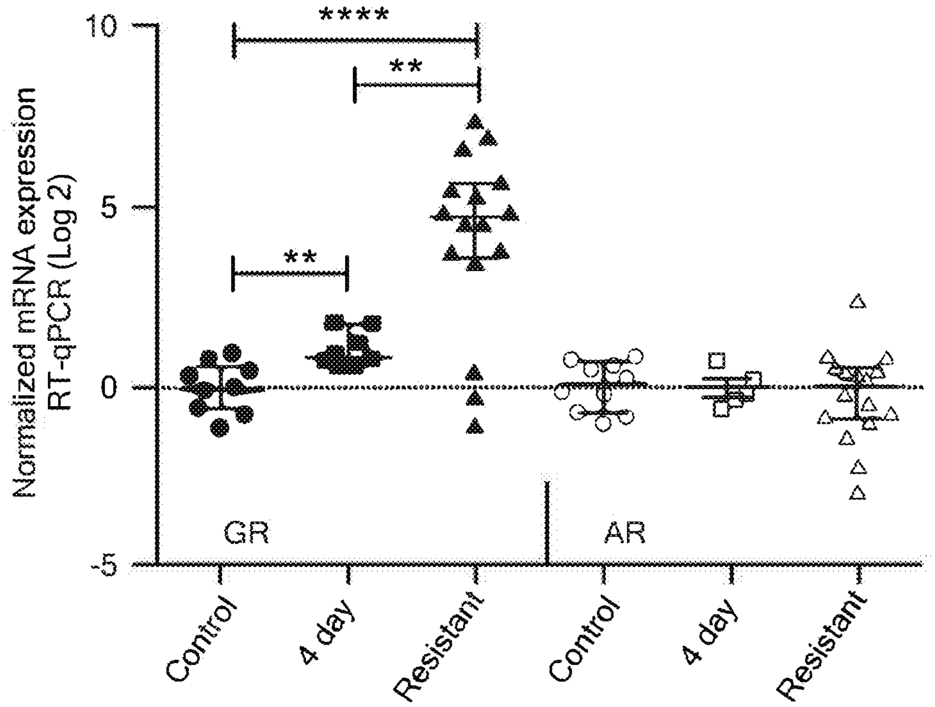
Figure 1D:
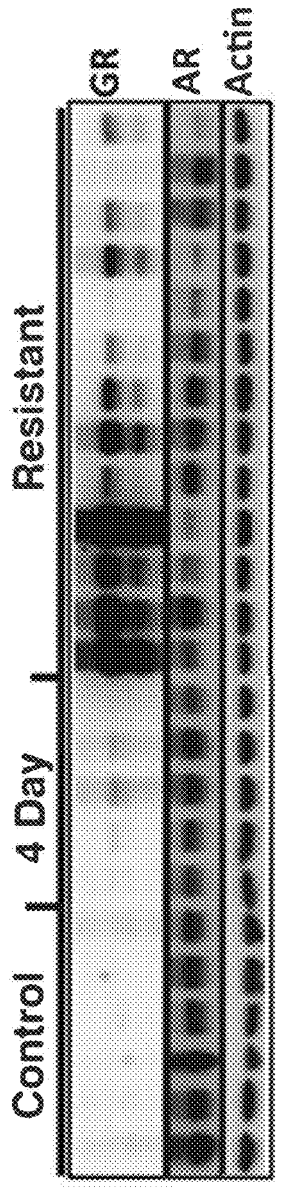

To explore this question further, an independent set of drug-resistant tumors was generated (the validation cohort), focusing on the two second generation antiandrogens in clinical use, enzalutamide and ARN-509 (FIG. 1B). GR mRNA levels in 10 control, 8 short term treated (4 day) and 16 resistant tumors were substantially higher in resistant tissues compared to control (median 26.9-fold increase) or 4 day treated tumors (FIG. 1C). Of the tissues analyzed by RT-qPCR, most were also analyzed for GR expression by western blot, based on availability of protein lysates (control n=6, 4 day n=5, resistant n=13). No GR was detected in control samples, minimal expression was noted in 4 day treated samples, and substantial expression was found in most resistant tumors in a pattern that tended to correlate with GR mRNA levels (FIG. 1D). There was no correlation between GR expression and the specific antiandrogen treatment used. In contrast to GR, AR RNA or proteins levels were not consistently different across the treatment groups (FIG. 1C,1D).

Figure 1E:
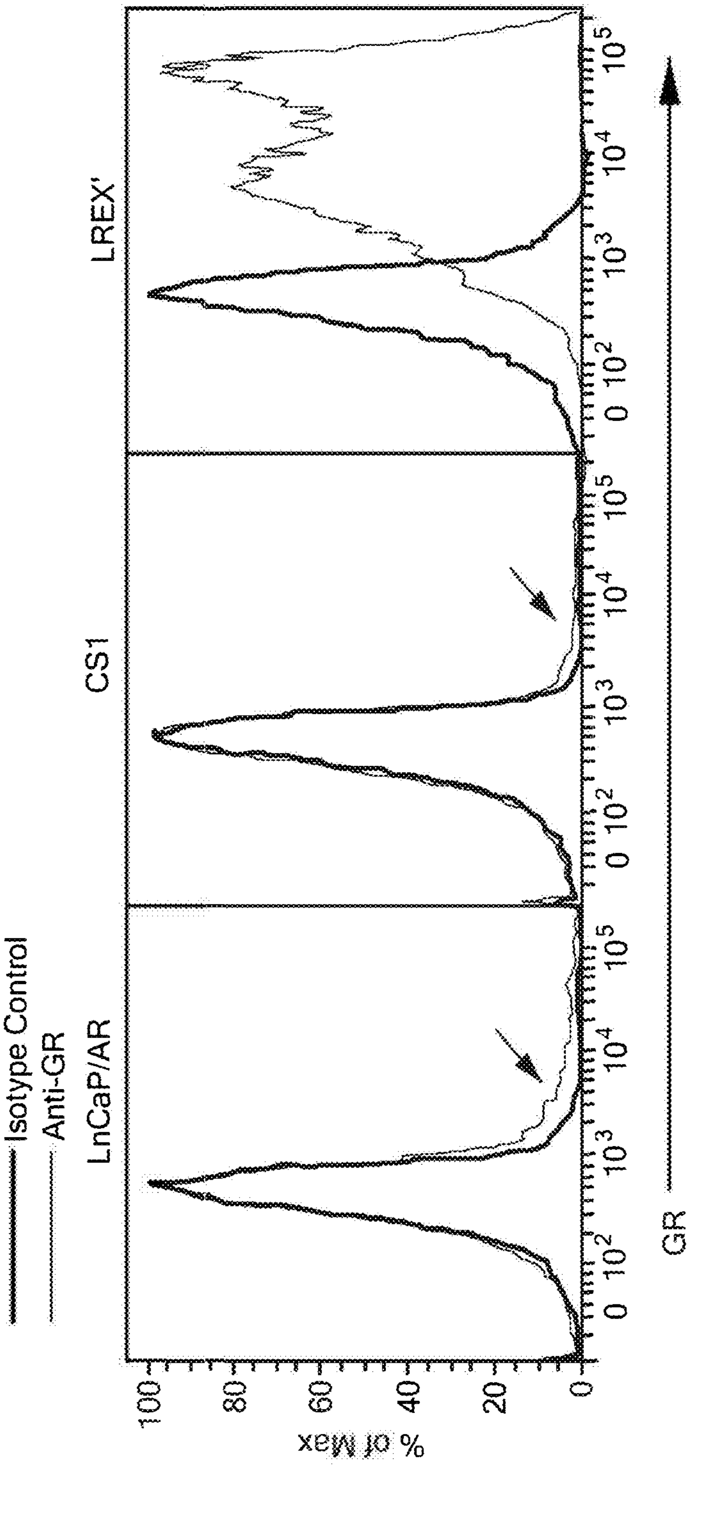
Figure 2A:
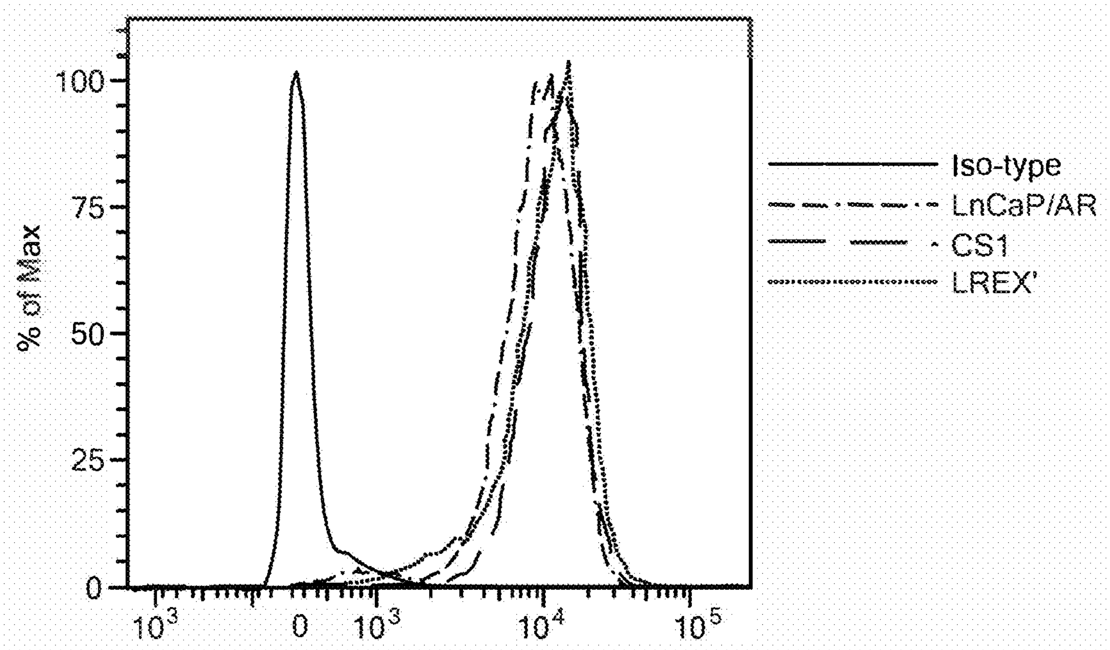
FIGS. 2A-2B show AR Expression in LREX' cells. A. Indicated cells were cultured in vitro, in charcoal stripped media without enzalutamide for 3 days and then analyzed for AR expression by intracellular AR flow cytometric analysis. B. LnCaP/AR control xenografts (n=6, same samples as in FIG. 1D) or enzalutamide (10 mg/kg) treated LREX' xenografts (n=8) were analyzed by GR and AR western blot. AR western blot signals were quantified using Image J software.

To explore AR and GR signaling in more detail, cells lines were established from control and drug-resistant tumors by adaptation to growth in vitro. LREX' (LnCaP/AR Resistant to Enzalutamide Xenograft derived) was derived from an enzalutamide-resistant tumor with high GR expression, and CS1 was derived from a vehicle treated tumor. A flow cytometry-based assay to measure GR expression on a cell-by-cell basis was also developed. In both LNCaP/AR and CS1, most cells showed no evidence of GR expression, with the exception of a small subpopulation (black arrow, discussed later) (FIG. 1E). In contrast, essentially all LREX' cells expressed GR. Intracellular AR staining confirmed that AR levels in LREX' did not notably differ from control cells (FIG. 2A).

LREX' Tumors are Dependent on GR for Enzalutamide-Resistant Growth

Figure 2B:
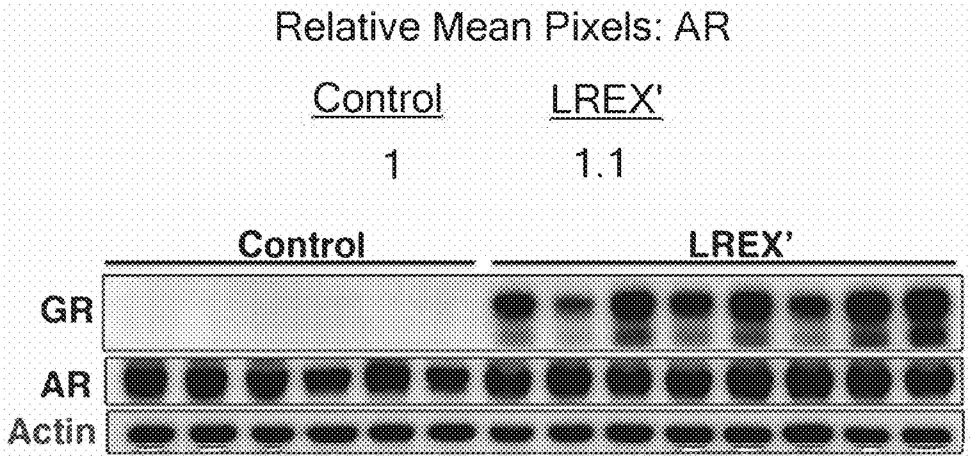
Figure 3A:
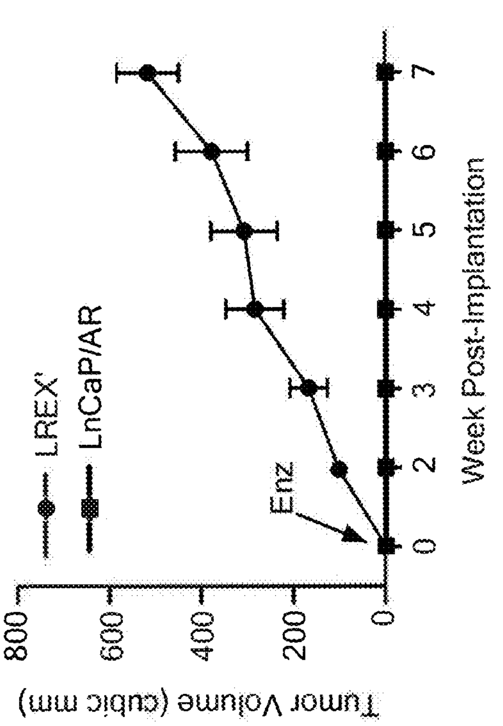
FIGS. 3A-3F show GR is necessary for resistance in the LREX' xenograft model. A. Mean tumor volume+/−s.e.m. of LREX' (n=20) or LnCaP/AR (n=14) cells in castrate mice treated with 10 mg/kg enzalutamide B. Mean tumor volumes+/−s.e.m. of CS1 in castrate mice treated with vehicle (n=10) or 10 mg/kg ARN-509 (n=10). C. GR immunohistochemistry (IHC) of enzalutamide (10 mg/kg)-treated LREX' tumors and vehicle-treated LnCaP/AR xenograft tissues. Blue arrow=endothelial/stromal cells, Black arrow=epithelial cell. D. Mean tumor volumes+/−s.e.m of LREX' xenografts in 10 mg/kg enzalutamide-treated castrated mice after infection with a non-targeting (n=14) or GR-targeting (n=12) hairpin. Comparison is by Mann-Whitney test. E. Tumor growth curve of CS1 in castrate mice after infection with the non-targeting (n=20) or GR-targeting (n=20) hairpin. F. Western blot analysis of GR expression in LREX' cells prior to implantation and of available tissues from D at day 49.
Figure 3B:
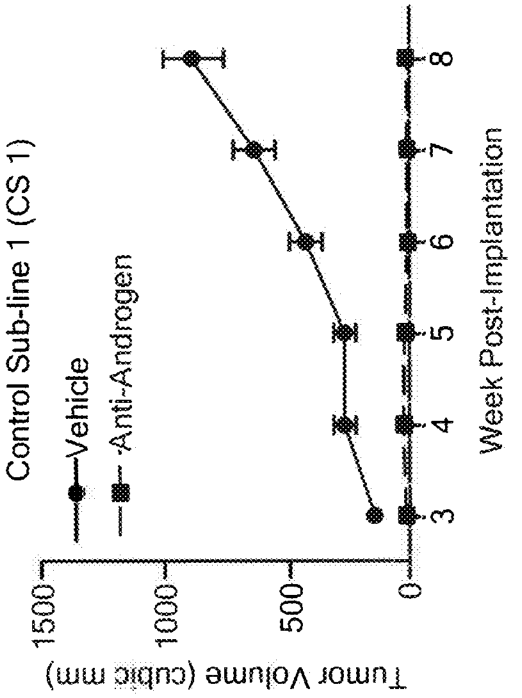
Figure 3C:
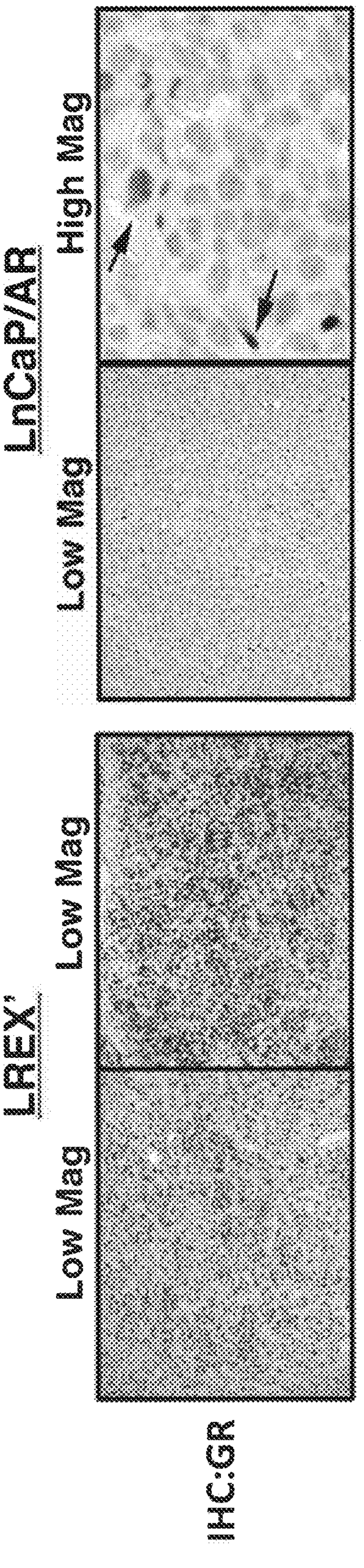

Having established the LREX' model as representative of high GR expression, it was then confirmed that these cells maintain a resistant phenotype in vivo. LREX' or control cells were injected into castrated mice that were then immediately initiated on antiandrogen treatment. LREX' showed robust growth whereas LNCaP/AR or CS1 lines were unable to establish tumors in the presence of antiandrogen (FIG. 3A,3B). Strong expression of GR was confirmed in multiple LREX' xenograft tumors by western blot and by IHC (FIG. 2B, 2C). Untreated LNCaP/AR tumors were negative for GR expression with the exception of rare GR-positive cells (FIG. 3C). Although many of these GR-positive cells had morphologic features of stromal or endothelial cells (blue arrows), some appeared epithelial (black arrow), consistent the with flow cytometry analysis (FIG. 1E, black arrows).

Figure 3D:
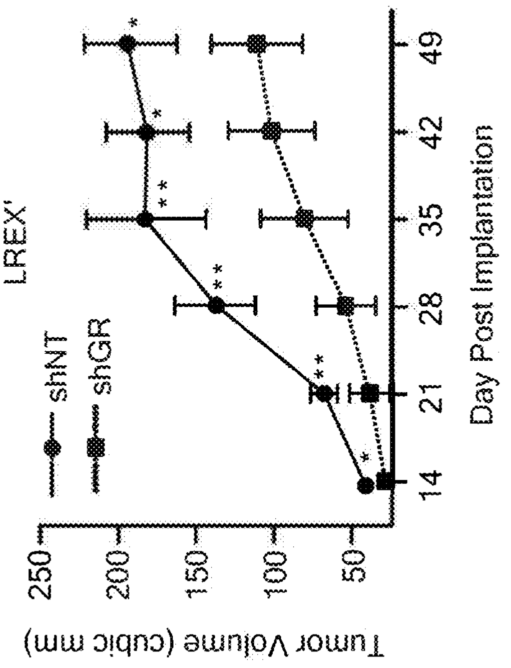
Figure 3E:
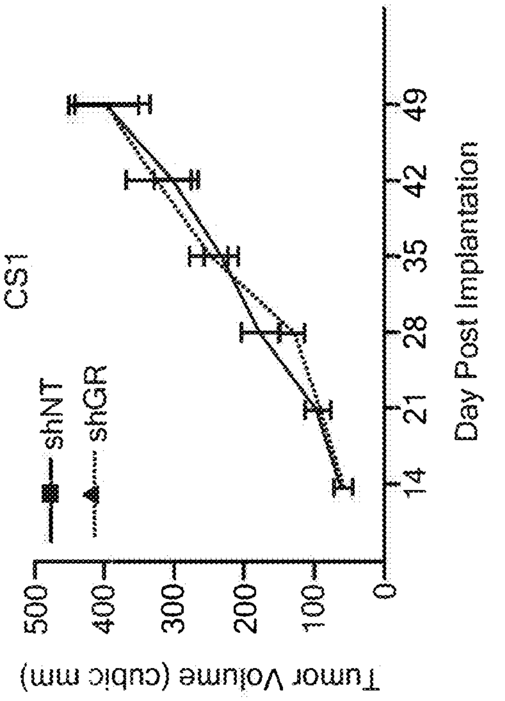
Figure 3F:
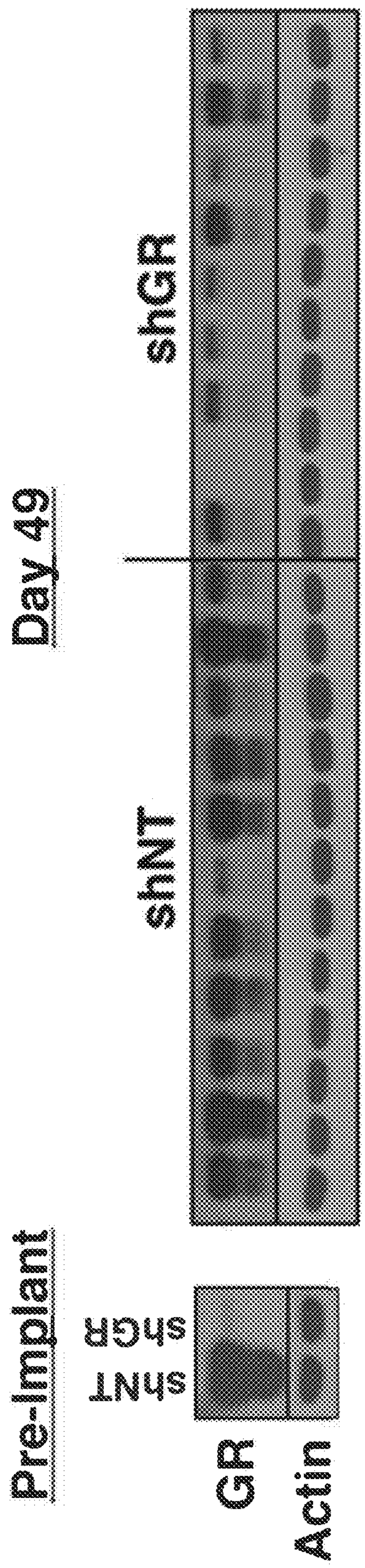

To determine whether GR expression is required to maintain the drug-resistant phenotype, LREX' cells were infected with a shRNA targeting GR (shGR) and stable knockdown of GR protein was confirmed (FIG. 3F). Tumor growth of shGR infected LREX' cells was significantly delayed relative to shNT (non targeted)-infected cells in castrated mice treated with enzalutamide (FIG. 3D). In contrast, shGR had no impact on the growth of GR-negative CS1 xenografts, diminishing the possibility of an off-target effect (FIG. 3E). Of note, shGR LREX' xenografts harvested on day 49 showed decreased GR protein knockdown compared to the pre-implantation levels, indicative of selective pressure against GR silencing in the setting of enzalutamide treatment (FIG. 3F). These findings provide direct evidence that GR drives enzalutamide resistance in vivo.

GR Expression is Associated with Clinical Resistance to Enzalutamide

Figure 4:
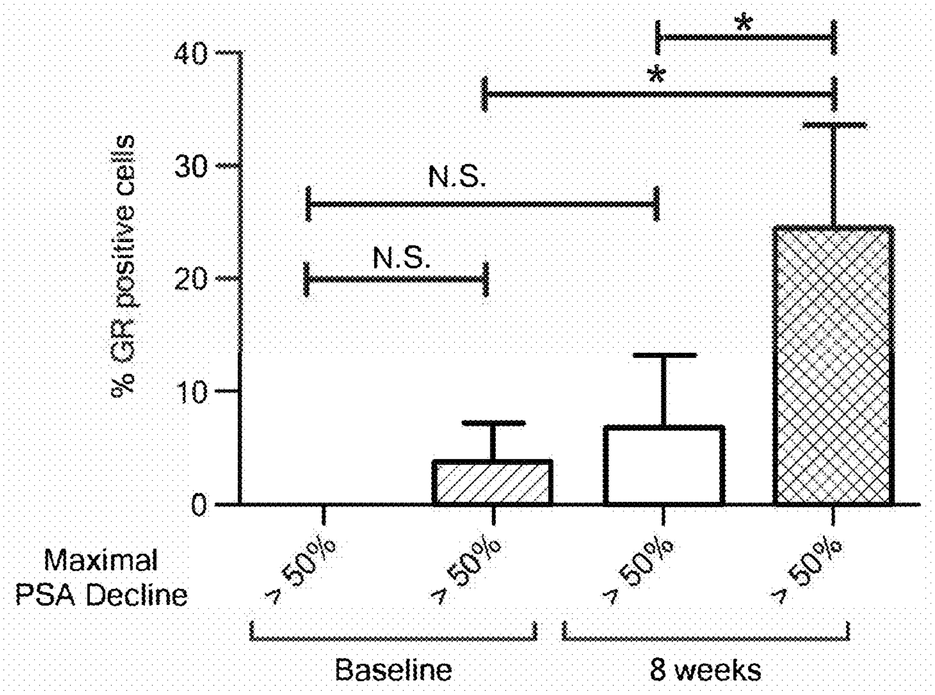
FIG. 4 shows GR induction dichotomized based on PSA response. GR IHC scores in matched baseline and 8 week samples dichotomized based on maximal PSA response+/−s.e.m. Comparisons are by Mann-Whitney test.
Figure 5D:
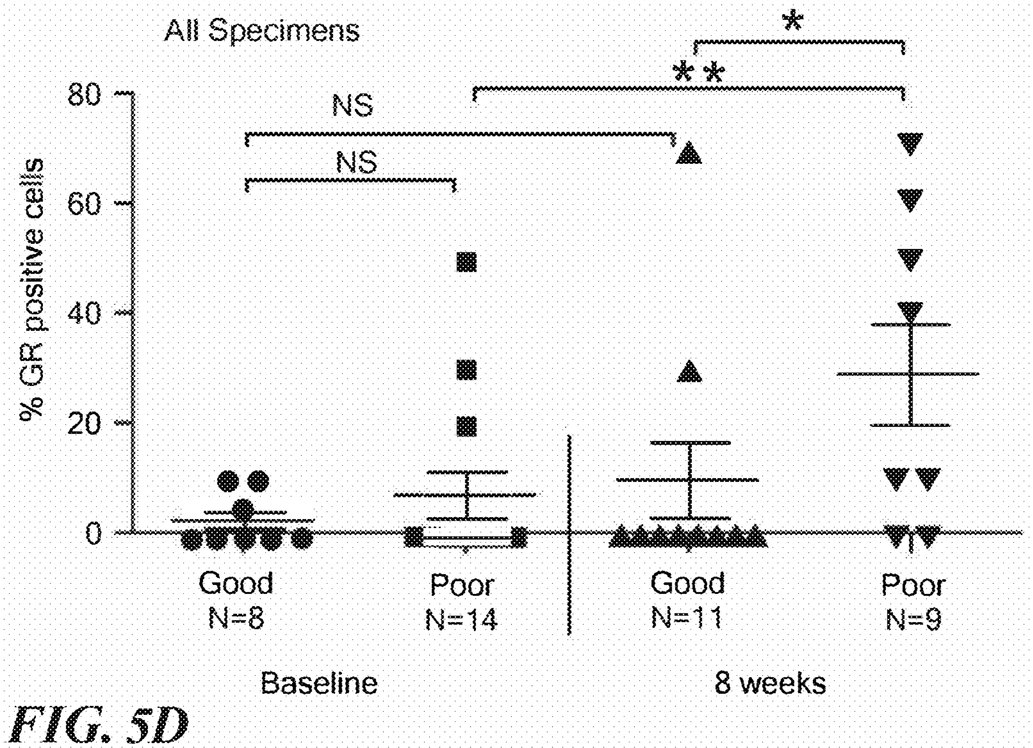
Figure 5E:
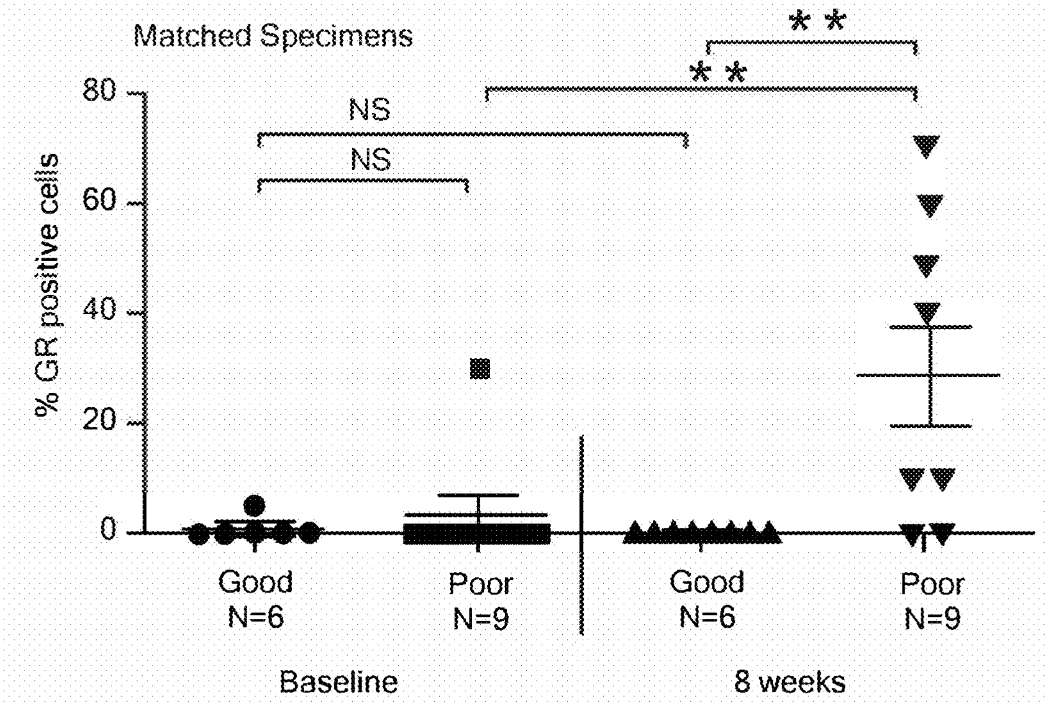
Figure 6:
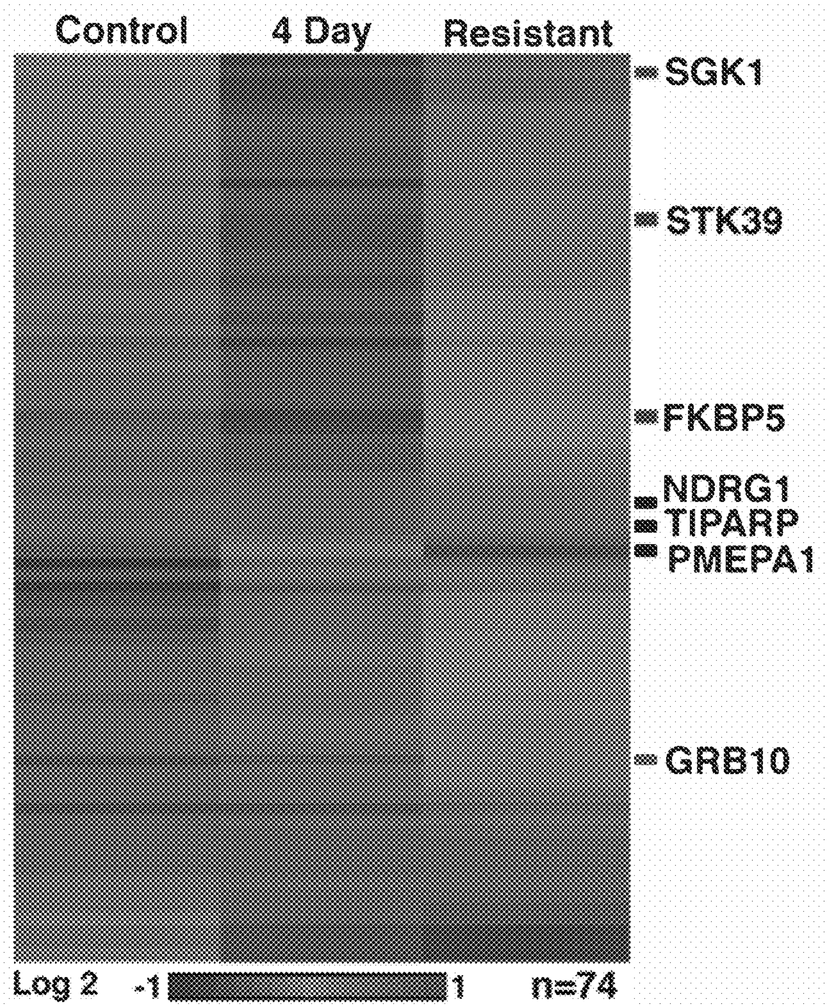
FIG. 6 presents expression of AR target genes in resistant tumors from validation cohort. Normalized expression array signal (Illumina HT-12) of a suite of 74 AR target genes in control (n=10), 4 day (n=8), and resistant tissues from the validation cohort described in FIG. 1 (n=12 of 16). The bottom quartile of GR expressing tissues were excluded from the analysis of the validation cohort tissues to minimize contamination from other resistance drivers. Genes are ranked by degree of restoration of expression in resistant tissue (Res-4 day)/(Control-4 day). All resistant tissues were continued on anti-androgen treatment through time of harvest.

To determine whether GR expression is a feature of clinical antiandrogen resistance, GR expression was evaluated in bone metastases from patients receiving enzalutamide. Bone marrow samples were obtained prior to enzalutamide treatment (baseline) and again after 8 weeks of treatment, as previously reported in a cohort of abiraterone-treated patients (Efstathiou et al., 2012). Using a GR IHC assay optimized for use in bone marrow samples, the percentage of GR-positive tumor cells was quantified and the data was dichotomized based on clinical response. Patients who continued to benefit from therapy for greater than 6 months were defined as good responders, while those in whom therapy was discontinued earlier than 6 months due to a lack of clinical benefit were classified as poor responders (FIG. 5A). Consistent with the designation of good versus poor clinical response based on treatment status at 6 months, 11 of 13 good responders but only 1 of 14 poor responders had a maximal PSA decline greater than 50% (FIG. 5C). Akin to the findings in the preclinical model, GR positivity at baseline was low: 3% of tumor cells in good responders and 8% in poor responders. Of note, 3 of 22 tumors had evidence of high GR expression at baseline (>20% of tumor cells) and all three had a poor clinical response (FIG. 5C,D). At 8 weeks, the mean percentage of GR positive cells was higher than baseline levels in both response groups but was more significantly elevated in poor responders (29% vs 8%, p=0.009). In addition, the percentage of GR-positive cells at 8 weeks was significantly higher in poor compared to good responders (29% versus 10%, p=0.02) (FIG. 5C,D), and similar results were obtained when the analysis was limited to patients from whom matched baseline and 8 week samples were available for analysis (FIG. 5E). Furthermore, when GR IHC data was dichotomized based on PSA decline instead of clinical response, GR induction was also associated with a limited PSA decline (FIG. 4). These findings establish a correlation between GR expression and clinical response to enzalutamide and raise the possibility that AR inhibition may induce GR expression in some patients. The fact that PSA levels also correlate with GR expression raises the question of whether transcriptional regulation of a canonical AR target gene may be regulated by GR.

GR Expressing Drug-Resistant Tumors Show Uneven Restoration of AR Target Genes

Figure 7A:
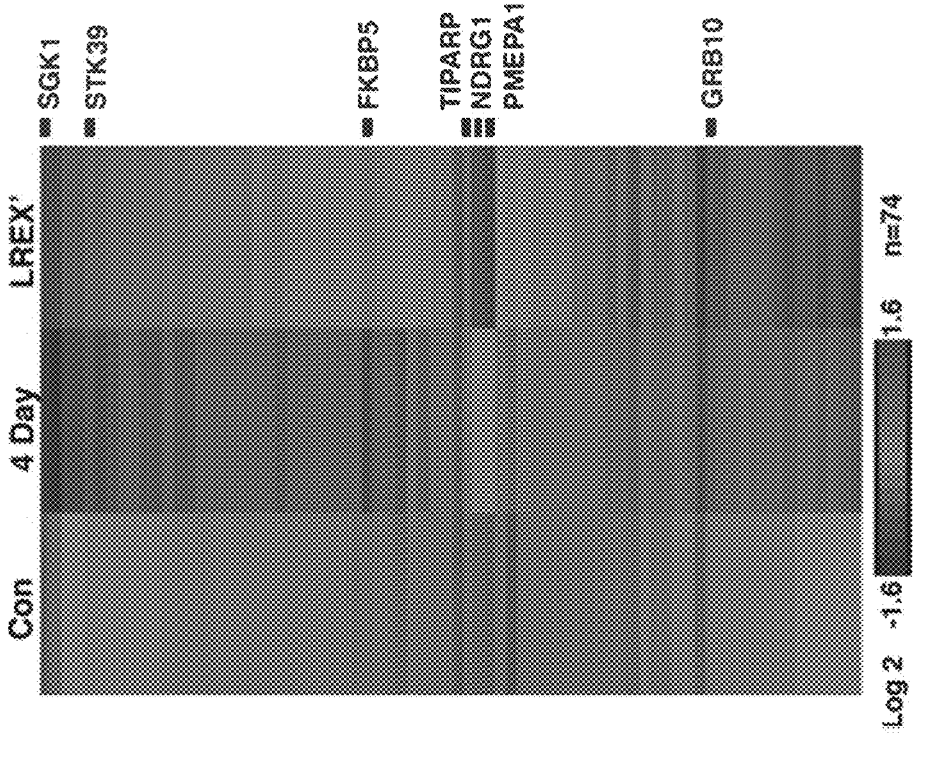
FIGS. 7A-7D demonstrates variable expression of AR target genes in LREX', in vivo, and after glucocorticoid treatment, in vitro. A. Normalized expression array signal (Illumina HT-12) of a suite of 74 AR target genes in control (n=10), 4 day (n=8), and LREX' (n=8, right) xenograft tumors. Genes are ranked by degree of restoration of expression in resistant tissue ((Res-4 day)/(Control-4 day)). All resistant tissues were continued on anti-androgen treatment through time of harvest. B. Fractional restoration values of each of the 74 AR targets in LREX' xenografts (n=8) or resistant tissues from the validation cohort (n=12). C. GR mRNA in resistant tissues used in B. D. Expression of AR target genes in the LREX' cell line in steroid depleted media after 8 hours of treatment with the indicated agonists, in vitro. Enzalutamide=10 micromolar, V=Vehicle.+/−s.e.m.

Having implicated GR as a potential mediator of antiandrogen resistance, it was next determined whether restored AR pathway activity also plays a role by comparing the mRNA transcript levels of 74 direct AR target genes in control, 4 day, and resistant tumors from the validation cohort (FIGS. 5A-E) as well as eight LREX' tumors (FIG. 7A).

Consistent with the data generated in the pilot cohort (FIG. 1A), some AR target genes in resistant tissues showed elevated levels relative to control (SGK1, STK39) while other genes (NDRG1, TIPARP, PMEPA1) showed no evidence of restored expression.

Figure 7B:
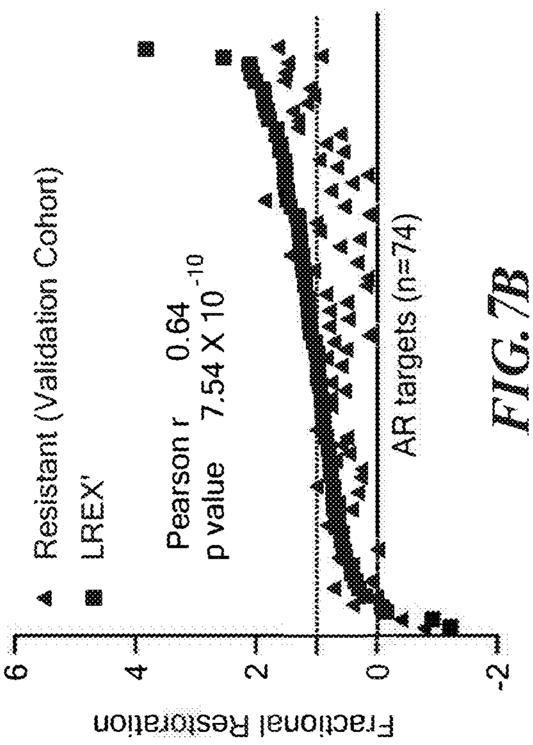
Figure 7C:
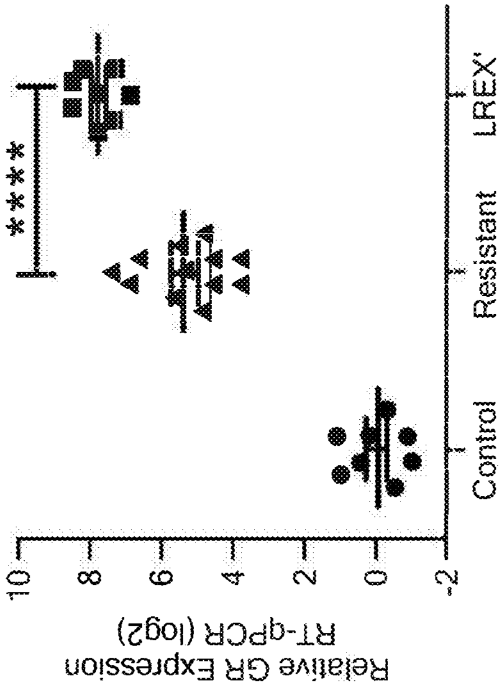

To examine restoration of AR signaling across the entire set of 74 target genes, a fractional restoration value was calculated using log 2 transformed expression values and the equation (Resistant−4 day)/(Control−4 day). With this approach, a gene whose expression in resistant tissue equals the expression in control tumors calculates as 1, while a gene whose expression in resistance equals its expression after 4 days of antiandrogen treatment equals 0. (Values greater than one indicate hyper-restoration in resistance relative to control and values below zero suggest further inhibition as compared to acute treatment.) These data confirmed that the pattern of restoration varied gene by gene, but this pattern was consistent in LREX' xenografts and in the validation cohort tumors (Pearson r 0.64, $p=7.54\times10^{-10}$, FIG. 7B). This finding is most consistent with a model in which AR remains inhibited in drug-resistant tumors but expression of certain AR target genes is restored by an alternative transcription factor, possibly GR. The fact that AR restoration values were somewhat higher in the LREX' analysis correlates with higher GR expression in these tumors (FIG. 7C).

GR Drives Expression of AR Target Genes in Resistant Tissues

Figure 7D:
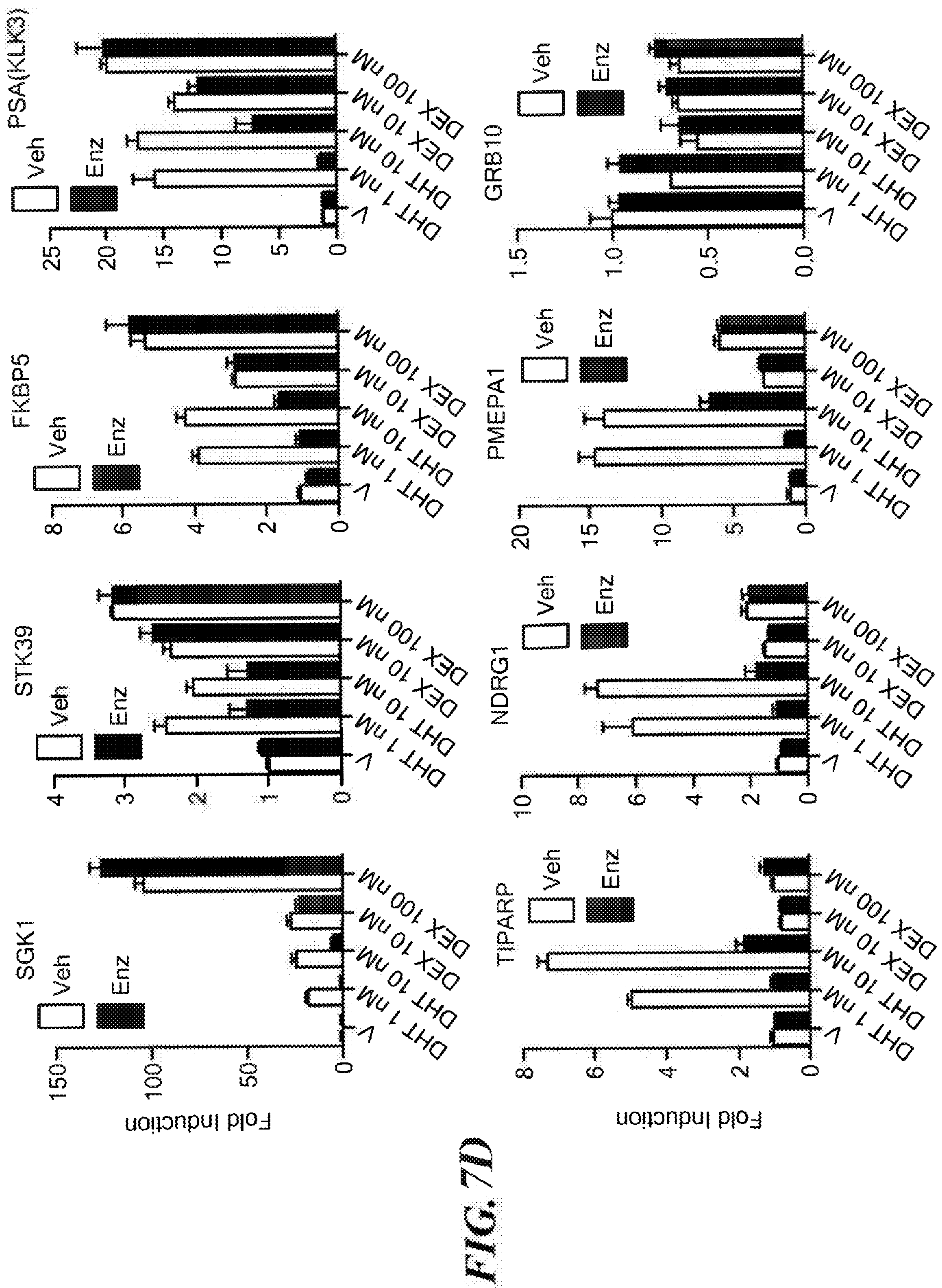

To determine if GR can drive expression of this subset of AR target genes, in vitro, DHT-induced (AR) and dexamethasone (Dex)-induced (GR) expression of 7 AR targets that represent the spectrum of restoration noted in the in vivo analysis were compared, as well as PSA (FIG. 7D). All 8 genes were regulated by DHT, and this regulation was blocked by enzalutamide. Thus, AR signaling remains intact and can be inhibited by antiandrogens in these drug-resistant cells, making an AR-dependent mechanism of drug resistance less likely.

Figure 8A:
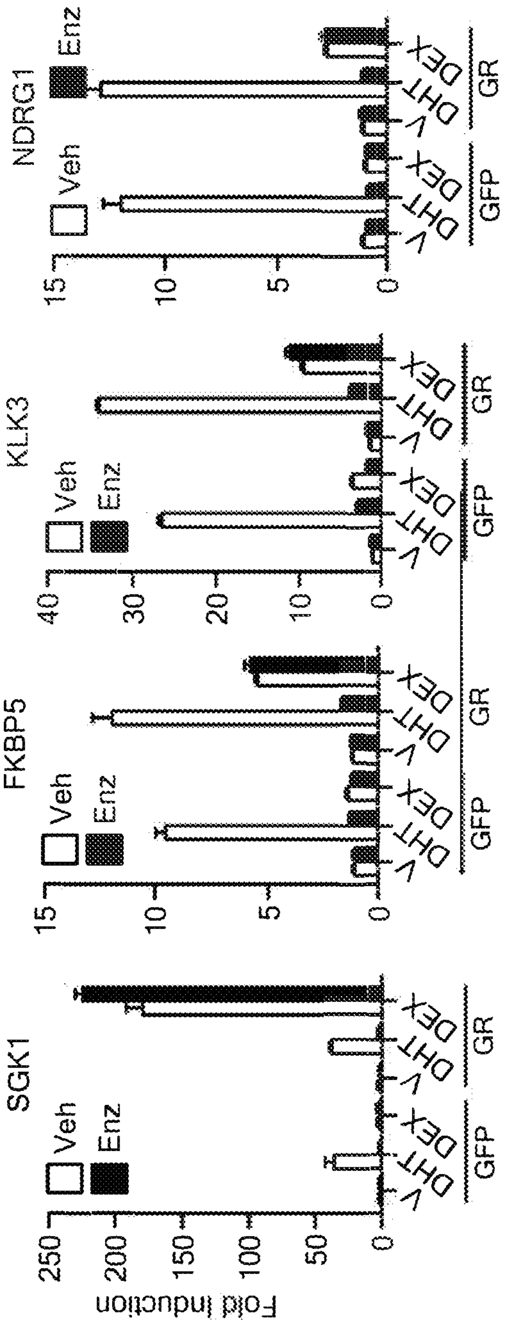
FIGS. 8A-8D show that dexamethasone activity is GR, and not AR, dependent. A. LnCaP/AR cells engineered to express GFP or GR were treated with indicated drugs. B. Western blot confirmation of GR expression in cells used in A. C. Co-treatment of LREX' cells with Dex and compound 15 and assessment of target gene expression. D. Control or AR siRNA knock-down in LREX' followed by treatment with indicated drugs. For S4A-S4D: V=Vehicle, DHT=1 nM, Dex=100 nM (unless otherwise indicated), CMP 15=1 micromolar, Enz=10 micromolar. Cells were treated in charcoal stripped media. Expression determined by RT-qPCR+/−s.e.m.
Figure 8B:
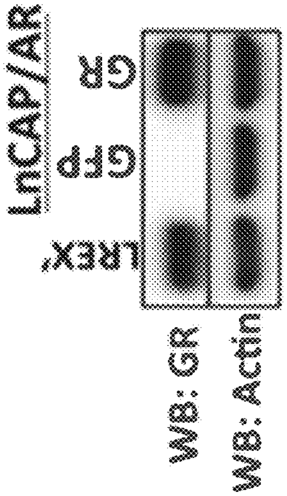
Figure 8C:
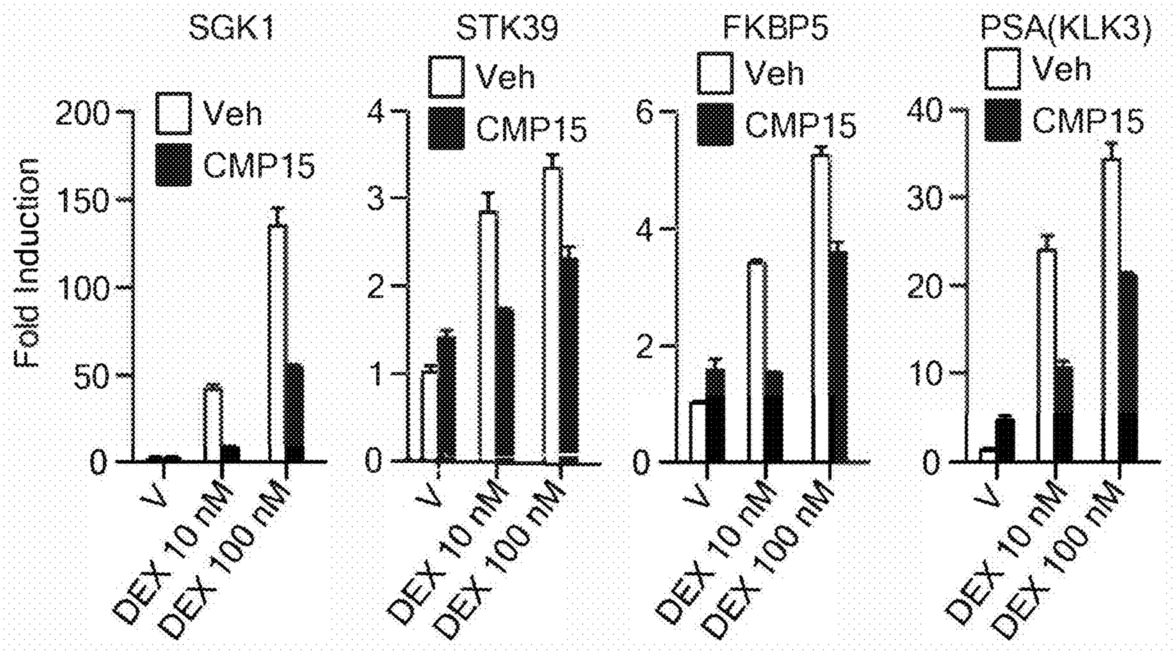
Figure 8D:
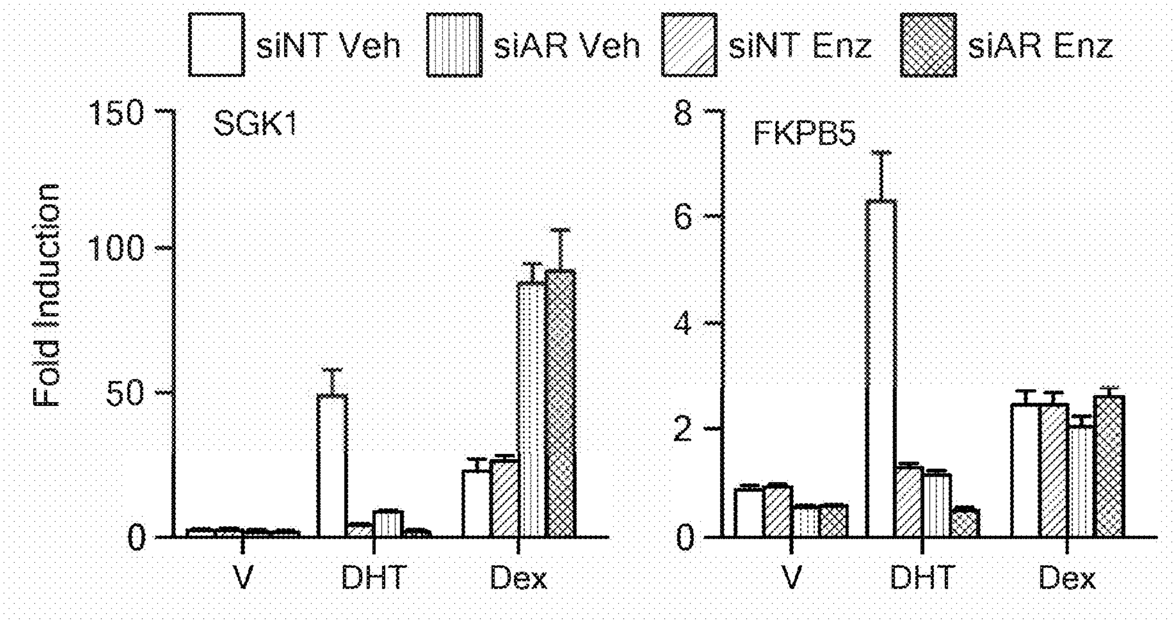

In contrast to DHT, the effect of Dex on these same target genes was variable but closely matched the pattern observed in drug resistant xenografts. For example, Dex strongly induced SGK1 and STK39 but did not induce TIPARP, NDRG1, and PMEPA1. Of note, KLK3 (PSA) was comparably induced by either DHT or Dex, providing evidence that persistent PSA expression in patients responding poorly to enzalutamide could be driven by GR. As expected, enzalutamide did not notably affect Dex activity. To confirm that this pattern of GR-dependent gene expression is not unique to LREX' cells, GR expressing retrovirus was introduced into parental LNCaP/AR cells and a similar pattern of DHT- versus Dex-induced gene expression was observed (FIG. 8A, 8B). To be sure that the effects of Dex in these models are mediated through GR, cells were co-treated with a previously described competitive GR antagonist that lacks AR binding called compound 15 (Wang et al., 2006). Compound 15 significantly decreased expression of Dex-induced genes, confirming that Dex activity in the LREX' model is GR-dependent (FIG. 8C). Lastly, siRNA experiments targeting AR confirmed that AR is not necessary for Dex-mediated gene activation (FIG. 8D). Collectively these experiments demonstrate that GR is able to drive expression of certain AR target genes independent of AR.

AR and GR have Overlapping Transcriptomes and Cistromes

Figure 9A:
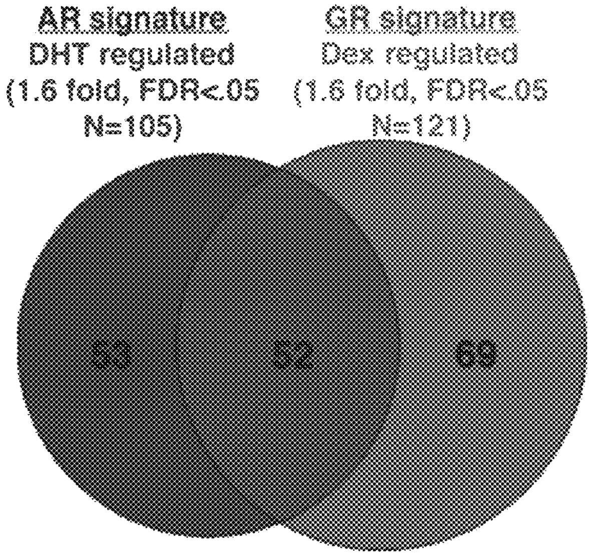
FIGS. 9A-9F show comparative AR and GR transcriptome and cistrome analysis in LREX'. A. Venn diagram of AR and GR signature gene lists. AR or GR signatures were defined as all genes showing >1.6 (or <−1.6) fold change (FDR <. 05) after 8 hours of addition of DHT (1 nM) or Dex (100 nM) to charcoal stripped media, respectively. B. Heat map depiction of expression changes of AR signature genes (left) or GR signature genes (right) associated with the indicated treatment. Enzalutamide=10 micromolar. C. Expression of AR- or GR-induced signature genes (as defined in A.) were compared in DHT (1 nM) or Dex (100 nM) treated samples. GR signature genes that also had higher expression in Dex samples (>1.1 fold, FDR <0.05) were designated as GR-selective (n=67) and AR signature genes that showed higher expression in DHT samples (>1.1 fold, FDR <0.05) were designated as AR-selective (n=39). D. Expression of AR- and GR-selective genes in LREX' and control tumors in vivo compared by Gene Set Enrichment Analysis (GSEA). E. AR cistrome defined by AR ChIP-seq after DHT (1 nM) treatment of LREX' in vitro in charcoal stripped media. Percent of AR defined peaks that overlap with GR peaks found by GR ChIP-seq after Dex (100 nm) treatment of LREX' in vitro are shown in pie graph. Top binding motifs in AR-unique and AR/GR overlap peaks are indicated below. F. GR cistrome defined by GR ChIP-seq after Dex treatment of LREX' in vitro in charcoal stripped media. Percent of GR peaks that overlap with AR peaks found by AR ChIP-seq after DHT (1 nM) treatment of LREX' in vitro are shown in pie graph. Top binding motifs in GR-unique and AR/GR overlap peaks are indicated below.
Figure 9B:
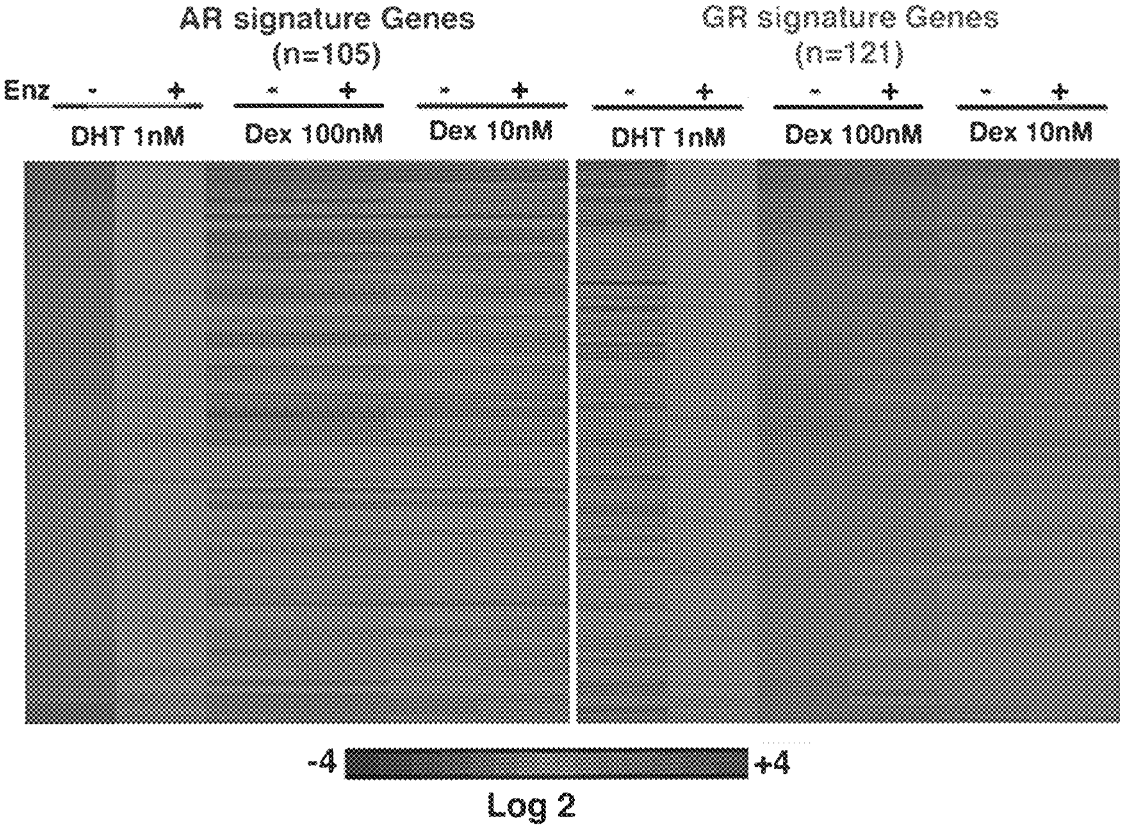

To explore AR and GR transcriptomes in an unbiased fashion, expression profiling after short-term treatment of LREX' cells with DHT or Dex was performed in the presence or absence of enzalutamide. AR and GR signatures were respectively defined as all genes with absolute expression change greater than 1.6 fold (FDR<0.05) after 1 nM DHT or 100 nM Dex treatment (Table 4). Of the 105 AR signature genes and 121 GR signature genes, 52 were common to both lists (FIG. 9A). An even larger proportion of AR or GR signature genes (>80%) showed evidence of regulation by the reciprocal receptor using different thresholds for expression differences (Table 4). Heatmap analysis of these genes confirmed significant overlap in DHT- versus Dex-induced gene expression and showed that Dex-induced gene expression is not impacted by enzalutamide treatment (FIG. 9B). These findings support the hypothesis that GR activity can bypass enzalutamide-mediated AR inhibition by regulating a distinct but significantly overlapping transcriptome.

Figure 9C:
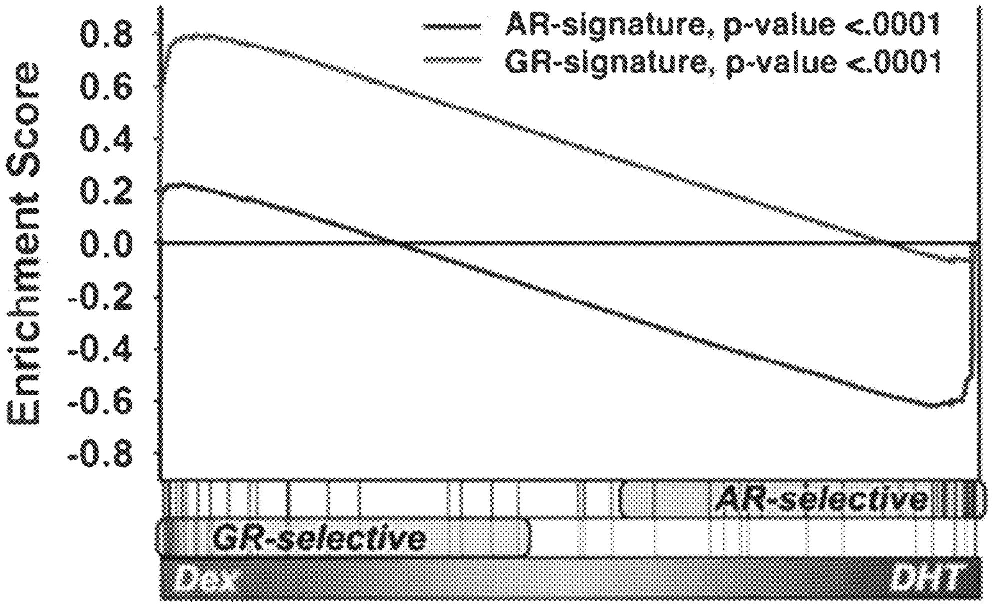
Figure 9D:
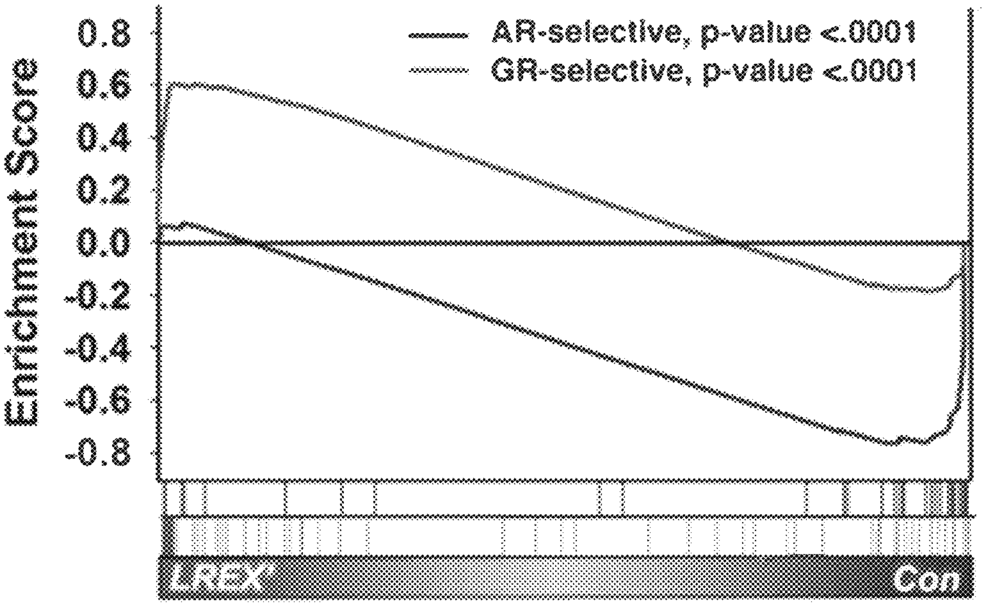

Whether transcriptomes of enzalutamide-resistant tumors are more likely to be explained by AR- or GR-driven gene expression using gene set enrichment analysis (GSEA) was next addressed. To define gene sets that distinguish AR and GR activity, expression of AR and GR signature genes was first evaluated by GSEA in the DHT- and Dex-treated samples from which they were derived. As expected, GR signature genes were enriched in the Dex-treated samples and AR signature genes were enriched with DHT treatment (FIG. 9C). Because several of the genes did not distinguish AR and GR status due to their overlapping transcriptional activities, the lists were refined into AR selective genes (defined as the AR induced signature genes that were also more highly expressed in DHT treated samples relative to Dex treated samples, n=39) and GR selective genes (defined as the converse, n=67) (Table 4). GSEA analysis of these selective gene lists revealed that GR selective genes were strongly enriched in the enzalutamide-resistant LREX' tumors whereas AR selective genes were strongly enriched in the control tumors (FIG. 9D). These data provide compelling, unbiased evidence that drug resistance is associated with a transition from AR- to GR-driven transcriptional activity.

Figure 9E:
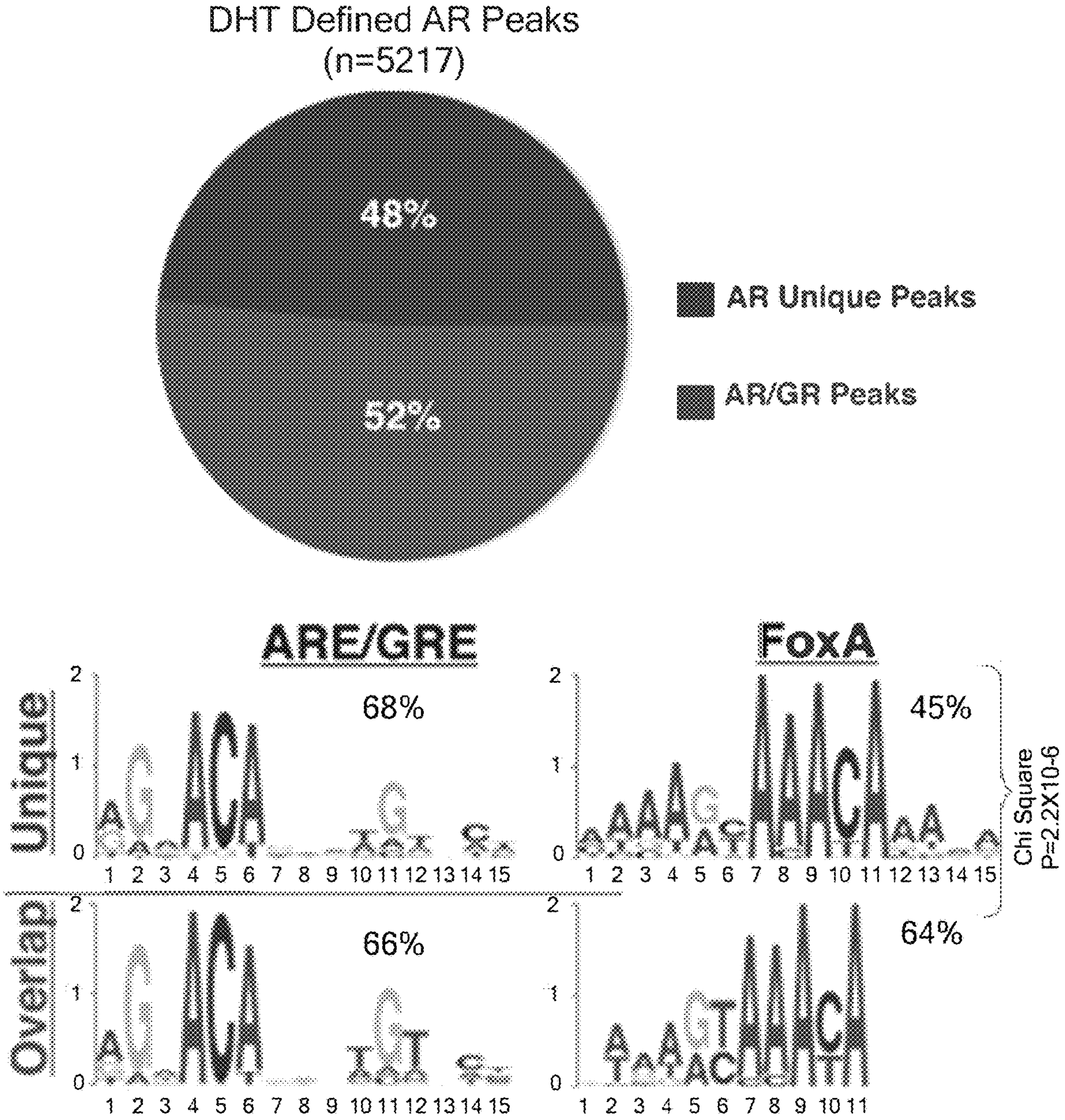
Figure 10A:
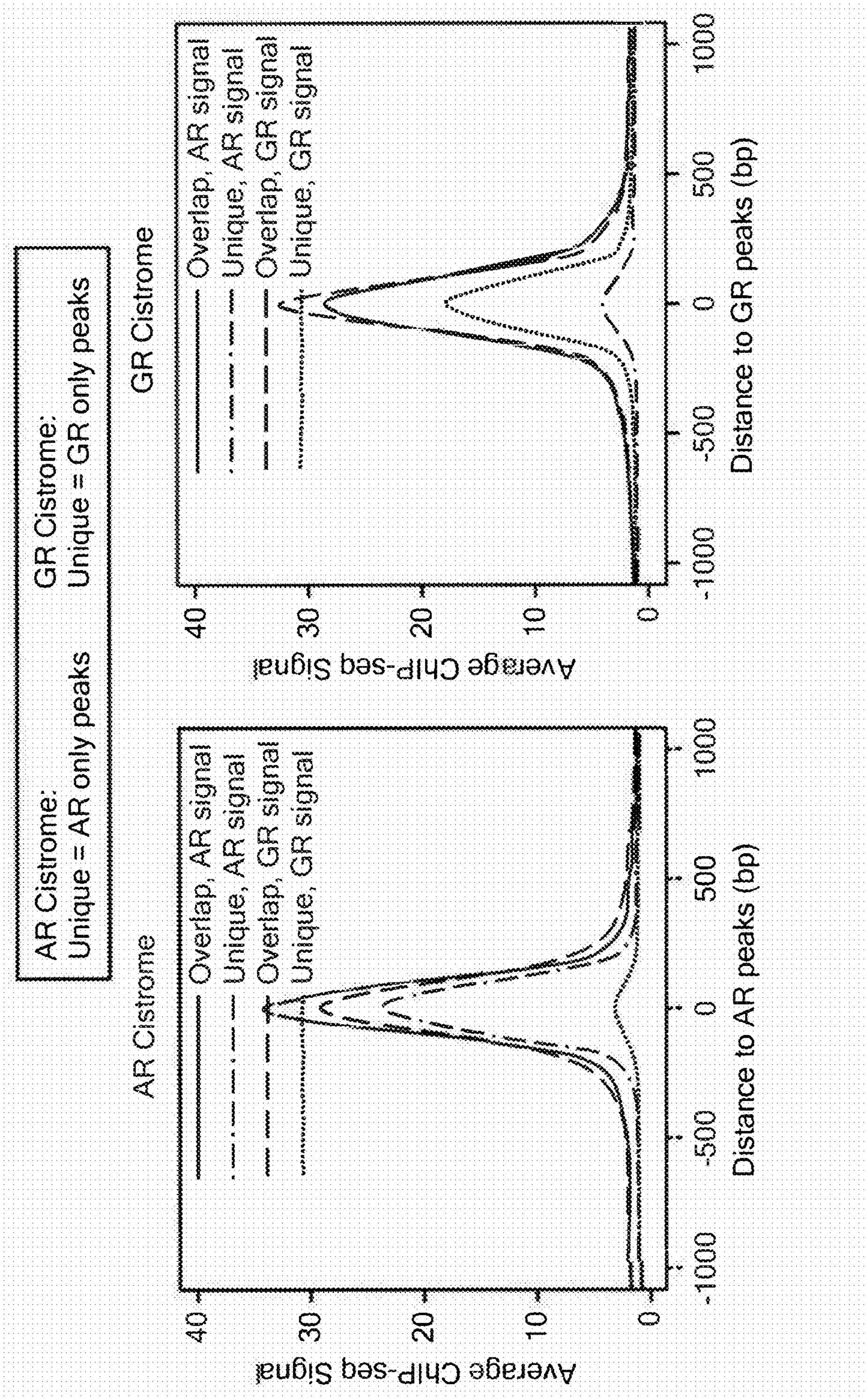
FIGS. 10A-10D show comparative AR and GR cistrome analysis. A. ChIP-seq signal strength for AR or GR at unique and overlap peaks in the AR or GR defined cistromes. B. AR and GR ChIP-qPCR at indicated AR target genes after treatment of LREX' in steroid depleted media with DHT (1 nm), Dex (100 nM), and/or enzalutamide (10 micromolar) for 1 hour as indicated+/−s.d. C. Integration of transcriptome and cistrome analysis. 56 AR signature genes transcriptionally regulated by DHT in LREX' were also found to have AR binding peak. Of those, 49 also showed at least modest regulation by Dex (1.2 fold, p<0.05). The percent of the 49 genes showing Dex regulation (yes) or the 7 showing no Dex regulation (no) that have an AR/GR overlap peak is shown.

One prediction of this model is that GR should occupy a substantial portion of AR binding sites in drug resistant cells. To address this question, ChIP-seq experiments were conducted to define AR and GR DNA binding sites in LREX' cells after DHT and Dex treatment respectively. Of note, 52% of the AR binding sites identified after DHT treatment were bound by GR after Dex treatment (FIG. 9E). The remaining 48% of AR peaks were examined more closely to be sure that these peaks were not scored as GR negative simply because they fell just below the threshold set by our peak calling parameters. When the average AR and GR signal was plotted as a measure of the relative strength of AR and GR peaks, little evidence was found of GR binding at the AR unique sites (FIG. 10A), confirming that these peaks were indeed unique to AR. Next motif analysis was conducted to explore potential differences between AR/GR overlap versus AR unique sites. The core ARE/GRE consensus sequence was present in both groups (66% and 68% of peaks) but AR/GR overlap peaks were relatively enriched for the FoxA1 motif (64% versus 45% of peaks, p=2.2×10-

Figure 9F:
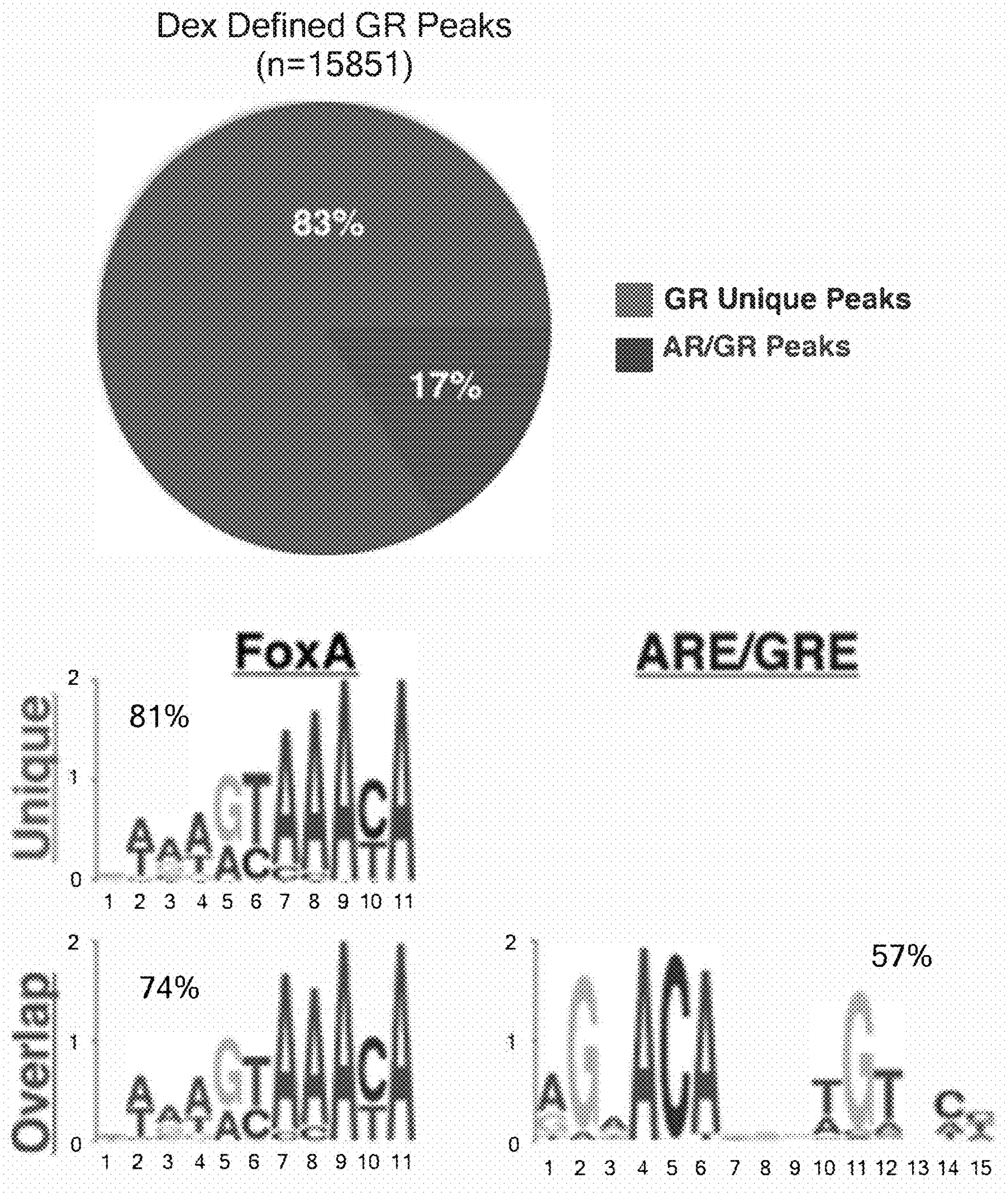

16) (FIG. 9E). Similar analysis of the GR cistrome defined GR unique and AR/GR overlap peaks and revealed that a higher proportion of GR binding sites were unique to GR. Interestingly, GR unique peaks were highly enriched for the FoxA motif (FIG. 9F), while the classic ARE/GRE was not reported by the motif discovery algorithm (MEME) and was found only 25% of the time.

Figure 10B:
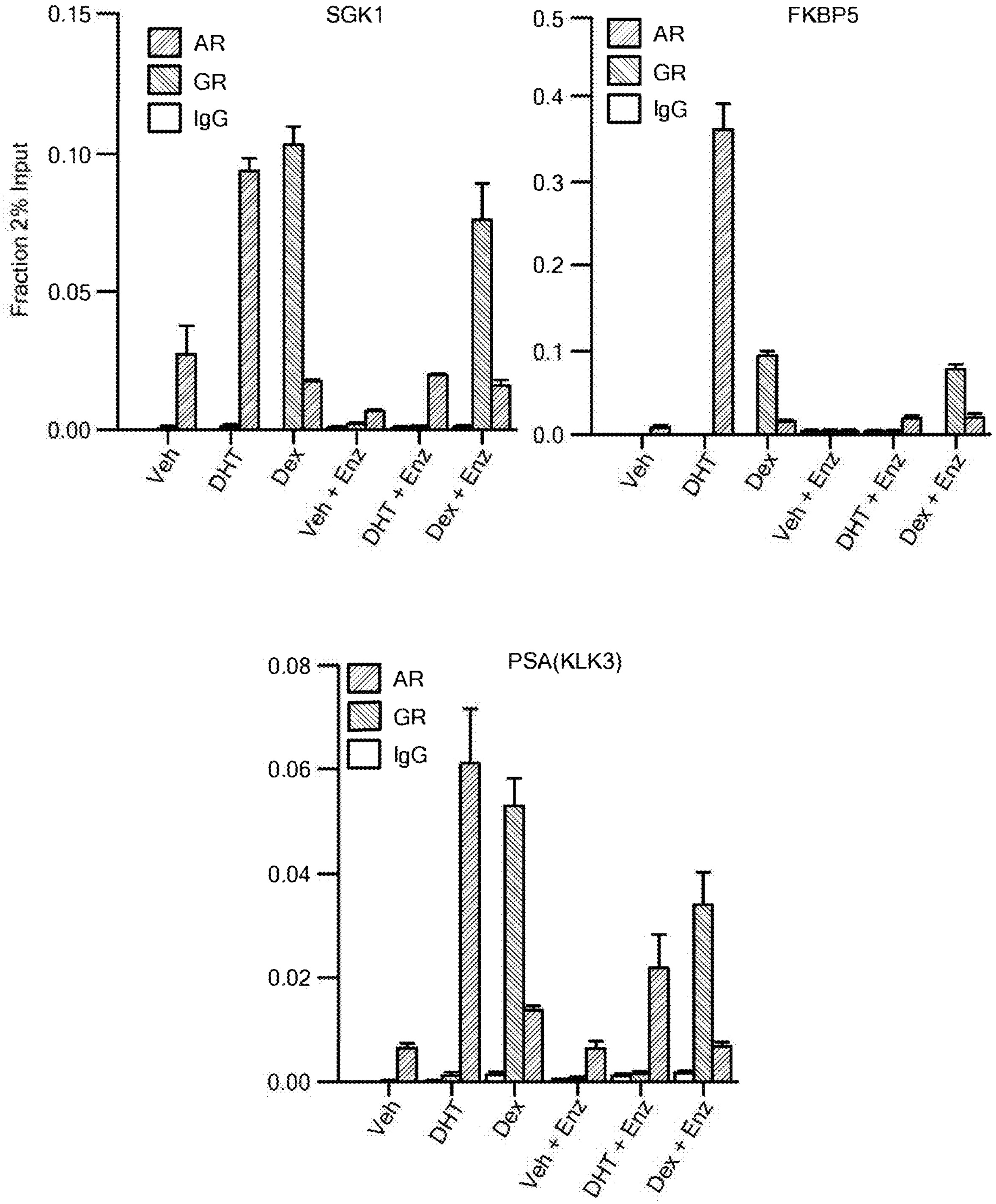
Figure 10C:
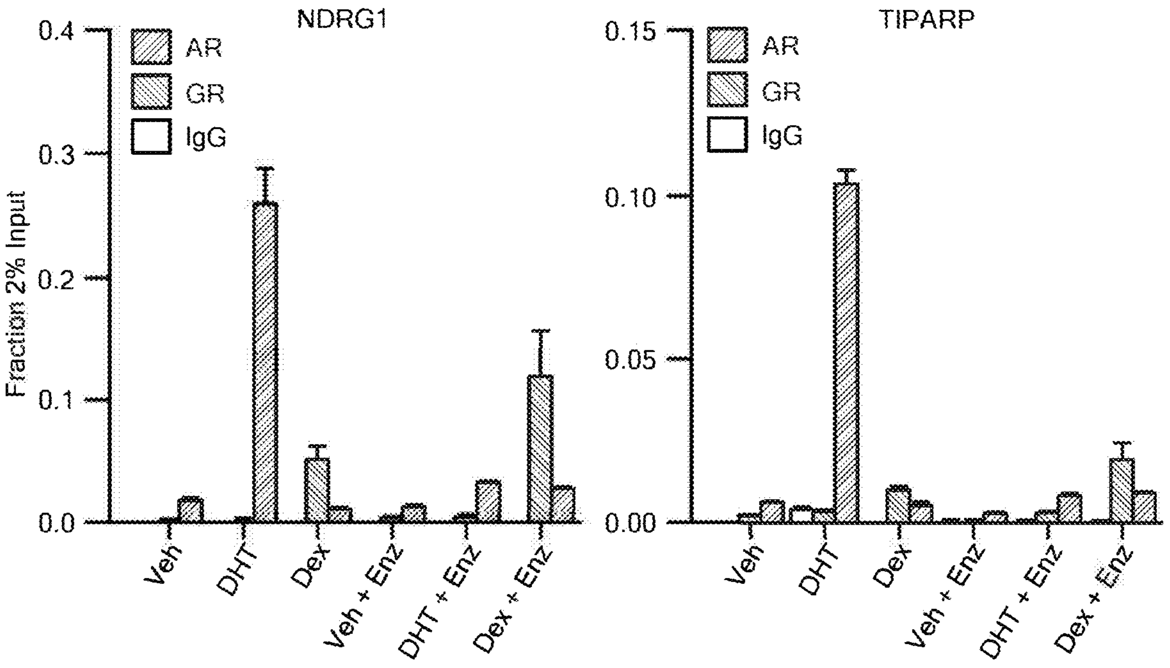
Figure 10D:
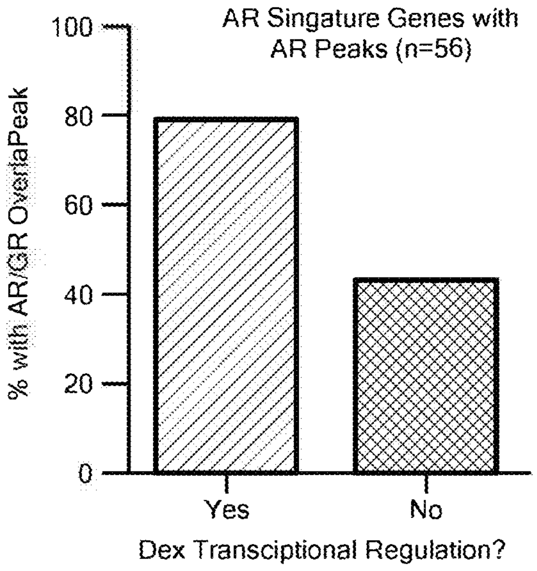

Although these cistrome studies provide evidence of substantial overlap between AR and GR binding sites in enzaluamide-resistant cells, several lines of evidence indicate that the transcriptional differences in DHT- versus Dex-induced gene expression cannot be explained solely by DNA binding. For example, ChIP RT-qPCR experiments showed significant AR and GR DNA binding at genes induced by both receptors (SGK1, FKBP5, PSA) but also at genes such as NDRG1 that are transcriptionally activated by DHT but not Dex (FIG. 10B). Integrative ChIP-seq and transcriptome analysis provided further evidence that DNA binding is not sufficient to determine transcriptional competence. Of the 56 AR signature genes found to have an AR binding peak, 49 showed at least some transcriptional regulation by GR (1.2 fold expression change, $p<0.05$). 38 of these 49 GR regulated genes (78%) had an overlapping AR/GR binding peak, confirming substantial overlap at co-regulated genes. But GR peaks were also found in 3 of the 7 AR targets genes (43%) with no apparent GR transcriptional regulation (FIG. 10C). Others have reported evidence of allosteric regulation of hormone receptor complexes by specific DNA sequences independent of binding affinity (Meijsing et al., 2009), a phenomenon that may also be relevant here.

Figure 11A:
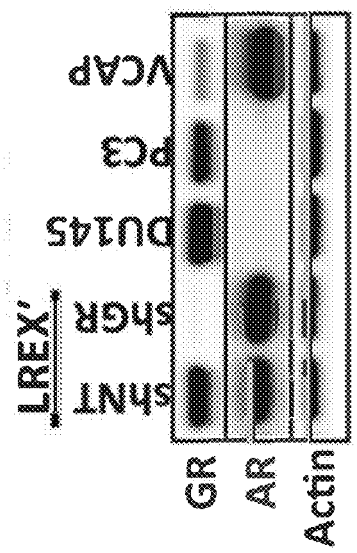
Figure 11B:
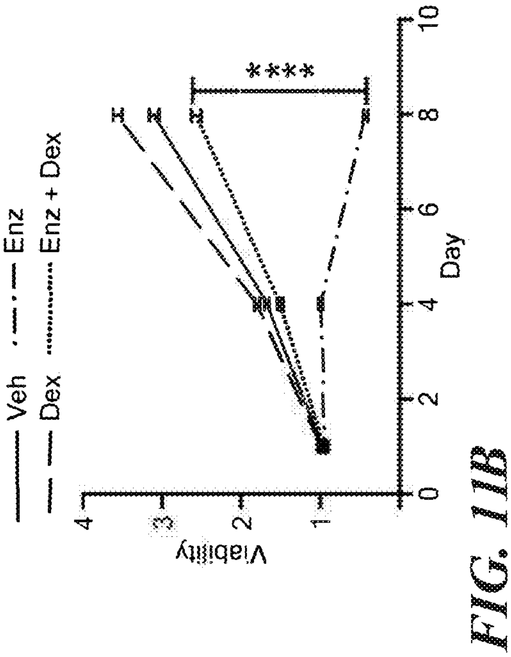
Figure 11C:
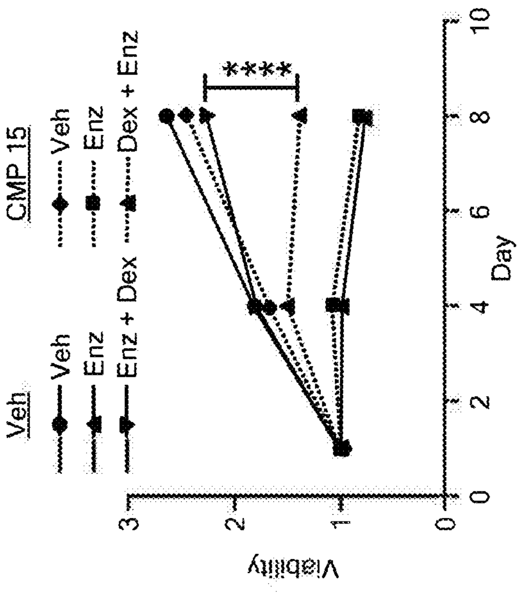
Figure 11D:
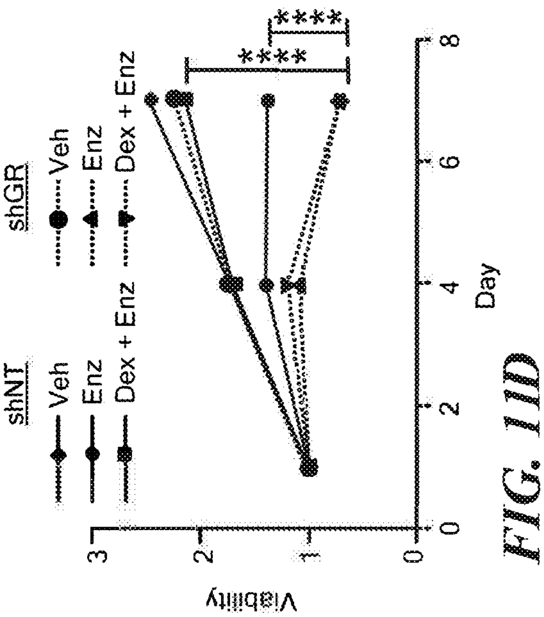

Activation of GR by Dexamethasone is Sufficient to Confer Enzalutamide Resistance Whereas LNCaP/AR cells acquire GR expression after prolonged exposure to enzalutamide, some prostate cancer cell lines derived from CRPC patients (DU145, PC3, VCaP) express endogenous GR (FIG. 11A). DU 145 and PC3 cells are AR-negative and hence resistant to enzalutamide but VCaP cells are enzalutamide-sensitive in vitro (Tran et al., 2009). IHC analysis showed diffuse, primarily cytoplasmic GR expression under standard culture conditions that lack glucocorticoid supplementation (FIG. 12A). To test if GR activation by addition of glucocorticoids impacts antiandrogen sensitivity, VCaP cells were treated with enzalutamide in the presence or absence of Dex. Enzalutamide inhibited growth as expected, but co-treatment with Dex reversed this growth inhibition (FIG. 11B). Additional studies with the GR antagonist, compound 15, or with GR shRNA restored enzalutamide sensitivity, provided pharmacologic and genetic evidence that GR confers resistance (FIG. 11C, 11D, 11E). Of note, GR knockdown (which inhibits GR more completely than compound 15, which has mixed agonist/antagonist properties(Wang et al., 2006)) augmented the activity of enzalutamide even in the absence of Dex (FIG. 11D,F), suggesting that even the weak basal GR activity seen under our standard cultures conditions can confer relative resistance to enzalutamide. This result also suggests that a pure GR antagonist could enhance the activity of enzalutamide in prostate cancers co-expressing GR and AR.

Figure 11H:
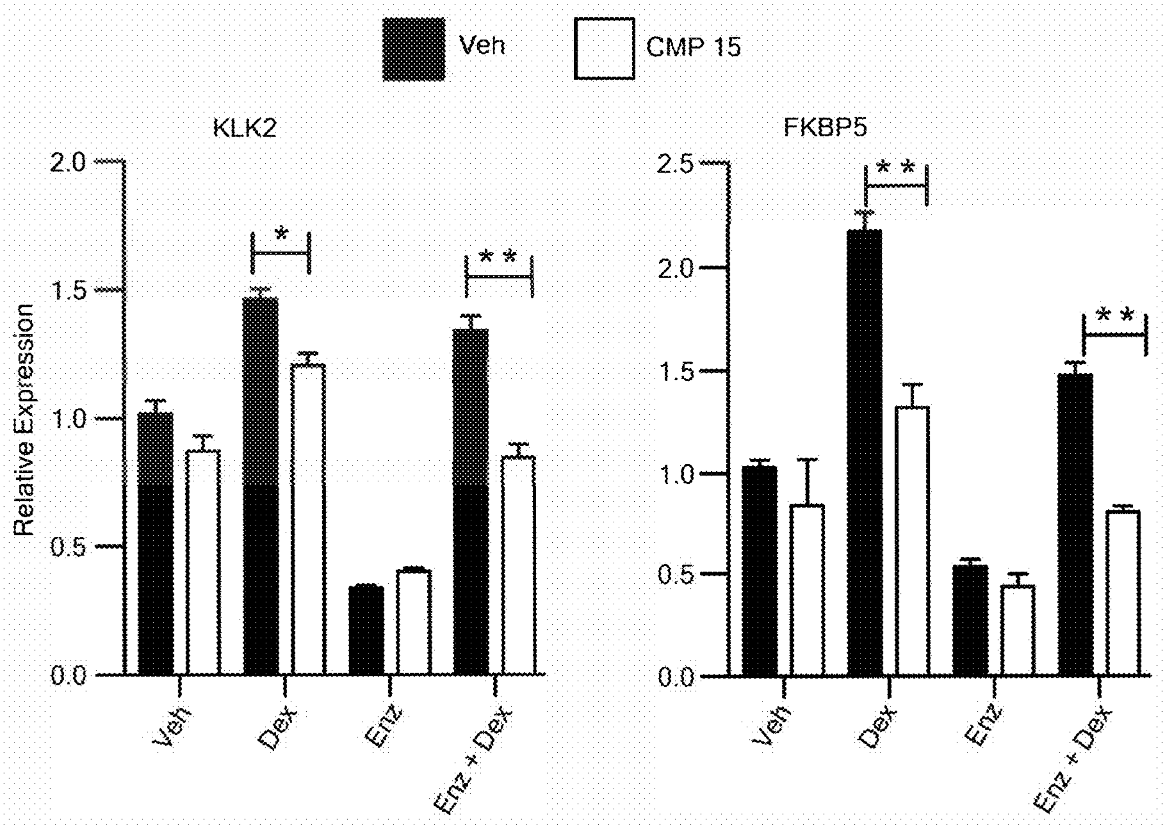
Figure 12C:
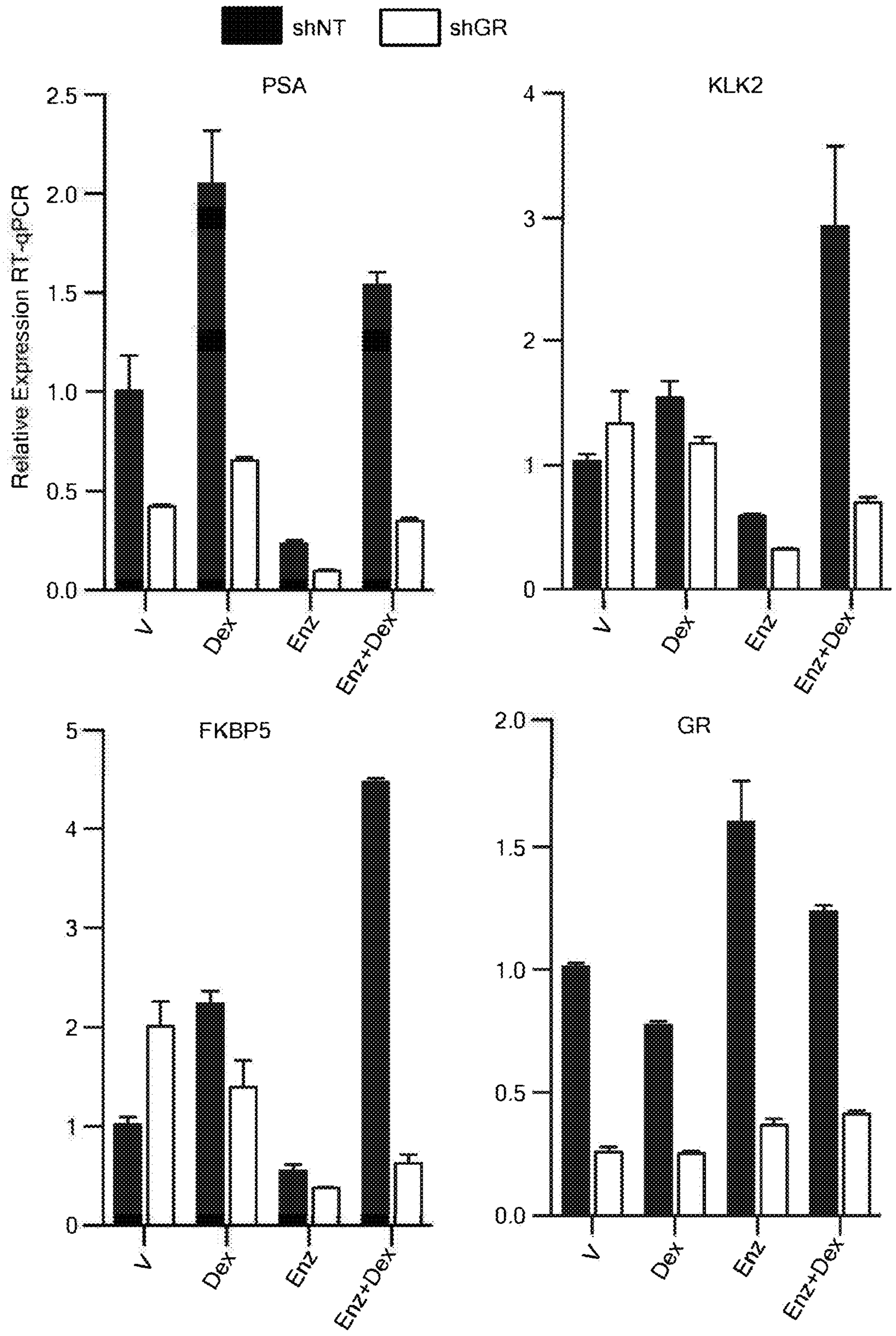

To determine if Dex activates a subset of AR target genes in VCaP (as observed in the LREX' model), a list of AR target genes was derived in VCaP cells exposed to DHT and it was asked whether Dex could modulate these same AR target genes in the presence of enzalutamide. Dex restored expression of some targets (KLK2, FKBP5, HOMER2, SLC45A3) but not others (DHCR24, SLC2A3, TRPM8, TMEM79), analogous to the uneven restoration observed in the LNCaP/AR model (FIG. 11G). Dex also induced expression of the clinical biomarker PSA in these cells, further supporting the hypothesis that GR can drive PSA progression in enzalutamide-resistant patients (FIGS. 12B, C). To confirm that Dex activated genes via the glucocorticoid receptor, the effect of compound 15 was evaluated on Dex induced transcriptional activity. As expected, compound 15 reduced Dex induction of the GR targets KLK2 and FKBP5 (FIG. 11H). Similarly, GR knock-down prevented Dex-mediated induction of target genes (FIG. 12C). As in the LREX' system (Table 4), the vast majority of genes robustly regulated by GR activation in VCaP cells were also regulated by AR activation with DHT (Table 5). These findings extend the hypothesis that GR promotes enzalutamide resistance largely by replacing AR activity at a subset of genes to a second model system.

A Subset of Prostate Cancers are Primed for GR Induction in the Setting of AR Inhibition In considering potential mechanisms for increased GR expression in drug-resistant tumors, several observations were noted that suggested two distinct models. First, flow cytometry analysis of LNCaP/AR and CS1 cells revealed GR expression in a rare subset of cells (FIG. 1E), raising the possibility that these cells clonally expand under the selective pressure of antiandrogen therapy. Consistent with this model, rare GR-positive cells were observed in a tissue microarray analysis of 59 untreated primary prostate cancers (Table 6). However, a modest (~2 fold) but significant increase in GR mRNA levels in LNCaP/AR xenografts was observed after only 4 days of antiandrogen treatment, reminiscent of an older report of increased GR expression in normal ventral rat prostate after castration (Davies and Rushmere, 1990). These findings suggest a second model of adaptive resistance whereby AR inhibition causes an increase in GR levels due to loss of AR-mediated negative feedback.

Figure 13A:
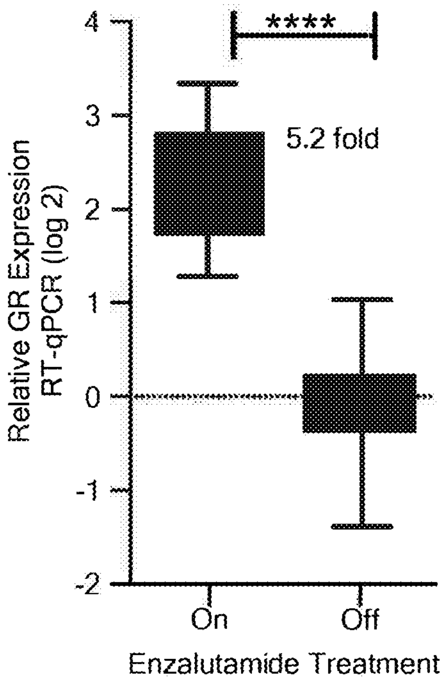
FIGS. 13A-13G show resistant cells are primed for GR induction upon AR inhibition. A. GR mRNA in LREX' xenografts. Tumors were injected into castrated mice and immediately treated with 10 mg/kg enzalutamide (n=20) for 7 weeks. Half of the mice were then continued on 10 mg/kg enzalutamide (n=10) or discontinued for 8 days (n=10). B. LREX' are maintained in vitro in the presence of enzalutamide 1 micromolar. GR mRNA was assessed in LREX' cell line after passage for indicate number of days in standard fetal bovine serum containing media without enzalutamide. C. GR mRNA in LREX' cultured in charcoal stripped media for 48 hours and then treated for 8 hours with vehicle or DHT with or without 10 micromolar enzalutamide. D. AR ChIP-qPCR with LREX' cultured in charcoal stripped media and then treated for 1 hour with DHT (1 nM) or Dex (100 nM) at an intronic enhancer site+/−s.d. E. Intracellular GR flow cytometric analysis of indicated cells at indicated times points. AUC=area under curve. Enzalutamide=1 micromolar F. Plotted median fluorescence (minus background) values from E and FIG. 14C. For both LREX plots, $R^2$ values for non-linear regression analysis is >0.98. G. Model of GR induction in resistant tissues.
Figure 13B:
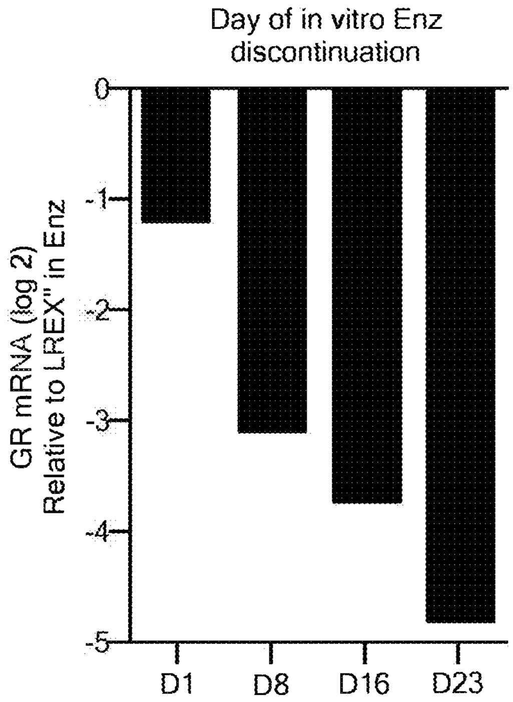
Figure 13C:
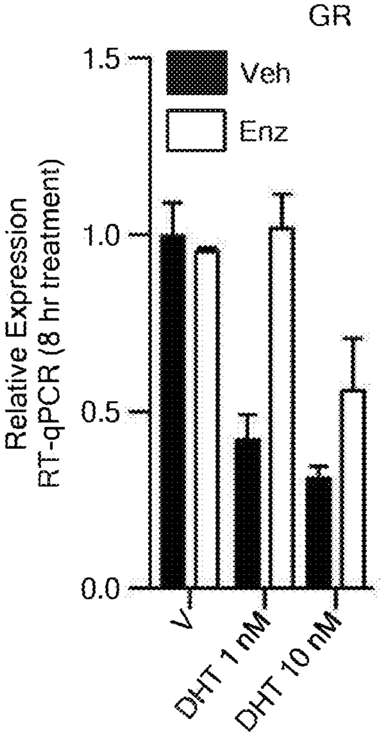
Figure 13D:
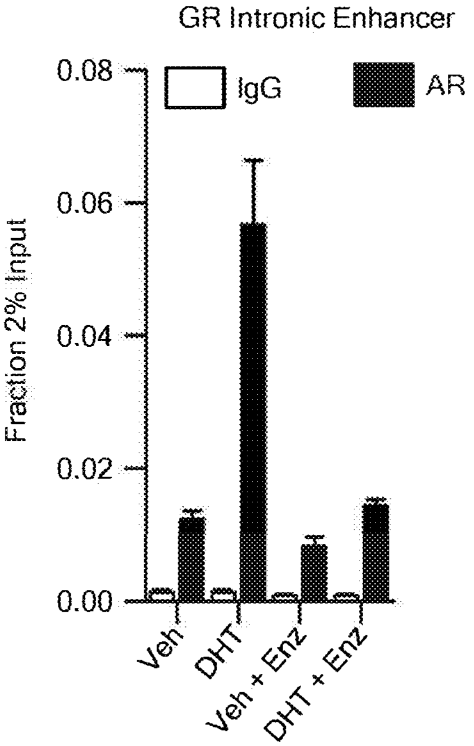

To investigate the relationship between AR activity and GR expression, whether the high level of GR expression in LREX' tumors is maintained after discontinuation of enzalutamide was examined. Remarkably, GR mRNA levels dropped by ~5 fold 8 days after treatment discontinuation (FIG. 13A). Because enzalutamide has a prolonged half-life in mice (Tran et al., 2009), it is difficult to make definitive conclusions about negative feedback loops using in vivo models. Therefore, similar enzalutamide withdrawal experiments were conducted in LREX' cells cultured in vitro. GR mRNA levels dropped as early as 1 day after discontinuation and continued to decline throughout the 23 days of the experiment (FIG. 13B). Additional experiments with LREX' cells using earlier timepoints in charcoal stripped media showed reduced GR mRNA levels after only 8 hours DHT exposure and this reduction was reversed by co-treatment with enzalutamide (FIG. 13C). This reduction correlated precisely with the recruitment of an AR binding peak in an intronic enhancer of GR identified by ChIP, suggesting AR directly represses GR expression in these cells (FIG. 13D).

Figure 13E:
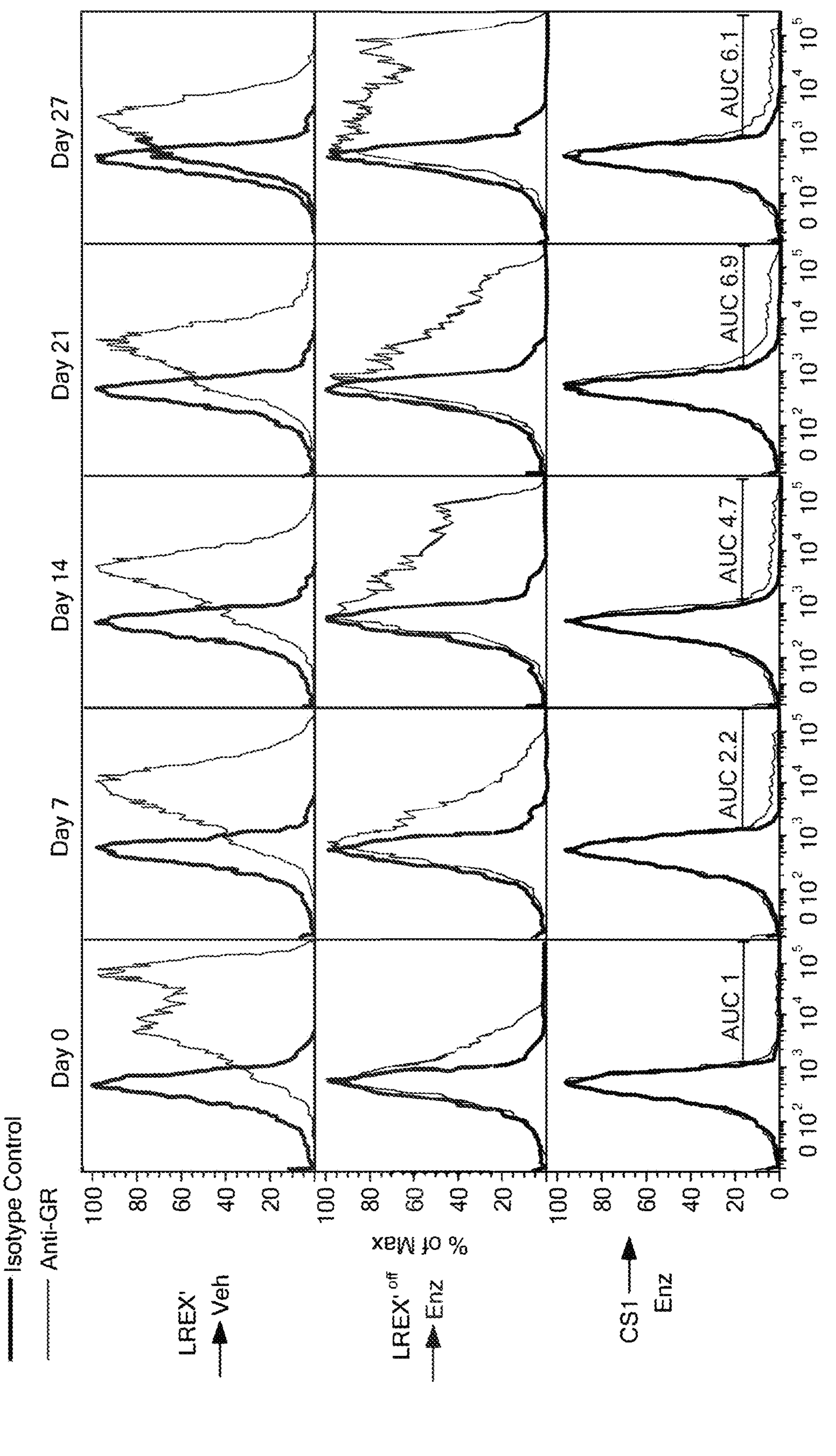
Figure 14A:
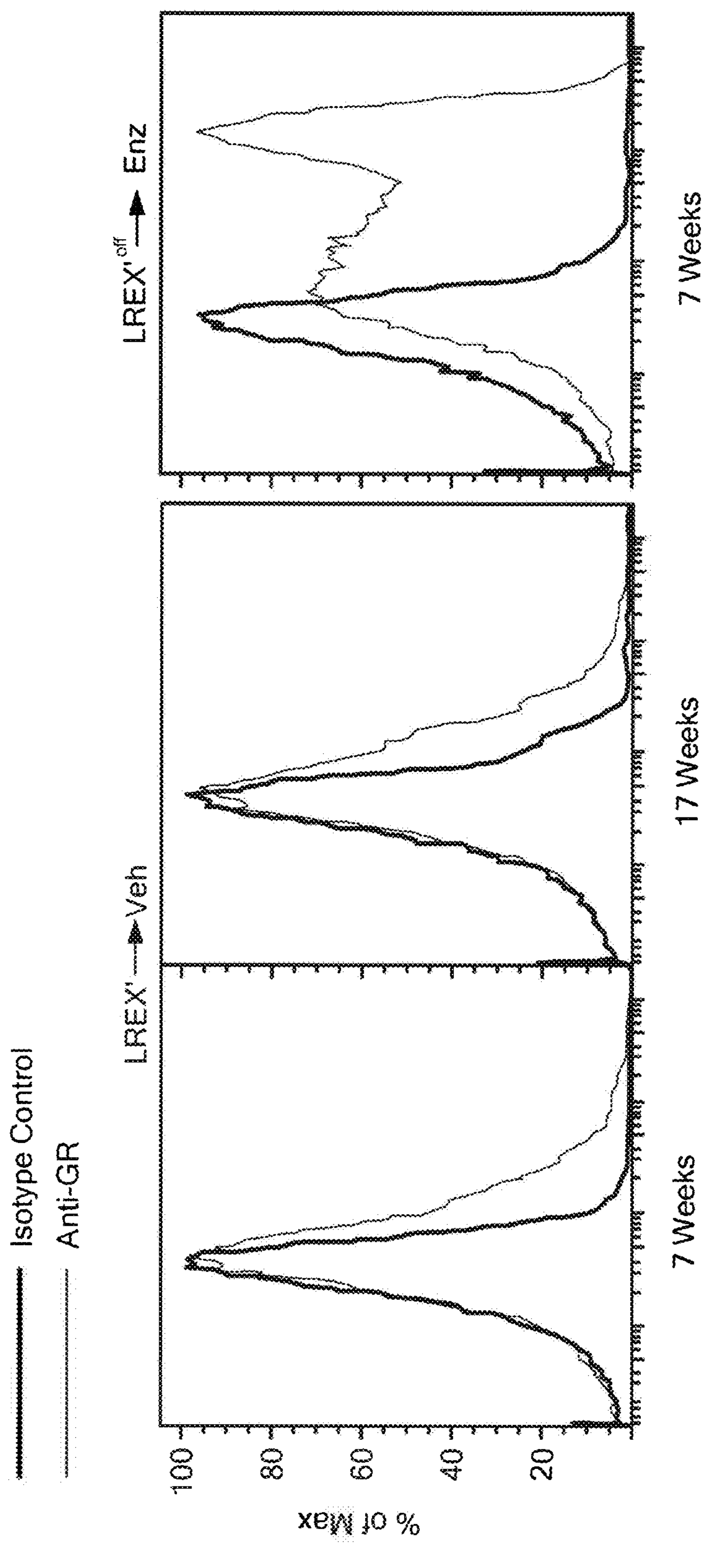
FIGS. 14A-14C shows GR expression in resistant and sensitive cells A. GR intracellular staining and flow cytometric analysis of LREX' or LREX'$^{off}$ cells after either vehicle (left) or 1 micromolar enzalutamide (right) treatment for indicated time. B. Relative cell numbers determined by cell counting (Vi-cell) of indicated cells with vehicle or 1 micro-molar enzalutamide treatment. C. Intracellular GR flow cytometric analysis of indicated cells at indicated times points. AUC=area under curve. Enzalutamide=1 micromolar.

To determine if the loss of GR expression upon enzalutamide withdrawal occurs across the entire cell population or is restricted to a subset of cells, flow cytometry experiments were conducted, where a shift in median signal intensity can be used to identify expression changes in the bulk cell population. (Expression changes limited to a minority subpopulation would not affect the median and would instead be identified as a tail population by histogram plot.) An exponential decay in median GR protein signal was observed (half-life 7.6 days) (FIG. 13E,top row, 13F), confirming that the loss in GR expression occurs across the entire LREX' cell population. Extension of this experiment to later time points (17 weeks) revealed a plateau in loss of GR expression by 7 weeks (FIG. 14A).

Next the reciprocal experiment of re-exposure of LREX' cells to enzalutamide following GR downregulation after prolonged enzalutamide withdrawal (LREX'$^{off}$) was conducted. GR expression was regained with induction kinetics essentially reciprocating the rate of decay previously seen with removal of drug (doubling time 6.8 days), establishing that the resistant line remained poised for GR induction in the setting of AR inhibition (FIG. 13E,F). Consistent with the time scale, continued drug exposure for 7 weeks was associated with a clear shift in GR expression in essentially all cells (FIG. 14A).

Figure 13F:
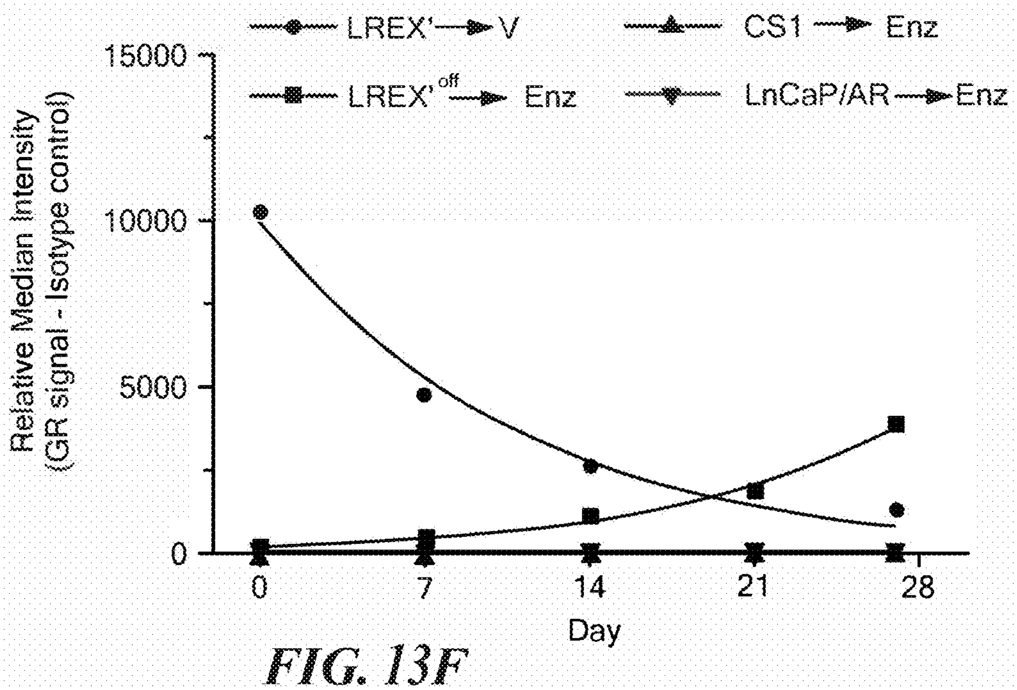
Figure 13G:
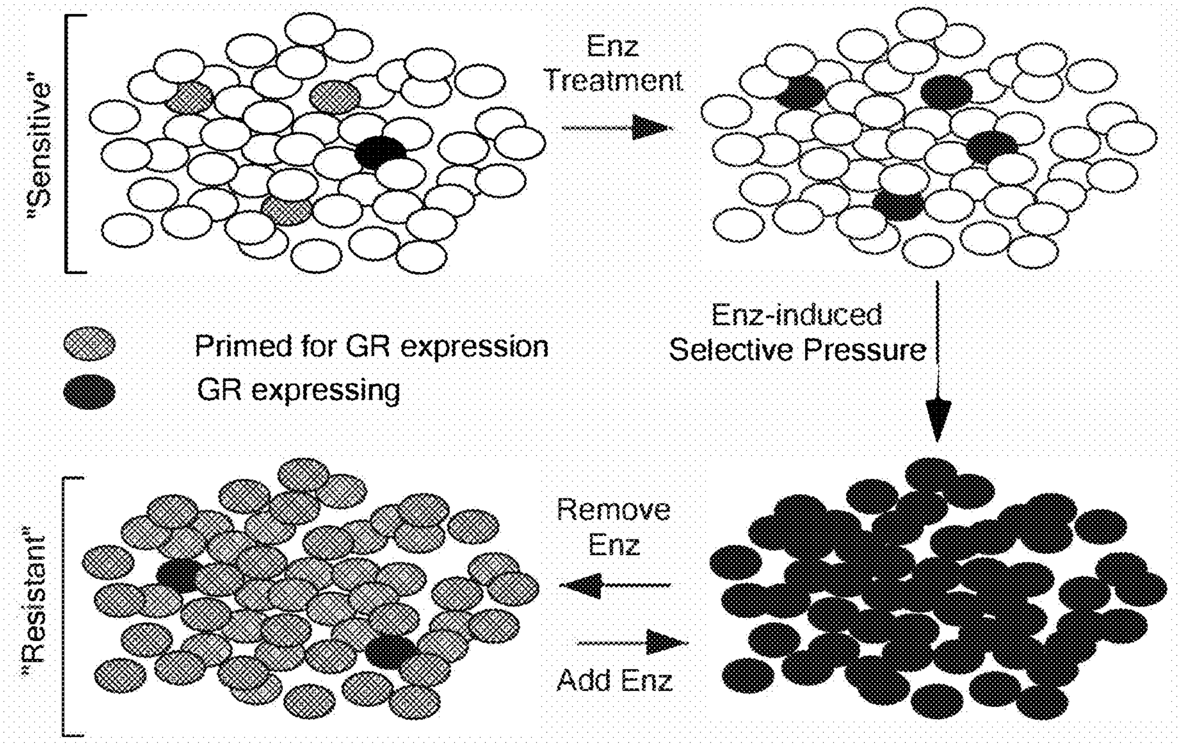
Figure 14B:
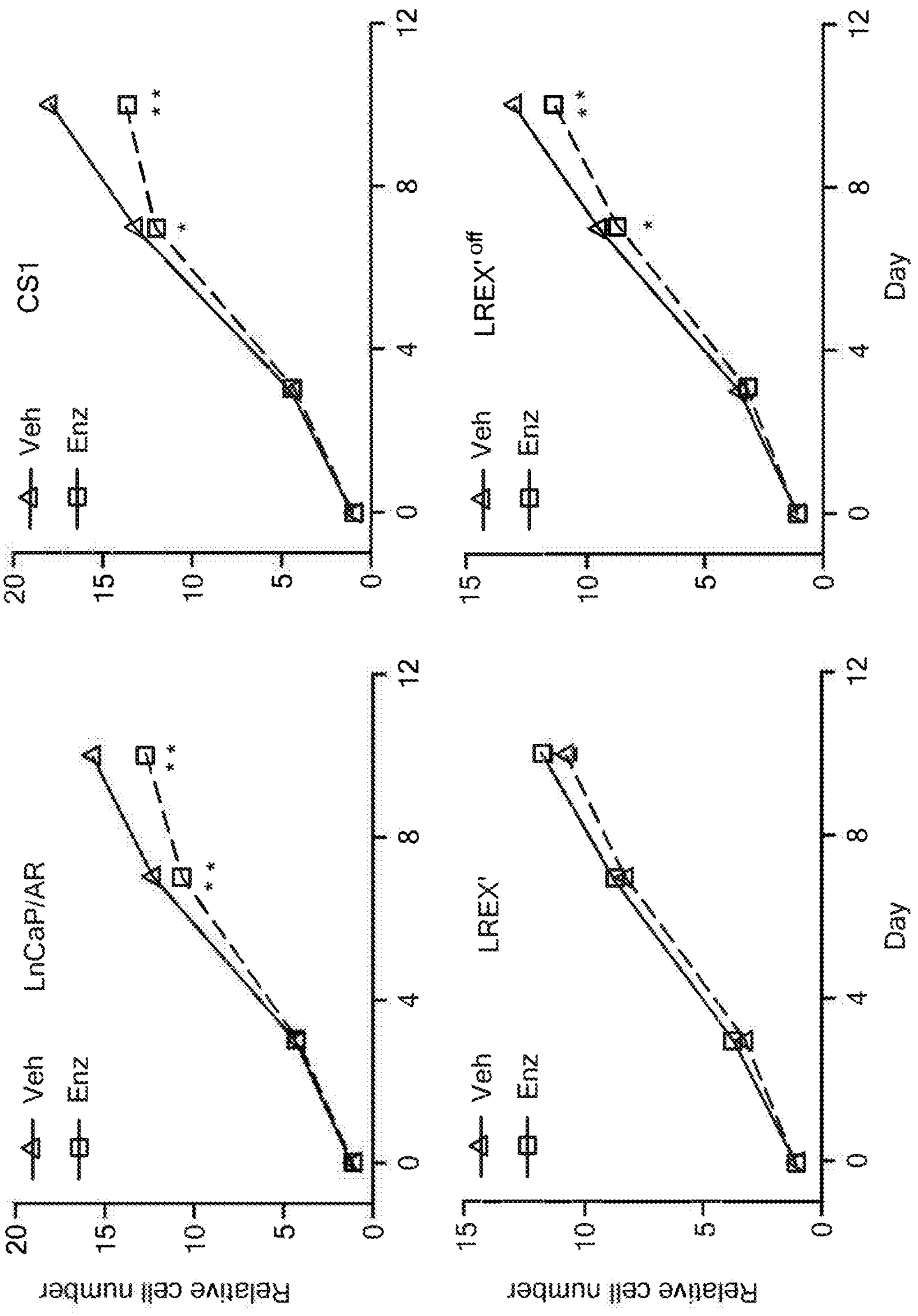
Figure 14C:
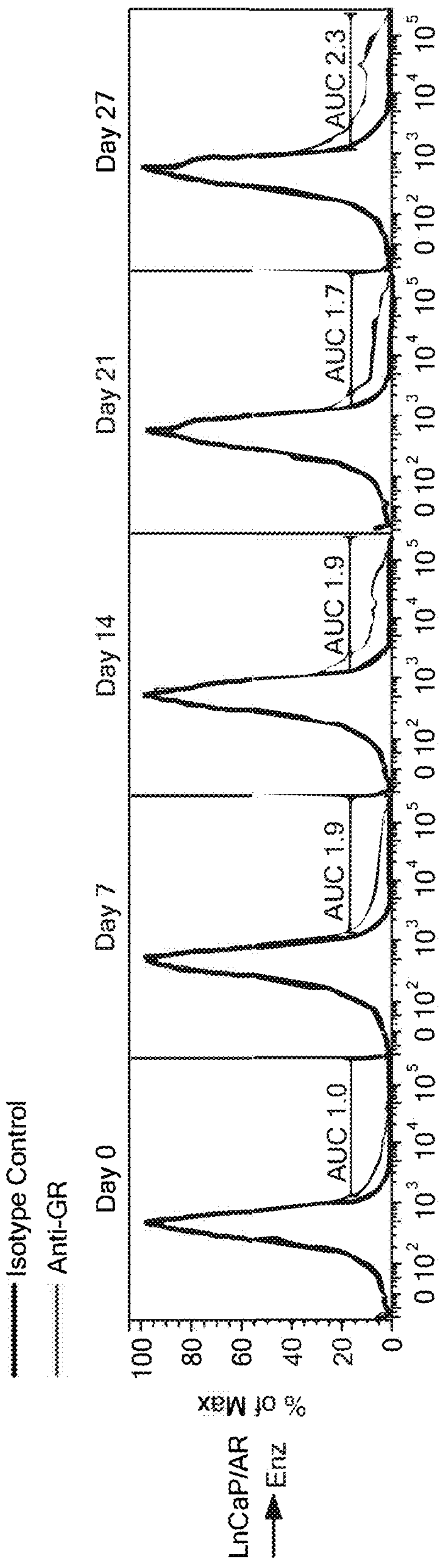

It was next determined if AR inhibition is sufficient to induce GR expression in LNCaP/AR or CS1 cells that had not previously been exposed to enzalutamide. In contrast to LREX', there was no change in median expression intensity in CS1 or LnCaP/AR over the 4 week experiment, indicating that most cells do not turn on GR expression simply as a consequence of AR inhibition (FIGS. 13E, 13F, 14C). However, the area under the GR staining population did increase. Given the weak antiproliferative effect of enzalutamide in vitro (FIG. 14B), the results presented herein suggest that this increase in GR expression is most likely explained by loss of AR-mediated negative feedback rather than by clonal expansion. Together, these findings support a model in which a subset of prostate cancer cells are "primed" for GR induction in the context of AR inhibition through an adaptive resistance mechanism (via AR-mediated negative feedback). The results presented herein suggest that these cells then clonally expand under the selective pressure of AR blockade, eventually emerging as drug-resistant tumors whose expression profiles may resemble those of AR-driven tumors but are driven by GR (FIG. 13G).

TABLE 2A

| Pilot Cohort | | | | |
|---|---|---|---|---|
| Anti-Androgen Group | Mean Tumor Volume ($mm^3$): Day 0 | % Regression: D 28 Mean | Mean Tumor Volume ($mm^3$) at harvest | Day of Harvest: Mean |
| All (n = 15) | 364 | 76% | 467 | D163 |
| RD162 (n = 9) | 379 | 80% | 554 | D173 |
| ARN-509 (n = 6) | 341 | 71% | 337 | D145 |

TABLE 2B

| Illumina HT-12 data Probeset ID | LNCAP/AR Fold Change with DHT | p-value |
|---|---|---|
| SGK1 | 7.05 | 1.98E−12 |
| KCNN2 | 2.85 | 1.17E−09 |
| PMEPA1 | 2.76 | 8.22E−10 |
| NCAPD3 | 2.39 | 1.31E−06 |
| SNAI2 | 2.03 | 4.77E−09 |
| LONRF1 | 1.68 | 4.36E−06 |
| SPOCK1 | 1.66 | 1.70E−05 |
| UGT2B17 | −1.26 | 0.000392588 |
| UGT2B15 | −1.36 | 0.00216714 |
| CAMK2N1 | −3.33 | 1.34E−07 |
| PMP22 | −4.49 | 1.31E−12 |

TABLE 2C

| Validation Cohort | | | |
|---|---|---|---|
| Drug Treatment | GR mRNA Expression | Western Blot | Other Resistance Mechanism |
| ARN | 172.1 | Y | |
| Enz | 127.7 | Y | |
| ARN | 103.8 | Y | |
| Enz | 53.0 | N | |
| ARN | 47.4 | Y | |
| ARN | 41.6 | Y | |
| ARN | 30.2 | Y | |
| Enz | 29.8 | N | |
| Enz | 24.2 | Y | |
| Enz | 24.0 | Y | |
| ARN | 14.5 | Y | |
| Enz | 14.3 | N | |
| ARN | 11.4 | Y | AR mutation |
| ARN | 1.4 | Y | |
| ARN | 0.8 | Y | |
| Enz | 0.5 | Y | CDH2 expressing |

TABLE 3

| Fractional Restoration of AR targets in resistance | | |
|---|---|---|
| Probeset | Fractional Restoration Resistant (Validation Cohort) | Fractional Restoration LREX' |
| ADAMTS1 | 0.104737035 | 0.224681263 |
| ARHGAP28 | 0.298572591 | 1.112766385 |
| ATAD2 | 0.980888318 | 1.302557125 |
| ATP1B1 | 0.054334091 | 1.552059641 |
| AURKA | 1.055812896 | 1.012376027 |
| C11ORF82 | 1.022088793 | 0.879681046 |
| C12ORF26 | 0.559908334 | 0.856561712 |
| C14ORF4 | 0.638697558 | 1.686188564 |
| C7ORF68 | 0.57401979 | 1.169336795 |
| CAP2 | 0.953992059 | 0.69853094 |
| CCNA2 | 0.732665467 | 1.071889661 |
| CKB | 1.066887783 | 1.021144279 |
| COBL | 0.575676657 | 1.028916763 |
| COL4A5 | 1.383819191 | 1.816840842 |
| COLEC12 | 0.884755155 | 1.134950911 |
| CYBASC3 | 0.618319396 | 0.622717671 |
| DDC | 0.252818617 | 1.346416329 |
| ENPP5 | 0.872211171 | 1.566327079 |
| ERBB2 | 0.584956319 | 0.450288253 |
| ERRFI1 | 0.344869039 | 0.791369105 |
| FADS1 | 0.783280213 | 1.534588169 |
| FAM111A | 1.06151086 | 1.91087708 |
| FKBP5 | 0.507369877 | 0.746124849 |
| GINS2 | 0.818809571 | 0.993454642 |
| GLRX2 | 0.163895682 | 0.394469677 |
| GMNN | 1.437188789 | 2.125173731 |
| GRB10 | 0.661692232 | 1.464197128 |
| HK2 | 0.857807757 | 0.944175379 |
| HMMR | 0.586811723 | 0.611488201 |
| HOMER2 | 0.718856843 | 0.835066652 |
| IRX3 | 1.504573197 | 2.101495745 |
| IRX5 | 1.58503456 | 2.04652588 |
| KCNN2 | 0.50426061 | −0.058662743 |
| LAMA5 | 0.594448349 | 1.614096978 |
| LOC338758 | 1.10031621 | 1.892542273 |
| LOC643911 | 1.430495646 | 1.277746127 |
| LPAR3 | 0.223276924 | 0.760020748 |
| MAPK6 | 0.6794877 | 0.712027157 |
| MELK | 0.822946788 | 0.951119531 |
| MLF1IP | 0.801888795 | 0.320087012 |
| NCAPG | 0.830147149 | 0.930073778 |
| NDC80 | 0.858582224 | 0.931146158 |
| NDRG1 | 0.110736515 | −0.89658973 |
| NLGN1 | 0.452084841 | 1.549812463 |
| NRP1 | 0.735034964 | 1.018946919 |
| ODC1 | 0.685851438 | 0.758202603 |
| PLEKHB1 | 1.006632446 | 1.321859712 |
| PLXDC2 | 1.457006773 | 1.696602557 |

TABLE 3-continued

| Fractional Restoration of AR targets in resistance | | |
|---|---|---|
| Probeset | Fractional Restoration Resistant (Validation Cohort) | Fractional Restoration LREX' |
| PMEPA1 | −0.518193024 | −1.216512966 |
| PPFIA2 | 0.399925636 | 1.270985117 |
| PRKD1 | 0.730293325 | 1.553606953 |
| PTGER4 | 0.500131315 | 1.14695717 |
| PTGFR | −0.163702714 | 1.289011102 |
| RND3 | 1.462746581 | 1.845253498 |
| SEMA6A | 0.324521397 | 1.214013023 |
| SESN1 | 0.500071071 | 1.204301228 |
| SGK | 1.594552221 | 3.860391513 |
| SGK1 | 0.908306288 | 2.583445858 |
| SLC45A3 | 0.666206634 | 0.572479739 |
| SLC7A5 | 1.788159088 | 1.505143938 |
| SMA4 | 1.007154273 | 1.905171027 |
| SORL1 | 0.393127568 | 0.792003324 |
| STK39 | 0.847407901 | 1.627660166 |
| TIPARP | 0.091937709 | −0.095853867 |
| TK1 | 1.103253735 | 1.239068469 |
| TLL1 | 0.042830568 | 0.578273664 |
| TMEM38B | 0.52248819 | 0.967647176 |
| TPX2 | 0.969128419 | 0.760244607 |
| TRIM45 | 0.797043275 | 1.170614157 |
| TSC22D3 | 0.502868149 | 0.808846273 |
| TSKU | 0.60338297 | 1.278936716 |
| TTK | 0.650518354 | 0.807578623 |
| TXNIP | 0.761305485 | 1.155255054 |
| ZWILCH | 0.621821416 | 0.45158825 |

TABLE 4

AR and GR signature genes corresponding to FIG. 9. Top: GR signature genes showing at least modest regulation by AR, or conversely, AR signature genes showing at least modest regulation by GR are annotated. Most (>80%) AR and GR signature genes show some evidence of regulation by the reciprocal receptor. Bottom: GR and AR selective genes used for GSEA analysis

| GR signature probesets (Dex 1.6 fold FDR < .05) | Significant regulation by AR (DHT 1.20 fold p < .05)? | AR signature probesets (DHT 1.6 fold FDR < .05) | Significant regulation by GR (Dex 1.20 fold p < .05)? |
|---|---|---|---|
| ABCC4 | Y | ABCC4 | Y |
| ABHD2 | Y | ALDH1A3 | Y |
| ACTA2 | N | BAMBI | Y |
| ALDH1A3 | Y | BDNF | Y |
| ATAD2 | N | C17ORF48 | Y |
| AZGP1 | N | C19ORF48 | Y |
| BAMBI | Y | C1ORF116 | Y |
| BCL6 | N | CBLN2 | Y |
| BRDT | Y | CEBPD | Y |
| C11ORF92 | Y | CHST2 | Y |
| C17ORF48 | Y | CRISPLD2 | Y |
| C19ORF48 | Y | CROT | N |
| C1ORF116 | Y | CYP7A1 | Y |
| C1ORF149 | Y | DKFZP761P0423 | N |
| C6ORF85 | Y | DNM1L | Y |
| C7ORF63 | Y | EDG7 | Y |
| C9ORF152 | N | ELL2 | Y |
| CEBPD | Y | ENDOD1 | N |
| CGNL1 | N | ERN1 | Y |
| CHKA | Y | ERRFI1 | Y |
| CRY2 | Y | F2RL1 | Y |
| DBC1 | Y | FAM105A | Y |
| DDIT4 | Y | FAM110B | Y |
| EDG7 | Y | FAM113B | Y |
| EEF2K | Y | FAM49A | Y |
| ELL2 | Y | FKBP5 | Y |
| EMP1 | N | FRK | Y |
| ERRFI1 | Y | FZD5 | Y |
| F2RL1 | Y | GADD45G | Y |
| FAM105A | Y | GCNT1 | Y |
| FAM49A | Y | GCNT3 | Y |

TABLE 4-continued

AR and GR signature genes corresponding to FIG. 9. Top: GR signature genes showing at least modest regulation by AR, or conversely, AR signature genes showing at least modest regulation by GR are annotated. Most (>80%) AR and GR signature genes show some evidence of regulation by the reciprocal receptor. Bottom: GR and AR selective genes used for GSEA analysis

| | | | |
|---|---|---|---|
| FKBP5 | Y | GRHL2 | Y |
| FLJ22795 | Y | HERC5 | Y |
| FOXO3 | Y | HEY1 | Y |
| GADD45B | Y | HMOX2 | Y |
| GHR | Y | HS.25318 | Y |
| HERC5 | Y | KIAA0194 | N |
| HMOX2 | Y | KLF15 | Y |
| HOMER2 | Y | KLF5 | Y |
| HS.99472 | Y | KLK2 | Y |
| HSD11B2 | Y | KLK4 | Y |
| IL6R | Y | LIPG | Y |
| KBTBD11 | Y | LPAR3 | Y |
| KIAA0040 | N | LRIG1 | Y |
| KIAA1370 | Y | MBOAT2 | Y |
| KLF15 | Y | MGC87042 | Y |
| KLF5 | Y | MLPH | Y |
| KLF9 | N | MTMR9 | Y |
| KLK3 | Y | MUC13 | Y |
| KLK4 | Y | NAPEPLD | Y |
| KRT80 | Y | NAT8B | N |
| LIN7B | N | NDRG1 | Y |
| LINCR | Y | NEDD4L | Y |
| LOC100008588 | Y | NFKBIA | Y |
| LOC100130886 | Y | NKX3-1 | Y |
| LOC100131392 | Y | NPPC | N |
| LOC100134006 | N | ORM1 | N |
| LOC340970 | Y | ORM2 | N |
| LOC346702 | Y | PAK1IP1 | Y |
| LOC399939 | Y | PDE9A | Y |
| LOC440040 | N | PIK3AP1 | Y |
| LOC648509 | Y | PMEPA1 | Y |
| LOC728431 | N | PMP22 | N |
| LPAR3 | Y | PPFIBP2 | Y |
| MAP3K8 | Y | PRAGMIN | Y |
| MBOAT2 | Y | PRR15L | Y |
| MEAF6 | Y | PSCD1 | N |
| MGC87042 | Y | PSD | Y |
| MT1X | N | RAB20 | Y |
| MTMR9 | Y | RASD1 | Y |
| NDRG1 | Y | RDH10 | Y |
| NEDD4L | Y | RHOU | Y |
| NFKBIA | Y | RND3 | Y |
| NKX3-1 | Y | RNF160 | Y |
| NPC1 | Y | SGK | Y |
| NRP1 | Y | SGK1 | Y |
| PDE9A | Y | SHRM | Y |
| PER1 | Y | SIPA1L2 | Y |
| PGC | N | SLC16A6 | Y |
| PGLYRP2 | N | SLC26A3 | Y |
| PHLDA1 | Y | SLC2A12 | Y |
| PLGLB1 | Y | SLC2A3 | N |
| PNLIP | Y | SLC36A1 | N |
| PPAP2A | N | SLC45A3 | Y |
| PRKCD | Y | SNAI2 | Y |
| PRR15L | Y | SNORD54 | Y |
| PSD | Y | SPSB1 | Y |
| RASD1 | Y | ST6GALNAC1 | N |
| RDH10 | Y | STEAP2 | Y |
| RGS2 | N | SYTL2 | Y |
| RHOB | Y | TIPARP | N |
| RHOU | Y | TMPRSS2 | Y |
| RND3 | Y | TSC22D1 | Y |
| RNF160 | Y | TSKU | Y |
| S100P | Y | TUBA3C | Y |
| SCNN1G | N | TUBA3D | Y |
| SGK | Y | TUBA3E | Y |
| SGK1 | Y | UAP1 | N |
| SIPA1L2 | Y | VASN | Y |
| SLC25A18 | Y | WNT7B | N |
| SLC26A3 | Y | ZBTB16 | Y |
| SLC2A12 | Y | ZMIZ1 | Y |
| SLC31A2 | Y | ZNF385B | N |
| SLC45A3 | Y | ZNF533 | N |

TABLE 4-continued

AR and GR signature genes corresponding to FIG. 9. Top: GR signature genes showing at least modest regulation by AR, or conversely, AR signature genes showing at least modest regulation by GR are annotated. Most (>80%) AR and GR signature genes show some evidence of regulation by the reciprocal receptor. Bottom: GR and AR selective genes used for GSEA analysis

| | | | |
|---|---|---|---|
| SNAI2 | Y | ZNF703 | N |
| SPRYD5 | N | | |
| SPSB1 | Y | | |
| STEAP2 | Y | | |
| STK39 | Y | | |
| SYTL2 | Y | | |
| TBC1D8 | Y | | |
| TMPRSS2 | Y | | |
| TRIM48 | Y | | |
| TSKU | Y | | |
| TUBA3C | Y | | |
| TUBA3D | Y | | |
| TUBA3E | Y | | |
| ZBTB16 | Y | | |
| ZC3H12A | Y | | |
| ZMIZ1 | Y | | |
| ZNF812 | N | | |

| GR selective gene set | AR selective gene set |
|---|---|
| ABHD2 | ABCC4 |
| ACTA2 | C1ORF116 |
| ATAD2 | CROT |
| AZGP1 | DKFZP761P0423 |
| BCL6 | ENDOD1 |
| C1ORF149 | ERN1 |
| C6ORF85 | FAM110B |
| C7ORF63 | FRK |
| C9ORF152 | FZD5 |
| CEBPD | GADD45G |
| CGNL1 | GCNT1 |
| CHKA | GRHL2 |
| CRY2 | HEY1 |
| DBC1 | KIAA0194 |
| DDIT4 | LRIG1 |
| EEF2K | MTMR9 |
| EMP1 | NDRG1 |
| ERRFI1 | NKX3-1 |
| FKBP5 | NPPC |
| FLI22795 | ORM1 |
| FOXO3 | ORM2 |
| GADD45B | PAK1IP1 |
| GHR | PIK3AP1 |
| HERC5 | PMEPA1 |
| HOMER2 | PRAGMIN |
| HSD11B2 | PSCD1 |
| KBTBD11 | RASD1 |
| KIAA0040 | RHOU |
| KLF15 | SHRM |
| KLF9 | SLC2A3 |
| KRT80 | SLC36A1 |
| LIN7B | SLC45A3 |
| LOC100130886 | TIPARP |
| LOC100131392 | TMPRSS2 |
| LOC100134006 | TSC22D1 |
| LOC340970 | UAP1 |
| LOC399939 | WNT7B |
| LOC440040 | ZNF385B |
| LOC728431 | ZNF533 |
| MEAF6 | |
| MT1X | |
| NPC1 | |
| NRP1 | |
| PGC | |
| PGLYRP2 | |
| PHLDA1 | |
| PNLIP | |
| PPAP2A | |
| PRKCD | |
| PRR15L | |
| RGS2 | |
| RHOB | |

TABLE 4-continued

AR and GR signature genes corresponding to FIG. 9. Top: GR signature genes showing at least modest regulation by AR, or conversely, AR signature genes showing at least modest regulation by GR are annotated. Most (>80%) AR and GR signature genes show some evidence of regulation by the reciprocal receptor. Bottom: GR and AR selective genes used for GSEA analysis

| |
|---|
| S100P |
| SCNN1G |
| SGK |
| SGK1 |
| SLC25A18 |
| SPRYD5 |
| SPSB1 |
| STK39 |
| TRIM48 |
| TUBA3C |
| TUBA3D |
| TUBA3E |
| ZBTB16 |
| ZMIZ1 |
| ZNF812 |

TABLE 5

Regulation of GR regulated Genes in VCAP by AR

| VCAP: Dex Regulated Genes (1.5 fold, FDR < .05) Gene | Significant change with DHT? |
|---|---|
| ACSL3 | Yes (FDR < .05) |
| C21ORF34 | Yes (FDR < .05) |
| CAMK2N1 | Yes (FDR < .05) |
| CXCR7 | Yes (FDR < .05) |
| EAF2 | Yes (FDR < .05) |
| ELL2 | Yes (FDR < .05) |
| ERRFI1 | Yes (FDR < .05) |
| FKBP5 | Yes (FDR < .05) |
| HOMER2 | Yes (FDR < .05) |
| HS.570267 | Yes (FDR < .05) |
| MYBPC1 | Yes (FDR < .05) |
| OPRK1 | Yes (FDR < .05) |
| REG4 | Yes (FDR < .05) |
| SEC11C | Yes (FDR < .05) |
| STK39 | Yes (FDR < .05) |
| ZCCHC6 | Yes (FDR < .05) |
| ARHGAP28 | Yes (p < .05) |
| C11ORF92 | Yes (p < .05) |
| CAPN5 | Yes (p < .05) |
| CEBPD | Yes (p < .05) |
| CRELD2 | Yes (p < .05) |
| HSPA5 | Yes (p < .05) |
| KLF9 | Yes (p < .05) |
| PDIA4 | Yes (p < .05) |
| SGK1 | Yes (p < .05) |
| TRA1P2 | Yes (p < .05) |
| ZBTB16 | Yes (p < .05) |
| MAOA | No |
| SCNN1A | No |

TABLE 6

GR staining (IHC) of Tissue Microarray

| Primary (untreated) PCa Distribution | n = 59 # of tumors | Median Intensity (1-3) |
|---|---|---|
| Absent | 34 | 0 |
| Focal | 6 | 1 |
| Low | 7 | 1 |
| Intermediate | 11 | 1 |
| Diffuse | 1 | 2 |

Distribution (% of cells staining): Absent = 0%, Focal < 20%, Low 20-50%, Intermediate 50-90%, Diffuse > 90%

Discussion

Following the recent approvals of the next generation AR pathway inhibitors abiraterone and enzalutamide, the treatment of metastatic prostate cancer has evolved to a two-stage process. Initially patients receive conventional androgen deprivation therapy, typically with a gonadotropin-releasing hormone agonist that lowers testosterone (castration), often in conjunction with an anti-androgen such as bicalutamide. Preclinical and clinical studies have conclusively demonstrated that acquired resistance to conventional androgen deprivation therapy is caused by restoration of AR pathway activation, primarily due to increased AR expression. These discoveries provided the rationale for the development of next generation AR therapies.

The results presented herein demonstrate that acquired resistance to at least one of these new next generation therapies, enzalutamide, can occur via a different mechanism—increased expression of GR. The evidence for GR-driven resistance emerged from two independent preclinical models (LNCaP/AR and VCaP) and was supported by correlative data showing increased GR expression in patients with enzalutamide resistance. Consistent with mechanistic studies showing that GR can function independently of AR, increased GR expression was also associated with ARN-509 resistance, potentially forecasting a general mechanism of resistance to antiandrogens. Whether increased GR expression plays a role in abiraterone resistance remains to be determined. Unlike enzalutamide and ARN-509, abiraterone impairs AR signaling by lowering residual systemic and intratumoral androgen levels and preclinical evidence suggests that abiraterone resistance may be associated with increased AR expression (Mostaghel et al., 2011). The results presented herein suggest that tumors can efficiently overcome the ligand deficiency conferred by traditional androgen-deprivation therapy or abiraterone by simply elevating AR levels, whereas the increased selection pressure conferred by second-generation antiandrogens requires an alternative strategy such as GR bypass or AR mutation (Balbas et al., 2013; Joseph et al., 2013; Korpal et al., 2013).

Comparative AR and GR transcriptome studies supported a model whereby GR bypasses enzalutamide-mediated AR blockade without the need for any restored AR function. This model is further supported by ChIP-seq analyses showing that GR can bind to just over half of all AR binding sites in enzalutamide resistant cells. Importantly, GR occupied a large number of sites that are not bound by AR, raising the possibility of a distinct GR transcriptional program that could contribute to resistance. However, transcriptome analysis found that a large majority of genes robustly regulated by GR were also regulated by AR. For this reason, the results presented herein suggest that the antiandrogen resistance conferred by GR is most likely mediated by one or more of the unevenly restored AR target genes rather than a distinct set of "GR only" target genes. It will be of interest to explore whether just one or a small number of downstream targets are responsible for resistance and also why GR fails to activate transcription at the vast majority of the "GR unique" binding sites. It is postulated that variables such as chromatin context, co-factors and other signaling events may be important.

The GR bypass model of AR pathway blockade presented herein is reminiscent of recent reports that kinase inhibitor blockade in various cancers can be overcome by upregulation of other kinases and/or their ligands (Engelman et al., 2007; Johannessen et al., 2010; Straussman et al., 2012; Wilson et al., 2012). The results presented herein comprise the first example of nuclear receptor bypass as a mechanism of acquired resistance to nuclear receptor blockade. In the case of kinase inhibitors, bypass is just one of many potential resistance mechanisms that also includes direct mutation of the kinase target and lineage switching to histologically distinct phenotypes that no longer require the drug target for survival (Katayama et al., 2012). The same may be true here based on the fact that a subset of drug-resistant LNCaP/AR tumors had minimal GR expression, raising the possibility of other resistance drivers. For example, one of these low GR tumors contained the F876L AR mutation that converts both ARN-509 and enzalutamide to agonists and is associated with clinical resistance (Balbas et al., 2013; Joseph et al., 2013; Korpal et al., 2013). A second low GR tumor expressed high levels of N-Cadherin (Table 2C), which can confer AR independence by morphological conversion to a tumor with mesenchymal features (Tanaka et al., 2010).

Expression of GR in antiandrogen-resistant prostate tumors appears to occur by a mechanism that includes features of adaptive resistance (via AR-mediated negative feedback of GR expression) as well as clonal selection. The results presented herein showed that AR inhibition induced strong GR expression in drug-resistant prostate cancer cells as well as in a subset of drug-naïve cells that are somehow "primed" to respond. The molecular basis for this "primed" state remains to be defined but, based on the reversibility of GR expression in the presence or absence of AR inhibition, is likely to involve an epigenetic mechanism. Knowledge of baseline tumor GR expression in patients, as well as the "primed" state of these tumor cells, could have clinical relevance as a treatment response biomarker. Baseline GR expression may predict a poor clinical outcome and, based on the increase in GR expression in some patients after 8 weeks of treatment, that the "priming" phenomenon observed in the models presented herein may also be relevant in patients.

Whatever the precise mechanism regulating GR expression, one immediate implication is that corticosteroid therapy could be detrimental to prostate cancer patients in certain clinical contexts. Corticosteroids are currently administered routinely with both docetaxel and abiraterone to prevent side effects from each of these therapies. The data presented herein suggest that corticosteroids might promote tumor progression in men whose tumors express GR. Indeed, reanalysis of the phase 3 clinical trial AFFIRM that demonstrated a survival benefit with enzalutamide treatment found that men receiving corticosteroids had a significantly worse survival that those who did not (Scher et al., 2012b) (Scher et al., 2012a). It is worth noting that corticosteroids can also confer clinical benefit in CRPC, an effect attributed to feedback suppression of pituitary ACTH production and resultant decrease in adrenal androgen production (Attard et al., 2009). This duality of potential glucocorticoid effects should prompt a reexamination of the appropriate clinical context for corticosteroid therapy.

The data presented herein also suggest that combined inhibition of both GR and AR could prolong the duration of response with next generation AR antagonists. Clinical studies of the GR antagonist mefipristone in patients with excess glucocorticoid production (Cushing syndrome) demonstrate that GR can be inhibited in humans with an acceptable risk-benefit profile (Fleseriu et al., 2012). Unfortunately both mefipristone and a related GR antagonist ORG34517 activate AR target gene expression, likely by direct AR agonism since mefipristone binds and activates AR (Klokk et al., 2007). The ability of compound 15 to overcome GR driven resistance should stimulate further efforts to optimize GR-specific antagonists that lack "off target" AR effects for use in preventing or overcoming enzalutamide resistance.

REFERENCES

Attard, G., Reid, A. H., A'Hern, R., Parker, C., Oommen, N. B., Folkerd, E., Messiou, C., Molife, L. R., Maier, G., Thompson, E., et al. (2009). Selective inhibition of CYP17 with abiraterone acetate is highly active in the treatment of castration-resistant prostate cancer. J Clin Oncol 27, 3742-3748.

Bailey, T. L., Boden, M., Buske, F. A., Frith, M., Grant, C. E., Clementi, L., Ren, J., Li, W. W., and Noble, W. S. (2009). MEME SUITE: tools for motif discovery and searching. Nucleic Acids Res 37, W202-208.

Balbas, M. D., Evans, M. J., Hosfield, D. J., Wongvipat, J., Arora, V. K., Watson, P. A., Chen, Y., Greene, G. L., Shen, Y., and Sawyers, C. L. (2013). Overcoming mutation-based resistance to antiandrogens with rational drug design. eLife 2, e00499.

Chapman, P. B., Hauschild, A., Robert, C., Haanen, J. B., Ascierto, P., Larkin, J., Dummer, R., Garbe, C., Testori, A., Maio, M., et al. (2011). Improved survival with vemurafenib in melanoma with BRAF V600E mutation. The New England journal of medicine 364, 2507-2516.

Chen, C. D., Welsbie, D. S., Tran, C., Baek, S. H., Chen, R., Vessella, R., Rosenfeld, M. G., and Sawyers, C. L. (2004). Molecular determinants of resistance to antiandrogen therapy. Nat Med 10, 33-39.

Clegg, N. J., Wongvipat, J., Joseph, J. D., Tran, C., Ouk, S., Dilhas, A., Chen, Y., Grillot, K., Bischoff, E. D., Cai, L., et al. (2012). ARN-509: a novel antiandrogen for prostate cancer treatment. Cancer research 72, 1494-1503.

Davies, P., and Rushmere, N. K. (1990). Association of glucocorticoid receptors with prostate nuclear sites for androgen receptors and with androgen response elements. Journal of molecular endocrinology 5, 117-127.

de Bono, J. S., Logothetis, C. J., Molina, A., Fizazi, K., North, S., Chu, L., Chi, K. N., Jones, R. J., Goodman, O. B., Jr., Saad, F., et al. (2011). Abiraterone and increased survival in metastatic prostate cancer. The New England journal of medicine 364, 1995-2005.

Demetri, G. D., von Mehren, M., Blanke, C. D., Van den Abbeele, A. D., Eisenberg, B., Roberts, P. J., Heinrich, M. C., Tuveson, D. A., Singer, S., Janicek, M., et al. (2002). Efficacy and safety of imatinib mesylate in advanced gastrointestinal stromal tumors. The New England journal of medicine 347, 472-480.

Efstathiou, E., Titus, M., Tsavachidou, D., Tzelepi, V., Wen, S., Hoang, A., Molina, A., Chieffo, N., Smith, L. A., Karlou, M., et al. (2012). Effects of abiraterone acetate on androgen signaling in castrate-resistant prostate cancer in bone. J Clin Oncol 30, 637-643.

Engelman, J. A., Zejnullahu, K., Mitsudomi, T., Song, Y., Hyland, C., Park, J. O., Lindeman, N., Gale, C. M., Zhao, X., Christensen, J., et al. (2007). MET amplification leads to gefitinib resistance in lung cancer by activating ERBB3 signaling. Science 316, 1039-1043.

Fleseriu, M., Biller, B. M., Findling, J. W., Molitch, M. E., Schteingart, D. E., and Gross, C. (2012). Mifepristone, a glucocorticoid receptor antagonist, produces clinical and metabolic benefits in patients with Cushing's syndrome. The Journal of clinical endocrinology and metabolism 97, 2039-2049.

Glickman, M. S., and Sawyers, C. L. (2012). Converting cancer therapies into cures: lessons from infectious diseases. Cell 148, 1089-1098.

Johannessen, C. M., Boehm, J. S., Kim, S. Y., Thomas, S. R., Wardwell, L., Johnson, L. A., Emery, C. M., Stransky, N., Cogdill, A. P., Barretina, J., et al. (2010). COT drives resistance to RAF inhibition through MAP kinase pathway reactivation. Nature 468, 968-972.

Joseph, J. D., Lu, N., Qian, J., Sensintaffar, J., Shao, G., Brigham, D., Moon, M., Chow Maneval, E., Chen, I., Darimont, B., et al. (2013). A clinically relevant androgen receptor mutation confers resistance to 2nd generation anti-androgens enzalutamide and ARN-509. Cancer discovery.

Katayama, R., Shaw, A. T., Khan, T. M., Mino-Kenudson, M., Solomon, B. J., Halmos, B., Jessop, N. A., Wain, J. C., Yeo, A. T., Benes, C., et al. (2012). Mechanisms of acquired crizotinib resistance in ALK-rearranged lung Cancers. Sci Transl Med 4, 120ra117.

Klokk, T. I., Kurys, P., Elbi, C., Nagaich, A. K., Hendarwanto, A., Slagsvold, T., Chang, C. Y., Hager, G. L., and Saatcioglu, F. (2007). Ligand-specific dynamics of the androgen receptor at its response element in living cells. Mol Cell Biol 27, 1823-1843.

Korpal, M., Korn, J. M., Gao, X., Rakiec, D. P., Ruddy, D. A., Doshi, S., Yuan, J., Kovats, S. G., Kim, S., Cooke, V. G., et al. (2013). An F876L Mutation in Androgen Receptor Confers Genetic and Phenotypic Resistance to MDV3100 (Enzalutamide). Cancer discovery.

Langmead, B., Trapnell, C., Pop, M., and Salzberg, S. L. (2009). Ultrafast and memory-efficient alignment of short DNA sequences to the human genome. Genome Biol 10, R25.

Maemondo, M., Inoue, A., Kobayashi, K., Sugawara, S., Oizumi, S., Isobe, H., Gemma, A., Harada, M., Yoshizawa, H., Kinoshita, I., et al. (2010). Gefitinib or chemotherapy for non-small-cell lung cancer with mutated EGFR. The New England journal of medicine 362, 2380-2388.

Mangelsdorf, D. J., Thummel, C., Beato, M., Herrlich, P., Schutz, G., Umesono, K., Blumberg, B., Kastner, P., Mark, M., Chambon, P., et al. (1995). The nuclear receptor superfamily: the second decade. Cell 83, 835-839.

Meijsing, S. H., Pufall, M. A., So, A. Y., Bates, D. L., Chen, L., and Yamamoto, K. R. (2009). DNA binding site sequence directs glucocorticoid receptor structure and activity. Science 324, 407-410.

Mostaghel, E. A., Marck, B. T., Plymate, S. R., Vessella, R. L., Balk, S., Matsumoto, A. M., Nelson, P. S., and Montgomery, R. B. (2011). Resistance to CYP17A1 inhibition with abiraterone in castration-resistant prostate cancer: induction of steroidogenesis and androgen receptor splice variants. Clin Cancer Res 17, 5913-5925.

Sawyers, C. L., Hochhaus, A., Feldman, E., Goldman, J. M., Miller, C. B., Ottmann, O. G., Schiffer, C. A., Talpaz, M., Guilhot, F., Deininger, M. W., et al. (2002). Imatinib induces hematologic and cytogenetic responses in patients with chronic myelogenous leukemia in myeloid blast crisis: results of a phase II study. Blood 99, 3530-3539.

Scher, H. I., Fizazi, K., Saad, F., Chi, K., Taplin, M.-E., Sternberg, C. N., Armstrong, A. J., Hirmand, M., Selby, B., and De Bono, J. S. (2012a). ASSOCIATION OF BASELINE CORTICOSTEROID WITH OUTCOMES IN A MULTIVARIATE ANALYSIS OF THE PHASE 3 AFFIRM STUDY OF ENZALUTAMIDE (ENZA), AN ANDROGEN RECEPTOR SIGNALING INHIBITOR (ARSI), ESMO, ed.

Scher, H. I., Fizazi, K., Saad, F., Taplin, M. E., Sternberg, C. N., Miller, K., de Wit, R., Mulders, P., Chi, K. N., Shore, N. D., et al. (2012b). Increased survival with enzalutamide in prostate cancer after chemotherapy. The New England journal of medicine 367, 1187-1197.

Straussman, R., Morikawa, T., Shee, K., Barzily-Rokni, M., Qian, Z. R., Du, J., Davis, A., Mongare, M. M., Gould, J., Frederick, D. T., et al. (2012). Tumour micro-environment elicits innate resistance to RAF inhibitors through HGF secretion. Nature 487, 500-504.

Tanaka, H., Kono, E., Tran, C. P., Miyazaki, H., Yamashiro, J., Shimomura, T., Fazli, L., Wada, R., Huang, J., Vessella, R. L., et al. (2010). Monoclonal antibody targeting of N-cadherin inhibits prostate cancer growth, metastasis and castration resistance. Nat Med 16, 1414-1420.

Tran, C., Ouk, S., Clegg, N. J., Chen, Y., Watson, P. A., Arora, V., Wongvipat, J., Smith-Jones, P. M., Yoo, D., Kwon, A., et al. (2009). Development of a second-generation antiandrogen for treatment of advanced prostate cancer. Science 324, 787-790.

Wang, J. C., Shah, N., Pantoja, C., Meijsing, S. H., Ho, J. D., Scanlan, T. S., and Yamamoto, K. R. (2006). Novel arylpyrazole compounds selectively modulate glucocorticoid receptor regulatory activity. Genes & development 20, 689-699.

Wilson, T. R., Fridlyand, J., Yan, Y., Penuel, E., Burton, L., Chan, E., Peng, J., Lin, E., Wang, Y., Sosman, J., et al. (2012). Widespread potential for growth-factor-driven resistance to anticancer kinase inhibitors. Nature 487, 505-509.

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome Biol 9, 8137.

Example 2: Traditional Androgen Treatments for Prostate Cancer

TABLE 6

| Prescribing information for the antiandrogen flutamide | |
|---|---|
| Indication & Dosage | Oral<br>Palliative treatment of prostatic carcinoma<br>Adult: 250 mg tid preferably at least 3 days before gonadorelin analogue treatment. |
| Administration | May be taken with or without food. |
| Contraindications | Hypersensitivity, severe hepatic impairment, pregnancy and lactation. |
| Hypersensitivity, severe hepatic impairment, pregnancy and lactation. | Perform liver function tests before starting treatment and at regular intervals. Treatment is not recommended in patients whose ALT values exceed twice the upper limit of normal. Regular assessment of prostate specific antigen level may help to monitor disease progression. Advise patient against discontinuing drug on their own. Exercise caution in patients with cardiac disease. |
| Adverse Drug Reactions | Hot flushes, loss of libido, impotence, gynaecomastia, nausea, vomiting, diarrhoea, increased appetite, sleep disturbances, skin reactions, anaemias, headache, dizziness, malaise, anxiety, hypertension, gastric and chest pain, oedema, blurred vision, hepatitis, jaundice, rash, thirst, pruritus, SLE-like syndrome, drowsiness, confusion, depression, nervousness. |
| Drug Interactions | Increased prothrombin time in patients on long-term warfarin treatment.<br>Potentially Fatal: Increased prothrombin time in patients on long-term warfarin treatment. |
| Pregnancy Category (US FDA) | Category D: There is positive evidence of human foetal risk, but the benefits from use in pregnant women may be acceptable despite the |

TABLE 6-continued

| Prescribing information for the antiandrogen flutamide | |
|---|---|
| | risk (e.g., if the drug is needed in a life-threatening situation or for a serious disease for which safer drugs cannot be used or are ineffective). |
| Storage | Oral: Store at 25° C. |
| Mechanism of Action | Flutamide is a nonsteroidal 'pure' antiandrogen which acts directly on the target tissues either by blocking androgen uptake or by inhibiting cytoplasmic and nuclear binding of androgen.<br>Distribution: Protein-binding: 90%<br>Metabolism: Rapid and extensive; converted to hydroxyflutamide.<br>Excretion: Urine, faeces (small amounts); 2 hrs (elimination half-life, metabolite). |
| MIMS Class | Hormonal Chemotherapy |
| ATC Classification | L02BB01 - flutamide; Belongs to the class of anti-androgens. |

From http://www.mims.com/USA/drug/info/flutamide/?type=full&mtype=generic

Example 3: Characterization of ABR173 and ABR167

Due to the need for a potent GR antagonist with either no AR activity or with potent dual AR/GR antagonism, "rational" design of derivatives with the desired pharmacology was performed based on molecular modeling of AR/GR ligands.

Figure 15:
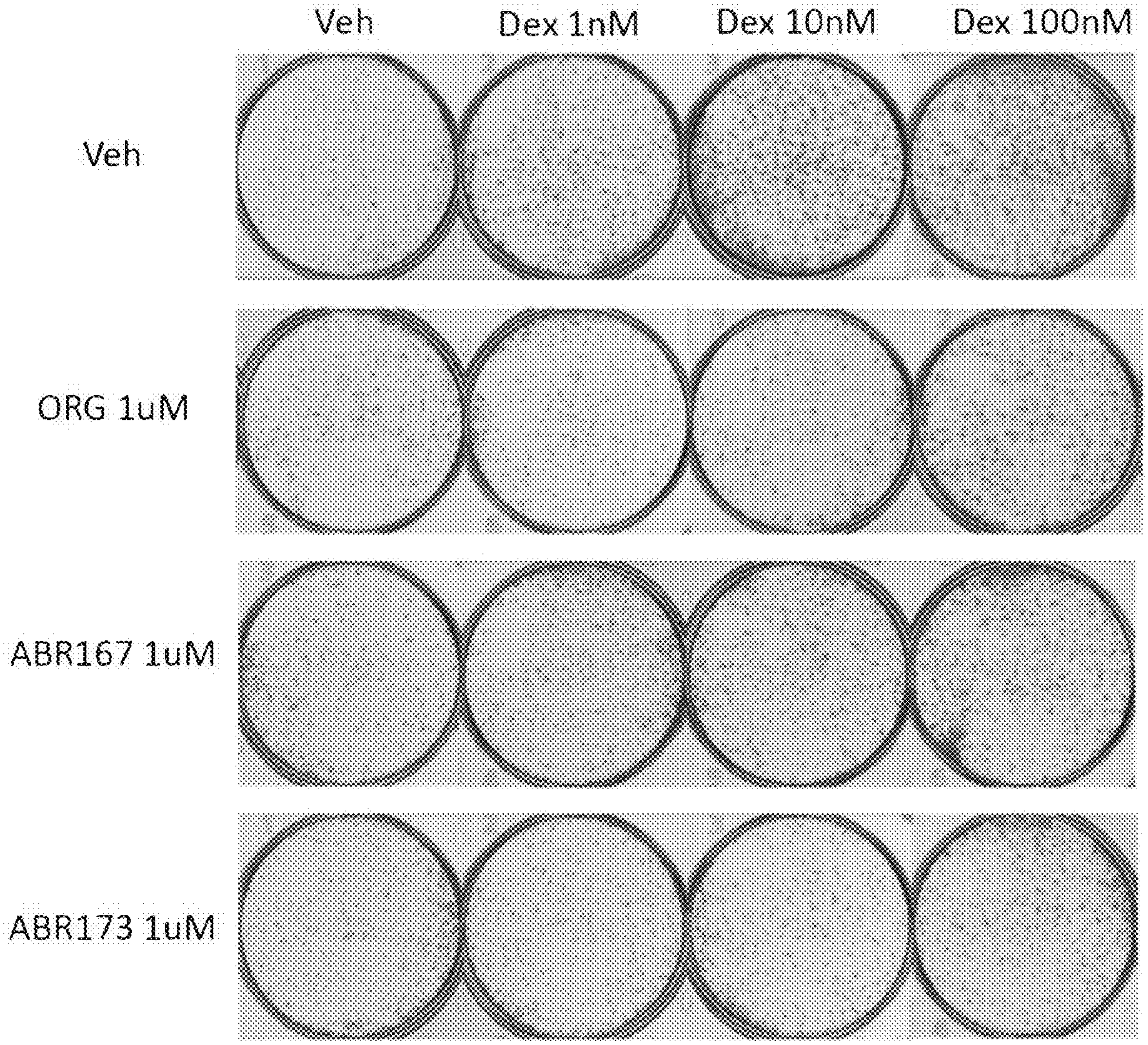
FIG. 15 shows assays measuring AB173, ABR167, and ORG34517 with different concentrations of dexamethasone (Dex).

As described above, DU145 cells are AR-negative and hence resistant to enzalutamide. Under these conditions, GR-dependent proliferation was examined. The two compounds of interest, ABR173 and ABR167, performed comparably to ORG 34517 (ORG) in assays with different concentrations of dexamethasone (Dex) (FIG. 15).

Figure 16:
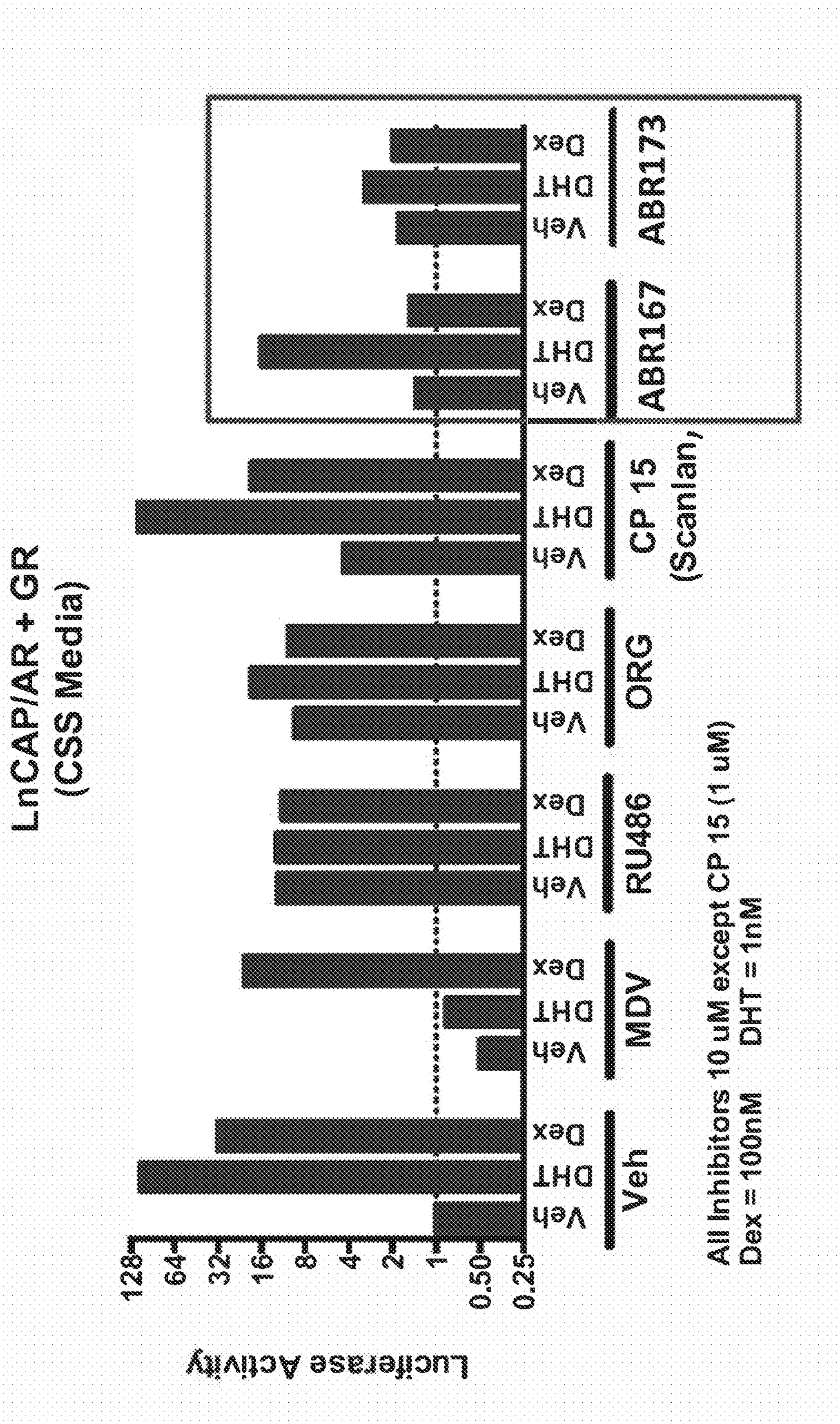
FIG. 16 shows effect of ABR167 and ABR173 at reversing the effect of Dex.

The novel compounds were also tested in a luciferase reporter assay in CSS media, utilizing retroviral Probasin-AR luciferase reporter. As shown in vehicle treated cells, neither ABR173 nor ABR167 had much agonist ability in this assay, though ABR167 did have a bit more than ABR173. Both compounds were effective at reversing the effect of Dex, a GR agonist, but not so successful at reversing the effect of DHR, an AR agonist (FIG. 16).

Figure 17:
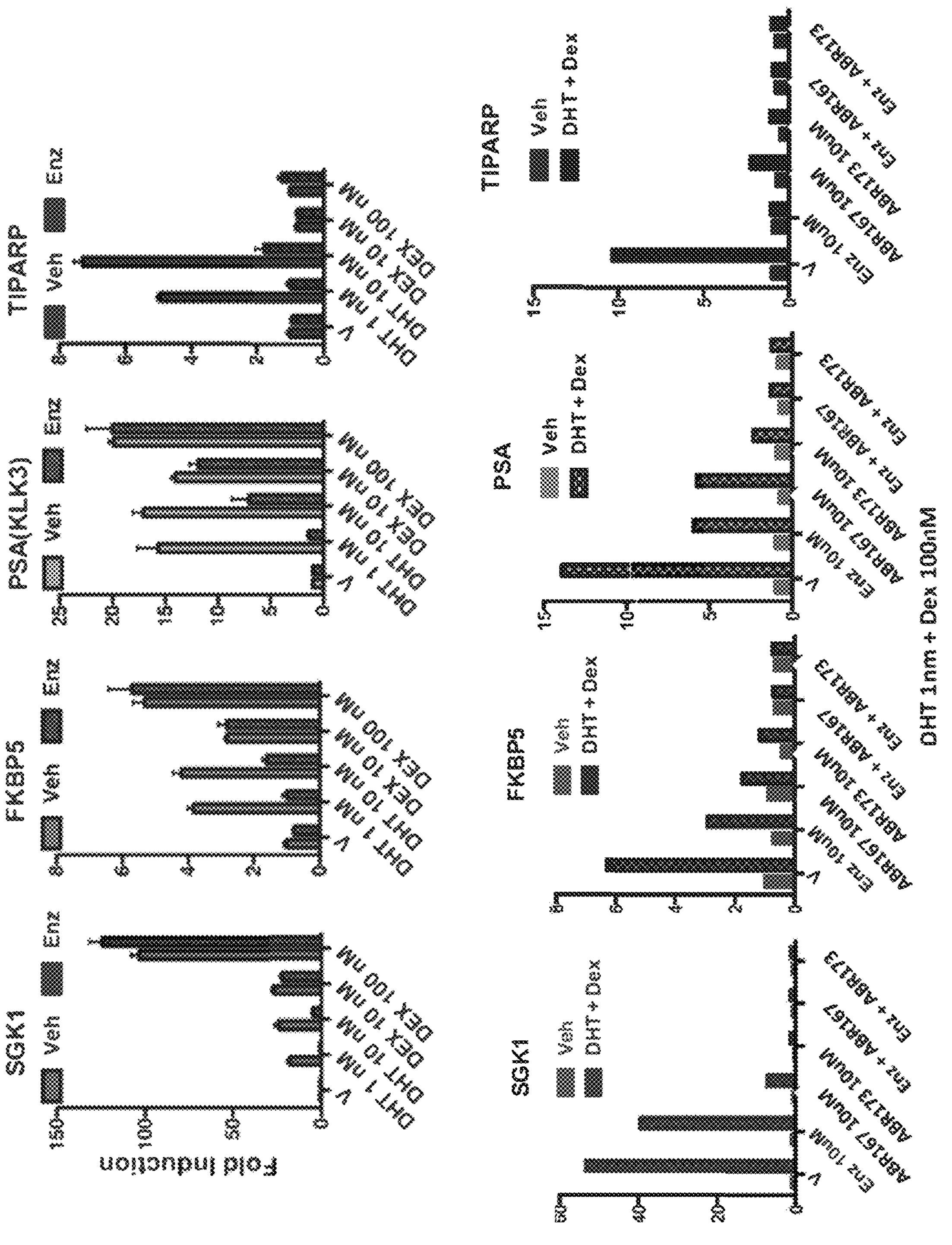
FIG. 17 shows agonist ability of ABR173 and ABR167.

In order to characterize the novel compounds in respect to their activation of endogenous genes in cells, LREX' cells in CSS were used. The compounds were tested in cells treated with vehicle or DHT+Dex (AR agonist and GR agonist). Additionally, some cells were tested with the novel compounds given individually, and others with a novel compound plus enzalutamide. The results demonstrate that ABR173 and ABR167 do not show agonist ability and both demonstrate dual GR/AR antagonist activity (FIG. 17).

Figure 18:
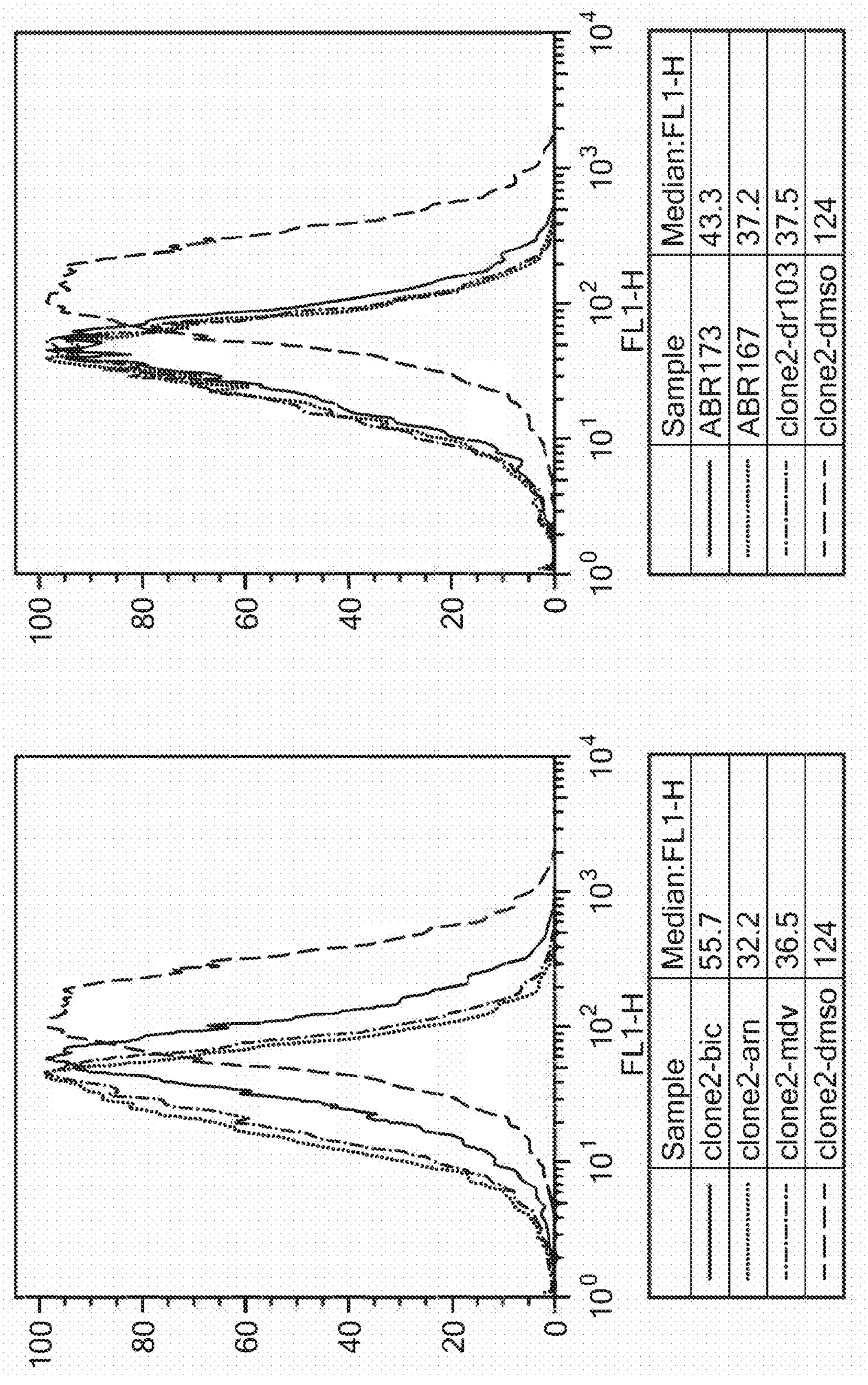
FIG. 18 shows effectiveness of ABR173 and ABR167 as compared to Enz/ARN-509.
Figure 19:
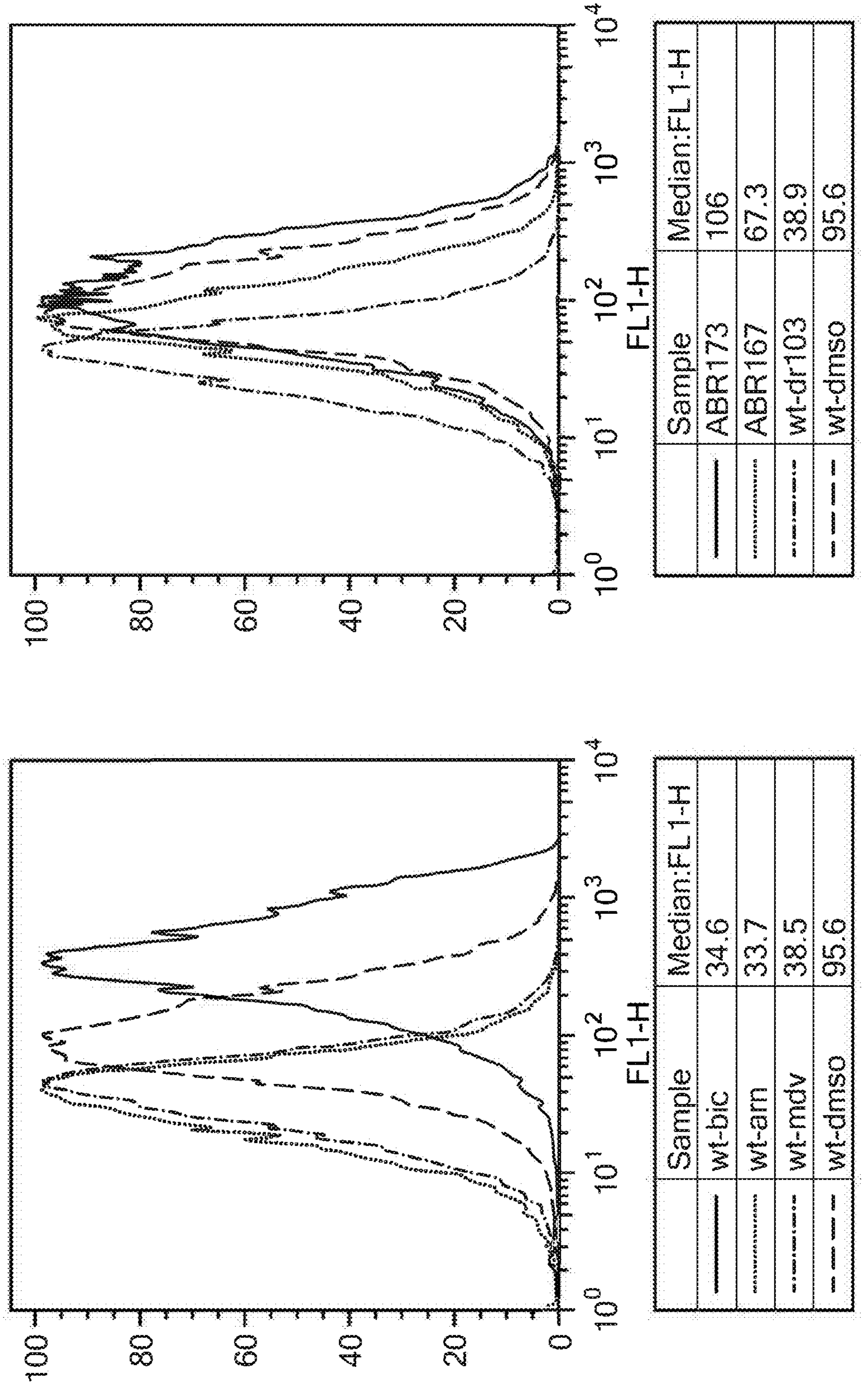
FIG. 19 shows that ABR173 and ABR167 were not as effectively antagonistic as Enz/ARN-509 in cells engineered to overexpress AR.
Figure 20:
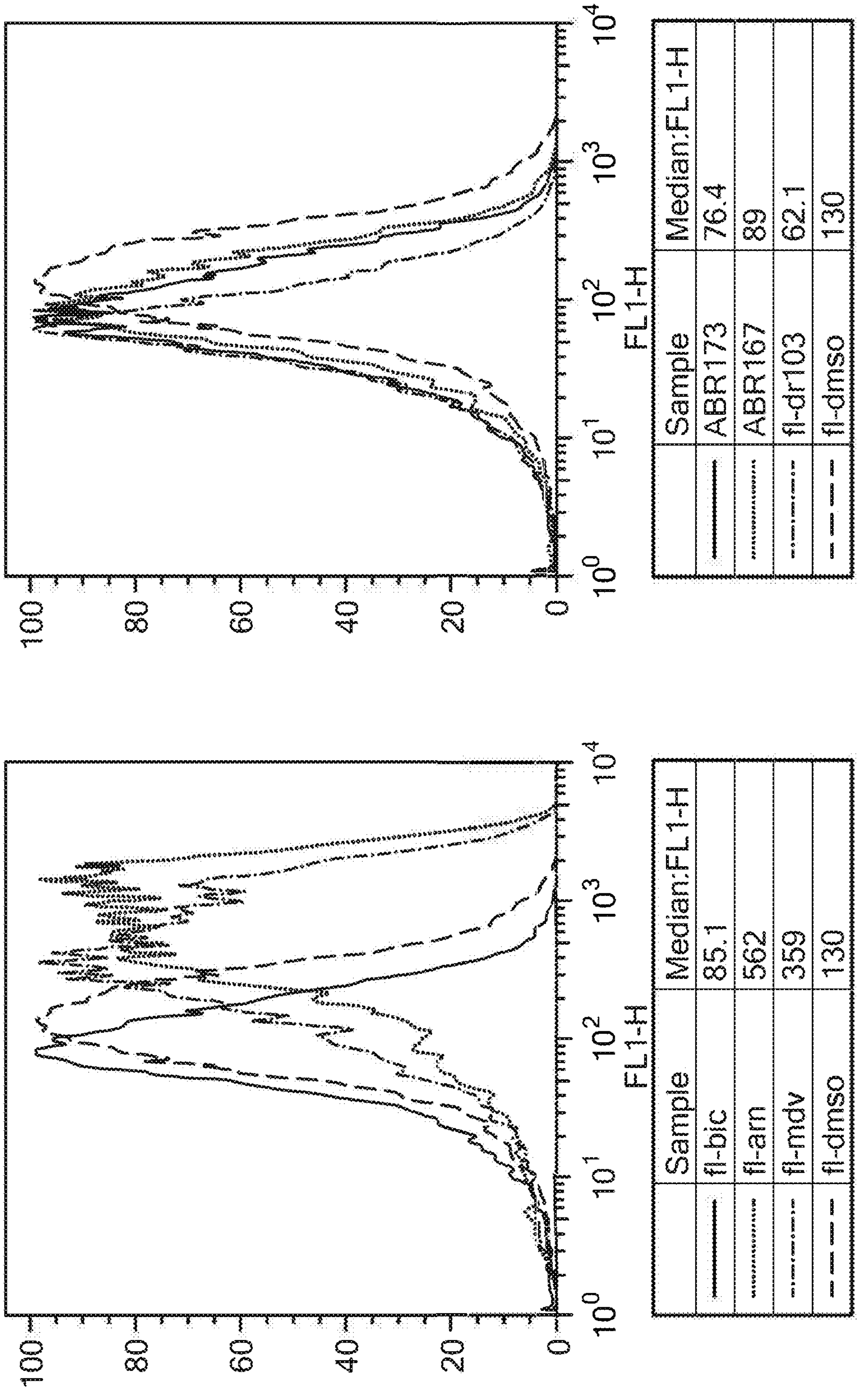
FIG. 20 shows that in LNCAP cells that overexpress the AR mutant AR F876L, the novel compounds ABR173 and ABR167 were more effective antagonists than Enz/ARN-509.

As described previously, LNCaP cells were used for an AR responsive GFP reporter assay in Fetal Bovine Serum (FBS). The novels compounds ABR173 and ABR167 were similarly effective to Enz/ARN-509 in this assay (FIG. 18). In cells engineered to overexpress AR, the novel compounds ABR173 and ABR167 were not as effectively antagonistic as Enz/ARN-509 (FIG. 19). However, in LNCAP cells that overexpress the AR mutant AR F876L, the novel compounds ABR173 and ABR167 were more effective antagonists than Enz/ARN-509 (FIG. 20).

Figure 21:
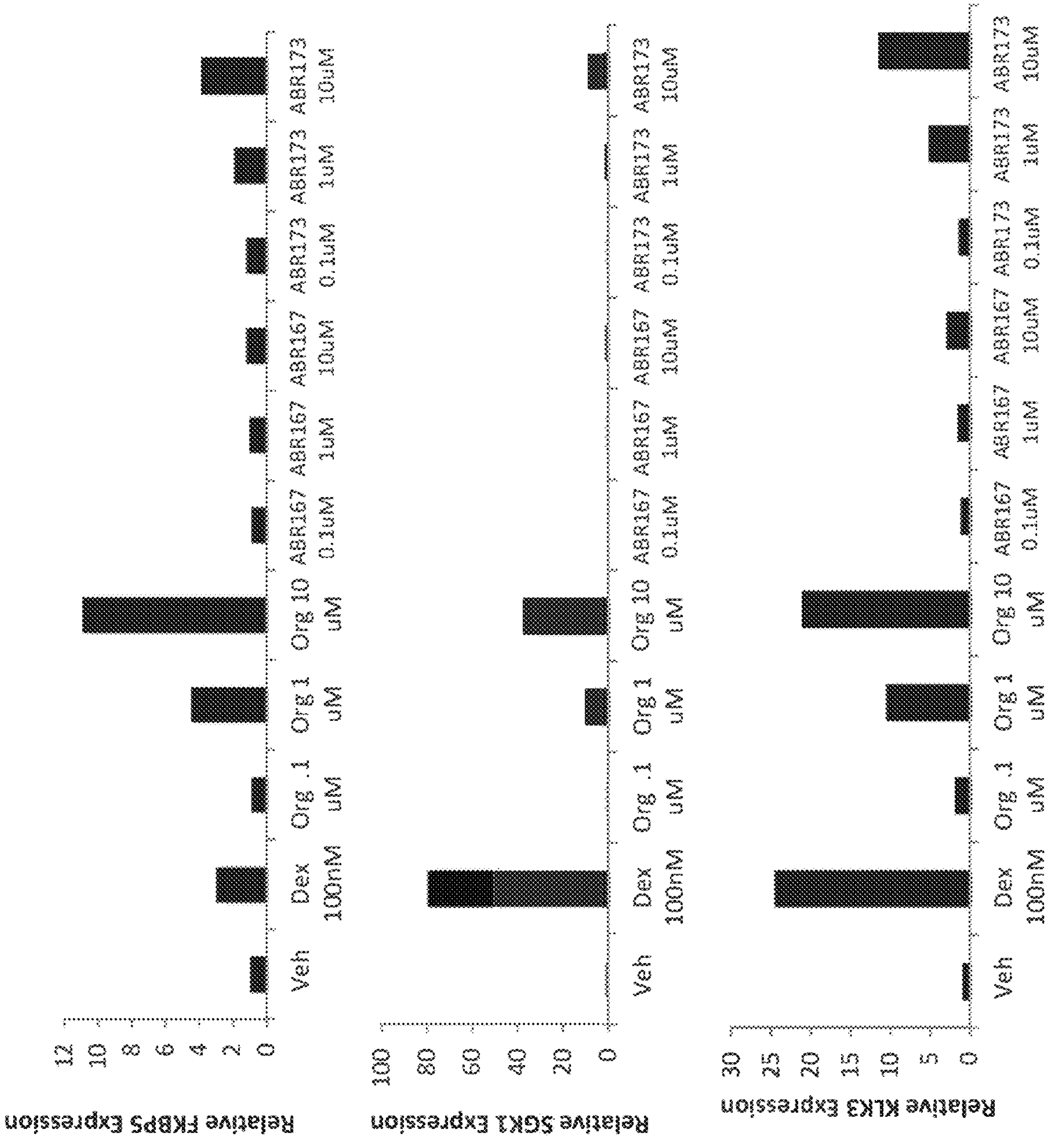
FIG. 21 shows that all 3 genes examined were induced by Dex and both ABR1 73 and ABR167 demonstrated mild agonist activity.

Both novel compounds were tested in LREX' cell line cultures in FBS with 1 μM Enz to examine their effects on endogenous target genes. All 3 genes examined were induced by Dex and both ABR173 and ABR167 demonstrated mild agonist activity (FIG. 21).

Figure 22:
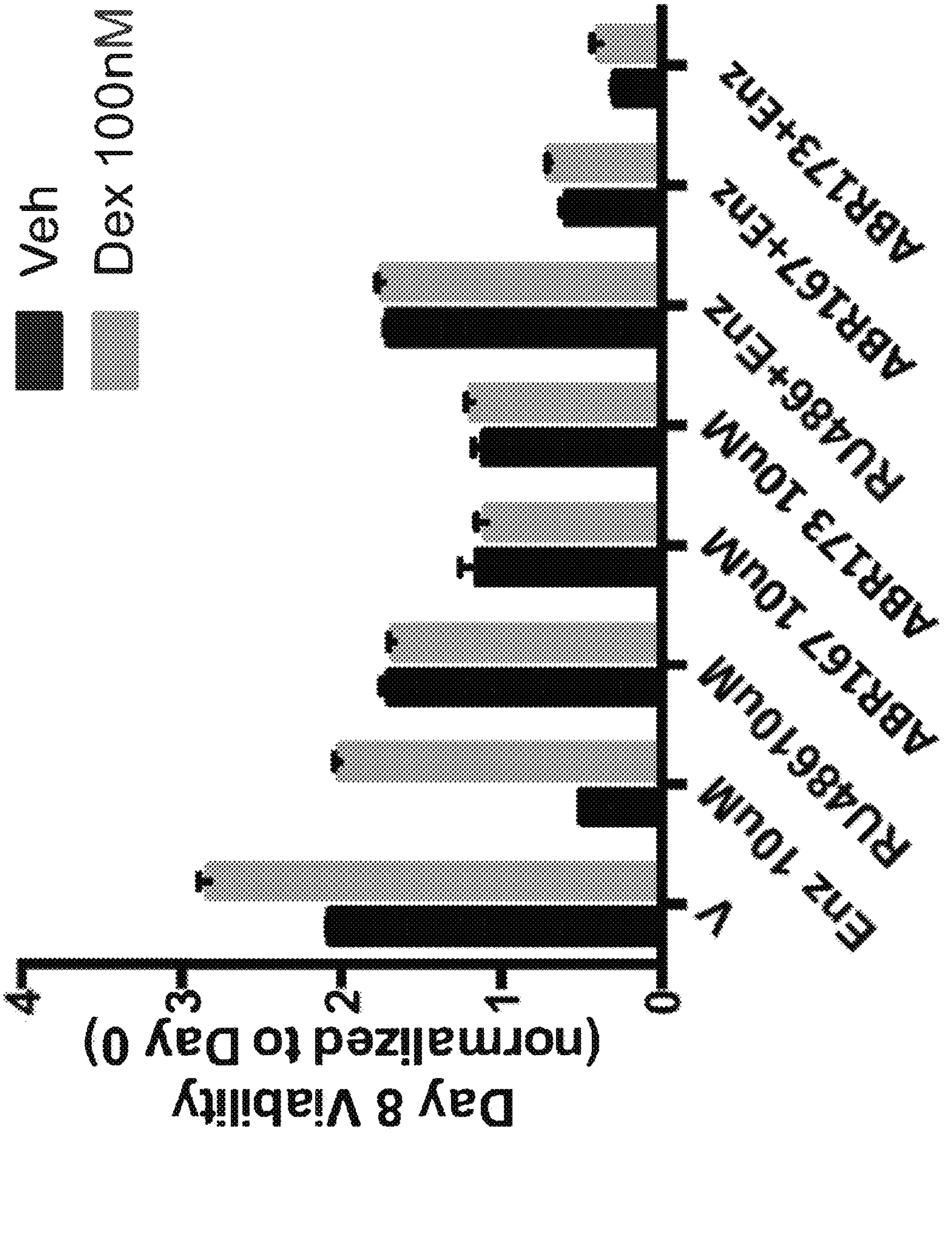
FIG. 22 shows that both ABR173 and ABR167 blocked the Dex induced resistance to Enz without compromising Enz function.
Figure 23:
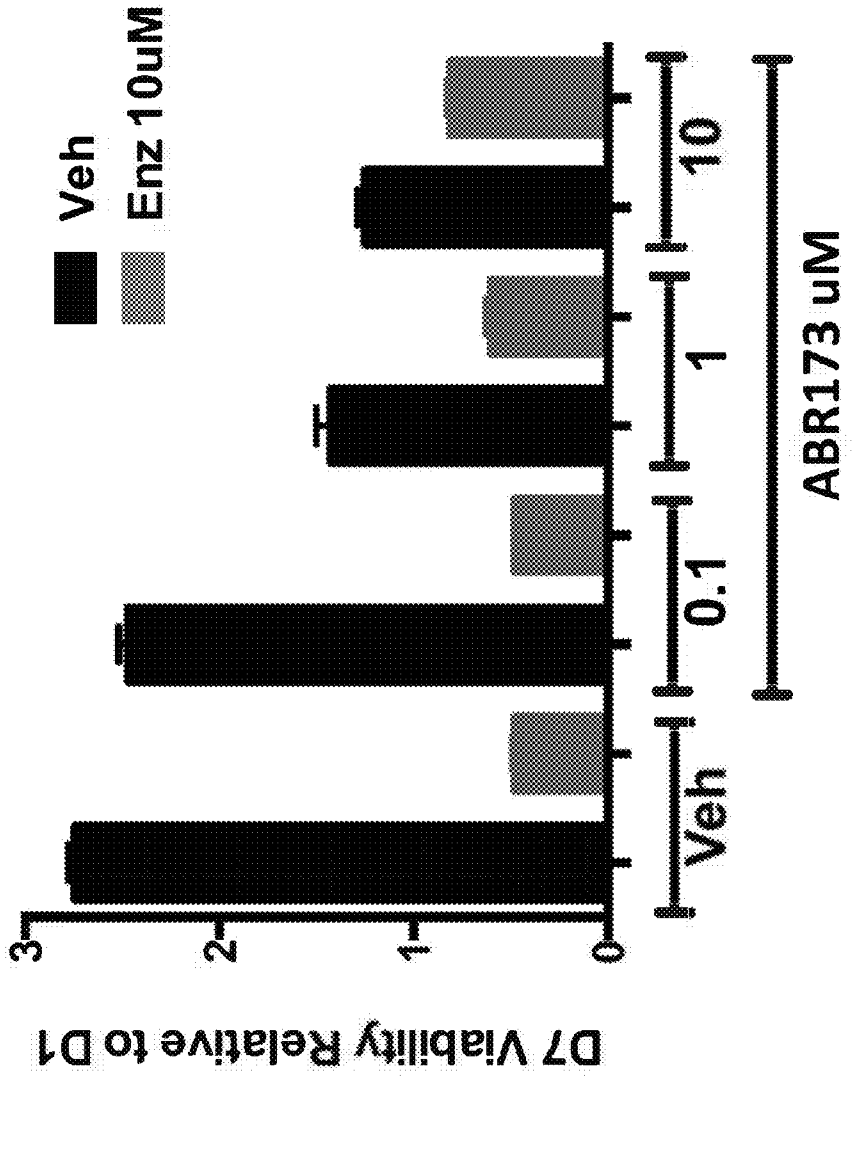
FIG. 23 shows that higher doses of ABR173 appear to slightly impair Enz efficacy.

An assay in VCaP cells (high levels of GR, low levels of AR) was performed to determine if the novel compounds could overcome the effect of Dex (GR agonist) without impairing the effect of Enz (AR antagonist). Both ABR173 and ABR167 blocked the Dex-induced resistance to Enz without compromising Enz function (FIG. 22). Additionally, the effect of ABR167+Enz is quite promising. The experiment was repeated with ABR173 because there might have been some non-specific effects due to a precipitate in an older batch of the compound. In this experiment, higher doses ABR173 appeared to slightly impair Enz efficacy (FIG. 23).

Figure 24:
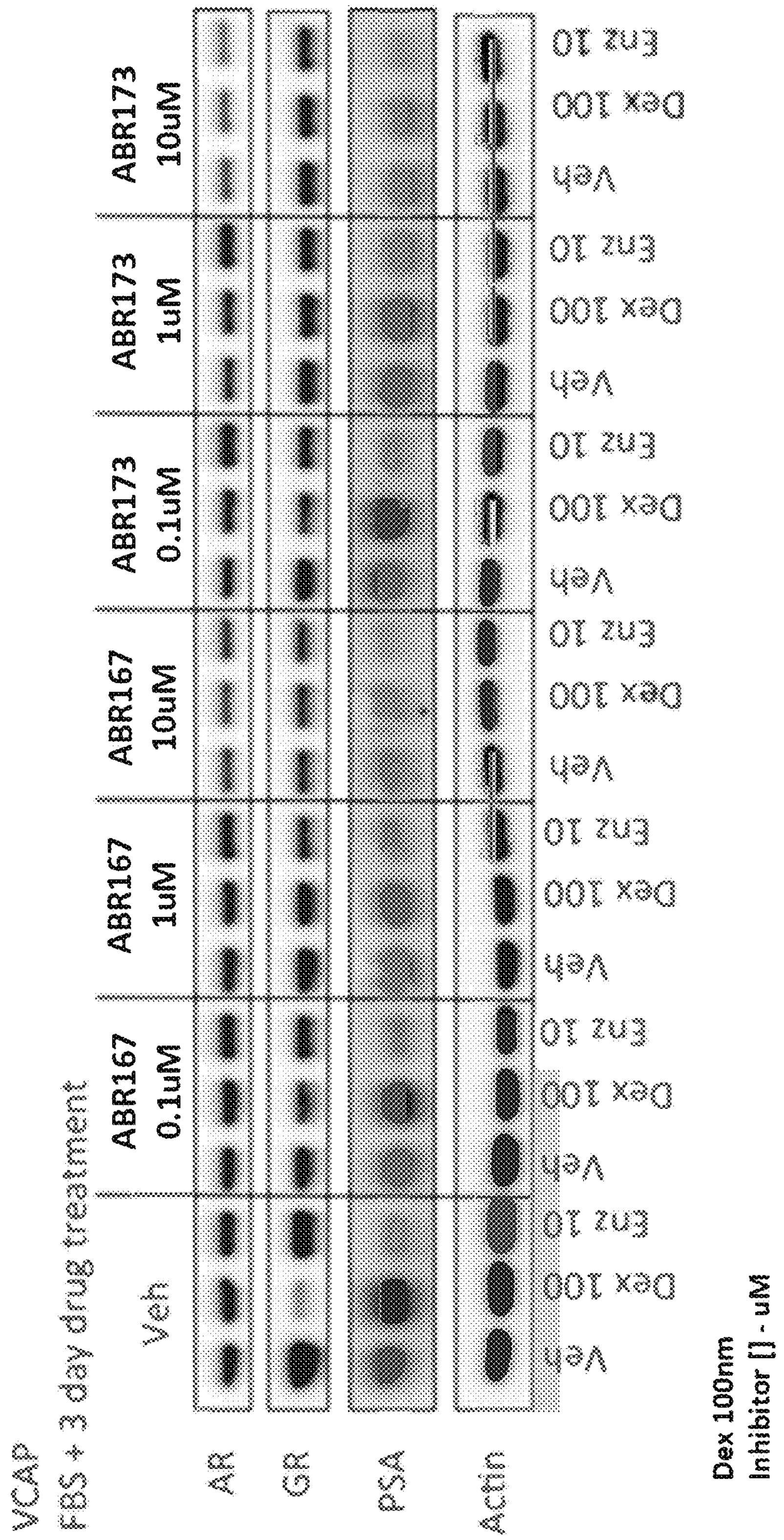
FIG. 24 shows that both ABR173 and ABR1 67 appeared to cause some GR protein degradation.
Figure 25:
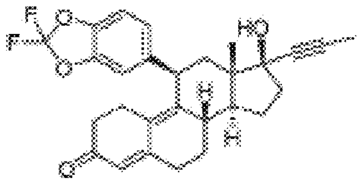
FIG. 25 shows certain compounds.
Figure 25:
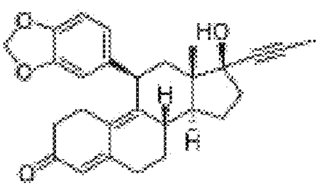
Figure 25:
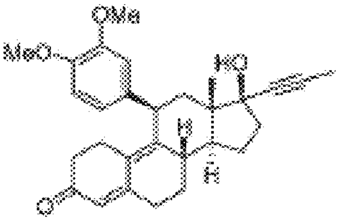
Figure 25:
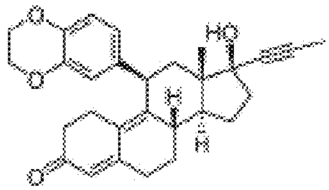
Figure 25:
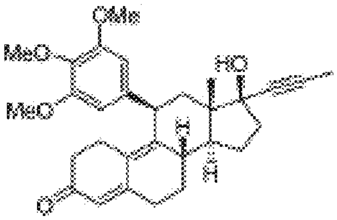
Figure 25:
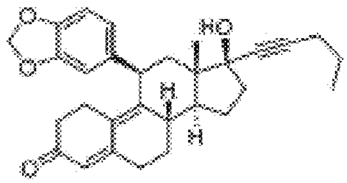
Figure 25:
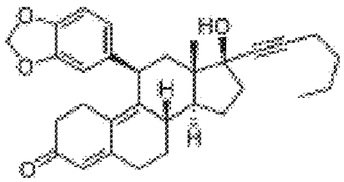
Figure 25:
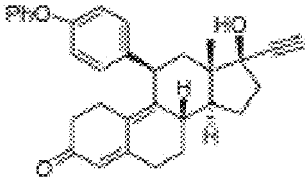
Figure 25:
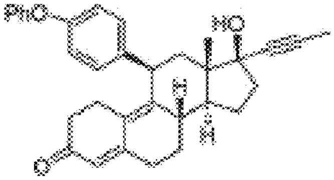
Figure 26:
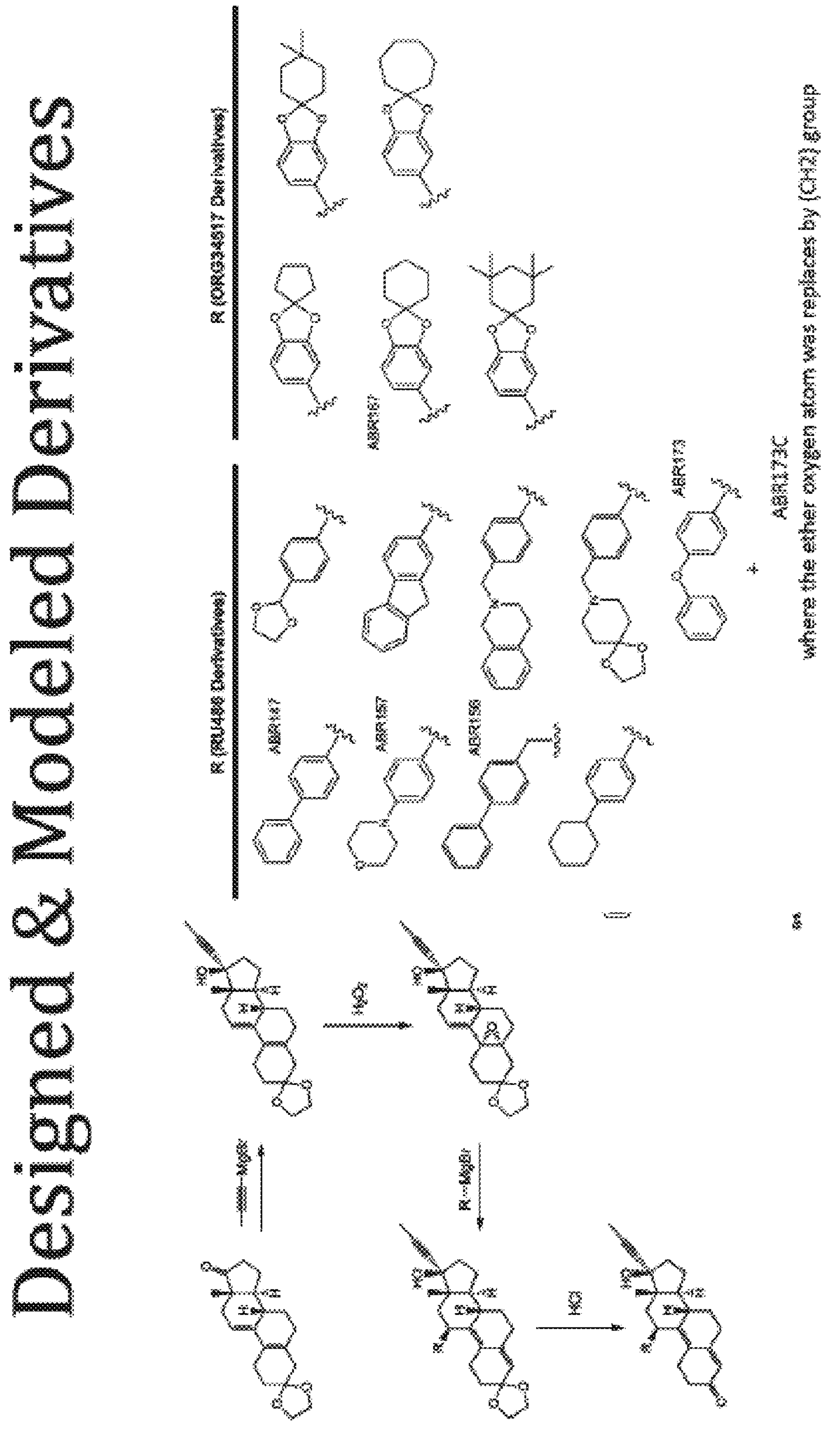
FIG. 26 shows designed and modeled derivatives.
Figure 27:
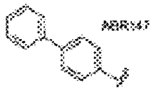
FIG. 27 shows a summary of 10-ns MD simulations.
Figure 27:
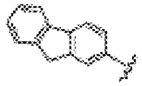
Figure 27:
Figure 27:
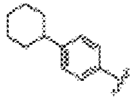
Figure 27:
Figure 27:
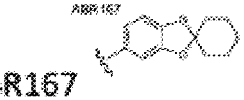
Figure 27:
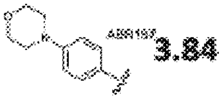
Figure 27:
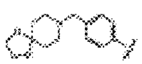
Figure 27:
Figure 27:
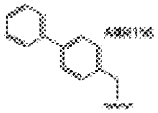
Figure 27:
Figure 27:
Figure 27:
Figure 27:

Finally, Western blots were performed to assess the effect of the novel compounds on AR and GR protein levels. Both ABR173 and ABR167 appeared to cause some GR protein degradation (FIG. 24).

Example 4: Three Dimensional Modeling Analyses

This Example describes the use of three-dimensional X-ray modeling data in the rational design of GR and AR inhibitors described herein (e.g., compounds of formula I). As described in Appendices C and D, modeling analyses were performed to understand which parts of known GR/AR inhibitors were in contact with helices 11 and 12. Without wishing to be bound by any particular theory, Applicant has observed that the conformation of these helices is generally indicative of whether a compound is acting as an inhibitor, wherein the helices are "compressed" when bound to an agonist, and "disordered" or spread apart when bound to an antagonist. By observing and/or predicting the molecular interactions that would be useful to achieve antagonism, compounds were designed that are antagonists but not agonists. For example, if additional moieties are placed in the correct position, it can result in steric interactions that drive the helices from an agonist conformation into an antagonist conformation. As described herein, chemical syntheses were then be used to validate the predictions.

Applicant observed that RU486 and $ORN_{34517}$ bind GR and AR in the same fashion, and the signature-defining structural moiety of these compounds points toward helix 11 and helix 12. By transposing RU486's GR binding into AR, Applicant observed that it binds analogously, but does not have the requisite structure to push against helices 11 and 12 to behave as antagonist. Applicant then designed compounds described herein to possess properly-positioned moieties for achieving the desired antagonist activity. Examples of such compounds and moieties are detailed in Appendices C and D, as well as described herein.

Example 5: Methods of Identifying Subjects and Monitoring Effects of Therapy

Methods of identifying subjects and/or monitoring the effect of therapy in a subject can include obtaining a sample from a subject and performing an analysis on the sample. Methods can also involve taking a plurality of samples over a designated period of time; in some such embodiments, samples are taken are regular intervals during or within the period of time.

Many techniques can be used both for identifying subjects and for monitoring the effect of therapy. One such method is to take bone marrow biopsy samples and then use a GR IHC assay optimized for use in bone marrow samples to quantify the percentage of GR-positive tumor cells. Another method is to obtain patient urine samples and test them for prostate cells that are shed during urination. High-throughput proteomics can be used to look at levels of GR or a GR-responsive entity such as SGK1 in serum or urine. Another technique, transcriptome sequencing, can be used to evaluate mRNA levels or GR or a GR-responsive entity such as SGK1.

Activation of GR or a GR-responsive entity such as SGK1 can be identified by activation state-specific antibodies that bind to a specific isoform of GR or a GR-responsive entity such as SGK1. One method of measuring activation is via activation state-specific antibodies that are conjugated to a label, preferably a fluorescent label, and more preferably a FRET label.

```
Sequences
Human AR Protein Sequence (GenBank: AAA51729.1)
                                                            SEQ ID NO: 1
MEVQLGLGRVYPRPPSKTYRGAFQNLFQSVREVIQNPGPRHPEAASAAPPGASLLLLQQQQQQQQQQQQQ

QQQQQQQQETSPRQQQQQQGEDGSPQAHRRGPTGYLVLDEEQQPSQPQSALECHPERGCVPEPGAAVAAS

KGLPQQLPAPPDEDDSAAPSTLSLLGPTFPGLSSCSADLKDILSEASTMQLLQQQQQEAVSEGSSSGRAR

EASGAPTSSKDNYLGGTSTISDNAKELCKAVSVSMGLGVEALEHLSPGEQLRGDCMYAPLLGVPPAVRPT

PCAPLAECKGSLLDDSAGKSTEDTAEYSPFKGGYTKGLEGESLGCSGSAAAGSSGTLELPSTLSLYKSGA

LDEAAAYQSRDYYNFPLALAGPPPPPPPPHPHARIKLENPLDYGSAWAAAAAQCRYGDLASLHGAGAAGP

GSGSPSAAASSSWHTLFTAEEGQLYGPCGGGGGGGGGGGGGGGGGGGGGGGGEAGAVAPYGYTRPPQGLA

GQESDFTAPDVWYPGGMVSRVPYPSPTCVKSEMGPWMDSYSGPYGDMRLETARDHVLPIDYYFPPQKTCL

ICGDEASGCHYGALTCGSCKVFFKRAAEGKQKYLCASRNDCTIDKFRRKNCPSCRLRKCYEAGMTLGARK

LKKLGNLKLQEEGEASSTTSPTEETTQKLTVSHIEGYECQPIFLNVLEAIEPGVVCAGHDNNQPDSFAAL

LSSLNELGERQLVHVVKWAKALPGFRNLHVDDQMAVIQYSWMGLMVFAMGWRSFTNVNSRMLYFAPDLVF

NEYRMHKSRMYSQCVRMRHLSQEFGWLQITPQEFLCMKALLLFSIIPVDGLKNQKFFDELRMNYIKELDR

IIACKRKNPTSCSRRFYQLTKLLDSVQPIARELHQFTFDLLIKSHMVSVDFPEMMAEIISVQVPKILSGK

VKPIYFHTQ
```

-continued

Human AR mRNA Sequence (GenBank: M20132.1)

SEQ ID NO: 2

TAATAACTCAGTTCTTATTTGCACCTACTTCAGTGGACACTGAATTTGGAAGGTGGAGGATTTTGTTTTT

TTCTTTTAAGATCTGGGCATCTTTTGAATCTACCCTTCAAGTATTAAGAGACAGACTGTGAGCCTAGCAG

GGCAGATCTTGTCCACCGTGTGTCTTCTTCTGCACGAGACTTTGAGGCTGTCAGAGCGCTTTTTGCGTGG

TTGCTCCCGCAAGTTTCCTTCTCTGGAGCTTCCCGCAGGTGGGCAGCTAGCTGCAGCGACTACCGCATCA

TCACAGCCTGTTGAACTCTTCTGAGCAAGAGAAGGGGAGGCGGGGTAAGGGAAGTAGGTGGAAGATTCAG

CCAAGCTCAAGGATGGAAGTGCAGTTAGGGCTGGGAAGGGTCTACCCTCGGCCGCCGTCCAAGACCTACC

GAGGAGCTTTCCAGAATCTGTTCCAGAGCGTGCGCGAAGTGATCCAGAACCCGGGCCCCAGGCACCCAGA

GGCCGCGAGCGCAGCACCTCCCGGCGCCAGTTTGCTGCTGCTGCAGCAGCAGCAGCAGCAGCAGCAGCAG

CAGCAGCAGCAGCAGCAGCAGCAGCAGCAGCAAGAGACTAGCCCCAGGCAGCAGCAGCAGCAGCAGG

GTGAGGATGGTTCTCCCCAAGCCCATCGTAGAGGCCCCACAGGCTACCTGGTCCTGGATGAGGAACAGCA

ACCTTCACAGCCGCAGTCGGCCCTGGAGTGCCACCCCGAGAGAGGTTGCGTCCCAGAGCCTGGAGCCGCC

GTGGCCGCCAGCAAGGGGCTGCCGCAGCAGCTGCCAGCACCTCCGGACGAGGATGACTCAGCTGCCCCAT

CCACGTTGTCCCTGCTGGGCCCCACTTTCCCCGGCTTAAGCAGCTGCTCCGCTGACCTTAAAGACATCCT

GAGCGAGGCCAGCACCATGCAACTCCTTCAGCAACAGCAGCAGGAAGCAGTATCCGAAGGCAGCAGCAGC

GGGAGAGCGAGGGAGGCCTCGGGGGCTCCCACTTCCTCCAAGGACAATTACTTAGGGGGCACTTCGACCA

TTTCTGACAACGCCAAGGAGTTGTGTAAGGCAGTGTCGGTGTCCATGGGCCTGGGTGTGGAGGCGTTGGA

GCATCTGAGTCCAGGGGAACAGCTTCGGGGGGATTGCATGTACGCCCCACTTTTGGGAGTTCCACCCGCT

GTGCGTCCCACTCCTTGTGCCCGATTGGCCGAATGCAAAGGTTCTCTGCTAGACGACAGCGCAGGCAAGA

GCACTGAAGATACTGCTGAGTATTCCCCTTTCAAGGGAGGTTACACCAAAGGGCTAGAAGGCGAGAGCCT

AGGCTGCTCTGGCAGCGCTGCAGCAGGGAGCTCCGGGACACTTGAACTGCCGTCTACCCTGTCTCTCTAC

AAGTCCGGAGCACTGGACGAGGCAGCTGCGTACCAGAGTCGCGACTACTACAACTTTCCACTGGCTCTGG

CCGGACCGCCGCCCCCTCCGCCGCCTCCCCATCCCCACGCTCGCATCAAGCTGGAGAACCCGCTGGACTA

CGGCAGCGCCTGGGCGGCTGCGGCGGCGCAGTGCCGCTATGGGGACCTGGCGAGCCTGCATGGCGCGGGT

GCAGCGGGACCCGGTTCTGGGTCACCCTCAGCCGCCGCTTCCTCATCCTGGCACACTCTCTTCACAGCCG

AAGAAGGCCAGTTGTATGGACCGTGTGGTGGTGGTGGGGGTGGTGGCGGCGGCGGCGGCGGCGGCGGCGG

CGGCGGCGGCGGCGGCGGCGGCGGCGGCGAGGCGGGAGCTGTAGCCCCCTACGGCTACACTCGGCCCCCT

CAGGGGCTGGCGGGCCAGGAAAGCGACTTCACCGCACCTGATGTGTGGTACCCTGGCGGCATGGTGAGCA

GAGTGCCCTATCCCAGTCCCACTTGTGTCAAAAGCGAAATGGGCCCCTGGATGGATAGCTACTCCGGACC

TTACGGGGACATGCGTTTGGAGACTGCCAGGGACCATGTTTTGCCCATTGACTATTACTTTCCACCCCAG

AAGACCTGCCTGATCTGTGGAGATGAAGCTTCTGGGTGTCACTATGGAGCTCTCACATGTGGAAGCTGCA

AGGTCTTCTTCAAAAGAGCCGCTGAAGGGAAACAGAAGTACCTGTGCGCCAGCAGAAATGATTGCACTAT

TGATAAATTCCGAAGGAAAAATTGTCCATCTTGTCGTCTTCGGAAATGTTATGAAGCAGGGATGACTCTG

GGAGCCCGGAAGCTGAAGAAACTTGGTAATCTGAAACTACAGGAGGAAGGAGAGGCTTCCAGCACCACCA

GCCCCACTGAGGAGACAACCCAGAAGCTGACAGTGTCACACATTGAAGGCTATGAATGTCAGCCCATCTT

TCTGAATGTCCTGGAAGCCATTGAGCCAGGTGTAGTGTGTGCTGGACACGACAACAACCAGCCCGACTCC

TTTGCAGCCTTGCTCTCTAGCCTCAATGAACTGGGAGAGAGACAGCTTGTACACGTGGTCAAGTGGGCCA

AGGCCTTGCCTGGCTTCCGCAACTTACACGTGGACGACCAGATGGCTGTCATTCAGTACTCCTGGATGGG

GCTCATGGTGTTTGCCATGGGCTGGCGATCCTTCACCAATGTCAACTCCAGGATGCTCTACTTCGCCCCT

GATCTGGTTTTCAATGAGTACCGCATGCACAAGTCCCGGATGTACAGCCAGTGTGTCCGAATGAGGCACC

TCTCTCAAGAGTTTGGATGGCTCCAAATCACCCCCCAGGAATTCCTGTGCATGAAAGCACTGCTACTCTT

-continued

CAGCATTATTCCAGTGGATGGGCTGAAAAATCAAAAATTCTTTGATGAACTTCGAATGAACTACATCAAG

GAACTCGATCGTATCATTGCATGCAAAAGAAAAAATCCCACATCCTGCTCAAGACGCTTCTACCAGCTCA

CCAAGCTCCTGGACTCCGTGCAGCCTATTGCGAGAGAGCTGCATCAGTTCACTTTTGACCTGCTAATCAA

GTCACACATGGTGAGCGTGGACTTTCCGGAAATGATGGCAGAGATCATCTCTGTGCAAGTGCCCAAGATC

CTTTCTGGGAAAGTCAAGCCCATCTATTTCCACACCCAGTGAAGCATTGGAAACCCTATTTCCCCACCCC

AGCTCATGCCCCCTTTCAGATGTCTTCTGCCTGTTATAACTCTGCACTACTCCTCTGCAGTGCCTTGGGG

AATTTCCTCTATTGATGTACAGTCTGTCATGAACATGTTCCTGAATTCTATTTGCTGGGCTTTTTTTTTC

TCTTTCTCTCCTTTCTTTTTCTTCTTCCCTCCCTATCTAACCCTCCCATGGCACCTTCAGACTTTGCTTC

CCATTGTGGCTCCTATCTGTGTTTTGAATGGTGTTGTATGCCTTTAAATCTGTGATGATCCTCATATGGC

CCAGTGTCAAGTTGTGCTTGTTTACAGCACTACTCTGTGCCAGCCACACAAACGTTTACTTATCTTATGC

CACGGGAAGTTTAGAGAGCTAAGATTATCTGGGGAAATCAAAACAAAAAACAAGCAAACAAAAAAAAAA

Human GR Isoform alpha Protein Sequence (NCBI Reference Sequence: NP_001018086.1)

SEQ ID NO: 3

MDSKESLTPGREENPSSVLAQERGDVMDFYKTLRGGATVKVSASSPSLAVASQSDSKQRRLLVDFPKGSV

SNAQQPDLSKAVSLSMGLYMGETETKVMGNDLGFPQQGQISLSSGETDLKLLEESIANLNRSTSVPENPK

SSASTAVSAAPTEKEFPKTHSDVSSEQQHLKGQTGTNGGNVKLYTTDQSTFDILQDLEFSSGSPGKETNE

SPWRSDLLIDENCLLSPLAGEDDSFLLEGNSNEDCKPLILPDTKPKIKDNGDLVLSSPSNVTLPQVKTEK

EDFIELCTPGVIKQEKLGTVYCQASFPGANIIGNKMSAISVHGVSTSGGQMYHYDMNTASLSQQQDQKPI

FNVIPPIPVGSENWNRCQGSGDDNLTSLGTLNFPGRTVFSNGYSSPSMRPDVSSPPSSSSTATTGPPPKL

CLVCSDEASGCHYGVLTCGSCKVFFKRAVEGQHNYLCAGRNDCIIDKIRRKNCPACRYRKCLQAGMNLEA

RKTKKKIKGIQQATTGVSQETSENPGNKTIVPATLPQLTPTLVSLLEVIEPEVLYAGYDSSVPDSTWRIM

TTLNMLGGRQVIAAVKWAKAIPGFRNLHLDDQMTLLQYSWMFLMAFALGWRSYRQSSANLLCFAPDLIIN

EQPETLPCMYDQCKHMLYVSSELHRLQVSYEEYLCMKTLLLLSSVPKDGLKSQELFDEIRMTYIKELGKA

IVKREGNSSQNWQRFYQLTKLLDSMHEVVENLLNYCFQTFLDKTMSIEFPEMLAEIITNQIPKYSNGNIK

KLLFHQK

Human GR Isoform alpha-B Protein Sequence (NCBI Reference Sequence: NP_001191187.1)

SEQ ID NO: 4

MDFYKTLRGGATVKVSASSPSLAVASQSDSKQRRLLVDFPKGSVSNAQQPDLSKAVSLSMGLYMGETETK

VMGNDLGFPQQGQISLSSGETDLKLLEESIANLNRSTSVPENPKSSASTAVSAAPTEKEFPKTHSDVSSE

QQHLKGQTGTNGGNVKLYTTDQSTFDILQDLEFSSGSPGKETNESPWRSDLLIDENCLLSPLAGEDDSFL

LEGNSNEDCKPLILPDTKPKIKDNGDLVLSSPSNVTLPQVKTEKEDFIELCTPGVIKQEKLGTVYCQASF

PGANIIGNKMSAISVHGVSTSGGQMYHYDMNTASLSQQQDQKPIFNVIPPIPVGSENWNRCQGSGDDNLT

SLGTLNFPGRTVFSNGYSSPSMRPDVSSPPSSSSTATTGPPPKLCLVCSDEASGCHYGVLTCGSCKVFFK

RAVEGQHNYLCAGRNDCIIDKIRRKNCPACRYRKCLQAGMNLEARKTKKKIKGIQQATTGVSQETSENPG

NKTIVPATLPQLTPTLVSLLEVIEPFVLYAGYDSSVPDSTWRIMTTLNMLGGRQVIAAVKWAKAIPGFRN

LHLDDQMTLLQYSWMFLMAFALGWRSYRQSSANLLCFAPDLIINEQRMTLPCMYDQCKHMLYVSSELHRL

QVSYEEYLCMKLLLLLSSVPKDGLKSQELFDEIRMTYIKELGKAIVKREGNSSQNWQRFYQLTKLLDSMH

EVVENLLNYCFQTFLDKTMSIEFPEMLAEIITNQIPKYSNGNIKKLLFHQK

Human GR Isoform alpha-C1 Protein Sequence (NCBI Reference Sequence: NP_001191188.1)

SEQ ID NO: 5

MGLYMGETETKVMGNDLGFPQQGQISLSSGETDLKLLEESIANLNRSTSVPENPKSSASTAVSAAPTEKE

FPKTHSDVSSEQQHLKGQTGTNGGNVKLYTTDQSTFDILQDLEFSSGSPGKETNESPWRSDLLIDENCLL

-continued

SPLAGEDDSFLLEGNSNEDCKPLILPDTKPKIKDNGDLVLSSPSNVTLPQVKTEKEDFIELCTPGVIKQE
KLGTVYCQASFPGANIIGNKMSAISVHGVSTSGGQMYHYDMNTASLSQQQDQKPIFNVIPPIPVGSENWN
RCQGSGDDNLTSLGTLNFPGRTVFSNGYSSPSMRPDVSSPPSSSSTATTGPPPKLCLVCSDEASGCHYGV
LTCGSCKVFFKRAVEGQHNYLCAGRNDCIIDKIRRKNCPACRYRKCLQAGMNLEARKTKKKIKGIQQATT
GVSQETSENPGNKTIVPATLPQLTPTLVSLLEVIEPEVLYAGYDSSVPDSTWRIMTTLNMLGGRQVIAAV
KWAKAIPGFRNLHLDDQMTLLQYSWMFLMAFALGWRSYRQSSANLLCFAPDLIINEQRMTLPCMYDQCKH
MLYVSSELHRLQVSYEEYLCMKTLLLLSSVPKDGLKSQELFDEIRMTYIKELGKAIVKREGNSSQNWQRF
YQLTKLLDSMHEVVENLLNYCFQTFLDKTMSIEFPEMLAEIITNQIPKYSNGNIKKLLFHQK

Human GR Isoform alpha-C2 Protein Sequence (NCBI Reference Sequence: NP_001191187.1)

SEQ ID NO: 6

MGETETKVMGNDLGFPQQGQISLSSGETDLKLLEESIANLNRSTSVPENPKSSASTAVSAAPTEKEFPKT
HSDVSSEQQHLKGQIGTNGGNVKLYTTDQSTFDILQDLEFSSGSPGKETNESPWRSDLLIDENCLLSPLA
GEDDSFLLEGNSNEDCKPLILPDTKPKIKDNGDLVLSSPSNVTLPQVKTEKEDFIELCTPGVIKQEKLGT
VYCQASFPGANIIGNKMSAISVHGVSTSGGQMYHYDMNTASLSQQQDQKPIFNVIPPIPVGSENWNRCQG
SGDDNLTSLGTLNFPGRTVFSNGYSSPSMRPDVSSPPSSSSTATTGPPPKLCLVCSDEASGCHYGVLTCG
SCKVFFKRAVEGQHNYLCAGRNDCIIDKIRRKNCPACRYRKCLQAGMNLEARKTKKKIKGIQQATTGVSQ
ETSENPGNKTIVPATLPQLTPTLVSLLEVIEPEVLYAGYDSSVPDSTWRIMTTLNMLGGRQVIAAVKWAK
AIPGFRNLHLDDQMTLLQYSWMFLMAFALGWRSYRQSSANLLCFAPDLIINEQRMTLPCMYDQCKHMLYV
SSELHRLQVSYEEYLCMKTLLLLSSVPKDGLKSQELFDEIRMTYIKELGKAIVKREGNSSQNWQRFYQLT
KLLDSMHEVVENLLNYCFQTFLDKTMSIEFPEMLAEIITNQIPKYSNGNIKKLLFHQK

Human GR Isoform alpha-C3 Protein Sequence (NCBI Reference Sequence: NP_001191190.1)

SEQ ID NO: 7

MGNDLGFPQQGQISLSSGETDLKLLEESIANLNRSTSVPENPKSSASTAVSAAPTEKEFPKTHSDVSSEQ
QHLKGQTGTNGGNVKLYTTDQSTFDILQDLEFSSGSPGKETNESPWRSDLLIDENCLLSPLAGEDDSFLL
EGNSNEDCKPLILPDTKPKIKDNGDLVLSSPSNVTLPQVKTEKEDFIELCTPGVIKQEKLGTVYCQASFP
GANIIGNKMSAISVHGVSTSGGQMYHYDMNTASLSQQQDQKPIFNVIPPIPVGSENWNRCQGSGDDNLTS
LGTLNFPGRTVFSNGYSSPSMRPDVSSPPSSSSTATTGPPPKLCLVCSDEASGCHYGVLTCGSCKVFFKR
AVEGQHNYLCAGRNDCIIDKIRRKNCPACRYRKCLQAGMNLEARKTKKKIKGIQQATTGVSQETSENPGN
KTIVPATLPQLTPTLVSLLEVIEPEVLYAGYDSSVPDSTWRIMTTLNMLGGRQVIAAVKWAKAIPGFRNL
HLDDQMILLQYSWMFLMAFALGWRSYRQSSANLLCFAPDLIINEQRMTLPCMYDQCKHMLYVSSELHRLQ
VSYEEYLCMKTLLLLSSVPKDGLKSQELFDEIRMTYIKELGKAIVKREGNSSQNWQRFYQLTKLLDSMHE
VVENLLNYCFQTFLDKTMSIEFPEMLAEIITNQIPKYSNGNIKKLLFHQK

Human GR Isoform alpha-D1 Protein Sequence (NCBI Reference Sequence: NP_001191191.1)

SEQ ID NO: 8

MSAISVHGVSTSGGQMYHYDMNTASLSQQQDQKPIFNVIPPIPVGSENWNRCQGSGDDNLTSLGTLNFPG
RTVFSNGYSSPSMRPDVSSPPSSSSTATTGPPPKLCLVCSDEASGCHYGVLTCGSCKVFFKRAVEGQHNY
LCAGRNDCIIDKIRRKNCPACRYRKCLQAGMNLEARKTKKKIKGIQQATTGVSQETSENPGNKTIVPATL
PQLIPTLVSLLEVIEPEVLYAGYDSSVPDSTWRIMTTLNMLGGRQVIAAVKWAKAIPGFRNLHLDDQMTL
LQYSWMFLMAFALGWRSYRQSSANLLCFAPDLIINEQRMTLPCMYDQCKHMLYVSSELHRLQVSYEEYLC
MKTLLLLSSVPKDGLKSQELFDEIRMTYIKELGKAIVKREGNSSQNWQRFYQLTKLLDSMHEVVENLLNY
CFQTFLDKTMSIEFPEMLAEIITNQIPKYSNGNIKKLLFHQK

-continued

Human GR Isoform alpha-D2 Protein Sequence (NCBI Reference Sequence: NP_001191192.1)

SEQ ID NO: 9

MYHYDMNTASLSQQQDQKPIFNVIPPIPVGSENWNRCQGSGDDNLTSLGTLNFPGRTVFSNGYSSPSMRP

DVSSPPSSSSTATTGPPPKLCLVCSDEASGCHYGVLTCGSCKVFFKRAVEGQHNYLCAGRNDCIIDKIRR

KNCPACRYRKCLQAGMNLEARKTKKKIKGIQQATTGVSQETSENPGNKTIVPATLPQLTPTLVSLLEVIE

PEVLYAGYDSSVPDSTWRIMTTLNMLGGRQVIAAVKWAKAIPGFRNLHLDDQMTLLQYSWMFLMAFALGW

RSYRQSSANLLCFAPDLIINEQRMTLPCMYDQCKHMLYVSSELHRLQVSYEEYLCMKTLLLLSSVPKDGL

KSQELFDEIRMTYIKELGKAIVKREGNSSQNWQRFYQLTKILDSMHEVVENLLNYCFQTFLDKTMSIEFP

EMLAEIITNQIPKYSNGNIKKLLFHQK

Human GR Isoform alpha-D3 Protein Sequence (NCBI Reference Sequence: NP_001191193.1)

SEQ ID NO: 10

MNTASLSQQQDQKPIFNVIPPIPVGSENWNRCQGSGDDNLTSLGTLNFPGRTVFSNGYSSPSMRPDVSSP

PSSSSTATTGPPPKLCLVCSDEASGCHYGVLTCSSCKVFFKRAVEGQHNYLCAGRNDCIIDKIRRKNCPA

CRYRKCLQAGMNLEARKTKKKIKGIQQATTGVSQETSENPGNKTIVPATLPQLTPTLVSLLEVIEPEVLY

AGYDSSVPDSTWRIMTTLNMLGGRQVIAAVKWAKAIPGFRNLHLDDQMTLLQYSWMFLMAFALGWRSYRQ

SSANLLCFAPDLIINEQRMTLPCMYDQCKHMLYVSSELHRLQVSYEEYLCMKTLLLLSSVPKDGLKSQEL

FDEIRMTYIKELGKAIVKREGNSSQNWQRFYQLTKLLDSMHEVVENLLNYCFQTFLDKTMSIEFPEMLAE

IITNQIPKYSNGNIKKLLFHQK

Human GR Isoform GR-P Protein Sequence (NCBI Reference Sequence: NP_001191193.1)

SEQ ID NO: 11

MDSKESLTPGREENPSSVLAQERGDVMDFYKTLRGGATVKVSASSPSLAVASQSDSKQRRLLVDFPKGSV

SNAQQPDLSKAVSLSMGLYMGETETKVMGNDLGFPQQGQISLSSGETDLKLLEESIANLNRSTSVPENPK

SSASTAVSAAPTEKEFPKTHSDVSSEQQHLKGQTGTNGGNVKLYTTDQSTFDILQDLEFSSGSPGKETNE

SPWRSDLLIDENCLLSPLAGEDDSFLLEGNSNEDCKPLILPDTKPKIKDNGDLVLSSPSNVTLPQVKTEK

EDFIELCTPGVIKQEKLGTVYCQASFPGANIIGNKMSAISVHGVSTSGGQMYHYDMNTASLSQQQDQKPI

ENVIPPIPVGSENWNRCQGSGDDNLTSLGTLNFPGRTVFSNGYSSPSMRPDVSSPPSSSSTATTGPPPKL

CLVCSDEASGCHYGVLTCGSCKVFFKRAVEGQHNYLCAGRNDCIIDKIRRKNCPACRYRKCLQAGMNLEA

RKTKKKIKGIQQATTGVSQETSENPGNKTIVPATLPQLTPTLVSLLEVIEPEVLYPGYDSSVPDSTWRIM

TTLNMLGGRQVIAAVKWAKAIPGFRNLHLDDQMTLLQYSWMFLMAFALGWRSYRQSSANLLCFAPDLIIN

EQRMTLPCMYDQCKHMLYVSSELHRLQVSYEEYLCMKTLLLLSSGW

Human GR Isoform gamma Protein Sequence (NCBI Reference Sequence: NP_001018086.1)

SEQ ID NO: 12

MDSKESLTPGREENPSSVLAQERGDVMDFYKTLRGGATVKVSASSPSLAVASQSDSKQRRLLVDFPKGSV

SNAQQPDLSKAVSLSMGLYMGETETKVMGNDLGFPQQGQISLSSGETDLKLLEESIANLNRSTSVPENPK

SSASTAVSAAPTEKEFPKTHSDVSSEQQHLKGQTGTNGGNVKLYTTDQSTFDILQDLEFSSGSPGKETNE

SPWRSDLLIDENCLLSPLAGEDDSFLLEGNSNEDCKPLILPDTKPKIKDNGDLVLSSPSNVTLPQVKTEK

EDFIELCTPGVIKQEKLGTVYCQASFPGANIIGNKMSAISVHGVSTSGGQMYHYDMNTASLSQQQDQKPI

FNVIPPIPVGSENWNRCQGSGDDNLTSLGTLNFPGRTVFSNGYSSPSMRPDVSSPPSSSSTATTGPPPKL

CLVCSDEASGCHYGVLTCGSCKVFFKRAVEGRQHNYLCAGRNDCIIDKIRRKNCPACRYRKCLQAGMNLE

ARKTKKKIKGIQQATTGVSQETSENPGNKTIVPATLPQLTPTLYSLLEVIEPEVLYAGYDSSVPDSTWRI

MTTLNMLGGRQVIAAVKWAKAIPGFRNLHLDDQMTLLQYSWMFLMAFALGWRSYRQSSANLLCFAPDLII

NEQRMTLPCMYDQCKHMLYVSSELHRLQVSYEEYLCMKTLLLLSSVPKDGLKSQELFDEIRMTYIKELGK

-continued

AIVKREGNSSQNWQRFYQLTKLLDSMHEVVENLLNYCFQTFLDKTMSIEFPEMLAEIITNQIPKYSNGNI

KKLLFHQK

Human GR Isoform beta Protein Sequence (NCBI Reference Sequence: NP_001018661.1)

SEQ ID NO: 13

MDSKESLTPGREENPSSVLAQERGDVMDFYKTLRGGATVKVSASSPSLAVASQSDSKQRRLLVDFPKGSV

SNAQQFDLSKAVSLSMGLYMGETETKVMGNDLGFPQQGQISLSSGETDLKLLEESIANLNRSTSVPENPK

SSASTAVSAAPTEKEFPKTHSDVSSEQQHLKGQTGTNGGNVKLYTTDQSTFDILQDLEFSSGSPGKETNE

SPWRSDLLIDENCLLSPLAGEDDSFLLEGNSNEDCKPLILPDTKPKIKDNGDLVLSSPSNVTLPQVKTEK

EDFIELCTPGVIKQEKLGTVYCQASFPGANIIGNKMSAISVHGVSTSGGQMYHYDMNTASLSQQQDQKPI

FNVIPPIPVGSENWNRCQGSGDDNLTSLGTLNFPGRTVFSNGYSSPSMRPDVSSPPSSSSTATTGPPPKL

CLVCSDEASGCHYGVLTCGSCKVFFKRAVEGQHNYLCAGRNDCIIDKIRRKNCPACRYRKCLQAGMNLEA

RKTKKKIKGIQQATTGVSQETSENPGNKTIVPATLPQLTPTLVSLLEVIEPEVLYAGYDSSVPDSTWRIM

TTLNMLGGRQVIAAVKWAKAIPGFRNLHLDDQMTLLQYSWMFLMAFALGWRSYRQSSANLLCFAPDLIIN

EQRMTLPCMYDQCKHMLYVSSELHRLQVSYEEYLCMKTLLLLSSVPKDGLKSQELFDEIRMTYIKELGKA

IVKREGNSSQNWQRFYQLTKLLDSMHENVMWLKPESTSHTLI

Human GR Transcript Variant 1 mRNA Sequence (NCBI Reference Sequence: NM_001204259.1)

SEQ ID NO: 14

GGCGCCGCCTCCACCCGCTCCCCGCTCGGTCCCGCTCGCTCGCCCAGGCCGGGCTGCCCTTTCGCGTGTC

CGCGCTCTCTTCCCTCCGCCGCCGCCTCCTCCATTTTGCGAGCTCGTGTCTGTGACGGGAGCCCGAGTCA

CCGCCTGCCCGTCGGGGACGGATTCTGTGGGTGGAAGGAGACGCCGCAGCCGGAGCGGCCGAAGCAGCTG

GGACCGGGACGGGGCACGCGCGCCCGGAACCTCGACCCGCGGAGCCCGGCGCGGGGCGGAGGGCTGGCTT

GTCAGCTGGGCAATGGGAGACTTTCTTAAATAGGGGCTCTCCCCCCACCCATGGAGAAAGGGGCGGCTGT

TTACTTCCTTTTTTTAGAAAAAAAAAATATATTTCCCTCCTGCTCCTTCTGCGTTCACAAGCTAAGTTGT

TTATCTCGGCTGCGGCGGGAACTGCGGACGGTGGCGGGCGAGCGGCTCCTCTGCCAGAGTTGATATTCAC

TGATGGACTCCAAAGAATCATTAACTCCTGGTAGAGAAGAAAACCCCAGCAGTGTGCTTGCTCAGGAGAG

GGGAGATGTGATGGACTTCTATAAAACCCTAAGAGGAGGAGCTACTGTGAAGGTTTCTGCGTCTTCACCC

TCACTGGCTGTCGCTTCTCAATCAGACTCCAAGCAGCGAAGACTTTTGGTTGATTTTCCAAAAGGCTCAG

TAAGCAATGCGCAGCAGCCAGATCTGTCCAAAGCAGTTTCACTCTCAATGGGACTGTATATGGGAGAGAC

AGAAACAAAAGTGATGGGAAATGACCTGGGATTCCCACAGCAGGGCCAAATCAGCCTTTCCTCGGGGGAA

ACAGACTTAAAGCTTTTGGAAGAAAGCATTGCAAACCTCAATAGGTCGACCAGTGTTCCAGAGAACCCCA

AGAGTTCAGCATCCACTGCTGTGTCTGCTGCCCCCACAGAGAAGGAGTTTCCAAAAACTCACTCTGATGT

ATCTTCAGAACAGCAACATTTGAAGGGCCAGACTGGCACCAACGGTGGCAATGTGAAATTGTATACCACA

GACCAAAGCACCTTTGACATTTTGCAGGATTTGGAGTTTTCTTCTGGGTCCCCAGGTAAAGAGACGAATG

AGAGTCCTTGGAGATCAGACCTGTTGATAGATGAAAACTGTTTGCTTTCTCCTCTGGCGGGAGAAGACGA

TTCATTCCTTTTGGAAGGAAACTCGAATGAGGACTGCAAGCCTCTCATTTTACCGGACACTAAACCCAAA

ATTAAGGATAATGGAGATCTGGTTTTGTCAAGCCCCAGTAATGTAACACTGCCCCAAGTGAAAACAGAAA

AAGAAGATTTCATCGAACTCTGCACCCCTGGGGTAATTAAGCAAGAGAAACTGGGCACAGTTTACTGTCA

GGCAAGCTTTCCTGGAGCAAATATAATTGGTAATAAAATGTCTGCCATTTCTGTTCATGGTGTGAGTACC

TCTGGAGGACAGATGTACCACTATGACATGAATACAGCATCCCTTTCTCAACAGCAGGATCAGAAGCCTA

TTTTTAATGTCATTCCACCAATTCCCGTTGGTTCCGAAAATTGGAATAGGTGCCAAGGATCTGGAGATGA

CAACTTGACTTCTCTGGGGACTCTGAACTTCCCTGGTCGAACAGTTTTTTCTAATGGCTATTCAAGCCCC

AGCATGAGACCAGATGTAAGCTCTCCTCCATCCAGCTCCTCAACAGCAACAACAGGACCACCTCCCAAAC

-continued

TCTGCCTGGTGTGCTCTGATGAAGCTTCAGGATGTCATTATGGAGTCTTAACTTGTGGAAGCTGTAAAGT

TTTCTTCAAAAGAGCAGTGGAAGGACAGCACAATTACCTATGTGCTGGAAGGAATGATTGCATCATCGAT

AAAATTCGAAGAAAAAACTGCCCAGCATGCCGCTATCGAAAATGTCTTCAGGCTGGAATGAACCTGGAAG

CTCGAAAAACAAAGAAAAAAATAAAAGGAATTCAGCAGGCCACTACAGGAGTCTCACAAGAAACCTCTGA

AAATCCTGGTAACAAAACAATAGTTCCTGCAACGTTACCACAACTCACCCCTACCCTGGTGTCACTGTTG

GAGGTTATTGAACCTGAAGTGTTATATGCAGGATATGATAGCTCTGTTCCAGACTCAACTTGGAGGATCA

TGACTACGCTCAACATGTTAGGAGGGCGGCAAGTGATTGCAGCAGTGAAATGGGCAAAGGCAATACCAGG

TTTCAGGAACTTACACCTGGATGACCAAATGACCCTACTGCAGTACTCCTGGATGTTTCTTATGGCATTT

GCTCTGGGGTGGAGATCATATAGACAATCAAGTGCAAACCTGCTGTGTTTTGCTCCTGATCTGATTATTA

ATGAGCAGAGAATGACTCTACCCTGCATGTACGACCAATGTAAACACATGCTGTATGTTTCCTCTGAGTT

ACACAGGCTTCAGGTATCTTATGAAGAGTATCTCTGTATGAAAACCTTACTGCTTCTCTCTTCAGTTCCT

AAGGACGGTCTGAAGAGCCAAGAGCTATTTGATGAAATTAGAATGACCTACATCAAAGAGCTAGGAAAAG

CCATTGTCAAGAGGGAAGGAAACTCCAGCCAGAACTGGCAGCGGTTTTATCAACTGACAAAACTCTTGGA

TTCTATGCATGAAGTGGTTGAAAATCTCCTTAACTATTGCTTCCAAACATTTTTGGATAAGACCATGAGT

ATTGAATTCCCCGAGATGTTAGCTGAAATCATCACCAATCAGATACCAAAATATTCAAATGGAAATATCA

AAAAACTTCTGTTTCATCAAAAGTGACTGCCTTAATAAGAATGGTTGCCTTAAAGAAAGTCGAATTAATA

GCTTTTATTGTATAAACTATCAGTTTGTCCTGTAGAGGTTTTGTTGTTTTATTTTTTATTGTTTTCATCT

GTTGTTTTGTTTTAAATACGCACTACATGTGGTTTATAGAGGGCCAAGACTTGGCAACAGAAGCAGTTGA

GTCGTCATCACTTTTCAGTGATGGGAGAGTAGATGGTGAAATTTATTAGTTAATATATCCCAGAAATTAG

AAACCTTAATATGTGGACGTAATCTCCACAGTCAAAGAAGGATGGCACCTAAACCACCAGTGCCCAAAGT

CTGTGTGATGAACTTTCTCTTCATACTTTTTTTCACAGTTGGCTGGATGAAATTTTCTAGACTTTCTGTT

GGTGTATCCCCCCCCTGTATAGTTAGGATAGCATTTTTGATTTATGCATGGAAACCTGAAAAAAAGTTTA

CAAGTGTATATCAGAAAAGGGAAGTTGTGCCTTTTATAGCTATTACTGTCTGGTTTTAACAATTTCCTTT

ATATTTAGTGAACTACGCTTGCTCATTTTTTCTTACATAATTTTTTATTCAAGTTATTGTACAGCTGTTT

AAGATGGGCAGCTAGTTCGTAGCTTTCCCAAATAAACTCTAAACATTAATCAATCATCTGTGTGAAAATG

GGTTGGTGCTTCTAACCTGATGGCACTTAGCTATCAGAAGACCACAAAAATTGACTCAAATCTCCAGTAT

TCTTGTCAAAAAAAAAAAAAAAAAAGCTCATATTTTGTATATATCTGCTTCAGTGGAGAATTATATAGGT

TGTGCAAATTAACAGTCCTAACTGGTATAGAGCACCTAGTCCAGTGACCTGCTGGGTAAACTGTGGATGA

TGGTTGCAAAAGACTAATTTAAAAAATAACTACCAAGAGGCCCTGTCTGTACCTAACGCCCTATTTTTGC

AATGGCTATATGGCAAGAAAGCTGGTAAACTATTTGTCTTTCAGGACCTTTTGAAGTAGTTTGTATAACT

TCTTAAAAGTTGTGATTCCAGATAACCAGCTGTAACACAGCTGAGAGACTTTTAATCAGACAAAGTAATT

CCTCTCACTAAACTTTACCCAAAAACTAAATCTCTAATATGGCAAAAATGGCTAGACACCCATTTTCACA

TTCCCATCTGTCACCAATTGGTTAATCTTTCCTGATGGTACAGGAAAGCTCAGCTACTGATTTTTGTGAT

TTAGAACTGTATGTCAGACATCCATGTTTGTAAAACTACACATCCCTAATGTGTGCCATAGAGTTTAACA

CAAGTCCTGTGAATTTCTTCACTGTTGAAAATTATTTTAAACAAAATAGAAGCTGTAGTAGCCCTTTCTG

TGTGCACCTTACCAACTTTCTGTAAACTCAAAACTTAACATATTTACTAAGCCACAAGAAATTTGATTTC

TATTCAAGGTGGCCAAATTATTTGTGTAATAGAAAACTGAAAATCTAATATTAAAAATATGGAACTTCTA

ATATATTTTTATATTTAGTTATAGTTTCAGATATATATCATATTGGTATTCACTAATCTGGGAAGGGAAG

GGCTACTGCAGCTTTACATGCAATTTATTAAAATGATTGTAAAATAGCTTGTATAGTGTAAAATAAGAAT

GATTTTTAGATGAGATTGTTTTATCATGACATGTTATATATTTTTTGTAGGGGTCAAAGAAATGCTGATG

-continued

GATAACCTATATGATTTATAGTTTGTACATGCATTCATACAGGCAGCGATGGTCTCAGAAACCAAACAGT

TTGCTCTAGGGGAAGAGGGAGATGGAGACTGGTCCTGTGTGCAGTGAAGGTTGCTGAGGCTCTGACCCAG

TGAGATTACAGAGGAAGTTATCCTCTGCCTCCCATTCTGACCACCCTTCTCATTCCAACAGTGAGTCTGT

CAGCGCAGGTTTAGTTTACTCAATCTCCCCTTGCACTAAAGTATGTAAAGTATGTAAACAGGAGACAGGA

AGGTGGTGCTTACATCCTTAAAGGCACCATCTAATAGCGGGTTACTTTCACATACAGCCCTCCCCCAGCA

GTTGAATGACAACAGAAGCTTCAGAAGTTTGGCAATAGTTTGCATAGAGGTACCAGCAATATGTAAATAG

TGCAGAATCTCATAGGTTGCCAATAATACACTAATTCCTTTCTATCCTACAACAAGAGTTTATTTCCAAA

TAAAATGAGGACATGTTTTTGTTTTCTTTGAATGCTTTTTGAATGTTATTTGTTATTTTCAGTATTTTGG

AGAAATTATTTAATAAAAAAACAATCATTTGCTTTTTGAATGCTCTCTAAAAGGGAATGTAATATTTTAA

GATGGTGTGTAACCCGGCTGGATAAATTTTTGGTGCCTAAGAAAACTGCTTGAATATTCTTATCAATGAC

AGTGTTAAGTTTCAAAAAGAGCTTCTAAAACGTAGATTATCATTCCTTTATAGAATGTTATGTGGTTAAA

ACCAGAAAGCACATCTCACACATTAATCTGATTTTCATCCCAACAATCTTGGCGCTCAAAAAATAGAACT

CAATGAGAAAAAGAAGATTATGTGCACTTCGTTGTCAATAATAAGTCAACTGATGCTCATCGACAACTAT

AGGAGGCTTTTCATTAAATGGGAAAAGAAGCTGTGCCCTTTTAGGATACGTGGGGGAAAAGAAAGTCATC

TTAATTATGTTTAATTGTGGATTTAAGTGCTATATGGTGGTGCTGTTTGAAAGCAGATTTATTTCCTATG

TATGTGTTATCTGGCCATCCCAACCCAAACTGTTGAAGTTTGTAGTAACTTCAGTGAGAGTTGGTTACTC

ACAACAAATCCTGAAAAGTATTTTTAGTGTTTGTAGGTATTCTGTGGGATACTATACAAGCAGAACTGAG

GCACTTAGGACATAACACTTTTGGGGTATATATATCCAAATGCCTAAAACTATGGGAGGAAACCTTGGCC

ACCCCAAAAGGAAAACTAACATGATTTGTGTCTATGAAGTGCTGGATAATTAGCATGGGATGAGCTCTGG

GCATGCCATGAAGGAAAGCCACGCTCCCTTCAGAATTCAGAGGCAGGGAGCAATTCCAGTTTCACCTAAG

TCTCATAATTTTAGTTCCCTTTTAAAAACCCTGAAAACTACATCACCATGGAATGAAAAATATTGTTATA

CAATACATTGATCTGTCAAACTTCCAGAACCATGGTAGCCTTCAGTGAGATTTCCATCTTGGCTGGTCAC

TCCCTGACTGTAGCTGTAGGTGAATGTGTTTTTGTGTGTGTGTGTCTGGTTTTAGTGTCAGAAGGGAAAT

AAAAGTGTAAGGAGGACACTTTAAACCCTTTGGGTGGAGTTTCGTAATTTCCCAGACTATTTTCAAGCAA

CCTGGTCCACCCAGGATTAGTGACCAGGTTTTCAGGAAAGGATTTGCTTCTCTCTAGAAAATGTCTGAAA

GGATTTTATTTTCTGATGAAAGGCTGTATGAAAATACCCTCCTCAAATAACTTGCTTAACTACATATAGA

TTCAAGTGTGTCAATATTCTATTTTGTATATTAAATGCTATATAATGGGGACAAATCTATATTATACTGT

GTATGGCATTATTAAGAAGCTTTTTCATTATTTTTTATCACAGTAATTTTAAAATGTGTAAAAATTAAAA

CCAGTGACTCCTGTTTAAAAATAAAAGTTGTAGTTTTTTATTCATGCTGAATAATAATCTGTAGTTAAAA

AAAAAGTGTCTTTTTACCTACGCAGTGAAATGTCAGACTGTAAAACCTTGTGTGGAAATGTTTAACTTTT

ATTTTTTCATTTAAATTTGCTGTTCTGGTATTACCAAACCACACATTTGTACCGAATTGGCAGTAAATGT

TAGCCATTTACAGCAATGCCAAATATGGAGAAACATCATAATAAAAAAATCTGCTTTTTCATTAAAAAAA

AAAAAAAAAAA

Human GR Transcript Variant 2 mRNA Sequence (NCBI Reference Sequence: NM_001018074.1)

SEQ ID NO: 15

AGGTTATGTAAGGGTTTGCTTTCACCCCATTCAAAAGGTACCTCTTCCTCTTCTCTTGCTCCCTCTCGCC

CTCATTCTTGTGCCTATGCAGACATTTGAGTAGAGGCGAATCACTTTCACTTCTGCTGGGGAAATTGCAA

CACGCTTCTTTAAATGGCAGAGAGAAGGAGAAAACTTAGATCTTCTGATACCAAATCACTGGACCTTAGA

AGGTCAGAAATCTTTCAAGCCCTGCAGGACCGTAAAATGCGCATGTGTCCAACGGAAGCACTGGGGCATG

AGTGGGGAAGGAATAGAAACAGAAAGAGGTTGATATTCACTGATGGACTCCAAAGAATCATTAACTCCTG

GTAGAGAAGAAAACCCCAGCAGTGTGCTTGCTCAGGAGAGGGGAGATGTGATGGACTTCTATAAAACCCT

-continued

AAGAGGAGGAGCTACTGTGAAGGTTTCTGCGTCTTCACCCTCACTGGCTGTCGCTTCTCAATCAGACTCC

AAGCAGCGAAGACTTTTGGTTGATTTTCCAAAAGGCTCAGTAAGCAATGCGCAGCAGCCAGATCTGTCCA

AAGCAGTTTCACTCTCAATGGGACTGTATATGGGAGAGACAGAAACAAAAGTGATGGGAAATGACCTGGG

ATTCCCACAGCAGGGCCAAATCAGCCTTTCCTCGGGGGAAACAGACTTAAAGCTTTTGGAAGAAAGCATT

GCAAACCTCAATAGGTCGACCAGTGTTCCAGAGAACCCCAAGAGTTCAGCATCCACTGCTGTGTCTGCTG

CCCCCACAGAGAAGGAGTTTCCAAAAACTCACTCTGATGTATCTTCAGAACAGCAACATTTGAAGGGCCA

GACTGGCACCAACGGTGGCAATGTGAAATTGTATACCACAGACCAAAGCACCTTTGACATTTTGCAGGAT

TTGGAGTTTTCTTCTGGGTCCCCAGGTAAAGAGACGAATGAGAGTCCTTGGAGATCAGACCTGTTGATAG

ATGAAAACTGTTTGCTTTCTCCTCTGGCGGGAGAAGACGATTCATTCCTTTTGGAAGGAAACTCGAATGA

GGACTGCAAGCCTCTCATTTTACCGGACACTAAACCCAAAATTAAGGATAATGGAGATCTGGTTTTGTCA

AGCCCCAGTAATGTAACACTGCCCCAAGTGAAAACAGAAAAAGAAGATTTCATCGAACTCTGCACCCCTG

GGGTAATTAAGCAAGAGATACTGGGCACAGTTTACTGTCAGGCAAGCTTTCCTGGAGCAAATATAATTGG

TAATAAAATGTCTGCCATTTCTGTTCATGGTGTGAGTACCTCTGGAGGACAGATGTACCACTATGACATG

AATACAGCATCCCTTTCTCAACAGCAGGATCAGAAGCCTATTTTTAATGTCATTCCACCAATTCCCGTTG

GTTCCGAAAATTGGAATAGGTGCCAAGGATCTGGAGATGACAACTTGACTTCTCTGGGGACTCTGAACTT

CCCTGGTCGAACAGTTTTTTCTAATGGCTATTCAAGCCCCAGCATGAGACCAGATGTAAGCTCTCCTCCA

TCCAGCTCCTCAACAGCAACAACAGGACCACCTCCCAAACTCTGCCTGGTGTGCTCTGATGAAGCTTCAG

GATGTCATTATGGAGTCTTAACTTGTGGAAGCTGTAAAGTTTTCTTCAAAAGAGCAGTGGAAGGACAGCA

CAATTACCTATGTGCTGGAAGGAATGATTGCATCATCGATAAAATTCGAAGAAAAAACTGCCCAGCATGC

CGCTATCGAAAATGTCTTCAGGCTGGAATGAACCTGGAAGCTCGAAAAACAAAGAAAAAAATAAAAGGAA

TTCAGCAGGCCACTACAGGAGTCTCACAAGAAACCTCTGAAAATCCTGGTAACAAAACAATAGTTCCTGC

AACGTTACCACAACTCACCCCTACCCTGGTGTCACTGTTGGAGGTTATTGAACCTGAAGTGTTATATGCA

GGATATGATAGCTCTGTTCCAGACTCAACTTGGAGGATCATGACTACGCTCAACATGTTAGGAGGGCGGC

AAGTGATTGCAGCAGTGAAATGGGCAAAGGCAATACCAGGTTTCAGGAACTTACACCTGGATGACCAAAT

GACCCTACTGCAGTACTCCTGGATGTTTCTTATGGCATTTGCTCTGGGGTGGAGATCATATAGACAATCA

AGTGCAAACCTGCTGTGTTTTGCTCCTGATCTGATTATTAATGAGCAGAGAATGACTCTACCCTGCATGT

ACGACCAATGTAAACACATGCTGTATGTTTCCTCTGAGTTACACAGGCTTCAGGTATCTTATGAAGAGTA

TCTCTGTATGAAAACCTTACTGCTTCTCTCTTCAGTTCCTAAGGACGGTCTGAAGAGCCAAGAGCTATTT

GATGAAATTAGAATGACCTACATCAAAGAGCTAGGAAAAGCCATTGTCAAGAGGGAAGGAAACTCCAGCC

AGAACTGGCAGCGGTTTTATCAACTGACAAAACTCTTGGATTCTATGCATGAAGTGGTTGAAAATCTCCT

TAACTATTGCTTCCAAACATTTTTGGATAAGACCATGAGTATTGAATTCCCCGAGATGTTAGCTGAAATC

ATCACCAATCAGATACCAAAATATTCAAATGGAAATATCAAAAAACTTCTGTTTCATCAAAAGTGACTGC

CTTAATAAGAATGGTTGCCTTAAAGAAAGTCGAATTAATAGCTTTTATTGTATAAACTATCAGTTTGTCC

TGTAGAGGTTTTGTTGTTTTATTTTTTATTGTTTTCATCTGTTGTTTTGTTTTAAATACGCACTACATGT

GGTTTATAGAGGGCCAAGACTTGGCAACAGAAGCAGTTGAGTCGTCATCACTTTTCAGTGATGGGAGAGT

AGATGGTGAAATTTATTAGTTAATATATCCCAGAAATTAGAAACCTTAATATGTGGACGTAATCTCCACA

GTCAAAGAAGGATGGCACCTAAACCACCAGTGCCCAAAGTCTGTGTGATGAACTTTCTCTTCATACTTTT

TTTCACAGTTGGCTGGATGAAATTTTCTAGACTTTCTGTTGGTGTATCCCCCCCCTGTATAGTTAGGATA

GCATTTTTGATTTATGCATGGAAACCTGAAAAAAAGTTTACAAGTGTATATCAGAAAAGGGAAGTTGTGC

CTTTTATAGCTATTACTGTCTGGTTTTAACAATTTCCTTTATATTTAGTGAACTACGCTTGCTCATTTTT

TCTTACATAATTTTTTATTCAAGTTATTGTACAGCTGTTTAAGATGGGCAGCTAGTTCGTAGCTTTCCCA

-continued

AATAAACTCTAAACATTAATCAATCATCTGTGTGAAAATGGGTTGGTGCTTCTAACCTGATGGCACTTAG

CTATCAGAAGACCACAAAAATTGACTCAAATCTCCAGTATTCTTGTCAAAAAAAAAAAAAAAAAAAGCTCA

TATTTTGTATATATCTGCTTCAGTGGAGAATTATATAGGTTGTGCAAATTAACAGTCCTAACTGGTATAG

AGCACCTAGTCCAGTGACCTGCTGGGTAAACTGTGGATGATGGTTGCAAAAGACTAATTTAAAAAATAAC

TACCAAGAGGCCCTGTCTGTACCTAACGCCCTATTTTTGCAATGGCTATATGGCAAGAAAGCTGGTAAAC

TATTTGTCTTTCAGGACCTTTTGAAGTAGTTTGTATAACTTCTTAAAAGTTGTGATTCCAGATAACCAGC

TGTAACACAGCTGAGAGACTTTTAATCAGACAAAGTAATTCCTCTCACTAAACTTTACCCAAAAACTAAA

TCTCTAATATGGCAAAAATGGCTAGACACCCATTTTCACATTCCCATCTGTCACCAATTGGTTAATCTTT

CCTGATGGTACAGGAAAGCTCAGCTACTGATTTTTGTGATTTAGAACTGTATGTCAGACATCCATGTTTG

TAAAACTACACATCCCTAATGTGTGCCATAGAGTTTAACACAAGTCCTGTGAATTTCTTCACTGTTGAAA

ATTATTTTAAACAAAATAGAAGCTGTAGTAGCCCTTTCTGTGTGCACCTTACCAACTTTCTGTAAACTCA

AAACTTAACATATTTACTAAGCCACAAGAAATTTGATTTCTATTCAAGGTGGCCAAATTATTTGTGTAAT

AGAAAACTGAAAATCTAATATTAAAAATATGGAACTTCTAATATATTTTTATATTTAGTTATAGTTTCAG

ATATATATCATATTGGTATTCACTAATCTGGGAAGGGAAGGGCTACTGCAGCTTTACATGCAATTTATTA

AAATGATTGTAAAATAGCTTGTATAGTGTAAAATAAGAATGATTTTTAGATGAGATTGTTTTATCATGAC

ATGTTATATATTTTTTGTAGGGGTCAAAGAAATGCTGATGGATAACCTATATGATTTATAGTTTGTACAT

GCATTCATACAGGCAGCGATGGTCTCAGAAACCAAACAGTTTGCTCTAGGGGAAGAGGGAGATGGAGACT

GGTCCTGTGTGCAGTGAAGGTTGCTGAGGCTCTGACCCAGTGAGATTACAGAGGAAGTTATCCTCTGCCT

CCCATTCTGACCACCCTTCTCATTCCAACAGTGAGTCTGTCAGCGCAGGTTTAGTTTACTCAATCTCCCC

TTGCACTAAAGTATGTAAAGTATGTAAACAGGAGACAGGAAGGTGGTGCTTACATCCTTAAAGGCACCAT

CTAATAGCGGGTTACTTTCACATACAGCCCTCCCCCAGCAGTTGAATGACAACAGAAGCTTCAGAAGTTT

GGCAATAGTTTGCATAGAGGTACCAGCAATATGTAAATAGTGCAGAATCTCATAGGTTGCCAATAATACA

CTAATTCCTTTCTATCCTACAACAAGAGTTTATTTCCAAATAAAATGAGGACATGTTTTTGTTTTCTTTG

AATGCTTTTTGAATGTTATTTGTTATTTTCAGTATTTTGGAGAAATTATTTAATAAAAAAACAATCATTT

GCTTTTTGAATGCTCTCTAAAAGGGAATGTAATATTTTAAGATGGTGTGTAACCCGGCTGGATAAATTTT

TGGTGCCTAAGAAAACTGCTTGAATATTCTTATCAATGACAGTGTTAAGTTTCAAAAAGAGCTTCTAAAA

CGTAGATTATCATTCCTTTATAGAATGTTATGTGGTTAAAACCAGAAAGCACATCTCACACATTAATCTG

ATTTTCATCCCAACAATCTTGGCGCTCAAAAAATAGAACTCAATGAGAAAAAGAAGATTATGTGCACTTC

GTTGTCAATAATAAGTCAACTGATGCTCATCGACAACTATAGGAGGCTTTTCATTAAATGGGAAAAGAAG

CTGTGCCCTTTTAGGATACGTGGGGGAAAAGAAAGTCATCTTAATTATGTTTAATTGTGGATTTAAGTGC

TATATGGTGGTGCTGTTTGAAAGCAGATTTATTTCCTATGTATGTGTTATCTGGCCATCCCAACCCAAAC

TGTTGAAGTTTGTAGTAACTTCAGTGAGAGTTGGTTACTCACAACAAATCCTGAAAAGTATTTTTAGTGT

TTGTAGGTATTCTGTGGGATACTATACAAGCAGAACTGAGGCACTTAGGACATAACACTTTTGGGGTATA

TATATCCAAATGCCTAAAACTATGGGAGGAAACCTTGGCCACCCCAAAAGGAAAACTAACATGATTTGTG

TCTATGAAGTGCTGGATAATTAGCATGGGATGAGCTCTGGGCATGCCATGAAGGAAAGCCACGCTCCCTT

CAGAATTCAGAGGCAGGGAGCAATTCCAGTTTCACCTAAGTCTCATAATTTTAGTTCCCTTTTAAAAACC

CTGAAAACTACATCACCATGGAATGAAAAATATTGTTATACAATACATTGATCTGTCAAACTTCCAGAAC

CATGGTAGCCTTCAGTGAGATTTCCATCTTGGCTGGTCACTCCCTGACTGTAGCTGTAGGTGAATGTGTT

TTTGTGTGTGTGTGTCTGGTTTTAGTGTCAGAAGGGAAATAAAAGTGTAAGGAGGACACTTTAAACCCTT

TGGGTGGAGTTTCGTAATTTCCCAGACTATTTTCAAGCAACCTGGTCCACCCAGGATTAGTGACCAGGTT

-continued

TTCAGGAAAGGATTTGCTTCTCTCTAGAAAATGTCTGAAAGGATTTTATTTTCTGATGAAAGGCTGTATG

AAAATACCCTCCTCAAATAACTTGCTTAACTACATATAGATTCAAGTGTGTCAATATTCTATTTTGTATA

TTAAATGCTATATAATGGGGACAAATCTATATTATACTGTGTATGGCATTATTAAGAAGCTTTTTCATTA

TTTTTTATCACAGTAATTTTAAAATGTGTAAAAATTAAAACCAGTGACTCCTGTTTAAAAATAAAAGTTG

TAGTTTTTTATTCATGCTGAATAATAATCTGTAGTTAAAAAAAAAGTGTCTTTTTACCTACGCAGTGAAA

TGTCAGACTGTAAAACCTTGTGTGGAAATGTTTAACTTTTATTTTTTCATTTAAATTTGCTGTTCTGGTA

TTACCAAACCACACATTTGTACCGAATTGGCAGTAAATGTTAGCCATTTACAGCAATGCCAAATATGGAG

AAACATCATAATAAAAAAATCTGCTTTTTCATTA

Human GR Transcript Variant 3 mRNA Sequence (NCBI Reference Sequence: NM_001018075.1)

SEQ ID NO: 16

AGGTTATGTAAGGGTTTGCTTTCACCCCATTCAAAAGGTACCTCTTCCTCTTCTCTTGCTCCCTCTCGCC

CTCATTCTTGTGCCTATGCAGACATTTGAGTAGAGGCGAATCACTTTCACTTCTGCTGGGGAAATTGCAA

CACGCTTCTTTAAATGGCAGAGAGAAGGAGAAAACTTAGATCTTCTGATACCAAATCACTGGACCTTAGA

AGTTGATATTCACTGATGGACTCCAAAGAATCATTAACTCCTGGTAGAGAAGAAAACCCCAGCAGTGTGC

TTGCTCAGGAGAGGGGAGATGTGATGGACTTCTATAAAACCCTAAGAGGAGGAGCTACTGTGAAGGTTTC

TGCGTCTTCACCCTCACTGGCTGTCGCTTCTCAATCAGACTCCAAGCAGCGAAGACTTTTGGTTGATTTT

CCAAAAGGCTCAGTAAGCAATGCGCAGCAGCCAGATCTGTCCAAAGCAGTTTCACTCTCAATGGGACTGT

ATATGGGAGAGACAGAAACAAAAGTGATGGGAAATGACCTGGGATTCCCACAGCAGGGCCAAATCAGCCT

TTCCTCGGGGGAAACAGACTTAAAGCTTTTGGAAGAAAGCATTGCAAACCTCAATAGGTCGACCAGTGTT

CCAGAGAACCCCAAGAGTTCAGCATCCACTGCTGTGTCTGCTGCCCCCACAGAGAAGGAGTTTCCAAAAA

CTCACTCTGATGTATCTTCAGAACAGCAACATTTGAAGGGCCAGACTGGCACCAACGGTGGCAATGTGAA

ATTGTATACCACAGACCAAAGCACCTTTGACATTTTGCAGGATTTGGAGTTTTCTTCTGGGTCCCCAGGT

AAAGAGACGAATGAGAGTCCTTGGAGATCAGACCTGTTGATAGATGAAAACTGTTTGCTTTCTCCTCTGG

CGGGAGAAGACGATTCATTCCTTTTGGAAGGAAACTCGAATGAGGACTGCAAGCCTCTCATTTTACCGGA

CACTAAACCCAAAATTAAGGATAATGGAGATCTGGTTTTGTCAAGCCCCAGTAATGTAACACTGCCCCAA

GTGAAAACAGAAAAAGAAGATTTCATCGAACTCTGCACCCCTGGGGTAATTAAGCAAGAGAAACTGGGCA

CAGTTTACTGTCAGGCAAGCTTTCCTGGAGCAAATATAATTGGTAATAAAATGTCTGCCATTTCTGTTCA

TGGTGTGAGTACCTCTGGAGGACAGATGTACCACTATGACATGAATACAGCATCCCTTTCTCAACAGCAG

GATCAGAAGCCTATTTTTAATGTCATTCCACCAATTCCCGTTGGTTCCGAAAATTGGAATAGGTGCCAAG

GATCTGGAGATGACAACTTGACTTCTCTGGGGACTCTGAACTTCCCTGGTCGAACAGTTTTTTCTAATGG

CTATTCAAGCCCCAGCATGAGACCAGATGTAAGCTCTCCTCCATCCAGCTCCTCAACAGCAACAACAGGA

CCACCTCCCAAACTCTGCCTGGTGTGCTCTGATGAAGCTTCAGGATGTCATTATGGAGTCTTAACTTGTG

GAAGCTGTAAAGTTTTCTTCAAAAGAGCAGTGGAAGGACAGCACAATTACCTATGTGCTGGAAGGAATGA

TTGCATCATCGATAAAATTCGAAGAAAAAACTGCCCAGCATGCCGCTATCGAAAATGTCTTCAGGCTGGA

ATGAACCTGGAAGCTCGAAAAACAAAGAAAAAAATAAAAGGAATTCAGCAGGCCACTACAGGAGTCTCAC

AAGAAACCTCTGAAAATCCTGGTAACAAAACAATAGTTCCTGCAACGTTACCACAACTCACCCCTACCCT

GGTGTCACTGTTGGAGGTTATTGAACCTGAAGTGTTATATGCAGGATATGATAGCTCTGTTCCAGACTCA

ACTTGGAGGATCATGACTACGCTCAACATGTTAGGAGGGCGGCAAGTGATTGCAGCAGTGAAATGGGCAA

AGGCAATACCAGGTTTCAGGAACTTACACCTGGATGACCAAATGACCCTACTGCAGTACTCCTGGATGTT

TCTTATGGCATTTGCTCTGGGGTGGAGATCATATAGACAATCAAGTGCAAACCTGCTGTGTTTTGCTCCT

GATCTGATTATTAATGAGCAGAGAATGACTCTACCCTGCATGTACGACCAATGTAAACACATGCTGTATG

-continued

TTTCCTCTGAGTTACACAGGCTTCAGGTATCTTATGAAGAGTATCTCTGTATGAAAACCTTACTGCTTCT

CTCTTCAGTTCCTAAGGACGGTCTGAAGAGCCAAGAGCTATTTGATGAAATTAGAATGACCTACATCAAA

GAGCTAGGAAAAGCCATTGTCAAGAGGGAAGGAAACTCCAGCCAGAACTGGCAGCGGTTTTATCAACTGA

CAAAACTCTTGGATTCTATGCATGAAGTGGTTGAAAATCTCCTTAACTATTGCTTCCAAACATTTTTGGA

TAAGACCATGAGTATTGAATTCCCCGAGATGTTAGCTGAAATCATCACCAATCAGATACCAAAATATTCA

AATGGAAATATCAAAAAACTTCTGTTTCATCAAAAGTGACTGCCTTAATAAGAATGGTTGCCTTAAAGAA

AGTCGAATTAATAGCTTTTATTGTATAAACTATCAGTTTGTCCTGTAGAGGTTTTGTTGTTTTATTTTTT

ATTGTTTTCATCTGTTGTTTTGTTTTAAATACGCACTACATGTGGTTTATAGAGGGCCAAGACTTGGCAA

CAGAAGCAGTTGAGTCGTCATCACTTTTCAGTGATGGGAGAGTAGATGGTGAAATTTATTAGTTAATATA

TCCCAGAAATTAGAAACCTTAATATGTGGACGTAATCTCCACAGTCAAAGAAGGATGGCACCTAAACCAC

CAGTGCCCAAAGTCTGTGTGATGAACTTTCTCTTCATACTTTTTTTCACAGTTGGCTGGATGAAATTTTC

TAGACTTTCTGTTGGTGTATCCCCCCCCTGTATAGTTAGGATAGCATTTTTGATTTATGCATGGAAACCT

GAAAAAAAGTTTACAAGTGTATATCAGAAAAGGGAAGTTGTGCCTTTTATAGCTATTACTGTCTGGTTTT

AACAATTTCCTTTATATTTAGTGAACTACGCTTGCTCATTTTTTCTTACATAATTTTTTATTCAAGTTAT

TGTACAGCTGTTTAAGATGGGCAGCTAGTTCGTAGCTTTCCCAAATAAACTCTAAACATTAATCAATCAT

CTGTGTGAAAATGGGTTGGTGCTTCTAACCTGATGGCACTTAGCTATCAGAAGACCACAAAAATTGACTC

AAATCTCCAGTATTCTTGTCAAAAAAAAAAAAAAAAAAAGCTCATATTTTGTATATATCTGCTTCAGTGGA

GAATTATATAGGTTGTGCAAATTAACAGTCCTAACTGGTATAGAGCACCTAGTCCAGTGACCTGCTGGGT

AAACTGTGGATGATGGTTGCAAAAGACTAATTTAAAAAATAACTACCAAGAGGCCCTGTCTGTACCTAAC

GCCCTATTTTTGCAATGGCTATATGGCAAGAAAGCTGGTAAACTATTTGTCTTTCAGGACCTTTTGAAGT

AGTTTGTATAACTTCTTAAAAGTTGTGATTCCAGATAACCAGCTGTAACACAGCTGAGAGACTTTTAATC

AGACAAAGTAATTCCTCTCACTAAACTTTACCCAAAAACTAAATCTCTAATATGGCAAAAATGGCTAGAC

ACCCATTTTCACATTCCCATCTGTCACCAATTGGTTAATCTTTCCTGATGGTACAGGAAAGCTCAGCTAC

TGATTTTTGTGATTTAGAACTGTATGTCAGACATCCATGTTTGTAAAACTACACATCCCTAATGTGTGCC

ATAGAGTTTAACACAAGTCCTGTGAATTTCTTCACTGTTGAAAATTATTTTAAACAAAATAGAAGCTGTA

GTAGCCCTTTCTGTGTGCACCTTACCAACTTTCTGTAAACTCAAAACTTAACATATTTACTAAGCCACAA

GAAATTTGATTTCTATTCAAGGTGGCCAAATTATTTGTGTAATAGAAAACTGAAAATCTAATATTAAAAA

TATGGAACTTCTAATATATTTTTATATTTAGTTATAGTTTCAGATATATATCATATTGGTATTCACTAAT

CTGGGAAGGGAAGGGCTACTGCAGCTTTACATGCAATTTATTAAAATGATTGTAAAATAGCTTGTATAGT

GTAAAATAAGAATGATTTTTAGATGAGATTGTTTTATCATGACATGTTATATATTTTTTGTAGGGGTCAA

AGAAATGCTGATGGATAACCTATATGATTTATAGTTTGTACATGCATTCATACAGGCAGCGATGGTCTCA

GAAACCAAACAGTTTGCTCTAGGGGAAGAGGGAGATGGAGACTGGTCCTGTGTGCAGTGAAGGTTGCTGA

GGCTCTGACCCAGTGAGATTACAGAGGAAGTTATCCTCTGCCTCCCATTCTGACCACCCTTCTCATTCCA

ACAGTGAGTCTGTCAGCGCAGGTTTAGTTTACTCAATCTCCCCTTGCACTAAAGTATGTAAAGTATGTAA

ACAGGAGACAGGAAGGTGGTGCTTACATCCTTAAAGGCACCATCTAATAGCGGGTTACTTTCACATACAG

CCCTCCCCCAGCAGTTGAATGACAACAGAAGCTTCAGAAGTTTGGCAATAGTTTGCATAGAGGTACCAGC

AATATGTAAATAGTGCAGAATCTCATAGGTTGCCAATAATACACTAATTCCTTTCTATCCTACAACAAGA

GTTTATTTCCAAATAAAATGAGGACATGTTTTTGTTTTCTTTGAATGCTTTTTGAATGTTATTTGTTATT

TTCAGTATTTTGGAGAAATTATTTAATAAAAAAACAATCATTTGCTTTTTGAATGCTCTCTAAAAGGGAA

TGTAATATTTTAAGATGGTGTGTAACCCGGCTGGATAAATTTTTGGTGCCTAAGAAAACTGCTTGAATAT

TCTTATCAATGACAGTGTTAAGTTTCAAAAAGAGCTTCTAAAACGTAGATTATCATTCCTTTATAGAATG

-continued

TTATGTGGTTAAAACCAGAAAGCACATCTCACACATTAATCTGATTTTCATCCCAACAATCTTGGCGCTC

AAAAAATAGAACTCAATGAGAAAAAGAAGATTATGTGCACTTCGTTGTCAATAATAAGTCAACTGATGCT

CATCGACAACTATAGGAGGCTTTTCATTAAATGGGAAAAGAAGCTGTGCCCTTTTAGGATACGTGGGGA

AAAGAAAGTCATCTTAATTATGTTTAATTGTGGATTTAAGTGCTATATGGTGGTGCTGTTTGAAAGCAGA

TTTATTTCCTATGTATGTGTTATCTGGCCATCCCAACCCAAACTGTTGAAGTTTGTAGTAACTTCAGTGA

GAGTTGGTTACTCACAACAAATCCTGAAAAGTATTTTTAGTGTTTGTAGGTATTCTGTGGGATACTATAC

AAGCAGAACTGAGGCACTTAGGACATAACACTTTTGGGGTATATATATCCAAATGCCTAAAACTATGGGA

GGAAACCTTGGCCACCCCAAAAGGAAAACTAACATGATTTGTGTCTATGAAGTGCTGGATAATTAGCATG

GGATGAGCTCTGGGCATGCCATGAAGGAAAGCCACGCTCCCTTCAGAATTCAGAGGCAGGGAGCAATTCC

AGTTTCACCTAAGTCTCATAATTTTAGTTCCCTTTTAAAAACCCTGAAAACTACATCACCATGGAATGAA

AAATATTGTTATACAATACATTGATCTGTCAAACTTCCAGAACCATGGTAGCCTTCAGTGAGATTTCCAT

CTTGGCTGGTCACTCCCTGACTGTAGCTGTAGGTGAATGTGTTTTTGTGTGTGTGTGTCTGGTTTTAGTG

TCAGAAGGGAAATAAAAGTGTAAGGAGGACACTTTAAACCCTTTGGGTGGAGTTTCGTAATTTCCCAGAC

TATTTTCAAGCAACCTGGTCCACCCAGGATTAGTGACCAGGTTTTCAGGAAAGGATTTGCTTCTCTCTAG

AAAATGTCTGAAAGGATTTTATTTTCTGATGAAAGGCTGTATGAAAATACCCTCCTCAAATAACTTGCTT

AACTACATATAGATTCAAGTGTGTCAATATTCTATTTTGTATATTAAATGCTATATAATGGGGACAAATC

TATATTATACTGTGTATGGCATTATTAAGAAGCTTTTTCATTATTTTTTATCACAGTAATTTTAAAATGT

GTAAAAATTAAAACCAGTGACTCCTGTTTAAAAATAAaAGTTGTAGTTTTTTATTCATGCTGAATAATAA

TCTGTAGTTAAAAAAAAAGTGTCTTTTTACCTACGCAGTGAAATGTCAGACTGTAAAACCTTGTGTGGAA

ATGTTTAACTTTTATTTTTTCATTTAAATTTGCTGTTCTGGTATTACCAAACCACACATTTGTACCGAAT

TGGCAGTAAATGTTAGCCATTTACAGCAATGCCAAATATGGAGAAACATCATAATAAAAAAATCTGCTTT

TTCATTA

Human GR Transcript Variant 4 mRNA Sequence (NCBI Reference Sequence: NM_001018076.1)

SEQ ID NO: 17

CTTCTCTCCCAGTGCGAGAGCGCGGCGGCGGCAGCTGAAGACCCGGCCGCCCAGATGATGCGGTGGTGGG

GGACCTGCCGGCACGCGACTCCCCCCGGGCCCAAATTGATATTCACTGATGGACTCCAAAGAATCATTAA

CTCCTGGTAGAGAAGAAAACCCCAGCAGTGTGCTTGCTCAGGAGAGGGGAGATGTGATGGACTTCTATAA

AACCCTAAGAGGAGGAGCTACTGTGAAGGTTTCTGCGTCTTCACCCTCACTGGCTGTCGCTTCTCAATCA

GACTCCAAGCAGCGAAGACTTTTGGTTGATTTTCCAAAAGGCTCAGTAAGCAATGCGCAGCAGCCAGATC

TGTCCAAAGCAGTTTCACTCTCAATGGGACTGTATATGGGAGAGACAGAAACAAAAGTGATGGGAAATGA

CCTGGGATTCCCACAGCAGGGCCAAATCAGCCTTTCCTCGGGGGAAACAGACTTAAAGCTTTTGGAAGAA

AGCATTGCAAACCTCAATAGGTCGACCAGTGTTCCAGAGAACCCCAAGAGTTCAGCATCCACTGCTGTGT

CTGCTGCCCCCACAGAGAAGGAGTTTCCAAAAACTCACTCTGATGTATCTTCAGAACAGCAACATTTGAA

GGGCCAGACTGGCACCAACGGTGGCAATGTGAAATTGTATACCACAGACCAAAGCACCTTTGACATTTTG

CAGGATTTGGAGTTTTCTTCTGGGTCCCCAGGTAAAGAGACGAATGAGAGTCCTTGGAGATCAGACCTGT

TGATAGATGAAAACTGTTTGCTTTCTCCTCTGGCGGGAGAAGACGATTCATTCCTTTTGGAAGGAAACTC

GAATGAGGACTGCAAGCCTCTCATTTTACCGGACACTAAACCCAAAATTAAGGATAATGGAGATCTGGTT

TTGTCAAGCCCCAGTAATGTAACACTGCCCCAAGTGAAAACAGAAAAAGAAGATTTCATCGAACTCTGCA

CCCCTGGGGTAATTAAGCAAGAGAAACTGGGCACAGTTTACTGTCAGGCAAGCTTTCCTGGAGCAAATAT

AATTGGTAATAAAATGTCTGCCATTTCTGTTCATGGTGTGAGTACCTCTGGAGGACAGATGTACCACTAT

GACATGAATACAGCATCCCTTTCTCAACAGCAGGATCAGAAGCCTATTTTTAATGTCATTCCACCAATTC

-continued

CCGTTGGTTCCGAAAATTGGAATAGGTGCCAAGGATCTGGAGATGACAACTTGACTTCTCTGGGGACTCT
GAACTTCCCTGGTCGAACAGTTTTTTCTAATGGCTATTCAAGCCCCAGCATGAGACCAGATGTAAGCTCT
CCTCCATCCAGCTCCTCAACAGCAACAACAGGACCACCTCCCAAACTCTGCCTGGTGTGCTCTGATGAAG
CTTCAGGATGTCATTATGGAGTCTTAACTTGTGGAAGCTGTAAAGTTTTCTTCAAAAGAGCAGTGGAAGG
ACAGCACAATTACCTATGTGCTGGAAGGAATGATTGCATCATCGATAAAATTCGAAGAAAAAACTGCCCA
GCATGCCGCTATCGAAAATGTCTTCAGGCTGGAATGAACCTGGAAGCTCGAAAAACAAAGAAAAAAATAA
AAGGAATTCAGCAGGCCACTACAGGAGTCTCACAAGAAACCTCTGAAAATCCTGGTAACAAAACAATAGT
TCCTGCAACGTTACCACAACTCACCCCTACCCTGGTGTCACTGTTGGAGGTTATTGAACCTGAAGTGTTA
TATGCAGGATATGATAGCTCTGTTCCAGACTCAACTTGGAGGATCATGACTACGCTCAACATGTTAGGAG
GGCGGCAAGTGATTGCAGCAGTGAAATGGGCAAAGGCAATACCAGGTTTCAGGAACTTACACCTGGATGA
CCAAATGACCCTACTGCAGTACTCCTGGATGTTTCTTATGGCATTTGCTCTGGGGTGGAGATCATATAGA
CAATCAAGTGCAAACCTGCTGTGTTTTGCTCCTGATCTGATTATTAATGAGCAGAGAATGACTCTACCCT
GCATGTACGACCAATGTAAACACATGCTGTATGTTTCCTCTGAGTTACACAGGCTTCAGGTATCTTATGA
AGAGTATCTCTGTATGAAAACCTTACTGCTTCTCTCTTCAGTTCCTAAGGACGGTCTGAAGAGCCAAGAG
CTATTTGATGAAATTAGAATGACCTACATCAAAGAGCTAGGAAAAGCCATTGTCAAGAGGGAAGGAAACT
CCAGCCAGAACTGGCAGCGGTTTTATCAACTGACAAAACTCTTGGATTCTATGCATGAAGTGGTTGAAAA
TCTCCTTAACTATTGCTTCCAAACATTTTTGGATAAGACCATGAGTATTGAATTCCCCGAGATGTTAGCT
GAAATCATCACCAATCAGATACCAAAATATTCAAATGGAAATATCAAAAAACTTCTGTTTCATCAAAAGT
GACTGCCTTAATAAGAATGGTTGCCTTAAAGAAAGTCGAATTAATAGCTTTTATTGTATAAACTATCAGT
TTGTCCTGTAGAGGTTTTGTTGTTTTATTTTTTATTGTTTTCATCTGTTGTTTTGTTTTAAATACGCACT
ACATGTGGTTTATAGAGGGCCAAGACTTGGCAACAGAAGCAGTTGAGTCGTCATCACTTTTCAGTGATGG
GAGAGTAGATGGTGAAATTTATTAGTTAATATATCCCAGAAATTAGAAACCTTAATATGTGGACGTAATC
TCCACAGTCAAAGAAGGATGGCACCTAAACCACCAGTGCCCAAAGTCTGTGTGATGAACTTTCTCTTCAT
ACTTTTTTTCACAGTTGGCTGGATGAAATTTTCTAGACTTTCTGTTGGTGTATCCCCCCCCTGTATAGTT
AGGATAGCATTTTTGATTTATGCATGGAAACCTGAAAAAAAGTTTACAAGTGTATATCAGAAAAGGGAAG
TTGTGCCTTTTATAGCTATTACTGTCTGGTTTTAACAATTTCCTTTATATTTAGTGAACTACGCTTGCTC
ATTTTTTCTTACATAATTTTTTATTCAAGTTATTGTACAGCTGTTTAAGATGGGCAGCTAGTTCGTAGCT
TTCCCAAATAAACTCTAAACATTAATCAATCATCTGTGTGAAAATGGGTTGGTGCTTCTAACCTGATGGC
ACTTAGCTATCAGAAGACCACAAAAATTGACTCAAATCTCCAGTATTCTTGTCAAAAAAAAAAAAAAAAA
AGCTCATATTTTGTATATATCTGCTTCAGTGGAGAATTATATAGGTTGTGCAAATTAACAGTCCTAACTG
GTATAGAGCACCTAGTCCAGTGACCTGCTGGGTAAACTGTGGATGATGGTTGCAAAAGACTAATTTAAAA
AATAACTACCAAGAGGCCCTGTCTGTACCTAACGCCCTATTTTTGCAATGGCTATATGGCAAGAAAGCTG
GTAAACTATTTGTCTTTCAGGACCTTTTGAAGTAGTTTGTATAACTTCTTAAAAGTTGTGATTCCAGATA
ACCAGCTGTAACACAGCTGAGAGACTTTTAATCAGACAAAGTAATTCCTCTCACTAAACTTTACCCAAAA
ACTAAATCTCTAATATGGCAAAAATGGCTAGACACCCATTTTCACATTCCCATCTGTCACCAATTGGTTA
ATCTTTCCTGATGGTACAGGAAAGCTCAGCTACTGATTTTTGTGATTTAGAACTGTATGTCAGACATCCA
TGTTTGTAAAACTACACATCCCTAATGTGTGCCATAGAGTTTAACACAAGTCCTGTGAATTTCTTCACTG
TTGAAAATTATTTTAAACAAAATAGAAGCTGTAGTAGCCCTTTCTGTGTGCACCTTACCAACTTTCTGTA
AACTCAAAACTTAACATATTTACTAAGCCACAAGAAATTTGATTTCTATTCAAGGTGGCCAAATTATTTG
TGTAATAGAAAACTGAAAATCTAATATTAAAAATATGGAACTTCTAATATATTTTTATATTTAGTTATAG

-continued

TTTCAGATATATATCATATTGGTATTCACTAATCTGGGAAGGGAAGGGCTACTGCAGCTTTACATGCAAT

TTATTAAAATGATTGTAAAATAGCTTGTATAGTGTAAAATAAGAATGATTTTTAGATGAGATTGTTTTAT

CATGACATGTTATATATTTTTTGTAGGGGTCAAAGAAATGCTGATGGATAACCTATATGATTTATAGTTT

GTACATGCATTCATACAGGCAGCGATGGTCTCAGAAACCAAACAGTTTGCTCTAGGGGAAGAGGGAGATG

GAGACTGGTCCTGTGTGCAGTGAAGGTTGCTGAGGCTCTGACCCAGTGAGATTACAGAGGAAGTTATCCT

CTGCCTCCCATTCTGACCACCCTTCTCATTCCAACAGTGAGTCTGTCAGCGCAGGTTTAGTTTACTCAAT

CTCCCCTTGCACTAAAGTATGTAAAGTATGTAAACAGGAGACAGGAAGGTGGTGCTTACATCCTTAAAGG

CACCATCTAATAGCGGGTTACTTTCACATACAGCCCTCCCCCAGCAGTTGAATGACAACAGAAGCTTCAG

AAGTTTGGCAATAGTTTGCATAGAGGTACCAGCAATATGTAAATAGTGCAGAATCTCATAGGTTGCCAAT

AATACACTAATTCCTTTCTATCCTACAACAAGAGTTTATTTCCAAATAAAATGAGGACATGTTTTTGTTT

TCTTTGAATGCTTTTTGAATGTTATTTGTTATTTTCAGTATTTTGGAGAAATTATTTAATAAAAAAACAA

TCATTTGCTTTTTGAATGCTCTCTAAAAGGGAATGTAATATTTTAAGATGGTGTGTAACCCGGCTGGATA

AATTTTTGGTGCCTAAGAAAACTGCTTGTATATTCTTATCAATGTCAGTGTTAAGTTTCAAAAAGAGCTT

CTAAAACGTAGATTATCATTCCTTTATAGAATGTTATGTGGTTAAAACCAGAAAGCACATCTCACACATT

AATCTGATTTTCATCCCAACAATCTTGGCGCTCAAAAAATAGAACTCAATGAGAAAAAGAAGATTATGTG

CACTTCGTTGTCAATAATAAGTCAACTGATGCTCATCGACAACTATAGGAGGCTTTTCATTAAATGGGAA

AAGAAGCTGTGCCCTTTTAGGATACGTGGGGGAAAAGAAAGTCATCTTAATTATGTTTAATTGTGGATTT

AAGTGCTATATGGTGGTGCTGTTTGAAAGCAGATTTATTTCCTATGTATGTGTTATCTGGCCATCCCAAC

CCAAACTGTTGAAGTTTGTAGTAACTTCAGTGAGAGTTGGTTACTCACAACAAATCCTGAAAAGTATTTT

TAGTGTTTGTAGGTATTCTGTGGGATACTATACAAGCAGAACTGAGGCACTTAGGACATAACACTTTTGG

GGTATATATATCCAAATGCCTAAAACTATGGGAGGAAACCTTGGCCACCCCAAAAGGAAAACTAACATGA

TTTGTGTCTATGAAGTGCTGGATAATTAGCATGGGATGAGCTCTGGGCATGCCATGAAGGAAAGCCACGC

TCCCTTCAGAATTCAGAGGCAGGGAGCAATTCCAGTTTCACCTAAGTCTCATAATTTTAGTTCCCTTTTA

AAAACCCTGAAAACTACATCACCATGGAATGAAAAATATTGTTATACAATACATTGATCTGTCAAACTTC

CAGAACCATGGTAGCCTTCAGTGAGATTTCCATCTTGGCTGGTCACTCCCTGACTGTAGCTGTAGGTGAA

TGTGTTTTTGTGTGTGTGTGTCTGGTTTTAGTGTCAGAAGGGAAATAAAAGTGTAAGGAGGACACTTTAA

ACCCTTTGGGTGGAGTTTCGTAATTTCCCAGACTATTTTCAAGCAACCTGGTCCACCCAGGATTAGTGAC

CAGGTTTTCAGGAAAGGATTTGCTTCTCTCTAGAAAATGTCTGAAAGGATTTTATTTTCTGATGAAAGGC

TGTATGAAAATACCCTCCTCAAATAACTTGCTTAACTACATATAGATTCAAGTGTGTCAATATTCTATTT

TGTATATTAAATGCTATATAATGGGGACAAATCTATATTATACTGTGTATGGCATTATTAAGAAGCTTTT

TCATTATTTTTTATCACAGTAATTTTAAAATGTGTAAAAATTAAAACCAGTGACTCCTGTTTAAAAATAA

AAGTTGTAGTTTTTTATTCATGCTGAATAATAATCTGTAGTTAAAAAAAAAGTGTCTTTTTACCTACGCA

GTGAAATGTCAGACTGTAAAACCTTGTGTGGAAATGTTTAACTTTTATTTTTTCATTTAAATTTGCTGTT

CTGGTATTACCAAACCACACATTTGTACCGAATTGGCAGTAAATGTTAGCCATTTACAGCAATGCCAAAT

ATGGAGAAACATCATAATAAAAAAATCTGCTTTTTCATTA

Human GR Transcript Variant 5 mRNA Sequence (NCBI Reference Sequence: NM_001018077.1)

SEQ ID NO: 18

AGGTTATGTAAGGGTTTGCTTTCACCCCATTCAAAAGGTACCTCTTCCTCTTCTCTTGCTCCCTCTCGCC

CTCATTCTTGTGCCTATGCAGACATTTGAGTAGAGGCGAATCACTTTCACTTCTGCTGGGGAAATTGCAA

CACGCTTCTTTAAATGGCAGAGAGAAGGAGAAAACTTAGATCTTCTGATACCAAATCACTGGACCTTAGA

AGGTCAGAAATCTTTCAAGCCCTGCAGGACCGTAAAATGCGCATGTGTCCAACGGAAGCACTGGGGCATG

-continued

AGTGGGGAAGGAATAGAAACAGAAAGAGGGTAAGAGAAGAAAAAAGGGAAAGTGGTGAAGGCAGGGAGGA

AAATTGCTTAGTGTGAATATGCACGCATTCATTTAGTTTTCAAATCCTTGTTGAGCATGATAAAATTCCC

AGCATCAGACCTCACATGTTGGTTTCCATTAGGATCTGCCTGGGGGAATATCTGCTGAATCAGTGGCTCT

GAGCTGAACTAGGAAATTCACCATAATTAGGAGAGTCACTGTATTTCTCTCCAAAAAAAAAAAAAGTTATA

CCCGAGAGACAGGATCTTCTGATCTGAAATTTTCTTCACTTCTGAAATTCTCTGGTTTGTGCTCATCGTT

GGTAGCTATTTGTTCATCAAGAGTTGTGTAGCTGGCTTCTTCTGAAAAAAGGAATCTGCGTCATATCTAA

GTCAGATTTCATTCTGGTGCTCTCAGAGCAGTTAGCCCAGGAAAGGGGCCAGCTTCTGTGACGACTGCTG

CAGAGGCAGGTGCAGTTTGTGTGCCACAGATATTAACTTTGATAAGCACTTAATGAGTGCCTTCTCTGTG

CGAGAATGGGGAGGAACAAAATGCAGCTCCTACCCTCCTCGGGCTTTAGTTGTACCTTAATAACAGGAAT

TTTCATCTGCCTGGCTCCTTTCCTCAAAGAACAAAGAAGACTTTGCTTCATTAAAGTGTCTGAGAAGGAA

GTTGATATTCACTGATGGACTCCAAAGAATCATTAACTCCTGGTAGAGAAGAAAACCCCAGCAGTGTGCT

TGCTCAGGAGAGGGGAGATGTGATGGACTTCTATAAAACCCTAAGAGGAGGAGCTACTGTGAAGGTTTCT

GCGTCTTCACCCTCACTGGCTGTCGCTTCTCAATCAGACTCCAAGCAGCGAAGACTTTTGGTTGATTTTC

CAAAAGGCTCAGTAAGCAATGCGCAGCAGCCAGATCTGTCCAAAGCAGTTTCACTCTCAATGGGACTGTA

TATGGGAGAGACAGAAACAAAAGTGATGGGAAATGACCTGGGATTCCCACAGCAGGGCCAAATCAGCCTT

TCCTCGGGGGAAACAGACTTAAAGCTTTTGGAAGAAAGCATTGCAAACCTCAATAGGTCGACCAGTGTTC

CAGAGAACCCCAAGAGTTCAGCATCCACTGCTGTGTCTGCTGCCCCCACAGAGAAGGAGTTTCCAAAAAC

TCACTCTGATGTATCTTCAGAACAGCAACATTTGAAGGGCCAGACTGGCACCAACGGTGGCAATGTGAAA

TTGTATACCACAGACCAAAGCACCTTTGACATTTTGCAGGATTTGGAGTTTTCTTCTGGGTCCCCAGGTA

AAGAGACGAATGAGAGTCCTTGGAGATCAGACCTGTTGATAGATGAAAACTGTTTGCTTTCTCCTCTGGC

GGGAGAAGACGATTCATTCCTTTTGGAAGGAAACTCGAATGAGGACTGCAAGCCTCTCATTTTACCGGAC

ACTAAACCCAAAATTAAGGATAATGGAGATCTGGTTTTGTCAAGCCCCAGTAATGTAACACTGCCCCAAG

TGAAAACAGAAAAAGAAGATTTCATCGAACTCTGCACCCCTGGGGTAATTAAGCAAGAGAAACTGGGCAC

AGTTTACTGTCAGGCAAGCTTTCCTGGAGCAAATATAATTGGTAATAAAATGTCTGCCATTTCTGTTCAT

GGTGTGAGTACCTCTGGAGGACAGATGTACCACTATGACATGAATACAGCATCCCTTTCTCAACAGCAGG

ATCAGAAGCCTATTTTTAATGTCATTCCACCAATTCCCGTTGGTTCCGAAAATTGGAATAGGTGCCAAGG

ATCTGGAGATGACAACTTGACTTCTCTGGGGACTCTGAACTTCCCTGGTCGAACAGTTTTTTCTAATGGC

TATTCAAGCCCCAGCATGAGACCAGATGTAAGCTCTCCTCCATCCAGCTCCTCAACAGCAACAACAGGAC

CACCTCCCAAACTCTGCCTGGTGTGCTCTGATGAAGCTTCAGGATGTCATTATGGAGTCTTAACTTGTGG

AAGCTGTAAAGTTTTCTTCAAAAGAGCAGTGGAAGGACAGCACAATTACCTATGTGCTGGAAGGAATGAT

TGCATCATCGATAAAATTCGAAGAAAAAACTGCCCAGCATGCCGCTATCGAAAATGTCTTCAGGCTGGAA

TGAACCTGGAAGCTCGAAAAACAAAGAAAAAAATAAAAGGAATTCAGCAGGCCACTACAGGAGTCTCACA

AGAAACCTCTGAAAATCCTGGTAACAAAACAATAGTTCCTGCAACGTTACCACAACTCACCCCTACCCTG

GTGTCACTGTTGGAGGTTATTGAACCTGAAGTGTTATATGCAGGATATGATAGCTCTGTTCCAGACTCAA

CTTGGAGGATCATGACTACGCTCAACATGTTAGGAGGGCGGCAAGTGATTGCAGCAGTGAAATGGGCAAA

GGCAATACCAGGTTTCAGGAACTTACACCTGGATGACCAAATGACCCTACTGCAGTACTCCTGGATGTTT

CTTATGGCATTTGCTCTGGGGTGGAGATCATATAGACAATCAAGTGCAAACCTGCTGTGTTTTGCTCCTG

ATCTGATTATTAATGAGCAGAGAATGACTCTACCCTGCATGTACGACCAATGTAAACACATGCTGTATGT

TTCCTCTGAGTTACACAGGCTTCAGGTATCTTATGAAGAGTATCTCTGTATGAAAACCTTACTGCTTCTC

TCTTCAGTTCCTAAGGACGGTCTGAAGAGCCAAGAGCTATTTGATGAAATTAGAATGACCTACATCAAAG

AGCTAGGAAAAGCCATTGTCAAGAGGGAAGGAAACTCCAGCCAGAACTGGCAGCGGTTTTATCAACTGAC

-continued

AAAACTCTTGGATTCTATGCATGAAGTGGTTGAAAATCTCCTTAACTATTGCTTCCAAACATTTTTGGAT

AAGACCATGAGTATTGAATTCCCCGAGATGTTAGCTGAAATCATCACCAATCAGATACCAAAATATTCAA

ATGGAAATATCAAAAAACTTCTGTTTCATCAAAAGTGACTGCCTTAATAAGAATGGTTGCCTTAAAGAAA

GTCGAATTAATAGCTTTTATTGTATAAACTATCAGTTTGTCCTGTAGAGGTTTTGTTGTTTTATTTTTTA

TTGTTTTCATCTGTTGTTTTGTTTTAAATACGCACTACATGTGGTTTATAGAGGGCCAAGACTTGGCAAC

AGAAGCAGTTGAGTCGTCATCACTTTTCAGTGATGGGAGAGTAGATGGTGAAATTTATTAGTTAATATAT

CCCAGAAATTAGAAACCTTAATATGTGGACGTAATCTCCACAGTCAAAGAAGGATGGCACCTAAACCACC

AGTGCCCAAAGTCTGTGTGATGAACTTTCTCTTCATACTTTTTTTCACAGTTGGCTGGATGAAATTTTCT

AGACTTTCTGTTGGTGTATCCCCCCCCTGTATAGTTAGGATAGCATTTTTGATTTATGCATGGAAACCTG

AAAAAAAGTTTACAAGTGTATATCAGAAAAGGGAAGTTGTGCCTTTTATAGCTATTACTGTCTGGTTTTA

ACAATTTCCTTTATATTTAGTGAACTACGCTTGCTCATTTTTTCTTACATAATTTTTTATTCAAGTTATT

GTACAGCTGTTTAAGATGGGCAGCTAGTTCGTAGCTTTCCCAAATAAACTCTAAACATTAATCAATCATC

TGTGTGAAAATGGGTTGGTGCTTCTAACCTGATGGCACTTAGCTATCAGAAGACCACAAAAATTGACTCA

AATCTCCAGTATTCTTGTCAAAAAAAAAAAAAAAAAAGCTCATATTTTGTATATATCTGCTTCAGTGGAG

AATTATATAGGTTGTGCAAATTAACAGTCCTAACTGGTATAGAGCACCTAGTCCAGTGACCTGCTGGGTA

AACTGTGGATGATGGTTGCAAAAGACTAATTTAAAAAATAACTACCAAGAGGCCCTGTCTGTACCTAACG

CCCTATTTTTGCAATGGCTATATGGCAAGAAAGCTGGTAAACTATTTGTCTTTCAGGACCTTTTGAAGTA

GTTTGTATAACTTCTTAAAAGTTGTGATTCCAGATAACCAGCTGTAACACAGCTGAGAGACTTTTAATCA

GACAAAGTAATTCCTCTCACTAAACTTTACCCAAAAACTAAATCTCTAATATGGCAAAAATGGCTAGACA

CCCATTTTCACATTCCCATCTGTCACCAATTGGTTAATCTTTCCTGATGGTACAGGAAAGCTCAGCTACT

GATTTTTGTGATTTAGAACTGTATGTCAGACATCCATGTTTGTAAAACTACACATCCCTAATGTGTGCCA

TAGAGTTTAACACAAGTCCTGTGAATTTCTTCACTGTTGAAAATTATTTTAAACAAAATAGAAGCTGTAG

TAGCCCTTTCTGTGTGCACCTTACCAACTTTCTGTAAACTCAAAACTTAACATATTTACTAAGCCACAAG

AAATTTGATTTCTATTCAAGGTGGCCAAATTATTTGTGTAATAGAAAACTGAAAATCTAATATTAAAAAT

ATGGAACTTCTAATATATTTTTATATTTAGTTATAGTTTCAGATATATATCATATTGGTATTCACTAATC

TGGGAAGGGAAGGGCTACTGCAGCTTTACATGCAATTTATTAAAATGATTGTAAAATAGCTTGTATAGTG

TAAAATAAGAATGATTTTTAGATGAGATTGTTTTATCATGACATGTTATATATTTTTTGTAGGGGTCAAA

GAAATGCTGATGGATAACCTATATGATTTATAGTTTGTACATGCATTCATACAGGCAGCGATGGTCTCAG

AAACCAAACAGTTTGCTCTAGGGGAAGAGGGAGATGGAGACTGGTCCTGTGTGCAGTGAAGGTTGCTGAG

GCTCTGACCCAGTGAGATTACAGAGGAAGTTATCCTCTGCCTCCCATTCTGACCACCCTTCTCATTCCAA

CAGTGAGTCTGTCAGCGCAGGTTTAGTTTACTCAATCTCCCCTTGCACTAAAGTATGTAAAGTATGTAAA

CAGGAGACAGGAAGGTGGTGCTTACATCCTTAAAGGCACCATCTAATAGCGGGTTACTTTCACATACAGC

CCTCCCCCAGCAGTTGAATGACAACAGAAGCTTCAGAAGTTTGGCAATAGTTTGCATAGAGGTACCAGCA

ATATGTAAATAGTGCAGAATCTCATAGGTTGCCAATAATACACTAATTCCTTTCTATCCTACAACAAGAG

TTTATTTCCAAATAAAATGAGGACATGTTTTTGTTTTCTTTGAATGCTTTTTGAATGTTATTTGTTATTT

TCAGTATTTTGGAGAAATTATTTAATAAAAAAACAATCATTTGCTTTTTGAATGCTCTCTAAAAGGGAAT

GTAATATTTTAAGATGGTGTGTAACCCGGCTGGATAAATTTTTGGTGCCTAAGAAAACTGCTTGAATATT

CTTATCAATGACAGTGTTAAGTTTCAAAAAGAGCTTCTAAAACGTAGATTATCATTCCTTTATAGAATGT

TATGTGGTTAAAACCAGAAAGCACATCTCACACATTAATCTGATTTTCATCCCAACAATCTTGGCGCTCA

AAAAATAGAACTCAATGAGAAAAAGAAGATTATGTGCACTTCGTTGTCAATAATAAGTCAACTGATGCTC

-continued

ATCGACAACTATAGGAGGCTTTTCATTAAATGGGAAAAGAAGCTGTGCCCTTTTAGGATACGTGGGGGAA

AAGAAAGTCATCTTAATTATGTTTAATTGTGGATTTAAGTGCTATATGGTGGTGCTGTTTGAAAGCAGAT

TTATTTCCTATGTATGTGTTATCTGGCCATCCCAACCCAAACTGTTGAAGTTTGTAGTAACTTCAGTGAG

AGTTGGTTACTCACAACAAATCCTGAAAAGTATTTTTAGTGTTTGTAGGTATTCTGTGGGATACTATACA

AGCAGAACTGAGGCACTTAGGACATAACACTTTTGGGGTATATATATCCAAATGCCTAAAACTATGGGAG

GAAACCTTGGCCACCCCAAAAGGAAAACTAACATGATTTGTGTCTATGAAGTGCTGGATAATTAGCATGG

GATGAGCTCTGGGCATGCCATGAAGGAAAGCCACGCTCCCTTCAGAATTCAGAGGCAGGGAGCAATTCCA

GTTTCACCTAAGTCTCATAATTTTAGTTCCCTTTTAAAAACCCTGAAAACTACATCACCATGGAATGAAA

AATATTGTTATACAATACATTGATCTGTCAAACTTCCAGAACCATGGTAGCCTTCAGTGAGATTTCCATC

TTGGCTGGTCACTCCCTGACTGTAGCTGTAGGTGAATGTGTTTTTGTGTGTGTGTGTCTGGTTTTAGTGT

CAGAAGGGAAATAAAAGTGTAAGGAGGACACTTTAAACCCTTTGGGTGGAGTTTCGTAATTTCCCAGACT

ATTTTCAAGCAACCTGGTCCACCCAGGATTAGTGACCAGGTTTTCAGGAAAGGATTTGCTTCTCTCTAGA

AAATGTCTGAAAGGATTTTATTTTCTGATGAAAGGCTGTATGAAAATACCCTCCTCAAATAACTTGCTTA

ACTACATATAGATTCAAGTGTGTCAATATTCTATTTTGTATATTAAATGCTATATAATGGGGACAAATCT

ATATTATACTGTGTATGGCATTATTAAGAAGCTTTTTCATTATTTTTTATCACAGTAATTTTAAAATGTG

TAAAAATTAAAACCAGTGACTCCTGTTTAAAAATAAAAGTTGTAGTTTTTTATTCATGCTGAATAATAAT

CTGTAGTTAAAAAAAAAGTGTCTTTTTACCTACGCAGTGAAATGTCAGACTGTAAAACCTTGTGTGGAAA

TGTTTAACTTTTATTTTTTCATTTAAATTTGCTGTTCTGGTATTACCAAACCACACATTTGTACCGAATT

GGCAGTAAATGTTAGCCATTTACAGCAATGCCAAATATGGAGAAACATCATAATAAAAAAATCTGCTTTT

TCATTA

Human GR Transcript Variant 6 mRNA Sequence (NCBI Reference Sequence: NM_001020825.1)

SEQ ID NO: 19

GGCGCCGCCTCCACCCGCTCCCCGCTCGGTCCCGCTCGCTCGCCCAGGCCGGGCTGCCCTTTCGCGTGTC

CGCGCTCTCTTCCCTCCGCCGCCGCCTCCTCCATTTTGCGAGCTCGTGTCTGTGACGGGAGCCCGAGTCA

CCGCCTGCCCGTCGGGGACGGATTCTGTGGGTGGAAGGAGACGCCGCAGCCGGAGCGGCCGAAGCAGCTG

GGACCGGGACGGGGCACGCGCGCCCGGAACCTCGACCCGCGGAGCCCGGCGCGGGGCGGAGGGCTGGCTT

GTCAGCTGGGCAATGGGAGACTTTCTTAAATAGGGGCTCTCCCCCCACCCATGGAGAAAGGGGCGGCTGT

TTACTTCCTTTTTTTAGAAAAAAAAAAATATATTTCCCTCCTGCTCCTTCTGCGTTCACAAGCTAAGTTGT

TTATCTCGGCTGCGGCGGGAACTGCGGACGGTGGCGGGCGAGCGGCTCCTCTGCCAGAGTTGATATTCAC

TGATGGACTCCAAAGAATCATTAACTCCTGGTAGAGAAGAAAACCCCAGCAGTGTGCTTGCTCAGGAGAG

GGGAGATGTGATGGACTTCTATAAAACCCTAAGAGGAGGAGCTACTGTGAAGGTTTCTGCGTCTTCACCC

TCACTGGCTGTCGCTTCTCAATCAGACTCCAAGCAGCGAAGACTTTTGGTTGATTTTCCAAAAGGCTCAG

TAAGCAATGCGCAGCAGCCAGATCTGTCCAAAGCAGTTTCACTCTCAATGGGACTGTATATGGGAGAGAC

AGAAACAAAAGTGATGGGAAATGACCTGGGATTCCCACAGCAGGGCCAAATCAGCCTTTCCTCGGGGGAA

ACAGACTTAAAGCTTTTGGAAGAAAGCATTGCAAACCTCAATAGGTCGACCAGTGTTCCAGAGAACCCCA

AGAGTTCAGCATCCACTGCTGTGTCTGCTGCCCCCACAGAGAAGGAGTTTCCAAAAACTCACTCTGATGT

ATCTTCAGAACAGCAACATTTGAAGGGCCAGACTGGCACCAACGGTGGCAATGTGAAATTGTATACCACA

GACCAAAGCACCTTTGACATTTTGCAGGATTTGGAGTTTTCTTCTGGGTCCCCAGGTAAAGAGACGAATG

AGAGTCCTTGGAGATCAGACCTGTTGATAGATGAAAACTGTTTGCTTTCTCCTCTGGCGGGAGAAGACGA

TTCATTCCTTTTGGAAGGAAACTCGAATGAGGACTGCAAGCCTCTCATTTTACCGGACACTAAACCCAAA

ATTAAGGATAATGGAGATCTGGTTTTGTCAAGCCCCAGTAATGTAACACTGCCCCAAGTGAAAACAGAAA

-continued
AAGAAGATTTCATCGAACTCTGCACCCCTGGGGTAATTAAGCAAGAGAAACTGGGCACAGTTTACTGTCA
GGCAAGCTTTCCTGGAGCAAATATAATTGGTAATAAAATGTCTGCCATTTCTGTTCATGGTGTGAGTACC
TCTGGAGGACAGATGTACCACTATGACATGAATACAGCATCCCTTTCTCAACAGCAGGATCAGAAGCCTA
TTTTTAATGTCATTCCACCAATTCCCGTTGGTTCCGAAAATTGGAATAGGTGCCAAGGATCTGGAGATGA
CAACTTGACTTCTCTGGGGACTCTGAACTTCCCTGGTCGAACAGTTTTTTCTAATGGCTATTCAAGCCCC
AGCATGAGACCAGATGTAAGCTCTCCTCCATCCAGCTCCTCAACAGCAACAACAGGACCACCTCCCAAAC
TCTGCCTGGTGTGCTCTGATGAAGCTTCAGGATGTCATTATGGAGTCTTAACTTGTGGAAGCTGTAAAGT
TTTCTTCAAAAGAGCAGTGGAAGGACAGCACAATTACCTATGTGCTGGAAGGAATGATTGCATCATCGAT
AAAATTCGAAGAAAAAACTGCCCAGCATGCCGCTATCGAAAATGTCTTCAGGCTGGAATGAACCTGGAAG
CTCGAAAAACAAAGAAAAAAATAAAAGGAATTCAGCAGGCCACTACAGGAGTCTCACAAGAAACCTCTGA
AAATCCTGGTAACAAAACAATAGTTCCTGCAACGTTACCACAACTCACCCCTACCCTGGTGTCACTGTTG
GAGGTTATTGAACCTGAAGTGTTATATGCAGGATATGATAGCTCTGTTCCAGACTCAACTTGGAGGATCA
TGACTACGCTCAACATGTTAGGAGGGCGGCAAGTGATTGCAGCAGTGAAATGGGCAAAGGCAATACCAGG
TTTCAGGAACTTACACCTGGATGACCAAATGACCCTACTGCAGTACTCCTGGATGTTTCTTATGGCATTT
GCTCTGGGGTGGAGATCATATAGACAATCAAGTGCAAACCTGCTGTGTTTTGCTCCTGATCTGATTATTA
ATGAGCAGAGAATGACTCTACCCTGCATGTACGACCAATGTAAACACATGCTGTATGTTTCCTCTGAGTT
ACACAGGCTTCAGGTATCTTATGAAGAGTATCTCTGTATGAAAACCTTACTGCTTCTCTCTTCAGTTCCT
AAGGACGGTCTGAAGAGCCAAGAGCTATTTGATGAAATTAGAATGACCTACATCAAAGAGCTAGGAAAAG
CCATTGTCAAGAGGGAAGGAAACTCCAGCCAGAACTGGCAGCGGTTTTATCAACTGACAAAACTCTTGGA
TTCTATGCATGAAAATGTTATGTGGTTAAAACCAGAAAGCACATCTCACACATTAATCTGATTTTCATCC
CAACAATCTTGGCGCTCAAAAAATAGAACTCAATGAGAAAAAGAAGATTATGTGCACTTCGTTGTCAATA
ATAAGTCAACTGATGCTCATCGACAACTATAGGAGGCTTTTCATTAAATGGGAAAAGAAGCTGTGCCCTT
TTAGGATACGTGGGGGAAAAGAAAGTCATCTTAATTATGTTTAATTGTGGATTTAAGTGCTATATGGTGG
TGCTGTTTGAAAGCAGATTTATTTCCTATGTATGTGTTATCTGGCCATCCCAACCCAAACTGTTGAAGTT
TGTAGTAACTTCAGTGAGAGTTGGTTACTCACAACAAATCCTGAAAAGTATTTTTAGTGTTTGTAGGTAT
TCTGTGGGATACTATACAAGCAGAACTGAGGCACTTAGGACATAACACTTTTGGGGTATATATATCCAAA
TGCCTAAAACTATGGGAGGAAACCTTGGCCACCCCAAAAGGAAAACTAACATGATTTGTGTCTATGAAGT
GCTGGATAATTAGCATGGGATGAGCTCTGGGCATGCCATGAAGGAAAGCCACGCTCCCTTCAGAATTCAG
AGGCAGGGAGCAATTCCAGTTTCACCTAAGTCTCATAATTTTAGTTCCCTTTTAAAAACCCTGAAAACTA
CATCACCATGGAATGAAAAATATTGTTATACAATACATTGATCTGTCAAACTTCCAGAACCATGGTAGCC
TTCAGTGAGATTTCCATCTTGGCTGGTCACTCCCTGACTGTAGCTGTAGGTGAATGTGTTTTTGTGTGTG
TGTGTCTGGTTTTAGTGTCAGAAGGGAAATAAAAGTGTAAGGAGGACACTTTAAACCCTTTGGGTGGAGT
TTCGTAATTTCCCAGACTATTTTCAAGCAACCTGGTCCACCCAGGATTAGTGACCAGGTTTTCAGGAAAG
GATTTGCTTCTCTCTAGAAAATGTCTGAAAGGATTTTATTTTCTGATGAAAGGCTGTATGAAAATACCCT
CCTCAAATAACTTGCTTAACTACATATAGATTCAAGTGTGTCAATATTCTATTTTGTATATTAAATGCTA
TATAATGGGGACAAATCTATATTATACTGTGTATGGCATTATTAAGAAGCTTTTTCATTATTTTTTATCA
CAGTAATTTTAAAATGTGTAAAAATTAAAACCAGTGACTCCTGTTTAAAAATAAAAGTTGTAGTTTTTTA
TTCATGCTGAATAATAATCTGTAGTTAAAAAAAAAGTGTCTTTTTACCTACGCAGTGAAATGTCAGACTG
TAAAACCTTGTGTGGAAATGTTTAACTTTTATTTTTTCATTTAAATTTGCTGTTCTGGTATTACCAAACC
ACACATTTGTACCGAATTGGCAGTAAATGTTAGCCATTTACAGCAATGCCAAATATGGAGAAACATCATA
ATAAAATCTGCTTTTTCATTA -continued Human GR Transcript Variant 7 mRNA Sequence (NCBI Reference Sequence: NM_001024094.1)

SEQ ID NO: 20

GGCGCCGCCTCCACCCGCTCCCCGCTCGGTCCCGCTCGCTCGCCCAGGCCGGGCTGCCCTTTCGCGTGTC

CGCGCTCTCTTCCCTCCGCCGCCGCCTCCTCCATTTTGCGAGCTCGTGTCTGTGACGGGAGCCCGAGTCA

CCGCCTGCCCGTCGGGGACGGATTCTGTGGGTGGAAGGAGACGCCGCAGCCGGAGCGGCCGAAGCAGCTG

GGACCGGGACGGGGCACGCGCGCCCGGAACCTCGACCCGCGGAGCCCGGCGCGGGGCGGAGGGCTGGCTT

GTCAGCTGGGCAATGGGAGACTTTCTTAAATAGGGGCTCTCCCCCCACCCATGGAGAAAGGGGCGGCTGT

TTACTTCCTTTTTTTAGAAAAAAAAAATATATTTCCCTCCTGCTCCTTCTGCGTTCACAAGCTAAGTTGT

TTATCTCGGCTGCGGCGGGAACTGCGGACGGTGGCGGGCGAGCGGCTCCTCTGCCAGAGTTGATATTCAC

TGATGGACTCCAAAGAATCATTAACTCCTGGTAGAGAAGAAAACCCCAGCAGTGTGCTTGCTCAGGAGAG

GGGAGATGTGATGGACTTCTATAAAACCCTAAGAGGAGGAGCTACTGTGAAGGTTTCTGCGTCTTCACCC

TCACTGGCTGTCGCTTCTCAATCAGACTCCAAGCAGCGAAGACTTTTGGTTGATTTTCCAAAAGGCTCAG

TAAGCAATGCGCAGCAGCCAGATCTGTCCAAAGCAGTTTCACTCTCAATGGGACTGTATATGGGAGAGAC

AGAAACAAAAGTGATGGGAAATGACCTGGGATTCCCACAGCAGGGCCAAATCAGCCTTTCCTCGGGGGAA

ACAGACTTAAAGCTTTTGGAAGAAAGCATTGCAAACCTCAATAGGTCGACCAGTGTTCCAGAGAACCCCA

AGAGTTCAGCATCCACTGCTGTGTCTGCTGCCCCCACAGAGAAGGAGTTTCCAAAAACTCACTCTGATGT

ATCTTCAGAACAGCAACATTTGAAGGGCCAGACTGGCACCAACGGTGGCAATGTGAAATTGTATACCACA

GACCAAAGCACCTTTGACATTTTGCAGGATTTGGAGTTTTCTTCTGGGTCCCCAGGTAAAGAGACGAATG

AGAGTCCTTGGAGATCAGACCTGTTGATAGATGAAAACTGTTTGCTTTCTCCTCTGGCGGGAGAAGACGA

TTCATTCCTTTTGGAAGGAAACTCGAATGAGGACTGCAAGCCTCTCATTTTACCGGACACTAAACCCAAA

ATTAAGGATAATGGAGATCTGGTTTTGTCAAGCCCCAGTAATGTAACACTGCCCCAAGTGAAAACAGAAA

AAGAAGATTTCATCGAACTCTGCACCCCTGGGGTAATTAAGCAAGAGAAACTGGGCACAGTTTACTGTCA

GGCAAGCTTTCCTGGAGCAAATATAATTGGTAATAAAATGTCTGCCATTTCTGTTCATGGTGTGAGTACC

TCTGGAGGACAGATGTACCACTATGACATGAATACAGCATCCCTTTCTCAACAGCAGGATCAGAAGCCTA

TTTTTAATGTCATTCCACCAATTCCCGTTGGTTCCGAAAATTGGAATAGGTGCCAAGGATCTGGAGATGA

CAACTTGACTTCTCTGGGGACTCTGAACTTCCCTGGTCGAACAGTTTTTTCTAATGGCTATTCAAGCCCC

AGCATGAGACCAGATGTAAGCTCTCCTCCATCCAGCTCCTCAACAGCAACAACAGGACCACCTCCCAAAC

TCTGCCTGGTGTGCTCTGATGAAGCTTCAGGATGTCATTATGGAGTCTTAACTTGTGGAAGCTGTAAAGT

TTTCTTCAAAAGAGCAGTGGAAGGTAGACAGCACAATTACCTATGTGCTGGAAGGAATGATTGCATCATC

GATAAAATTCGAAGAAAAAACTGCCCAGCATGCCGCTATCGAAAATGTCTTCAGGCTGGAATGAACCTGG

AAGCTCGAAAAACAAAGAAAAAAATAAAAGGAATTCAGCAGGCCACTACAGGAGTCTCACAAGAAACCTC

TGAAAATCCTGGTAACAAAACAATAGTTCCTGCAACGTTACCACAACTCACCCCTACCCTGGTGTCACTG

TTGGAGGTTATTGAACCTGAAGTGTTATATGCAGGATATGATAGCTCTGTTCCAGACTCAACTTGGAGGA

TCATGACTACGCTCAACATGTTAGGAGGGCGGCAAGTGATTGCAGCAGTGAAATGGGCAAAGGCAATACC

AGGTTTCAGGAACTTACACCTGGATGACCAAATGACCCTACTGCAGTACTCCTGGATGTTTCTTATGGCA

TTTGCTCTGGGGTGGAGATCATATAGACAATCAAGTGCAAACCTGCTGTGTTTTGCTCCTGATCTGATTA

TTAATGAGCAGAGAATGACTCTACCCTGCATGTACGACCAATGTAAACACATGCTGTATGTTTCCTCTGA

GTTACACAGGCTTCAGGTATCTTATGAAGAGTATCTCTGTATGAAAACCTTACTGCTTCTCTCTTCAGTT

CCTAAGGACGGTCTGAAGAGCCAAGAGCTATTTGATGAAATTAGAATGACCTACATCAAAGAGCTAGGAA

AAGCCATTGTCAAGAGGGAAGGAAACTCCAGCCAGAACTGGCAGCGGTTTTATCAACTGACAAAACTCTT

GGATTCTATGCATGAAGTGGTTGAAAATCTCCTTAACTATTGCTTCCAAACATTTTTGGATAAGACCATG

-continued

AGTATTGAATTCCCCGAGATGTTAGCTGAAATCATCACCAATCAGATACCAAAATATTCAAATGGAAATA
TCAAAAAACTTCTGTTTCATCAAAAGTGACTGCCTTAATAAGAATGGTTGCCTTAAAGAAAGTCGAATTA
ATAGCTTTTATTGTATAAACTATCAGTTTGTCCTGTAGAGGTTTTGTTGTTTTATTTTTTATTGTTTTCA
TCTGTTGTTTTGTTTTAAATACGCACTACATGTGGTTTATAGAGGGCCAAGACTTGGCAACAGAAGCAGT
TGAGTCGTCATCACTTTTCAGTGATGGGAGAGTAGATGGTGAAATTTATTAGTTAATATATCCCAGAAAT
TAGAAACCTTAATATGTGGACGTAATCTCCACAGTCAAAGAAGGATGGCACCTAAACCACCAGTGCCCAA
AGTCTGTGTGATGAACTTTCTCTTCATACTTTTTTTCACAGTTGGCTGGATGAAATTTTCTAGACTTTCT
GTTGGTGTATCCCCCCCCTGTATAGTTAGGATAGCATTTTTGATTTATGCATGGAAACCTGAAAAAAAGT
TTACAAGTGTATATCAGAAAAGGGAAGTTGTGCCTTTTATAGCTATTACTGTCTGGTTTTAACAATTTCC
TTTATATTTAGTGAACTACGCTTGCTCATTTTTTCTTACATAATTTTTTATTCAAGTTATTGTACAGCTG
TTTAAGATGGGCAGCTAGTTCGTAGCTTTCCCAAATAAACTCTAAACATTAATCAATCATCTGTGTGAAA
ATGGGTTGGTGCTTCTAACCTGATGGCACTTAGCTATCAGAAGACCACAAAAATTGACTCAAATCTCCAG
TATTCTTGTCAAAAAAAAAAAAAAAAAAAGCTCATATTTTGTATATATCTGCTTCAGTGGAGAATTATATA
GGTTGTGCAAATTAACAGTCCTAACTGGTATAGAGCACCTAGTCCAGTGACCTGCTGGGTAAACTGTGGA
TGATGGTTGCAAAAGACTAATTTAAAAAATAACTACCAAGAGGCCCTGTCTGTACCTAACGCCCTATTTT
TGCAATGGCTATATGGCAAGAAAGCTGGTAAACTATTTGTCTTTCAGGACCTTTTGAAGTAGTTTGTATA
ACTTCTTAAAAGTTGTGATTCCAGATAACCAGCTGTAACACAGCTGAGAGACTTTTAATCAGACAAAGTA
ATTCCTCTCACTAAACTTTACCCAAAAACTAAATCTCTAATATGGCAAAAATGGCTAGACACCCATTTTC
ACATTCCCATCTGTCACCAATTGGTTAATCTTTCCTGATGGTACAGGAAAGCTCAGCTACTGATTTTTGT
GATTTAGAACTGTATGTCAGACATCCATGTTTGTAAAACTACACATCCCTAATGTGTGCCATAGAGTTTA
ACACAAGTCCTGTGAATTTCTTCACTGTTGAAAATTATTTAAACAAAATAGAAGCTGTAGTAGCCCTTT
CTGTGTGCACCTTACCAACTTTCTGTAAACTCAAAACTTAACATATTTACTAAGCCACAAGAAATTTGAT
TTCTATTCAAGGTGGCCAAATTATTTGTGTAATAGAAAACTGAAAATCTAATATTAAAAATATGGAACTT
CTAATATATTTTTATATTTAGTTATAGTTTCAGATATATATCATATTGGTATTCACTAATCTGGGAAGGG
AAGGGCTACTGCAGCTTTACATGCAATTTATTAAAATGATTGTAAAATAGCTTGTATAGTGTAAAATAAG
AATGATTTTTAGATGAGATTGTTTTATCATGACATGTTATATATTTTTTGTAGGGGTCAAAGAAATGCTG
ATGGATAACCTATATGATTTATAGTTTGTACATGCATTCATACAGGCAGCGATGGTCTCAGAAACCAAAC
AGTTTGCTCTAGGGGAAGAGGGAGATGGAGACTGGTCCTGTGTGCAGTGAAGGTTGCTGAGGCTCTGACC
CAGTGAGATTACAGAGGAAGTTATCCTCTGCCTCCCATTCTGACCACCCTTCTCATTCCAACAGTGAGTC
TGTCAGCGCAGGTTTAGTTTACTCAATCTCCCCTTGCACTAAAGTATGTAAAGTATGTAAACAGGAGACA
GGAAGGTGGTGCTTACATCCTTAAAGGCACCATCTAATAGCGGGTTACTTTCACATACAGCCCTCCCCCA
GCAGTTGAATGACAACAGAAGCTTCAGAAGTTTGGCAATAGTTTGCATAGAGGTACCAGCAATATGTAAA
TAGTGCAGAATCTCATAGGTTGCCAATAATACACTAATTCCTTTCTATCCTACAACAAGAGTTTATTTCC
AAATAAAATGAGGACATGTTTTTGTTTTCTTTGAATGCTTTTTGAATGTTATTTGTTATTTTCAGTATTT
TGGAGAAATTATTTAATAAAAAAACAATCATTTGCTTTTTGAATGCTCTCTAAAAGGGAATGTAATATTT
TAAGATGGTGTGTAACCCGGCTGGATAAATTTTTGGTGCCTAAGAAAACTGCTTGAATATTCTTATCAAT
GACAGTGTTAAGTTTCAAAAAGAGCTTCTAAAACGTAGATTATCATTCCTTTATAGAATGTTATGTGGTT
AAAACCAGAAAGCACATCTCACACATTAATCTGATTTTCATCCCAACAATCTTGGCGCTCAAAAAATAGA
ACTCAATGAGAAAAAGAAGATTATGTGCACTTCGTTGTCAATAATAAGTCAACTGATGCTCATCGACAAC
TATAGGAGGCTTTTCATTAAATGGGAAAAGAAGCTGTGCCCTTTTAGGATACGTGGGGGAAAAGAAAGTC

-continued

ATCTTAATTATGTTTAATTGTGGATTTAAGTGCTATATGGTGGTGCTGTTTGAAAGCAGATTTATTTCCT

ATGTATGTGTTATCTGGCCATCCCAACCCAAACTGTTGAAGTTTGTAGTAACTTCAGTGAGAGTTGGTTA

CTCACAACAAATCCTGAAAAGTATTTTTAGTGTTTGTAGGTATTCTGTGGGATACTATACAAGCAGAACT

GAGGCACTTAGGACATAACACTTTTGGGGTATATATATCCAAATGCCTAAAACTATGGGAGGAAACCTTG

GCCACCCCAAAAGGAAAACTAACATGATTTGTGTCTATGAAGTGCTGGATAATTAGCATGGGATGAGCTC

TGGGCATGCCATGAAGGAAAGCCACGCTCCCTTCAGAATTCAGAGGCAGGGAGCAATTCCAGTTTCACCT

AAGTCTCATAATTTTAGTTCCCTTTTAAAAACCCTGAAAACTACATCACCATGGAATGAAAAATATTGTT

ATACAATACATTGATCTGTCAAACTTCCAGAACCATGGTAGCCTTCAGTGAGATTTCCATCTTGGCTGGT

CACTCCCTGACTGTAGCTGTAGGTGAATGTGTTTTTGTGTGTGTGTGTCTGGTTTTAGTGTCAGAAGGGA

AATAAAAGTGTAAGGAGGACACTTTAAACCCTTTGGGTGGAGTTTCGTAATTTCCCAGACTATTTTCAAG

CAACCTGGTCCACCCAGGATTAGTGACCAGGTTTTCAGGAAAGGATTTGCTTCTCTCTAGAAAATGTCTG

AAAGGATTTTATTTTCTGATGAAAGGCTGTATGAAAATACCCTCCTCAAATAACTTGCTTAACTACATAT

AGATTCAAGTGTGTCAATATTCTATTTTGTATATTAAATGCTATATAATGGGGACAAATCTATATTATAC

TGTGTATGGCATTATTAAGAAGCTTTTTCATTATTTTTTATCACAGTAATTTTAAAATGTGTAAAAATTA

AAACCAGTGACTCCTGTTTAAAAATAAAAGTTGTAGTTTTTTATTCATGCTGAATAATAATCTGTAGTTA

AAAAAAAAGTGTCTTTTTACCTACGCAGTGAAATGTCAGACTGTAAAACCTTGTGTGGAAATGTTTAACT

TTTATTTTTTCATTTAAATTTGCTGTTCTGGTATTACCAAACCACACATTTGTACCGAATTGGCAGTAAA

TGTTAGCCATTTACAGCAATGCCAAATATGGAGAAACATCATAATAAAAAAATCTGCTTTTTCATTA

Human GR Transcript Variant 8 mRNA Sequence (NCBI Reference Sequence: NM_001204265.1)

SEQ ID NO: 21

GGCGCCGCCTCCACCCGCTCCCCGCTCGGTCCCGCTCGCTCGCCCAGGCCGGGCTGCCCTTTCGCGTGTC

CGCGCTCTCTTCCCTCCGCCGCCGCCTCCTCCATTTTGCGAGCTCGTGTCTGTGACGGGAGCCCGAGTCA

CCGCCTGCCCGTCGGGGACGGATTCTGTGGGTGGAAGGAGACGCCGCAGCCGGAGCGGCCGAAGCAGCTG

GGACCGGGACGGGGCACGCGCGCCCGGAACCTCGACCCGCGGAGCCCGGCGCGGGGCGGAGGGCTGGCTT

GTCAGCTGGGCAATGGGAGACTTTCTTAAATAGGGGCTCTCCCCCCACCCATGGAGAAAGGGGCGGCTGT

TTACTTCCTTTTTTTAGAAAAAAAAAATATATTTCCCTCCTGCTCCTTCTGCGTTCACAAGCTAAGTTGT

TTATCTCGGCTGCGGCGGGAACTGCGGACGGTGGCGGGCGAGCGGCTCCTCTGCCAGAGTTGATATTCAC

TGATGGACTCCARAGAATCATTAACTCCTGGTAGAGAAGAAAACCCCAGCAGTGTGCTTGCTCAGGAGAG

GGGAGATGTGATGGACTTCTATAAAACCCTAAGAGGAGGAGCTACTGTGAAGGTTTCTGCGTCTTCACCC

TCACTGGCTGTCGCTTCTCAATCAGACTCCAAGCAGCGAAGACTTTTGGTTGATTTTCCAAAAGGCTCAG

TAAGCAATGCGCAGCAGCCAGATCTGTCCAAAGCAGTTTCACTCTCAATGGGACTGTATATGGGAGAGAC

AGAAACAAAAGTGATGGGAAATGACCTGGGATTCCCACAGCAGGGCCAAATCAGCCTTTCCTCGGGGGAA

ACAGACTTAAAGCTTTTGGAAGAAAGCATTGCAAACCTCAATAGGTCGACCAGTGTTCCAGAGAACCCCA

AGAGTTCAGCATCCACTGCTGTGTCTGCTGCCCCCACAGAGAAGGAGTTTCCAAAAACTCACTCTGATGT

ATCTTCAGAACAGCAACATTTGAAGGGCCAGACTGGCACCAACGGTGGCAATGTGAAATTGTATACCACA

GACCAAAGCACCTTTGACATTTTGCAGGATTTGGAGTTTTCTTCTGGGTCCCCAGGTAAAGAGACGAATG

AGAGTCCTTGGAGATCAGACCTGTTGATAGATGAAAACTGTTTGCTTTCTCCTCTGGCGGGAGAAGACGA

TTCATTCCTTTTGGAAGGAAACTCGAATGAGGACTGCAAGCCTCTCATTTTACCGGACACTAAACCCAAA

ATTAAGGATAATGGAGATCTGGTTTTGTCAAGCCCCAGTAATGTAACACTGCCCCAAGTGAAAACAGAAA

AAGAAGATTTCATCGAACTCTGCACCCCTGGGGTAATTAAGCAAGAGAAACTGGGCACAGTTTACTGTCA

GGCAAGCTTTCCTGGAGCAAATATAATTGGTAATAAAATGTCTGCCATTTCTGTTCATGGTGTGAGTACC

-continued

TCTGGAGGACAGATGTACCACTATGACATGAATACAGCATCCCTTTCTCAACAGCAGGATCAGAAGCCTA

TTTTTAATGTCATTCCACCAATTCCCGTTGGTTCCGAAAATTGGAATAGGTGCCAAGGATCTGGAGATGA

CAACTTGACTTCTCTGGGGACTCTGAACTTCCCTGGTCGAACAGTTTTTTCTAATGGCTATTCAAGCCCC

AGCATGAGACCAGATGTAAGCTCTCCTCCATCCAGCTCCTCAACAGCAACAACAGGACCACCTCCCAAAC

TCTGCCTGGTGTGCTCTGATGAAGCTTCAGGATGTCATTATGGAGTCTTAACTTGTGGAAGCTGTAAAGT

TTTCTTCAAAAGAGCAGTGGAAGGACAGCACAATTACCTATGTGCTGGAAGGAATGATTGCATCATCGAT

AAAATTCGAAGAAAAAACTGCCCAGCATGCCGCTATCGAAAATGTCTTCAGGCTGGAATGAACCTGGAAG

CTCGAAAAACAAAGAAAAAAATAAAAGGAATTCAGCAGGCCACTACAGGAGTCTCACAAGAAACCTCTGA

AAATCCTGGTAACAAAACAATAGTTCCTGCAACGTTACCACAACTCACCCCTACCCTGGTGTCACTGTTG

GAGGTTATTGAACCTGAAGTGTTATATGCAGGATATGATAGCTCTGTTCCAGACTCAACTTGGAGGATCA

TGACTACGCTCAACATGTTAGGAGGGCGGCAAGTGATTGCAGCAGTGAAATGGGCAAAGGCAATACCAGG

TTTCAGGAACTTACACCTGGATGACCAAATGACCCTACTGCAGTACTCCTGGATGTTTCTTATGGCATTT

GCTCTGGGGTGGAGATCATATAGACAATCAAGTGCAAACCTGCTGTGTTTTGCTCCTGATCTGATTATTA

ATGAGCAGAGAATGACTCTACCCTGCATGTACGACCAATGTAAACACATGCTGTATGTTTCCTCTGAGTT

ACACAGGCTTCAGGTATCTTATGAAGAGTATCTCTGTATGAAAACCTTACTGCTTCTCTCTTCAGGTTGG

TAGAACACCTTTTCACCTTATGTCAAAAGCATGAAATATGAAGGCCTAGAAACAAAGGTTAATTTATATA

CATAGTACTAATAATTATACCAAGTCTACTATTATTTCCTACTAGTCAGATGATTTTTATGAATGTAAAA

TATTAGAAAGGCACAGTAAGTGACACCAAGATTAATAAGACAAATAGGTATGGCAGAAACAGAGAGGTAT

ATGAGCTGCATAGGGATCTCTGTTGATAAGAATCTGTGTAGACTTTTTTCTCCTTCCTTCCTTTGATCTT

TGATCATGGGAAGACATGGAAAAAGAAAGCTAACTACAGTGATTTTGTCCACTACACTGTTATTTGGTTA

AAAATTTTAGTTTCCTAATGAGTATTAGCATGTATGAGAAATTATGGGAGAAAAAGGCGCATCCTAGAAA

AGGTGTGCTTAATTACTATTGGGGATTGGTTAACATAGCATGGGAGCTGGATTGTCAGAGATTCATTATC

TAGAAAATGGCAACAAGAGTTTATARAACGAACTTCTGTGAGATTACTTTTTAGCTAGCAAAGACAAAGA

TGTCCTTCAGTAGGTGAAGTGATAAACTATGATACATCCAGATGATGGAATACTATTGAGGACTAAAAAG

AAATAAGCTGTCAAGCCATGAAAACACATGGAGGGACGTTAAATGCATATTACTAAGTGAAAAAAGCTAA

TCTGAAAGGGCTACATACTGTGTGATTCTAACTATATAACATTCCATAAAAGGCAAAACTGTGAAGACAG

CAAAAAAAAATCAGCGGTTGCCAGGGTTTAGAAGGAAGGGAGGGATAAATGTGCAGAGCACAGAGGATTT

TTAGGGCAGTGAAAATACTTCGTATGATACTACAATGGTGGAAACATGTCATTATACATTTATCCAAACC

CAAAGAATGTCCACCACCAAGAGTGAACCCTCAACTATGGACTTTGGGTGATGATGTGTGGGACAGGAGG

TATATGAAAAATCTCTGTACCTTCCTCCCAATTTTGCTGTGAACTTAAAACTGCTCTAAAAAAAGTCTTT

TTTAAAAAAAGCTCTATGAACTAGTTGGTATTATAAACCTTAGGCCATTTCAAGTAAAAATTACATATCA

ATGTTTATTAAATACTGAGTTAATAGCTGAATACCTCTTTCATATACAAATAAGTACATTTGCAATTTTT

TAAAAAGTCTTAATTCCATTAGTAACTGTGGTTTCATAGTTGCCAAATAACTGTAAGCTATGGATGTTGC

ACAAGACTGTGATTTTATTTAATCATTTCATATCTATTTAAACATTTCCAAAGCGCACATTCATCTTAAT

GTTTTCACACTATTTTTGCTCAACAAAAAGTTATTTTATGTTAATGGATATAAGAAGTATTAATAATATT

TCAGTCAAGGCAAGAGAACCCGATAAAGATCATTGCTAGAGACGTTTAATGTTACCTGTAGCGGTACACT

TGTTAAAGAAGTGATTAAGCAGTTACATAAAATTCTGATCATAGCTTTGATTGATACCATGAAGGTATAA

TTCAGTGCCTGGATACTAACAACTTTACTTGTTTAAAAAAAAAA

-continued

Human serine/threonine-protein kinase Sgk1 isoform 1 Protein Sequence (NCBI Reference Sequence: NP_005618.2)

SEQ ID NO: 22

MTVKTEAAKGTLTYSRMRGMVAILIAFMKQRRMGLNDFIQKIANNSYACKHPEVQSILKISQPQEPELMN

ANPSPPPSPSQQINLGPSSNPHAKPSDFHFLKVIGKGSFGKVLLARHKAEEVFYAVKVLQKKAILKKKEE

KHIMSERNVLLKNVKHPFLVGLHFSFQTADKLYFVLDYINGGELFYHLQRERCFLEPRARFYAAEIASAL

GYLHSLNIVYRDLKPENILLDSQGHIVLTDFGLCKENIEHNSTTSTFCGTPEYLAPEVLHKQPYDRTVDW

WCLGAVLYEMLYGLPPFYSRNTAEMYDNILNKPLQLKPNITNSARHLLEGLLQKDRTKRLGAKDDFMEIK

SHVFFSLINWDDLINKKITPPFNPNVSGPNDLRHFDPEFTEEPVPNSIGKSPDSVLVTASVKEAAEAFLG

FSYAPPTDSFL

Human serine/threonine-protein kinase Sgk1 isoform 2 Protein Sequence (NCBI Reference Sequence: NP_001137148.1)

SEQ ID NO: 23

MVNKDMNGFPVKKCSAFQFFKKRVRRWIKSPMVSVDKHQSPSLKYTGSSMVHIPPGEPDFESSLCQTCLG

EHAFQRGVLPQENESCSWETQSGCEVREPCNHANILTKPDPRTFWTNDDPAFMKQRRMGLNDFIQKIANN

SYACKHPEVQSILKISQPQEPELMNANPSPPPSPSQQINLGPSSNPHAKPSDFHFLKVIGKGSFGKVLLA

RHKAEEVFYAVKVLQKKAILKKKEEKHIMSERNVLLKNVKHPFLVGLHFSFQTADKLYFVLDYINGGELF

YHLQRERCFLEPRARFYAAEIASALGYLHSLNIVYRDLKPENILLDSQGHIVLTDFGLCKENIEHNSTTS

TFCGTPEYLAPEVLHKQPYDRTVDWWCLGAVLYEMLYGLPPFYSRNTAEMYDNILNKPLQLKPNITNSAR

HLLEGLLQKDRTKRLGAKDDFMEIKSHVFFSLINWDDLINKKITPPFNPNVSGPNDLRHFDPEFTEEPVP

NSIGKSPDSVLVTASVKEAAEAFLGFSYAPPTDSFL

Human serine/threonine-protein kinase Sgk1 isoform 3 Protein Sequence (NCBI Reference Sequence: NP_001137149.1)

SEQ ID NO: 24

MSSQSSSLSEACSREAYSSHNWALPPASRSNPQPAYPWATRRMKEEAIKPPLKAFMKQRRMGLNDFIQKI

ANNSYACKHPEVQSILKISQPQEPELMNANPSPPPSPSQQINLGPSSNPHAKPSDFHELKVIGKGSFGKV

LLARHKAEEVFYAVKVLQKKAILKKKEEKHIMSERNVLLKNVKHPFLVGLHFSFQTADKLYFVLDYINGG

ELFYHLQRERCFLEPRARFYAAEIASALGYLHSLNIVYRDLKPENILLDSQGHIVLTDFGLCKENIEHNS

TTSTFCGTPEYLAPEVLHKQPYDRTVDWWCLGAVLYEMLYGLPPFYSRNTAEMYDNILNKPLQLKPNITN

SARHLLEGLLQKDRTKRLGAKDDFMEIKSHVFFSLINWDDLINKKITPPFNPNVSGPNDLRHFDPEFTEE

PVPNSIGKSPDSVLVTASVKEAAEAFLGFSYAPPTDSFL

Human serine/threonine-protein kinase Sgk1 isoform 4 Protein Sequence (NCBI Reference Sequence: NP_001137150.1)

SEQ ID NO: 25

MGEMQGALARARLESLLRPRHKKRAEAQKRSESFLLSGLAFMKQRRMGLNDFIQKIANNSYACKHPEVQS

ILKISQPQEPELMNANPSPPPSPSQQINLGPSSNPHAKPSDFHFLKVIGKGSFGKVLLARHKAEEVFYAV

KVLQKKAILKKKEEKHIMSERNVLLKNVKHPFLVGLHFSFQTADKLYFVLDYINGGELFYHLQRERCFLE

PRARFYAAEIASALGYLHSLNIVYRDLKPENILLDSQGHIVLTDFGLCKENIEHNSTTSTFCGTPEYLAP

EVLHKQPYDRTVDWWCLGAVLYEMLYGLPPFYSRNTAEMYDNILNKPLQLKPNITNSARHLLEGLLQKDR

TKRLGAKDDFMEIKSHVFFSLINWDDLINKKITPPFNPNVSGPNDLRHFDPEFTEEPVPNSIGKSPDSVL

VTASVKEAAEAFLGFSYAPPTDSFL

Human SGK1 Transcript Variant 1 mRNA Sequence (NCBI Reference Sequence: NM_005627.3)

SEQ ID NO: 26

TTTTTTATAAGGCCGAGCGCGCGGCCTGGCGCAGCATACGCCGAGCCGGTCTTTGAGCGCTAACGTCTTT

CTGTCTCCCCGCGGTGGTGATGACGGTGAAAACTGAGGCTGCTAAGGGCACCCTCACTTACTCCAGGATG

AGGGGCATGGTGGCAATTCTCATCGCTTTCATGAAGCAGAGGAGGATGGGTCTGAACGACTTTATTCAGA

AGATTGCCAATAACTCCTATGCATGCAAACACCCTGAAGTTCAGTCCATCTTGAAGATCTCCCAACCTCA

-continued

```
GGAGCCTGAGCTTATGAATGCCAACCCTTCTCCTCCACCAAGTCCTTCTCAGCAAATCAACCTTGGCCCG

TCGTCCAATCCTCATGCTAAACCATCTGACTTTCACTTCTTGAAAGTGATCGGAAAGGGCAGTTTTGGAA

AGGTTCTTCTAGCAAGACACAAGGCAGAAGAAGTGTTCTATGCAGTCAAAGTTTTACAGAAGAAAGCAAT

CCTGAAAAAGAAAGAGGAGAAGCATATTATGTCGGAGCGGAATGTTCTGTTGAAGAATGTGAAGCACCCT

TTCCTGGTGGGCCTTCACTTCTCTTTCCAGACTGCTGACAAATTGTACTTTGTCCTAGACTACATTAATG

GTGGAGAGTTGTTCTACCATCTCCAGAGGGAACGCTGCTTCCTGGAACCACGGGCTCGTTTCTATGCTGC

TGAAATAGCCAGTGCCTTGGGCTACCTGCATTCACTGAACATCGTTTATAGAGACTTAAAACCAGAGAAT

ATTTTGCTAGATTCACAGGGACACATTGTCCTTACTGACTTCGGACTCTGCAAGGAGAACATTGAACACA

ACAGCACAACATCCACCTTCTGTGGCACGCCGGAGTATCTCGCACCTGAGGTGCTTCATAAGCAGCCTTA

TGACAGGACTGTGGACTGGTGGTGCCTGGGAGCTGTCTTGTATGAGATGCTGTATGGCCTGCCGCCTTTT

TATAGCCGAAACACAGCTGAAATGTACGACAACATTCTGAACAAGCCTCTCCAGCTGAAACCAAATATTA

CAAATTCCGCAAGACACCTCCTGGAGGGCCTCCTGCAGAAGGACAGGACAAAGCGGCTCGGGGCCAAGGA

TGACTTCATGGAGATTAAGAGTCATGTCTTCTTCTCCTTAATTAACTGGGATGATCTCATTAATAAGAAG

ATTACTCCCCCTTTTAACCCAAATGTGAGTGGGCCCAACGACCTACGGCACTTTGACCCCGAGTTTACCG

AAGAGCCTGTCCCCAACTCCATTGGCAAGTCCCCTGACAGCGTCCTCGTCACAGCCAGCGTCAAGGAAGC

TGCCGAGGCTTTCCTAGGCTTTTCCTATGCGCCTCCCACGGACTCTTTCCTCTGAACCCTGTTAGGGCTT

GGTTTTAAAGGATTTTATGTGTGTTTCCGAATGTTTTAGTTAGCCTTTTGGTGGAGCCGCCAGCTGACAG

GACATCTTACAAGAGAATTTGCACATCTCTGGAAGCTTAGCAATCTTATTGCACACTGTTCGCTGGAAGC

TTTTTGAAGAGCACATTCTCCTCAGTGAGCTCATGAGGTTTTCATTTTTATTCTTCCTTCCAACGTGGTG

CTATCTCTGAAACGAGCGTTAGAGTGCCGCCTTAGACGGAGGCAGGAGTTTCGTTAGAAAGCGGACGCTG

TTCTAAAAAAGGTCTCCTGCAGATCTGTCTGGGCTGTGATGACGTATATTATGAAATGTGCCTTTTCTGA

AGAGATTGTGTTAGCTCCAAAGCTTTTCCTATCGCAGTGTTTCAGTTCTTTATTTTCCCTTGTGGATATG

CTGTGTGAACCGTCGTGTGAGTGTGGTATGCCTGATCACAGATGGATTTTGTTATAAGCATCAATGTGAC

ACTTGCAGGACACTACAACGTGGGACATTGTTTGTTTCTTCCATATTTGGAAGATAAATTTATGTGTAGA

CTTTTTTGTAAGATACGGTTAATAACTAAAATTTATTGAAATGGTCTTGCAATGACTCGTATTCAGATGC

TTAAAGAAAGCATTGCTGCTACAAATATTTCTATTTTTAGAAAGGGTTTTTATGGACCAATGCCCCAGTT

GTCAGTCAGAGCCGTTGGTGTTTTTCATTGTTTAAAATGTCACCTGTAAAATGGGCATTATTTATGTTTT

TTTTTTTGCATTCCTGATAATTGTATGTATTGTATAAAGAACGTCTGTACATTGGGTTATAACACTAGTA

TATTTAAACTTACAGGCTTATTTGTAATGTAAACCACCATTTTAATGTACTGTAATTAACATGGTTATAA

TACGTACAATCCTTCCCTCATCCCATCACACAACTTTTTTTGTGTGTGATAAACTGATTTTGGTTTGCAA

TAAAACCTTGAAAAATATTTACATATAAAAAAAA
```

Human SGK1 Transcript Variant 2 mRNA Sequence (NCBI Reference Sequence: NM_001143676.1)

SEQ ID NO: 27

```
AGATATTCATGAACCGTTGCTTCTTCCAGCCTCGCCTTCTCGCTCCCTCTGCCTTTCTGGCGCTGTTCTC

CCTCCCTCCCTCTGGCTTCTGCTCTTTCTTACTCCTTCTCTCAGCTGCTTAACTACAGCTCCCACTGGAA

CTTGCACAATCAAAAACAACTCTCCTCTCTCAAGCCGCCTCCAGGAGCGCATCACCTGGAGAAGAGCGAC

TCGCTCCCCGCGCCGGCCGCGGAAGAGCTGCCAGGTAGCTGGGGGCGGGGAGGCGTACCCTTCTCCCGCT

CGGTAAGAGCCACAGCATCTCCCCGGAGATTGGCCGTATCCCACCGTCCGGCCCCCAGGGTCCTGCAGCG

GTGATGCATATGTTTCGGAGCAATGATGGAAGGAGAAAAGCCGCTGTCGGTGGCAACTGAAAGTGGGGAG

AGGTTGCTGCAGTAGCTGGTGCTGCAGAATGCGCGAGTGAAGAACTGAGCCCCGCTAGATTCTCCATCCC

GCTCAGTCTTCATTAACTGTCTGCAGGAGGTAAACCGGGGAAACAGATATGCACTAACCAGGCGGGTGCC
```

-continued

AACCTGGATCTATAACTGTGAATTCCCCACGGTGGAAAATGGTAAACAAAGACATGAATGGATTCCCAGT

CAAGAAATGCTCAGCCTTCCAATTTTTTTAGAAGCGGGTACGAAGGTGGATCAAGAGCCCAATGGTCAGT

GTGGACAAGCATCAGAGTCCCAGCCTGAAGTACACCGGCTCCTCCATGGTGCACATCCCTCCAGGGGAGC

CAGACTTCGAGTCTTCCTTGTGTCAAACATGCCTGGGTGAACATGCTTTCCAAAGAGGGGTTCTCCCTCA

GGAGAACGAGTCATGTTCATGGGAAACTCAATCTGGGTGTGAAGTGAGAGAGCCATGTAATCATGCCAAC

ATCCTGACCAAGCCCGATCCAAGAACCTTCTGGACTAATGATGATCCAGCTTTCATGAAGCAGAGGAGGA

TGGGTCTGAACGACTTTATTCAGAAGATTGCCAATAACTCCTATGCATGCAAACACCCTGAAGTTCAGTC

CATCTTGAAGATCTCCCAACCTCAGGAGCCTGAGCTTATGAATGCCAACCCTTCTCCTCCACCAAGTCCT

TCTCAGCAAATCAACCTTGGCCCGTCGTCCAATCCTCATGCTAAACCATCTGACTTTCACTTCTTGAAAG

TGATCGGAAAGGGCAGTTTTGGAAAGGTTCTTCTAGCAAGACACAAGGCAGAAGAAGTGTTCTATGCAGT

CAAAGTTTTACAGAAGAAAGCAATCCTGAAAAAGAAAGAGGAGAAGCATATTATGTCGGAGCGGAATGTT

CTGTTGAAGAATGTGAAGCACCCTTTCCTGGTGGGCCTTCACTCCTCTTTCCAGACTGCTGACAAATTGT

ACTTTGTCCTAGACTACATTAATGGTGGAGAGTTGTTCTACCATCTCCAGAGGGAACGCTGCTTCCTGGA

ACCACGGGCTCGTTTCTATGCTGCTGAAATAGCCAGTGCCTTGGGCTACCTGCATTCACTGAACATCGTT

TATAGAGACTTAAAACCAGAGAATATTTTGCTAGATTCACAGGGACACATTGTCCTTACTGACTTCGGAC

TCTGCAAGGAGAACATTGAACACAACAGCACAACATCCACCTTCTGTGGCACGCCGGAGTATCTCGCACC

TGAGGTGCTTCATAAGCAGCCTTATGACAGGACTGTGGACTGGTGGTGCCTGGGAGCTGTCTTGTATGAG

ATGCTGTATGGCCTGCCGCCTTTTTATAGCCGAAACACAGCTGAAATGTACGACAACATTCTGAACAAGC

CTCTCCAGCTGAAACCAAATATTACAAATTCCGCAAGACACCTCCTGGAGGGCCTCCTGCAGAAGGACAG

GACAAAGCGGCTCGGGGCCAAGGATGACTTCATGGAGATTAAGAGTCATGTCTTCTTCTCCTTAATTAAC

TGGGATGATCTCATTAATAAGAAGATTACTCCCCCTTTTAACCCAAATGTGAGTGGGCCCAACGACCTAC

GGCACTTTGACCCCGAGTTTACCGAAGAGCCTGTCCCCAACTCCATTGGCAAGTCCCCTGACAGCGTCCT

CGTCACAGCCAGCGTCAAGGAAGCTGCCGAGGCTTTCCTAGGCTTTTCCTATGCGCCTCCCACGGACTCT

TTCCTCTGAACCCTGTTAGGGCTTGGTTTTAAAGGATTTTATGTGTGTTTCCGAATGTTTTAGTTAGCCT

TTTGGTGGAGCCGCCAGCTGACAGGACATCTTACAAGAGAATTTGCACATCTCTGGAAGCTTAGCAATCT

TATTGCACACTGTTCGCTGGAAGCTTTTTGAAGAGCACATTCTCCTCAGTGAGCTCATGAGGTTTTCATT

TTTATTCTTCCTTCCAACGTGGTGCTATCTCTGAAACGAGCGTTAGAGTGCCGCCTTAGACGGAGGCAGG

AGTTTCGTTAGAAAGCGGACGCTGTTCTAAAAAAGGTCTCCTGCAGATCTGTCTGGGCTGTGATGACGAA

TATTATGAAATGTGCCTTTTCTGAAGAGATTGTGTTAGCTCCAAAGCTTTTCCTATCGCAGTGTTTCAGT

TCTTTATTTTCCCTTGTGGATATGCTGTGTGAACCGTCGTGTGAGTGTGGTATGCCTGATCACAGATGGA

TTTTGTTATAAGCATCAATGTGACACTTGCAGGACACTACAACGTGGGACATTGTTTGTTTCTTCCATAT

TTGGAAGATAAATTTATGTGTAGACTTTTTTGTAAGATACGGTTAATAACTAAAATTTATTGAAATGGTC

TTGCAATGACTCGTATTCAGATGCTTAAAGAAAGCATTGCTGCTACAAATATTTCTATTTTTAGAAAGGG

TTTTTATGGACCAATGCCCCAGTTGTCAGTCAGAGCCGTTGGTGTTTTTCATTGTTTAAAATGTCACCTG

TAAAATGGGCATTATTTATGTTTTTTTTTTTGCATTCCTGATAATTGTATGTATTGTATAAAGAACGTCT

GTACATTGGGTTATAACACTAGTATATTTAAACTTACAGGCTTATTTGTAATGTAAACCACCATTTTAAT

GTACTGTAATTAACATGGTTATAATACGTACAATCCTTCCCTCATCCCATCACACAACTTTTTTTGTGTG

TGATAAACTGATTTTGGTTTGCAATAAAACCTTGAAAAATATTTACATATAAAAAAA

-continued

Human SGK1 Transcript Variant 3 mRNA Sequence (NCBI Reference Sequence: NM001143677.1)

SEQ ID NO: 28

AAGTGGGGTTCATAACAGAACAGGGATAGCCGTCTCTGGCTCGTGCTCTCATGTCATCTCAGAGTTCCAG

CTTATCAGAGGCATGTAGCAGGGAGGCTTATTCCAGCCATAACTGGGCTCTACCTCCAGCCTCCAGAAGT

AATCCCCAACCTGCATATCCTTGGGCAACCCGAAGAATGAAAGAAGAAGCTATAAAACCCCCTTTGAAAG

CTTTCATGAAGCAGAGGAGGATGGGTCTGAACGACTTTATTCAGAAGATTGCCAATAACTCCTATGCATG

CAAACACCCTGAAGTTCAGTCCATCTTGAAGATCTCCCAACCTCAGGAGCCTGAGCTTATGAATGCCAAC

CCTTCTCCTCCACCAAGTCCTTCTCAGCAAATCAACCTTGGCCCGTCGTCCAATCCTCATGCTAAACCAT

CTGACTTTCACTTCTTGAAAGTGATCGGAAAGGGCAGTTTTGGAAAGGTTCTTCTAGCAAGACACAAGGC

AGAAGAAGTGTTCTATGCAGTCAAAGTTTTACAGAAGAAAGCAATCCTGAAAAAGAAAGAGGAGAAGCAT

ATTATGTCGGAGCGGAATGTTCTGTTGAAGAATGTGAAGCACCCTTTCCTGGTGGGCCTTCACTTCTCTT

TCCAGACTGCTGACAAATTGTACTTTGTCCTAGACTACATTAATGGTGGAGAGTTGTTCTACCATCTCCA

GAGGGAACGCTGCTTCCTGGAACCACGGGCTCGTTTCTATGCTGCTGAAATAGCCAGTGCCTTGGGCTAC

CTGCATTCACTGAACATCGTTTATAGAGACTTAAAACCAGAGAATATTTTGCTAGATTCACAGGGACACA

TTGTCCTTACTGACTTCGGACTCTGCAAGGAGAACATTGAACACAACAGCACAACATCCACCTTCTGTGG

CACGCCGGAGTATCTCGCACCTGAGGTGCTTCATAAGCAGCCTTATGACAGGACTGTGGACTGGTGGTGC

CTGGGAGCTGTCTTGTATGAGATGCTGTATGGCCTGCCGCCTTTTTATAGCCGAAACACAGCTGAAATGT

ACGACAACATTCTGAACAAGCCTCTCCAGCTGAAACCAAATATTACAAATTCCGCAAGACACCTCCTGGA

GGGCCTCCTGCAGAAGGACAGGACAAAGCGGCTCGGGGCCAAGGATGACTTCATGGAGATTAAGAGTCAT

GTCTTCTTCTCCTTAATTAACTGGGATGATCTCATTAATAAGAAGATTACTCCCCCTTTTAACCCAAATG

TGAGTGGGCCCAACGACCTACGGCACTTTGACCCCGAGTTTACCGAAGAGCCTGTCCCCAACTCCATTGG

CAAGTCCCCTGACAGCGTCCTCGTCACAGCCAGCGTCAAGGAAGCTGCCGAGGCTTTCCTAGGCTTTTCC

TATGCGCCTCCCACGGACTCTTTCCTCTGAACCCTGTTAGGGCTTGGTTTTAAAGGATTTTATGTGTGTT

TCCGAATGTTTTAGTTAGCCTTTTGGTGGAGCCGCCAGCTGACAGGACATCTTACAAGAGAATTTGCACA

TCTCTGGAAGCTTAGCAATCTTATTGCACACTGTTCGCTGGAAGCTTTTTGAAGAGCACATTCTCCTCAG

TGAGCTCATGAGGTTTTCATTTTTATTCTTCCTTCCAACGTGGTGCTATCTCTGAAACGAGCGTTAGAGT

GCCGCCTTAGACGGAGGCAGGAGTTTCGTTAGAAAGCGGACGCTGTTCTAAAAAAGGTCTCCTGCAGATC

TGTCTGGGCTGTGATGACGAATATTATGAAATGTGCCTTTTCTGAAGAGATTGTGTTAGCTCCAAAGCTT

TTCCTATCGCAGTGTTTCAGTTCTTTATTTTCCCTTGTGGATATGCTGTGTGAACCGTCGTGTGAGTGTG

GTATGCCTGATCACAGATGGATTTTGTTATAAGCATCAATGTGACACTTGCAGGACACTACAACGTGGGA

CATTGTTTGTTTCTTCCATATTTGGAAGATAAATTTATGTGTAGACTTTTTTGTAAGATACGGTTAATAA

CTAAAATTTATTGAAATGGTCTTGCAATGACTCGTATTCAGATGCTTAAAGAAAGCATTGCTGCTACAAA

TATTTCTATTTTTAGAAAGGGTTTTTATGGACCAATGCCCCAGTTGTCAGTCAGAGCCGTTGGTGTTTTT

CATTGTTTAAAATGTCACCTGTAAAATGGGCATTATTTATGTTTTTTTTTTTGCATTCCTGATAATTGTA

TGTATTGTATAAAGAACGTCTGTACATTGGGTTATAACACTAGTATATTTAAACTTACAGGCTTATTTGT

AATGTAAACCACCATTTTAATGTACTGTAATTAACATGGTTATAATACGTACAATCCTTCCCTCATCCCA

TCACACAACTTTTTTTGTGTGTGATAAACTGATTTTGGTTTGCAATAAAACCTTGAAAAATATTTACATA

TAAAAAAAA

Human SGK1 Transcript Variant 4 mRNA Sequence (NCBI Reference Sequence: NM_001143678.1)

SEQ ID NO: 29

ACATTCCTGACCTCTCCCTCCCCCTTTTCCCTCTTTCTTTCCTTCCTTCCTCCTCTTCCAAGTTCTGGGA

TTTTTCAGCCTTGCTTGGTTTTGGCCAAAAGCACAAAAAAGGCGTTTTCGGAAGCGACCCGACCGTGCAC

-continued

AAGGGCCATTTGTTTGTTTTGGGACTCGGGGCAGGAAATCTTGCCCGGCCTGAGTCACGGCGGCTCCTTC

AAGGAAACGTCAGTGCTCGCCGGTCGCTCTCGTCTGCCGCGCGCCCCGCCGCCCGCTGCCCATGGGGGAG

ATGCAGGGCGCGCTGGCCAGAGCCCGGCTCGAGTCCCTGCTGCGGCCCCGCCACAAAAAGAGGGCCGAGG

CGCAGAAAAGGAGCGAGTCCTTCCTGCTGAGCGGACTGGCTTTCATGAAGCAGAGGAGGATGGGTCTGAA

CGACTTTATTCAGAAGATTGCCAATAACTCCTATGCATGCAAACACCCTGAAGTTCAGTCCATCTTGAAG

ATCTCCCAACCTCAGGAGCCTGAGCTTATGAATGCCAACCCTTCTCCTCCACCAAGTCCTTCTCAGCAAA

TCAACCTTGGCCCGTCGTCCAATCCTCATGCTAAACCATCTGACTTTCACTTCTTGAAAGTGATCGGAAA

GGGCAGTTTTGGAAAGGTTCTTCTAGCAAGACACAAGGCAGAAGAAGTGTTCTATGCAGTCAAAGTTTTA

CAGAAGAAAGCAATCCTGAAAAAGAAAGAGGAGAAGCATATTATGTCGGAGCGGAATGTTCTGTTGAAGA

ATGTGAAGCACCCTTTCCTGGTGGGCCTTCACTTCTCTTTCCAGACTGCTGACAAATTGTACTTTGTCCT

AGACTACATTAATGGTGGAGAGTTGTTCTACCATCTCCAGAGGGAACGCTGCTTCCTGGAACCACGGGCT

CGTTTCTATGCTGCTGAAATAGCCAGTGCCTTGGGCTACCTGCATTCACTGAACATCGTTTATAGAGACT

TAAAACCAGAGAATATTTTGCTAGATTCACAGGGACACATTGTCCTTACTGACTTCGGACTCTGCAAGGA

GAACATTGAACACAACAGCACAACATCCACCTTCTGTGGCACGCCGGAGTATCTCGCACCTGAGGTGCTT

CATAAGCAGCCTTATGACAGGACTGTGGACTGGTGGTGCCTGGGAGCTGTCTTGTATGAGATGCTGTATG

GCCTGCCGCCTTTTTATAGCCGAAACACAGCTGAAATGTACGACAACATTCTGAACAAGCCTCTCCAGCT

GAAACCAAATATTACAAATTCCGCAAGACACCTCCTGGAGGGCCTCCTGCAGAAGGACAGGACAAAGCGG

CTCGGGGCCAAGGATGACTTCATGGAGATTAAGAGTCATGTCTTCTTCTCCTTAATTAACTGGGATGATC

TCATTAATAAGAAGATTACTCCCCCTTTTAACCCAAATGTGAGTGGGCCCAACGACCTACGGCACTTTGA

CCCCGAGTTTACCGAAGAGCCTGTCCCCAACTCCATTGGCAAGTCCCCTGACAGCGTCCTCGTCACAGCC

AGCGTCAAGGAAGCTGCCGAGGCTTTCCTAGGCTTTTCCTATGCGCCTCCCACGGACTCTTTCCTCTGAA

CCCTGTTAGGGCTTGGTTTTAAAGGATTTTATGTGTGTTTCCGAATGTTTTAGTTAGCCTTTTGGTGGAG

CCGCCAGCTGACAGGACATCTTACAAGAGAATTTGCACATCTCTGGAAGCTTAGCAATCTTATTGCACAC

TGTTCGCTGGAAGCTTTTTGAAGAGCACATTCTCCTCAGTGAGCTCATGAGGTTTTCATTTTTATTCTTC

CTTCCAACGTGGTGCTATCTCTGAAACGAGCGTTAGAGTGCCGCCTTAGACGGAGGCAGGAGTTTCGTTA

GAAAGCGGACGCTGTTCTAAAAAAGGTCTCCTGCAGATCTGTCTGGGCTGTGATGACGAATATTATGAAA

TGTGCCTTTTCTGAAGAGATTGTGTTAGCTCCAAAGCTTTTCCTATCGCAGTGTTTCAGTTCTTTATTTT

CCCTTGTGGATATGCTGTGTGAACCGTCGTGTGAGTGTGGTATGCCTGATCACAGATGGATTTTGTTATA

AGCATCAATGTGACACTTGCAGGACACTACAACGTGGGACATTGTTTGTTTCTTCCATATTTGGAAGATA

AATTTATGTGTAGACTTTTTTGTAAGATACGGTTAATAACTAAAATTTATTGAAATGGTCTTGCAATGAC

TCGTATTCAGATGCTTAAAGAAAGCATTGCTGCTACAAATATTTCTATTTTTAGAAAGGGTTTTTATGGA

CCAATGCCCCAGTTGTCAGTCAGAGCCGTTGGTGTTTTTCATTGTTTAAAATGTCACCTGTAAAATGGGC

ATTATTTATGTTTTTTTTTTTGCATTCCTGATAATTGTATGTATTGTATAAAGAACGTCTGTACATTGGG

TTATAACACTAGTATATTTAAACTTACAGGCTTATTTGTAATGTAAACCACCATTTTAATGTACTGTAAT

TAACATGGTTATAATACGTACAATCCTTCCCTCATCCCATCACACAACTTTTTTTGTGTGTGATAAACTG

ATTTTGGTTTGCAATAAAACCTTGAAAAATATTTACATATAAAAAAAA

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A method of treating castration resistant prostate cancer or doubly resistant prostate cancer comprising administering to a subject in need thereof a compound having the structure of formula I or III:

I

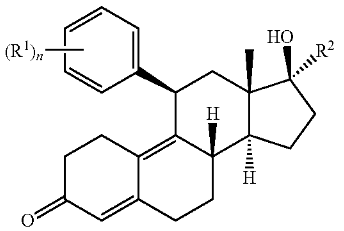

III

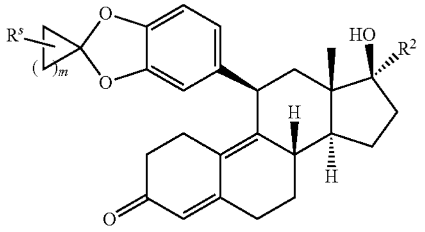

or a pharmaceutically acceptable salt thereof, wherein:

each $R^1$ is —OR, wherein R is optionally substituted phenyl;

$R^2$ is optionally substituted unsaturated $C_{2-6}$ aliphatic;

$R^s$ is —H, —OH, —$NH_2$, —$CH_3$, —Br, —Cl, —F, —I, or —O—$C_{1-6}$alkyl;

m is an integer between 1-8; and n is 1.

2. The method of claim 1, wherein $R^2$ is selected from the group consisting of ethyn-1-yl, 1-propyn-1-yl, 1-butyn-1-yl, ethen-1-yl, 1-propen-1-yl, and 1-buten-1-yl.

3. The method of claim 1, wherein $R^2$ is 1-propyn-1-yl.

4. The method of claim 1, wherein the compound has the structure of formula II-a or formula III-a:

II-a

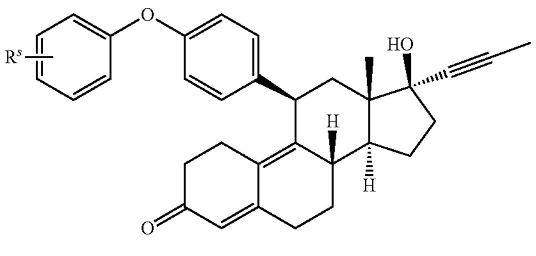

-continued

III-a

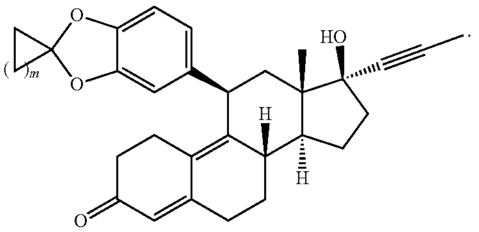

5. The method of claim 1, wherein the compound has the structure of formula IV:

IV

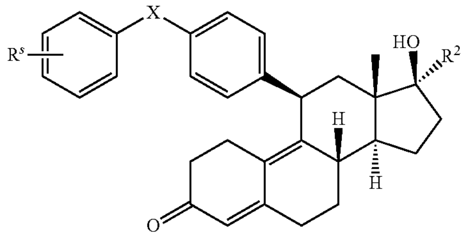

or a pharmaceutically acceptable salt thereof.

6. The method of claim 1, wherein the compound is selected from:

I-1

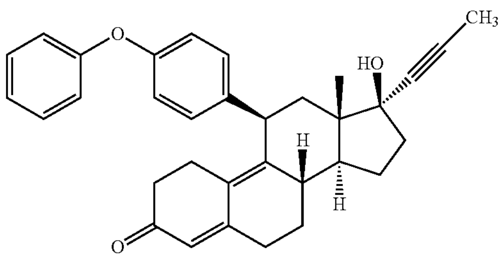

I-2

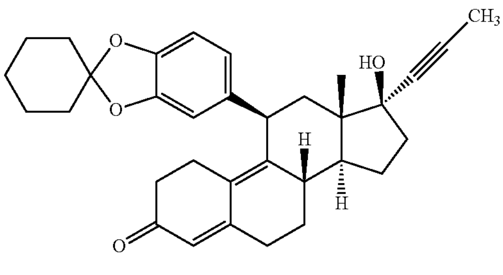

-continued
I-7
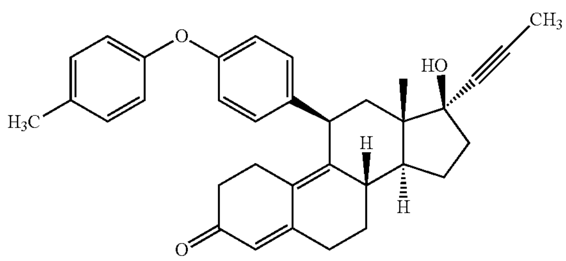
I-8
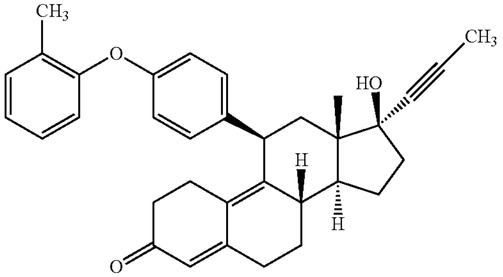
I-9
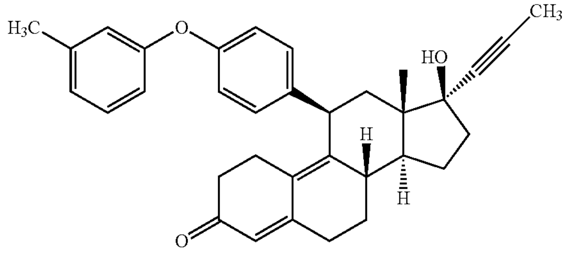
I-10
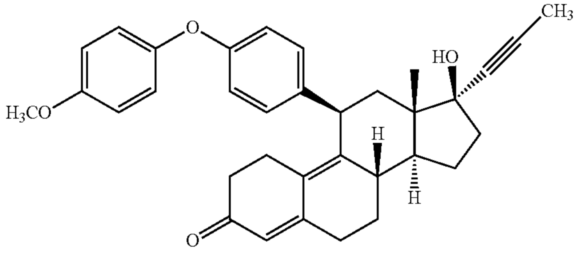
-continued
I-14
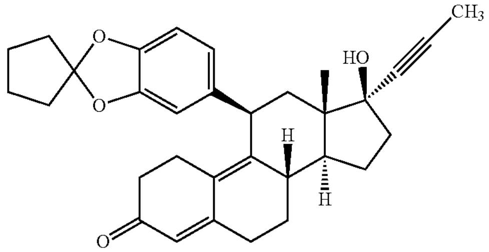
I-15
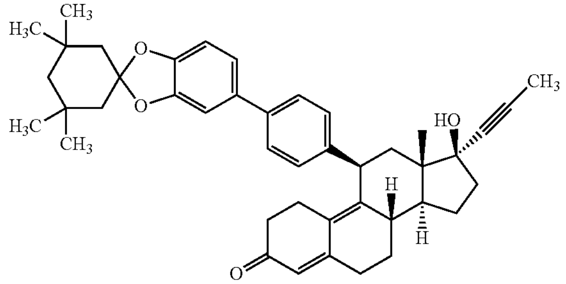
I-16
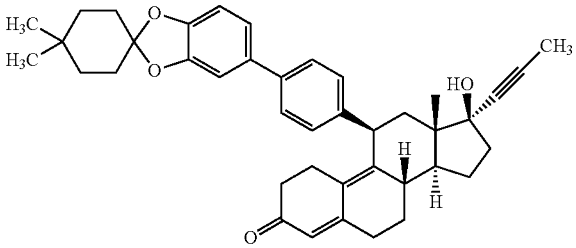
I-17
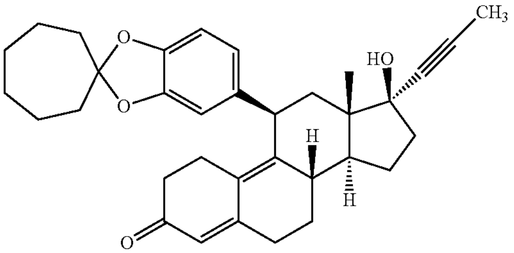
or a pharmaceutically acceptable salt thereof.
7. The method of claim 1, wherein the compound is administered to the subject in need thereof in combination with an androgen receptor inhibitor.
* * * * *

UNITED STATES PATENT AND TRADEMARK OFFICE

CERTIFICATE OF CORRECTION

PATENT NO. : 10,919,929 B2
APPLICATION NO. : 15/103283
DATED : February 16, 2021
INVENTOR(S) : Vivek Arora et al.

It is certified that error appears in the above-identified patent and that said Letters Patent is hereby corrected as shown below:

In the Claims

Column 254, Lines 42-43: Please replace the text "The method of claim 1, wherein the compound is selected from" with --A method of treating castration resistant prostate cancer or doubly resistant prostate cancer comprising administering to a subject in need thereof a compound selected from--.

Column 256, Lines 14-24: Please replace the structure

" 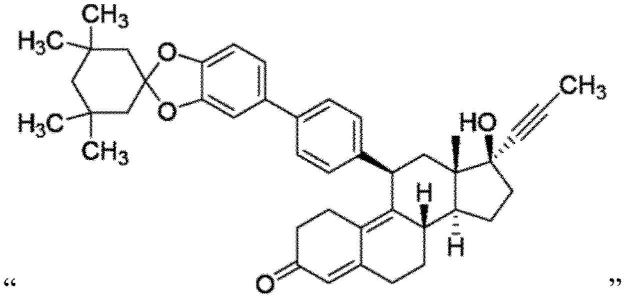 " with the structure

-- 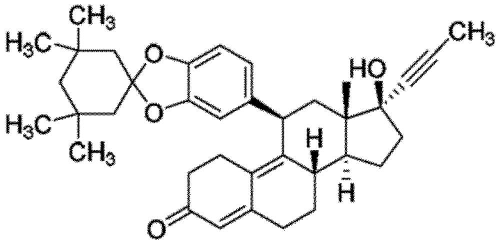 --.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*

Column 256, Lines 25-35: Please replace the structure

" 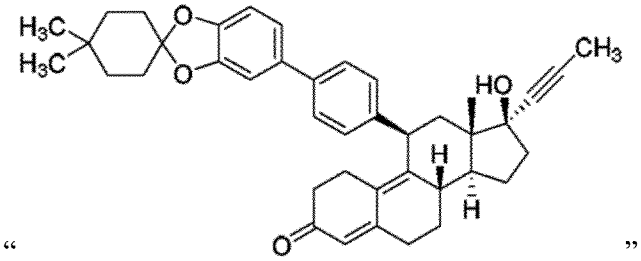 " with the structure

--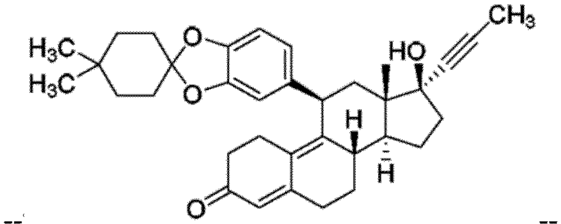 --.

Column 256, Line 49: Please replace the text "with an androgen receptor inhibitor" with --with an androgen receptor inhibitor selected from the group consisting of 3,3 '-diindolylmethane (DIM), abiraterone acetate, ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, and turosteride--.

SEQUENCE LISTING

```
<160> NUMBER OF SEQ ID NOS: 51

<210> SEQ ID NO 1
<211> LENGTH: 919
<212> TYPE: PRT
<213> ORGANISM: Homo sapiens

<400> SEQUENCE: 1

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gln Gln Gly Glu Asp Gly Ser Pro Gln
                85                  90                  95

Ala His Arg Arg Gly Pro Thr Gly Tyr Leu Val Leu Asp Glu Glu Gln
            100                 105                 110

Gln Pro Ser Gln Pro Gln Ser Ala Leu Glu Cys His Pro Glu Arg Gly
        115                 120                 125

Cys Val Pro Glu Pro Gly Ala Ala Val Ala Ala Ser Lys Gly Leu Pro
    130                 135                 140

Gln Gln Leu Pro Ala Pro Pro Asp Glu Asp Asp Ser Ala Ala Pro Ser
145                 150                 155                 160

Thr Leu Ser Leu Leu Gly Pro Thr Phe Pro Gly Leu Ser Ser Cys Ser
                165                 170                 175

Ala Asp Leu Lys Asp Ile Leu Ser Glu Ala Ser Thr Met Gln Leu Leu
            180                 185                 190

Gln Gln Gln Gln Gln Glu Ala Val Ser Glu Gly Ser Ser Ser Gly Arg
        195                 200                 205

Ala Arg Glu Ala Ser Gly Ala Pro Thr Ser Ser Lys Asp Asn Tyr Leu
    210                 215                 220

Gly Gly Thr Ser Thr Ile Ser Asp Asn Ala Lys Glu Leu Cys Lys Ala
225                 230                 235                 240

Val Ser Val Ser Met Gly Leu Gly Val Glu Ala Leu Glu His Leu Ser
                245                 250                 255

Pro Gly Glu Gln Leu Arg Gly Asp Cys Met Tyr Ala Pro Leu Leu Gly
            260                 265                 270

Val Pro Pro Ala Val Arg Pro Thr Pro Cys Ala Pro Leu Ala Glu Cys
        275                 280                 285

Lys Gly Ser Leu Leu Asp Asp Ser Ala Gly Lys Ser Thr Glu Asp Thr
    290                 295                 300

Ala Glu Tyr Ser Pro Phe Lys Gly Gly Tyr Thr Lys Gly Leu Glu Gly
305                 310                 315                 320

Glu Ser Leu Gly Cys Ser Gly Ser Ala Ala Ala Gly Ser Ser Gly Thr
                325                 330                 335
```

```
Leu Glu Leu Pro Ser Thr Leu Ser Leu Tyr Lys Ser Gly Ala Leu Asp
            340                 345                 350

Glu Ala Ala Ala Tyr Gln Ser Arg Asp Tyr Tyr Asn Phe Pro Leu Ala
        355                 360                 365

Leu Ala Gly Pro Pro Pro Pro Pro Pro Pro Pro His Pro His Ala Arg
    370                 375                 380

Ile Lys Leu Glu Asn Pro Leu Asp Tyr Gly Ser Ala Trp Ala Ala Ala
385                 390                 395                 400

Ala Ala Gln Cys Arg Tyr Gly Asp Leu Ala Ser Leu His Gly Ala Gly
                405                 410                 415

Ala Ala Gly Pro Gly Ser Gly Ser Pro Ser Ala Ala Ala Ser Ser Ser
            420                 425                 430

Trp His Thr Leu Phe Thr Ala Glu Glu Gly Gln Leu Tyr Gly Pro Cys
        435                 440                 445

Gly Gly Gly Gly Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro Tyr
465                 470                 475                 480

Gly Tyr Thr Arg Pro Pro Gln Gly Leu Ala Gly Gln Glu Ser Asp Phe
                485                 490                 495

Thr Ala Pro Asp Val Trp Tyr Pro Gly Gly Met Val Ser Arg Val Pro
            500                 505                 510

Tyr Pro Ser Pro Thr Cys Val Lys Ser Glu Met Gly Pro Trp Met Asp
        515                 520                 525

Ser Tyr Ser Gly Pro Tyr Gly Asp Met Arg Leu Glu Thr Ala Arg Asp
    530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
                565                 570                 575

Gly Ser Cys Lys Val Phe Phe Lys Arg Ala Ala Glu Gly Lys Gln Lys
            580                 585                 590

Tyr Leu Cys Ala Ser Arg Asn Asp Cys Thr Ile Asp Lys Phe Arg Arg
        595                 600                 605

Lys Asn Cys Pro Ser Cys Arg Leu Arg Lys Cys Tyr Glu Ala Gly Met
    610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Glu Thr Thr
                645                 650                 655

Gln Lys Leu Thr Val Ser His Ile Glu Gly Tyr Glu Cys Gln Pro Ile
            660                 665                 670

Phe Leu Asn Val Leu Glu Ala Ile Glu Pro Gly Val Val Cys Ala Gly
        675                 680                 685

His Asp Asn Asn Gln Pro Asp Ser Phe Ala Ala Leu Leu Ser Ser Leu
    690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
                725                 730                 735

Ile Gln Tyr Ser Trp Met Gly Leu Met Val Phe Ala Met Gly Trp Arg
            740                 745                 750

Ser Phe Thr Asn Val Asn Ser Arg Met Leu Tyr Phe Ala Pro Asp Leu
```

```
        755                 760                 765

Val Phe Asn Glu Tyr Arg Met His Lys Ser Arg Met Tyr Ser Gln Cys
    770                 775                 780

Val Arg Met Arg His Leu Ser Gln Glu Phe Gly Trp Leu Gln Ile Thr
785                 790                 795                 800

Pro Gln Glu Phe Leu Cys Met Lys Ala Leu Leu Leu Phe Ser Ile Ile
                805                 810                 815

Pro Val Asp Gly Leu Lys Asn Gln Lys Phe Phe Asp Glu Leu Arg Met
            820                 825                 830

Asn Tyr Ile Lys Glu Leu Asp Arg Ile Ile Ala Cys Lys Arg Lys Asn
        835                 840                 845

Pro Thr Ser Cys Ser Arg Arg Phe Tyr Gln Leu Thr Lys Leu Leu Asp
    850                 855                 860

Ser Val Gln Pro Ile Ala Arg Glu Leu His Gln Phe Thr Phe Asp Leu
865                 870                 875                 880

Leu Ile Lys Ser His Met Val Ser Val Asp Phe Pro Glu Met Met Ala
                885                 890                 895

Glu Ile Ile Ser Val Gln Val Pro Lys Ile Leu Ser Gly Lys Val Lys
            900                 905                 910

Pro Ile Tyr Phe His Thr Gln
        915


<210> SEQ ID NO 2
<211> LENGTH: 3569
<212> TYPE: DNA
<213> ORGANISM: Homo sapiens

<400> SEQUENCE: 2

taataactca gttcttattt gcacctactt cagtggacac tgaatttgga aggtggagga     60

ttttgttttt ttcttttaag atctgggcat cttttgaatc tacccttcaa gtattaagag    120

acagactgtg agcctagcag ggcagatctt gtccaccgtg tgtcttcttc tgcacgagac    180

tttgaggctg tcagagcgct tttgcgtgg ttgctcccgc aagtttcctt ctctggagct    240

tcccgcaggt gggcagctag ctgcagcgac taccgcatca tcacagcctg ttgaactctt    300

ctgagcaaga gaaggggagg cggggtaagg gaagtaggtg gaagattcag ccaagctcaa    360

ggatggaagt gcagttaggg ctgggaaggg tctaccctcg gccgccgtcc aagacctacc    420

gaggagcttt ccagaatctg ttccagagcg tgcgcgaagt gatccagaac ccgggcccca    480

ggcacccaga ggccgcgagc gcagcacctc ccggcgccag tttgctgctg ctgcagcagc    540

agcagcagca gcagcagcag cagcagcagc agcagcagca gcagcagcag cagcaagaga    600

ctagccccag gcagcagcag cagcagcagg gtgaggatgg ttctccccaa gcccatcgta    660

gaggccccac aggctacctg gtcctggatg aggaacagca accttcacag ccgcagtcgg    720

ccctggagtg ccaccccgag agaggttgcg tcccagagcc tggagccgcc gtggccgcca    780

gcaaggggct gccgcagcag ctgccagcac ctccggacga ggatgactca gctgccccat    840

ccacgttgtc cctgctgggc cccactttcc ccggcttaag cagctgctcc gctgacctta    900

aagacatcct gagcgaggcc agcaccatgc aactccttca gcaacagcag caggaagcag    960

tatccgaagg cagcagcagc gggagagcga gggaggcctc gggggctccc acttcctcca   1020

aggacaatta cttagggggc acttcgacca tttctgacaa cgccaaggag ttgtgtaagg   1080

cagtgtcggt gtccatgggc ctgggtgtgg aggcgttgga gcatctgagt ccaggggaac   1140

agcttcgggg ggattgcatg tacgccccac ttttgggagt tccacccgct gtgcgtccca   1200
```

-continued

```
ctccttgtgc cccattggcc gaatgcaaag gttctctgct agacgacagc gcaggcaaga   1260
gcactgaaga tactgctgag tattcccctt tcaagggagg ttacaccaaa gggctagaag   1320
gcgagagcct aggctgctct ggcagcgctg cagcagggag ctccgggaca cttgaactgc   1380
cgtctaccct gtctctctac aagtccggag cactggacga ggcagctgcg taccagagtc   1440
gcgactacta caactttcca ctggctctgg ccggaccgcc gccccctccg ccgcctcccc   1500
atccccacgc tcgcatcaag ctggagaacc cgctggacta cggcagcgcc tgggcggctg   1560
cggcggcgca gtgccgctat ggggacctgg cgagcctgca tggcgcgggt gcagcgggac   1620
ccggttctgg gtcaccctca gccgccgctt cctcatcctg gcacactctc ttcacagccg   1680
aagaaggcca gttgtatgga ccgtgtggtg gtggtggggg tggtggcggc ggcggcggcg   1740
gcggcggcgg cggcggcggc ggcggcggcg gcggcggcga ggcgggagct gtagcccccct   1800
acggctacac tcggcccccct caggggctgg cgggccagga aagcgacttc accgcacctg   1860
atgtgtggta ccctggcggc atggtgagca gagtgcccta tcccagtccc acttgtgtca   1920
aaagcgaaat gggcccctgg atggatagct actccggacc ttacggggac atgcgtttgg   1980
agactgccag ggaccatgtt ttgcccattg actattactt tccaccccag aagacctgcc   2040
tgatctgtgg agatgaagct tctgggtgtc actatggagc tctcacatgt ggaagctgca   2100
aggtcttctt caaaagagcc gctgaaggga aacagaagta cctgtgcgcc agcagaaatg   2160
attgcactat tgataaattc cgaaggaaaa attgtccatc ttgtcgtctt cggaaatgtt   2220
atgaagcagg gatgactctg ggagcccgga agctgaagaa acttggtaat ctgaaactac   2280
aggaggaagg agaggcttcc agcaccacca gccccactga ggagacaacc cagaagctga   2340
cagtgtcaca cattgaaggc tatgaatgtc agcccatctt tctgaatgtc ctggaagcca   2400
ttgagccagg tgtagtgtgt gctggacacg acaacaacca gcccgactcc tttgcagcct   2460
tgctctctag cctcaatgaa ctgggagaga gacagcttgt acacgtggtc aagtgggcca   2520
aggccttgcc tggcttccgc aacttacacg tggacgacca gatggctgtc attcagtact   2580
cctggatggg gctcatggtg tttgccatgg gctggcgatc cttcaccaat gtcaactcca   2640
ggatgctcta cttcgcccct gatctggttt tcaatgagta ccgcatgcac aagtcccgga   2700
tgtacagcca gtgtgtccga atgaggcacc tctctcaaga gtttggatgg ctccaaatca   2760
ccccccagga attcctgtgc atgaaagcac tgctactctt cagcattatt ccagtggatg   2820
ggctgaaaaa tcaaaaattc tttgatgaac ttcgaatgaa ctacatcaag gaactcgatc   2880
gtatcattgc atgcaaaaga aaaaatccca catcctgctc aagacgcttc taccagctca   2940
ccaagctcct ggactccgtg cagcctattg cgagagagct gcatcagttc acttttgacc   3000
tgctaatcaa gtcacacatg gtgagcgtgg actttccgga aatgatggca gagatcatct   3060
ctgtgcaagt gcccaagatc ctttctggga aagtcaagcc catctatttc cacacccagt   3120
gaagcattgg aaaccctatt tccccacccc agctcatgcc ccctttcaga tgtcttctgc   3180
ctgttataac tctgcactac tcctctgcag tgccttgggg aatttcctct attgatgtac   3240
agtctgtcat gaacatgttc ctgaattcta tttgctgggc tttttttttc tctttctctc   3300
ctttcttttt cttcttccct ccctatctaa ccctcccatg gcaccttcag actttgcttc   3360
ccattgtggc tcctatctgt gttttgaatg gtgttgtatg cctttaaatc tgtgatgatc   3420
ctcatatggc ccagtgtcaa gttgtgcttg tttacagcac tactctgtgc cagccacaca   3480
aacgtttact tatcttatgc cacgggaagt ttagagagct aagattatct ggggaaatca   3540
```

```
aaacaaaaaa caagcaaaca aaaaaaaaa                                       3569


<210> SEQ ID NO 3
<211> LENGTH: 777
<212> TYPE: PRT
<213> ORGANISM: Homo sapiens

<400> SEQUENCE: 3

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365
```

-continued

```
Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
    770                 775
```

-continued

<210> SEQ ID NO 4
<211> LENGTH: 751
<212> TYPE: PRT
<213> ORGANISM: Homo sapiens

<400> SEQUENCE: 4

Met Asp Phe Tyr Lys Thr Leu Arg Gly Gly Ala Thr Val Lys Val Ser
1 5 10 15

Ala Ser Ser Pro Ser Leu Ala Val Ala Ser Gln Ser Asp Ser Lys Gln
20 25 30

Arg Arg Leu Leu Val Asp Phe Pro Lys Gly Ser Val Ser Asn Ala Gln
35 40 45

Gln Pro Asp Leu Ser Lys Ala Val Ser Leu Ser Met Gly Leu Tyr Met
50 55 60

Gly Glu Thr Glu Thr Lys Val Met Gly Asn Asp Leu Gly Phe Pro Gln
65 70 75 80

Gln Gly Gln Ile Ser Leu Ser Ser Gly Glu Thr Asp Leu Lys Leu Leu
85 90 95

Glu Glu Ser Ile Ala Asn Leu Asn Arg Ser Thr Ser Val Pro Glu Asn
100 105 110

Pro Lys Ser Ser Ala Ser Thr Ala Val Ser Ala Ala Pro Thr Glu Lys
115 120 125

Glu Phe Pro Lys Thr His Ser Asp Val Ser Ser Glu Gln Gln His Leu
130 135 140

Lys Gly Gln Thr Gly Thr Asn Gly Gly Asn Val Lys Leu Tyr Thr Thr
145 150 155 160

Asp Gln Ser Thr Phe Asp Ile Leu Gln Asp Leu Glu Phe Ser Ser Gly
165 170 175

Ser Pro Gly Lys Glu Thr Asn Glu Ser Pro Trp Arg Ser Asp Leu Leu
180 185 190

Ile Asp Glu Asn Cys Leu Leu Ser Pro Leu Ala Gly Glu Asp Asp Ser
195 200 205

Phe Leu Leu Glu Gly Asn Ser Asn Glu Asp Cys Lys Pro Leu Ile Leu
210 215 220

Pro Asp Thr Lys Pro Lys Ile Lys Asp Asn Gly Asp Leu Val Leu Ser
225 230 235 240

Ser Pro Ser Asn Val Thr Leu Pro Gln Val Lys Thr Glu Lys Glu Asp
245 250 255

Phe Ile Glu Leu Cys Thr Pro Gly Val Ile Lys Gln Glu Lys Leu Gly
260 265 270

Thr Val Tyr Cys Gln Ala Ser Phe Pro Gly Ala Asn Ile Ile Gly Asn
275 280 285

Lys Met Ser Ala Ile Ser Val His Gly Val Ser Thr Ser Gly Gly Gln
290 295 300

Met Tyr His Tyr Asp Met Asn Thr Ala Ser Leu Ser Gln Gln Gln Asp
305 310 315 320

Gln Lys Pro Ile Phe Asn Val Ile Pro Pro Ile Pro Val Gly Ser Glu
325 330 335

Asn Trp Asn Arg Cys Gln Gly Ser Gly Asp Asp Asn Leu Thr Ser Leu
340 345 350

Gly Thr Leu Asn Phe Pro Gly Arg Thr Val Phe Ser Asn Gly Tyr Ser
355 360 365

Ser Pro Ser Met Arg Pro Asp Val Ser Ser Pro Pro Ser Ser Ser Ser
370 375 380

-continued

Thr Ala Thr Thr Gly Pro Pro Pro Lys Leu Cys Leu Val Cys Ser Asp
385 390 395 400

Glu Ala Ser Gly Cys His Tyr Gly Val Leu Thr Cys Gly Ser Cys Lys
405 410 415

Val Phe Phe Lys Arg Ala Val Glu Gly Gln His Asn Tyr Leu Cys Ala
420 425 430

Gly Arg Asn Asp Cys Ile Ile Asp Lys Ile Arg Arg Lys Asn Cys Pro
435 440 445

Ala Cys Arg Tyr Arg Lys Cys Leu Gln Ala Gly Met Asn Leu Glu Ala
450 455 460

Arg Lys Thr Lys Lys Lys Ile Lys Gly Ile Gln Gln Ala Thr Thr Gly
465 470 475 480

Val Ser Gln Glu Thr Ser Glu Asn Pro Gly Asn Lys Thr Ile Val Pro
485 490 495

Ala Thr Leu Pro Gln Leu Thr Pro Thr Leu Val Ser Leu Leu Glu Val
500 505 510

Ile Glu Pro Glu Val Leu Tyr Ala Gly Tyr Asp Ser Ser Val Pro Asp
515 520 525

Ser Thr Trp Arg Ile Met Thr Thr Leu Asn Met Leu Gly Gly Arg Gln
530 535 540

Val Ile Ala Ala Val Lys Trp Ala Lys Ala Ile Pro Gly Phe Arg Asn
545 550 555 560

Leu His Leu Asp Asp Gln Met Thr Leu Leu Gln Tyr Ser Trp Met Phe
565 570 575

Leu Met Ala Phe Ala Leu Gly Trp Arg Ser Tyr Arg Gln Ser Ser Ala
580 585 590

Asn Leu Leu Cys Phe Ala Pro Asp Leu Ile Ile Asn Glu Gln Arg Met
595 600 605

Thr Leu Pro Cys Met Tyr Asp Gln Cys Lys His Met Leu Tyr Val Ser
610 615 620

Ser Glu Leu His Arg Leu Gln Val Ser Tyr Glu Glu Tyr Leu Cys Met
625 630 635 640

Lys Thr Leu Leu Leu Leu Ser Ser Val Pro Lys Asp Gly Leu Lys Ser
645 650 655

Gln Glu Leu Phe Asp Glu Ile Arg Met Thr Tyr Ile Lys Glu Leu Gly
660 665 670

Lys Ala Ile Val Lys Arg Glu Gly Asn Ser Ser Gln Asn Trp Gln Arg
675 680 685

Phe Tyr Gln Leu Thr Lys Leu Leu Asp Ser Met His Glu Val Val Glu
690 695 700

Asn Leu Leu Asn Tyr Cys Phe Gln Thr Phe Leu Asp Lys Thr Met Ser
705 710 715 720

Ile Glu Phe Pro Glu Met Leu Ala Glu Ile Ile Thr Asn Gln Ile Pro
725 730 735

Lys Tyr Ser Asn Gly Asn Ile Lys Lys Leu Leu Phe His Gln Lys
740 745 750

<210> SEQ ID NO 5
<211> LENGTH: 692
<212> TYPE: PRT
<213> ORGANISM: Homo sapiens

<400> SEQUENCE: 5

Met Gly Leu Tyr Met Gly Glu Thr Glu Thr Lys Val Met Gly Asn Asp
1 5 10 15

-continued

```
Leu Gly Phe Pro Gln Gln Gly Gln Ile Ser Leu Ser Ser Gly Glu Thr
            20                  25                  30

Asp Leu Lys Leu Leu Glu Glu Ser Ile Ala Asn Leu Asn Arg Ser Thr
        35                  40                  45

Ser Val Pro Glu Asn Pro Lys Ser Ser Ala Ser Thr Ala Val Ser Ala
    50                  55                  60

Ala Pro Thr Glu Lys Glu Phe Pro Lys Thr His Ser Asp Val Ser Ser
65                  70                  75                  80

Glu Gln Gln His Leu Lys Gly Gln Thr Gly Thr Asn Gly Gly Asn Val
                85                  90                  95

Lys Leu Tyr Thr Thr Asp Gln Ser Thr Phe Asp Ile Leu Gln Asp Leu
            100                 105                 110

Glu Phe Ser Ser Gly Ser Pro Gly Lys Glu Thr Asn Glu Ser Pro Trp
        115                 120                 125

Arg Ser Asp Leu Leu Ile Asp Glu Asn Cys Leu Leu Ser Pro Leu Ala
    130                 135                 140

Gly Glu Asp Asp Ser Phe Leu Leu Glu Gly Asn Ser Asn Glu Asp Cys
145                 150                 155                 160

Lys Pro Leu Ile Leu Pro Asp Thr Lys Pro Lys Ile Lys Asp Asn Gly
                165                 170                 175

Asp Leu Val Leu Ser Ser Pro Ser Asn Val Thr Leu Pro Gln Val Lys
            180                 185                 190

Thr Glu Lys Glu Asp Phe Ile Glu Leu Cys Thr Pro Gly Val Ile Lys
        195                 200                 205

Gln Glu Lys Leu Gly Thr Val Tyr Cys Gln Ala Ser Phe Pro Gly Ala
    210                 215                 220

Asn Ile Ile Gly Asn Lys Met Ser Ala Ile Ser Val His Gly Val Ser
225                 230                 235                 240

Thr Ser Gly Gly Gln Met Tyr His Tyr Asp Met Asn Thr Ala Ser Leu
                245                 250                 255

Ser Gln Gln Gln Asp Gln Lys Pro Ile Phe Asn Val Ile Pro Pro Ile
            260                 265                 270

Pro Val Gly Ser Glu Asn Trp Asn Arg Cys Gln Gly Ser Gly Asp Asp
        275                 280                 285

Asn Leu Thr Ser Leu Gly Thr Leu Asn Phe Pro Gly Arg Thr Val Phe
    290                 295                 300

Ser Asn Gly Tyr Ser Ser Pro Ser Met Arg Pro Asp Val Ser Ser Pro
305                 310                 315                 320

Pro Ser Ser Ser Ser Thr Ala Thr Thr Gly Pro Pro Pro Lys Leu Cys
                325                 330                 335

Leu Val Cys Ser Asp Glu Ala Ser Gly Cys His Tyr Gly Val Leu Thr
            340                 345                 350

Cys Gly Ser Cys Lys Val Phe Phe Lys Arg Ala Val Glu Gly Gln His
        355                 360                 365

Asn Tyr Leu Cys Ala Gly Arg Asn Asp Cys Ile Ile Asp Lys Ile Arg
    370                 375                 380

Arg Lys Asn Cys Pro Ala Cys Arg Tyr Arg Lys Cys Leu Gln Ala Gly
385                 390                 395                 400

Met Asn Leu Glu Ala Arg Lys Thr Lys Lys Lys Ile Lys Gly Ile Gln
                405                 410                 415

Gln Ala Thr Thr Gly Val Ser Gln Glu Thr Ser Glu Asn Pro Gly Asn
            420                 425                 430
```

Lys Thr Ile Val Pro Ala Thr Leu Pro Gln Leu Thr Pro Thr Leu Val
435 440 445

Ser Leu Leu Glu Val Ile Glu Pro Glu Val Leu Tyr Ala Gly Tyr Asp
450 455 460

Ser Ser Val Pro Asp Ser Thr Trp Arg Ile Met Thr Thr Leu Asn Met
465 470 475 480

Leu Gly Gly Arg Gln Val Ile Ala Ala Val Lys Trp Ala Lys Ala Ile
485 490 495

Pro Gly Phe Arg Asn Leu His Leu Asp Asp Gln Met Thr Leu Leu Gln
500 505 510

Tyr Ser Trp Met Phe Leu Met Ala Phe Ala Leu Gly Trp Arg Ser Tyr
515 520 525

Arg Gln Ser Ser Ala Asn Leu Leu Cys Phe Ala Pro Asp Leu Ile Ile
530 535 540

Asn Glu Gln Arg Met Thr Leu Pro Cys Met Tyr Asp Gln Cys Lys His
545 550 555 560

Met Leu Tyr Val Ser Ser Glu Leu His Arg Leu Gln Val Ser Tyr Glu
565 570 575

Glu Tyr Leu Cys Met Lys Thr Leu Leu Leu Leu Ser Ser Val Pro Lys
580 585 590

Asp Gly Leu Lys Ser Gln Glu Leu Phe Asp Glu Ile Arg Met Thr Tyr
595 600 605

Ile Lys Glu Leu Gly Lys Ala Ile Val Lys Arg Glu Gly Asn Ser Ser
610 615 620

Gln Asn Trp Gln Arg Phe Tyr Gln Leu Thr Lys Leu Leu Asp Ser Met
625 630 635 640

His Glu Val Val Glu Asn Leu Leu Asn Tyr Cys Phe Gln Thr Phe Leu
645 650 655

Asp Lys Thr Met Ser Ile Glu Phe Pro Glu Met Leu Ala Glu Ile Ile
660 665 670

Thr Asn Gln Ile Pro Lys Tyr Ser Asn Gly Asn Ile Lys Lys Leu Leu
675 680 685

Phe His Gln Lys
690

<210> SEQ ID NO 6
<211> LENGTH: 688
<212> TYPE: PRT
<213> ORGANISM: Homo sapiens

<400> SEQUENCE: 6

Met Gly Glu Thr Glu Thr Lys Val Met Gly Asn Asp Leu Gly Phe Pro
1 5 10 15

Gln Gln Gly Gln Ile Ser Leu Ser Ser Gly Glu Thr Asp Leu Lys Leu
20 25 30

Leu Glu Glu Ser Ile Ala Asn Leu Asn Arg Ser Thr Ser Val Pro Glu
35 40 45

Asn Pro Lys Ser Ser Ala Ser Thr Ala Val Ser Ala Ala Pro Thr Glu
50 55 60

Lys Glu Phe Pro Lys Thr His Ser Asp Val Ser Ser Glu Gln Gln His
65 70 75 80

Leu Lys Gly Gln Thr Gly Thr Asn Gly Gly Asn Val Lys Leu Tyr Thr
85 90 95

Thr Asp Gln Ser Thr Phe Asp Ile Leu Gln Asp Leu Glu Phe Ser Ser
100 105 110

```
Gly Ser Pro Gly Lys Glu Thr Asn Glu Ser Pro Trp Arg Ser Asp Leu
        115                 120                 125

Leu Ile Asp Glu Asn Cys Leu Leu Ser Pro Leu Ala Gly Glu Asp Asp
    130                 135                 140

Ser Phe Leu Leu Glu Gly Asn Ser Asn Glu Asp Cys Lys Pro Leu Ile
145                 150                 155                 160

Leu Pro Asp Thr Lys Pro Lys Ile Lys Asp Asn Gly Asp Leu Val Leu
                165                 170                 175

Ser Ser Pro Ser Asn Val Thr Leu Pro Gln Val Lys Thr Glu Lys Glu
            180                 185                 190

Asp Phe Ile Glu Leu Cys Thr Pro Gly Val Ile Lys Gln Glu Lys Leu
        195                 200                 205

Gly Thr Val Tyr Cys Gln Ala Ser Phe Pro Gly Ala Asn Ile Ile Gly
    210                 215                 220

Asn Lys Met Ser Ala Ile Ser Val His Gly Val Ser Thr Ser Gly Gly
225                 230                 235                 240

Gln Met Tyr His Tyr Asp Met Asn Thr Ala Ser Leu Ser Gln Gln Gln
                245                 250                 255

Asp Gln Lys Pro Ile Phe Asn Val Ile Pro Pro Ile Pro Val Gly Ser
            260                 265                 270

Glu Asn Trp Asn Arg Cys Gln Gly Ser Gly Asp Asp Asn Leu Thr Ser
        275                 280                 285

Leu Gly Thr Leu Asn Phe Pro Gly Arg Thr Val Phe Ser Asn Gly Tyr
    290                 295                 300

Ser Ser Pro Ser Met Arg Pro Asp Val Ser Ser Pro Pro Ser Ser Ser
305                 310                 315                 320

Ser Thr Ala Thr Thr Gly Pro Pro Pro Lys Leu Cys Leu Val Cys Ser
                325                 330                 335

Asp Glu Ala Ser Gly Cys His Tyr Gly Val Leu Thr Cys Gly Ser Cys
            340                 345                 350

Lys Val Phe Phe Lys Arg Ala Val Glu Gly Gln His Asn Tyr Leu Cys
        355                 360                 365

Ala Gly Arg Asn Asp Cys Ile Ile Asp Lys Ile Arg Arg Lys Asn Cys
    370                 375                 380

Pro Ala Cys Arg Tyr Arg Lys Cys Leu Gln Ala Gly Met Asn Leu Glu
385                 390                 395                 400

Ala Arg Lys Thr Lys Lys Lys Ile Lys Gly Ile Gln Gln Ala Thr Thr
                405                 410                 415

Gly Val Ser Gln Glu Thr Ser Glu Asn Pro Gly Asn Lys Thr Ile Val
            420                 425                 430

Pro Ala Thr Leu Pro Gln Leu Thr Pro Thr Leu Val Ser Leu Leu Glu
        435                 440                 445

Val Ile Glu Pro Glu Val Leu Tyr Ala Gly Tyr Asp Ser Ser Val Pro
    450                 455                 460

Asp Ser Thr Trp Arg Ile Met Thr Thr Leu Asn Met Leu Gly Gly Arg
465                 470                 475                 480

Gln Val Ile Ala Ala Val Lys Trp Ala Lys Ala Ile Pro Gly Phe Arg
                485                 490                 495

Asn Leu His Leu Asp Asp Gln Met Thr Leu Leu Gln Tyr Ser Trp Met
            500                 505                 510

Phe Leu Met Ala Phe Ala Leu Gly Trp Arg Ser Tyr Arg Gln Ser Ser
        515                 520                 525
```

```
Ala Asn Leu Leu Cys Phe Ala Pro Asp Leu Ile Ile Asn Glu Gln Arg
    530                 535                 540

Met Thr Leu Pro Cys Met Tyr Asp Gln Cys Lys His Met Leu Tyr Val
545                 550                 555                 560

Ser Ser Glu Leu His Arg Leu Gln Val Ser Tyr Glu Glu Tyr Leu Cys
                565                 570                 575

Met Lys Thr Leu Leu Leu Leu Ser Ser Val Pro Lys Asp Gly Leu Lys
            580                 585                 590

Ser Gln Glu Leu Phe Asp Glu Ile Arg Met Thr Tyr Ile Lys Glu Leu
        595                 600                 605

Gly Lys Ala Ile Val Lys Arg Glu Gly Asn Ser Ser Gln Asn Trp Gln
    610                 615                 620

Arg Phe Tyr Gln Leu Thr Lys Leu Leu Asp Ser Met His Glu Val Val
625                 630                 635                 640

Glu Asn Leu Leu Asn Tyr Cys Phe Gln Thr Phe Leu Asp Lys Thr Met
                645                 650                 655

Ser Ile Glu Phe Pro Glu Met Leu Ala Glu Ile Ile Thr Asn Gln Ile
            660                 665                 670

Pro Lys Tyr Ser Asn Gly Asn Ile Lys Lys Leu Leu Phe His Gln Lys
        675                 680                 685


<210> SEQ ID NO 7
<211> LENGTH: 680
<212> TYPE: PRT
<213> ORGANISM: Homo sapiens

<400> SEQUENCE: 7

Met Gly Asn Asp Leu Gly Phe Pro Gln Gln Gly Gln Ile Ser Leu Ser
1               5                   10                  15

Ser Gly Glu Thr Asp Leu Lys Leu Leu Glu Glu Ser Ile Ala Asn Leu
            20                  25                  30

Asn Arg Ser Thr Ser Val Pro Glu Asn Pro Lys Ser Ser Ala Ser Thr
        35                  40                  45

Ala Val Ser Ala Ala Pro Thr Glu Lys Glu Phe Pro Lys Thr His Ser
    50                  55                  60

Asp Val Ser Ser Glu Gln Gln His Leu Lys Gly Gln Thr Gly Thr Asn
65                  70                  75                  80

Gly Gly Asn Val Lys Leu Tyr Thr Thr Asp Gln Ser Thr Phe Asp Ile
                85                  90                  95

Leu Gln Asp Leu Glu Phe Ser Ser Gly Ser Pro Gly Lys Glu Thr Asn
            100                 105                 110

Glu Ser Pro Trp Arg Ser Asp Leu Leu Ile Asp Glu Asn Cys Leu Leu
        115                 120                 125

Ser Pro Leu Ala Gly Glu Asp Asp Ser Phe Leu Leu Glu Gly Asn Ser
    130                 135                 140

Asn Glu Asp Cys Lys Pro Leu Ile Leu Pro Asp Thr Lys Pro Lys Ile
145                 150                 155                 160

Lys Asp Asn Gly Asp Leu Val Leu Ser Ser Pro Ser Asn Val Thr Leu
                165                 170                 175

Pro Gln Val Lys Thr Glu Lys Glu Asp Phe Ile Glu Leu Cys Thr Pro
            180                 185                 190

Gly Val Ile Lys Gln Glu Lys Leu Gly Thr Val Tyr Cys Gln Ala Ser
        195                 200                 205

Phe Pro Gly Ala Asn Ile Ile Gly Asn Lys Met Ser Ala Ile Ser Val
    210                 215                 220
```

-continued

```
His Gly Val Ser Thr Ser Gly Gly Gln Met Tyr His Tyr Asp Met Asn
225                 230                 235                 240

Thr Ala Ser Leu Ser Gln Gln Gln Asp Gln Lys Pro Ile Phe Asn Val
                245                 250                 255

Ile Pro Pro Ile Pro Val Gly Ser Glu Asn Trp Asn Arg Cys Gln Gly
            260                 265                 270

Ser Gly Asp Asp Asn Leu Thr Ser Leu Gly Thr Leu Asn Phe Pro Gly
        275                 280                 285

Arg Thr Val Phe Ser Asn Gly Tyr Ser Ser Pro Ser Met Arg Pro Asp
    290                 295                 300

Val Ser Ser Pro Pro Ser Ser Ser Ser Thr Ala Thr Thr Gly Pro Pro
305                 310                 315                 320

Pro Lys Leu Cys Leu Val Cys Ser Asp Glu Ala Ser Gly Cys His Tyr
                325                 330                 335

Gly Val Leu Thr Cys Gly Ser Cys Lys Val Phe Phe Lys Arg Ala Val
            340                 345                 350

Glu Gly Gln His Asn Tyr Leu Cys Ala Gly Arg Asn Asp Cys Ile Ile
        355                 360                 365

Asp Lys Ile Arg Arg Lys Asn Cys Pro Ala Cys Arg Tyr Arg Lys Cys
    370                 375                 380

Leu Gln Ala Gly Met Asn Leu Glu Ala Arg Lys Thr Lys Lys Lys Ile
385                 390                 395                 400

Lys Gly Ile Gln Gln Ala Thr Thr Gly Val Ser Gln Glu Thr Ser Glu
                405                 410                 415

Asn Pro Gly Asn Lys Thr Ile Val Pro Ala Thr Leu Pro Gln Leu Thr
            420                 425                 430

Pro Thr Leu Val Ser Leu Leu Glu Val Ile Glu Pro Glu Val Leu Tyr
        435                 440                 445

Ala Gly Tyr Asp Ser Ser Val Pro Asp Ser Thr Trp Arg Ile Met Thr
    450                 455                 460

Thr Leu Asn Met Leu Gly Gly Arg Gln Val Ile Ala Ala Val Lys Trp
465                 470                 475                 480

Ala Lys Ala Ile Pro Gly Phe Arg Asn Leu His Leu Asp Asp Gln Met
                485                 490                 495

Thr Leu Leu Gln Tyr Ser Trp Met Phe Leu Met Ala Phe Ala Leu Gly
            500                 505                 510

Trp Arg Ser Tyr Arg Gln Ser Ser Ala Asn Leu Leu Cys Phe Ala Pro
        515                 520                 525

Asp Leu Ile Ile Asn Glu Gln Arg Met Thr Leu Pro Cys Met Tyr Asp
    530                 535                 540

Gln Cys Lys His Met Leu Tyr Val Ser Ser Glu Leu His Arg Leu Gln
545                 550                 555                 560

Val Ser Tyr Glu Glu Tyr Leu Cys Met Lys Thr Leu Leu Leu Leu Ser
                565                 570                 575

Ser Val Pro Lys Asp Gly Leu Lys Ser Gln Glu Leu Phe Asp Glu Ile
            580                 585                 590

Arg Met Thr Tyr Ile Lys Glu Leu Gly Lys Ala Ile Val Lys Arg Glu
        595                 600                 605

Gly Asn Ser Ser Gln Asn Trp Gln Arg Phe Tyr Gln Leu Thr Lys Leu
    610                 615                 620

Leu Asp Ser Met His Glu Val Val Glu Asn Leu Leu Asn Tyr Cys Phe
625                 630                 635                 640
```

```
Gln Thr Phe Leu Asp Lys Thr Met Ser Ile Glu Phe Pro Glu Met Leu
                645                 650                 655

Ala Glu Ile Ile Thr Asn Gln Ile Pro Lys Tyr Ser Asn Gly Asn Ile
            660                 665                 670

Lys Lys Leu Leu Phe His Gln Lys
        675                 680


<210> SEQ ID NO 8
<211> LENGTH: 462
<212> TYPE: PRT
<213> ORGANISM: Homo sapiens

<400> SEQUENCE: 8

Met Ser Ala Ile Ser Val His Gly Val Ser Thr Ser Gly Gly Gln Met
1               5                   10                  15

Tyr His Tyr Asp Met Asn Thr Ala Ser Leu Ser Gln Gln Gln Asp Gln
            20                  25                  30

Lys Pro Ile Phe Asn Val Ile Pro Pro Ile Pro Val Gly Ser Glu Asn
        35                  40                  45

Trp Asn Arg Cys Gln Gly Ser Gly Asp Asp Asn Leu Thr Ser Leu Gly
    50                  55                  60

Thr Leu Asn Phe Pro Gly Arg Thr Val Phe Ser Asn Gly Tyr Ser Ser
65                  70                  75                  80

Pro Ser Met Arg Pro Asp Val Ser Ser Pro Pro Ser Ser Ser Ser Thr
                85                  90                  95

Ala Thr Thr Gly Pro Pro Pro Lys Leu Cys Leu Val Cys Ser Asp Glu
            100                 105                 110

Ala Ser Gly Cys His Tyr Gly Val Leu Thr Cys Gly Ser Cys Lys Val
        115                 120                 125

Phe Phe Lys Arg Ala Val Glu Gly Gln His Asn Tyr Leu Cys Ala Gly
    130                 135                 140

Arg Asn Asp Cys Ile Ile Asp Lys Ile Arg Arg Lys Asn Cys Pro Ala
145                 150                 155                 160

Cys Arg Tyr Arg Lys Cys Leu Gln Ala Gly Met Asn Leu Glu Ala Arg
                165                 170                 175

Lys Thr Lys Lys Lys Ile Lys Gly Ile Gln Gln Ala Thr Thr Gly Val
            180                 185                 190

Ser Gln Glu Thr Ser Glu Asn Pro Gly Asn Lys Thr Ile Val Pro Ala
        195                 200                 205

Thr Leu Pro Gln Leu Thr Pro Thr Leu Val Ser Leu Leu Glu Val Ile
    210                 215                 220

Glu Pro Glu Val Leu Tyr Ala Gly Tyr Asp Ser Ser Val Pro Asp Ser
225                 230                 235                 240

Thr Trp Arg Ile Met Thr Thr Leu Asn Met Leu Gly Gly Arg Gln Val
                245                 250                 255

Ile Ala Ala Val Lys Trp Ala Lys Ala Ile Pro Gly Phe Arg Asn Leu
            260                 265                 270

His Leu Asp Asp Gln Met Thr Leu Leu Gln Tyr Ser Trp Met Phe Leu
        275                 280                 285

Met Ala Phe Ala Leu Gly Trp Arg Ser Tyr Arg Gln Ser Ser Ala Asn
    290                 295                 300

Leu Leu Cys Phe Ala Pro Asp Leu Ile Ile Asn Glu Gln Arg Met Thr
305                 310                 315                 320

Leu Pro Cys Met Tyr Asp Gln Cys Lys His Met Leu Tyr Val Ser Ser
                325                 330                 335
```

Glu Leu His Arg Leu Gln Val Ser Tyr Glu Glu Tyr Leu Cys Met Lys
340 345 350

Thr Leu Leu Leu Leu Ser Ser Val Pro Lys Asp Gly Leu Lys Ser Gln
355 360 365

Glu Leu Phe Asp Glu Ile Arg Met Thr Tyr Ile Lys Glu Leu Gly Lys
370 375 380

Ala Ile Val Lys Arg Glu Gly Asn Ser Ser Gln Asn Trp Gln Arg Phe
385 390 395 400

Tyr Gln Leu Thr Lys Leu Leu Asp Ser Met His Glu Val Val Glu Asn
405 410 415

Leu Leu Asn Tyr Cys Phe Gln Thr Phe Leu Asp Lys Thr Met Ser Ile
420 425 430

Glu Phe Pro Glu Met Leu Ala Glu Ile Ile Thr Asn Gln Ile Pro Lys
435 440 445

Tyr Ser Asn Gly Asn Ile Lys Lys Leu Leu Phe His Gln Lys
450 455 460

<210> SEQ ID NO 9
<211> LENGTH: 447
<212> TYPE: PRT
<213> ORGANISM: Homo sapiens

<400> SEQUENCE: 9

Met Tyr His Tyr Asp Met Asn Thr Ala Ser Leu Ser Gln Gln Gln Asp
1 5 10 15

Gln Lys Pro Ile Phe Asn Val Ile Pro Pro Ile Pro Val Gly Ser Glu
20 25 30

Asn Trp Asn Arg Cys Gln Gly Ser Gly Asp Asp Asn Leu Thr Ser Leu
35 40 45

Gly Thr Leu Asn Phe Pro Gly Arg Thr Val Phe Ser Asn Gly Tyr Ser
50 55 60

Ser Pro Ser Met Arg Pro Asp Val Ser Ser Pro Pro Ser Ser Ser Ser
65 70 75 80

Thr Ala Thr Thr Gly Pro Pro Pro Lys Leu Cys Leu Val Cys Ser Asp
85 90 95

Glu Ala Ser Gly Cys His Tyr Gly Val Leu Thr Cys Gly Ser Cys Lys
100 105 110

Val Phe Phe Lys Arg Ala Val Glu Gly Gln His Asn Tyr Leu Cys Ala
115 120 125

Gly Arg Asn Asp Cys Ile Ile Asp Lys Ile Arg Arg Lys Asn Cys Pro
130 135 140

Ala Cys Arg Tyr Arg Lys Cys Leu Gln Ala Gly Met Asn Leu Glu Ala
145 150 155 160

Arg Lys Thr Lys Lys Lys Ile Lys Gly Ile Gln Gln Ala Thr Thr Gly
165 170 175

Val Ser Gln Glu Thr Ser Glu Asn Pro Gly Asn Lys Thr Ile Val Pro
180 185 190

Ala Thr Leu Pro Gln Leu Thr Pro Thr Leu Val Ser Leu Leu Glu Val
195 200 205

Ile Glu Pro Glu Val Leu Tyr Ala Gly Tyr Asp Ser Ser Val Pro Asp
210 215 220

Ser Thr Trp Arg Ile Met Thr Thr Leu Asn Met Leu Gly Gly Arg Gln
225 230 235 240

Val Ile Ala Ala Val Lys Trp Ala Lys Ala Ile Pro Gly Phe Arg Asn

```
                245                 250                 255

Leu His Leu Asp Asp Gln Met Thr Leu Leu Gln Tyr Ser Trp Met Phe
            260                 265                 270

Leu Met Ala Phe Ala Leu Gly Trp Arg Ser Tyr Arg Gln Ser Ser Ala
        275                 280                 285

Asn Leu Leu Cys Phe Ala Pro Asp Leu Ile Ile Asn Glu Gln Arg Met
    290                 295                 300

Thr Leu Pro Cys Met Tyr Asp Gln Cys Lys His Met Leu Tyr Val Ser
305                 310                 315                 320

Ser Glu Leu His Arg Leu Gln Val Ser Tyr Glu Glu Tyr Leu Cys Met
                325                 330                 335

Lys Thr Leu Leu Leu Leu Ser Ser Val Pro Lys Asp Gly Leu Lys Ser
            340                 345                 350

Gln Glu Leu Phe Asp Glu Ile Arg Met Thr Tyr Ile Lys Glu Leu Gly
        355                 360                 365

Lys Ala Ile Val Lys Arg Glu Gly Asn Ser Ser Gln Asn Trp Gln Arg
    370                 375                 380

Phe Tyr Gln Leu Thr Lys Leu Leu Asp Ser Met His Glu Val Val Glu
385                 390                 395                 400

Asn Leu Leu Asn Tyr Cys Phe Gln Thr Phe Leu Asp Lys Thr Met Ser
                405                 410                 415

Ile Glu Phe Pro Glu Met Leu Ala Glu Ile Ile Thr Asn Gln Ile Pro
            420                 425                 430

Lys Tyr Ser Asn Gly Asn Ile Lys Lys Leu Leu Phe His Gln Lys
        435                 440                 445


<210> SEQ ID NO 10
<211> LENGTH: 442
<212> TYPE: PRT
<213> ORGANISM: Homo sapiens

<400> SEQUENCE: 10

Met Asn Thr Ala Ser Leu Ser Gln Gln Gln Asp Gln Lys Pro Ile Phe
1               5                   10                  15

Asn Val Ile Pro Pro Ile Pro Val Gly Ser Glu Asn Trp Asn Arg Cys
            20                  25                  30

Gln Gly Ser Gly Asp Asp Asn Leu Thr Ser Leu Gly Thr Leu Asn Phe
        35                  40                  45

Pro Gly Arg Thr Val Phe Ser Asn Gly Tyr Ser Ser Pro Ser Met Arg
    50                  55                  60

Pro Asp Val Ser Ser Pro Pro Ser Ser Ser Ser Thr Ala Thr Thr Gly
65                  70                  75                  80

Pro Pro Pro Lys Leu Cys Leu Val Cys Ser Asp Glu Ala Ser Gly Cys
                85                  90                  95

His Tyr Gly Val Leu Thr Cys Gly Ser Cys Lys Val Phe Phe Lys Arg
            100                 105                 110

Ala Val Glu Gly Gln His Asn Tyr Leu Cys Ala Gly Arg Asn Asp Cys
        115                 120                 125

Ile Ile Asp Lys Ile Arg Arg Lys Asn Cys Pro Ala Cys Arg Tyr Arg
    130                 135                 140

Lys Cys Leu Gln Ala Gly Met Asn Leu Glu Ala Arg Lys Thr Lys Lys
145                 150                 155                 160

Lys Ile Lys Gly Ile Gln Gln Ala Thr Thr Gly Val Ser Gln Glu Thr
                165                 170                 175
```

```
Ser Glu Asn Pro Gly Asn Lys Thr Ile Val Pro Ala Thr Leu Pro Gln
            180                 185                 190

Leu Thr Pro Thr Leu Val Ser Leu Leu Glu Val Ile Glu Pro Glu Val
        195                 200                 205

Leu Tyr Ala Gly Tyr Asp Ser Ser Val Pro Asp Ser Thr Trp Arg Ile
    210                 215                 220

Met Thr Thr Leu Asn Met Leu Gly Gly Arg Gln Val Ile Ala Ala Val
225                 230                 235                 240

Lys Trp Ala Lys Ala Ile Pro Gly Phe Arg Asn Leu His Leu Asp Asp
                245                 250                 255

Gln Met Thr Leu Leu Gln Tyr Ser Trp Met Phe Leu Met Ala Phe Ala
            260                 265                 270

Leu Gly Trp Arg Ser Tyr Arg Gln Ser Ser Ala Asn Leu Leu Cys Phe
        275                 280                 285

Ala Pro Asp Leu Ile Ile Asn Glu Gln Arg Met Thr Leu Pro Cys Met
    290                 295                 300

Tyr Asp Gln Cys Lys His Met Leu Tyr Val Ser Ser Glu Leu His Arg
305                 310                 315                 320

Leu Gln Val Ser Tyr Glu Glu Tyr Leu Cys Met Lys Thr Leu Leu Leu
                325                 330                 335

Leu Ser Ser Val Pro Lys Asp Gly Leu Lys Ser Gln Glu Leu Phe Asp
            340                 345                 350

Glu Ile Arg Met Thr Tyr Ile Lys Glu Leu Gly Lys Ala Ile Val Lys
        355                 360                 365

Arg Glu Gly Asn Ser Ser Gln Asn Trp Gln Arg Phe Tyr Gln Leu Thr
    370                 375                 380

Lys Leu Leu Asp Ser Met His Glu Val Val Glu Asn Leu Leu Asn Tyr
385                 390                 395                 400

Cys Phe Gln Thr Phe Leu Asp Lys Thr Met Ser Ile Glu Phe Pro Glu
                405                 410                 415

Met Leu Ala Glu Ile Ile Thr Asn Gln Ile Pro Lys Tyr Ser Asn Gly
            420                 425                 430

Asn Ile Lys Lys Leu Leu Phe His Gln Lys
        435                 440


<210> SEQ ID NO 11
<211> LENGTH: 676
<212> TYPE: PRT
<213> ORGANISM: Homo sapiens

<400> SEQUENCE: 11

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110
```

```
Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525
```

```
Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Gly Trp
        675


<210> SEQ ID NO 12
<211> LENGTH: 778
<212> TYPE: PRT
<213> ORGANISM: Homo sapiens

<400> SEQUENCE: 12

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220
```

Leu Ser Pro Leu Ala Gly Glu Asp Asp Ser Phe Leu Leu Glu Gly Asn
225 230 235 240

Ser Asn Glu Asp Cys Lys Pro Leu Ile Leu Pro Asp Thr Lys Pro Lys
245 250 255

Ile Lys Asp Asn Gly Asp Leu Val Leu Ser Ser Pro Ser Asn Val Thr
260 265 270

Leu Pro Gln Val Lys Thr Glu Lys Glu Asp Phe Ile Glu Leu Cys Thr
275 280 285

Pro Gly Val Ile Lys Gln Glu Lys Leu Gly Thr Val Tyr Cys Gln Ala
290 295 300

Ser Phe Pro Gly Ala Asn Ile Ile Gly Asn Lys Met Ser Ala Ile Ser
305 310 315 320

Val His Gly Val Ser Thr Ser Gly Gly Gln Met Tyr His Tyr Asp Met
325 330 335

Asn Thr Ala Ser Leu Ser Gln Gln Gln Asp Gln Lys Pro Ile Phe Asn
340 345 350

Val Ile Pro Pro Ile Pro Val Gly Ser Glu Asn Trp Asn Arg Cys Gln
355 360 365

Gly Ser Gly Asp Asp Asn Leu Thr Ser Leu Gly Thr Leu Asn Phe Pro
370 375 380

Gly Arg Thr Val Phe Ser Asn Gly Tyr Ser Ser Pro Ser Met Arg Pro
385 390 395 400

Asp Val Ser Ser Pro Pro Ser Ser Ser Ser Thr Ala Thr Thr Gly Pro
405 410 415

Pro Pro Lys Leu Cys Leu Val Cys Ser Asp Glu Ala Ser Gly Cys His
420 425 430

Tyr Gly Val Leu Thr Cys Gly Ser Cys Lys Val Phe Phe Lys Arg Ala
435 440 445

Val Glu Gly Arg Gln His Asn Tyr Leu Cys Ala Gly Arg Asn Asp Cys
450 455 460

Ile Ile Asp Lys Ile Arg Arg Lys Asn Cys Pro Ala Cys Arg Tyr Arg
465 470 475 480

Lys Cys Leu Gln Ala Gly Met Asn Leu Glu Ala Arg Lys Thr Lys Lys
485 490 495

Lys Ile Lys Gly Ile Gln Gln Ala Thr Thr Gly Val Ser Gln Glu Thr
500 505 510

Ser Glu Asn Pro Gly Asn Lys Thr Ile Val Pro Ala Thr Leu Pro Gln
515 520 525

Leu Thr Pro Thr Leu Val Ser Leu Leu Glu Val Ile Glu Pro Glu Val
530 535 540

Leu Tyr Ala Gly Tyr Asp Ser Ser Val Pro Asp Ser Thr Trp Arg Ile
545 550 555 560

Met Thr Thr Leu Asn Met Leu Gly Gly Arg Gln Val Ile Ala Ala Val
565 570 575

Lys Trp Ala Lys Ala Ile Pro Gly Phe Arg Asn Leu His Leu Asp Asp
580 585 590

Gln Met Thr Leu Leu Gln Tyr Ser Trp Met Phe Leu Met Ala Phe Ala
595 600 605

Leu Gly Trp Arg Ser Tyr Arg Gln Ser Ser Ala Asn Leu Leu Cys Phe
610 615 620

Ala Pro Asp Leu Ile Ile Asn Glu Gln Arg Met Thr Leu Pro Cys Met
625 630 635 640

```
Tyr Asp Gln Cys Lys His Met Leu Tyr Val Ser Ser Glu Leu His Arg
                645                 650                 655

Leu Gln Val Ser Tyr Glu Glu Tyr Leu Cys Met Lys Thr Leu Leu Leu
            660                 665                 670

Leu Ser Ser Val Pro Lys Asp Gly Leu Lys Ser Gln Glu Leu Phe Asp
        675                 680                 685

Glu Ile Arg Met Thr Tyr Ile Lys Glu Leu Gly Lys Ala Ile Val Lys
    690                 695                 700

Arg Glu Gly Asn Ser Ser Gln Asn Trp Gln Arg Phe Tyr Gln Leu Thr
705                 710                 715                 720

Lys Leu Leu Asp Ser Met His Glu Val Val Glu Asn Leu Leu Asn Tyr
                725                 730                 735

Cys Phe Gln Thr Phe Leu Asp Lys Thr Met Ser Ile Glu Phe Pro Glu
            740                 745                 750

Met Leu Ala Glu Ile Ile Thr Asn Gln Ile Pro Lys Tyr Ser Asn Gly
        755                 760                 765

Asn Ile Lys Lys Leu Leu Phe His Gln Lys
    770                 775


<210> SEQ ID NO 13
<211> LENGTH: 742
<212> TYPE: PRT
<213> ORGANISM: Homo sapiens

<400> SEQUENCE: 13

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240
```

```
Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655
```

-continued

```
Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Asn Val Met Trp Leu Lys Pro Glu Ser
                725                 730                 735

Thr Ser His Thr Leu Ile
            740


<210> SEQ ID NO 14
<211> LENGTH: 6801
<212> TYPE: DNA
<213> ORGANISM: Homo sapiens

<400> SEQUENCE: 14

ggcgccgcct ccacccgctc cccgctcggt cccgctcgct cgcccaggcc gggctgccct      60

ttcgcgtgtc cgcgctctct tccctccgcc gccgcctcct ccattttgcg agctcgtgtc     120

tgtgacggga gcccgagtca ccgcctgccc gtcggggacg gattctgtgg gtggaaggag     180

acgccgcagc cggagcggcc gaagcagctg ggaccgggac ggggcacgcg cgcccggaac     240

ctcgacccgc ggagcccggc gcggggcgga gggctggctt gtcagctggg caatgggaga     300

ctttcttaaa taggggctct ccccccaccc atggagaaag gggcggctgt ttacttcctt     360

tttttagaaa aaaaaaatat atttccctcc tgctccttct gcgttcacaa gctaagttgt     420

ttatctcggc tgcggcggga actgcggacg gtggcgggcg agcggctcct ctgccagagt     480

tgatattcac tgatggactc caaagaatca ttaactcctg gtagagaaga aaaccccagc     540

agtgtgcttg ctcaggagag gggagatgtg atggacttct ataaaaccct aagaggagga     600

gctactgtga aggtttctgc gtcttcaccc tcactggctg tcgcttctca atcagactcc     660

aagcagcgaa gacttttggt tgattttcca aaaggctcag taagcaatgc gcagcagcca     720

gatctgtcca aagcagtttc actctcaatg ggactgtata tgggagagac agaaacaaaa     780

gtgatgggaa atgacctggg attcccacag cagggccaaa tcagcctttc ctcgggggaa     840

acagacttaa agcttttgga agaaagcatt gcaaacctca ataggtcgac cagtgttcca     900

gagaacccca agagttcagc atccactgct gtgtctgctg cccccacaga gaaggagttt     960

ccaaaaactc actctgatgt atcttcagaa cagcaacatt tgaagggcca gactggcacc    1020

aacggtggca atgtgaaatt gtataccaca gaccaaagca cctttgacat tttgcaggat    1080

ttggagtttt cttctgggtc cccaggtaaa gagacgaatg agagtccttg gagatcagac    1140

ctgttgatag atgaaaactg tttgctttct cctctggcgg gagaagacga ttcattcctt    1200

ttggaaggaa actcgaatga ggactgcaag cctctcattt taccggacac taaacccaaa    1260

attaaggata atggagatct ggttttgtca agccccagta atgtaacact gccccaagtg    1320

aaaacagaaa aagaagattt catcgaactc tgcacccctg gggtaattaa gcaagagaaa    1380

ctgggcacag tttactgtca ggcaagcttt cctggagcaa atataattgg taataaaatg    1440

tctgccattt ctgttcatgg tgtgagtacc tctggaggac agatgtacca ctatgacatg    1500

aatacagcat ccctttctca acagcaggat cagaagccta tttttaatgt cattccacca    1560

attcccgttg gttccgaaaa ttggaatagg tgccaaggat ctggagatga caacttgact    1620
```

-continued

```
tctctgggga ctctgaactt ccctggtcga acagtttttt ctaatggcta ttcaagcccc   1680
agcatgagac cagatgtaag ctctcctcca tccagctcct caacagcaac aacaggacca   1740
cctcccaaac tctgcctggt gtgctctgat gaagcttcag gatgtcatta tggagtctta   1800
acttgtggaa gctgtaaagt tttcttcaaa agagcagtgg aaggacagca caattaccta   1860
tgtgctggaa ggaatgattg catcatcgat aaaattcgaa gaaaaaactg cccagcatgc   1920
cgctatcgaa aatgtcttca ggctggaatg aacctggaag ctcgaaaaac aaagaaaaaa   1980
ataaaaggaa ttcagcaggc cactacagga gtctcacaag aaacctctga aaatcctggt   2040
aacaaaacaa tagttcctgc aacgttacca caactcaccc ctaccctggt gtcactgttg   2100
gaggttattg aacctgaagt gttatatgca ggatatgata gctctgttcc agactcaact   2160
tggaggatca tgactacgct caacatgtta ggagggcggc aagtgattgc agcagtgaaa   2220
tgggcaaagg caataccagg tttcaggaac ttacacctgg atgaccaaat gaccctactg   2280
cagtactcct ggatgtttct tatggcattt gctctggggt ggagatcata tagacaatca   2340
agtgcaaacc tgctgtgttt tgctcctgat ctgattatta atgagcagag aatgactcta   2400
ccctgcatgt acgaccaatg taaacacatg ctgtatgttt cctctgagtt acacaggctt   2460
caggtatctt atgaagagta tctctgtatg aaaaccttac tgcttctctc ttcagttcct   2520
aaggacggtc tgaagagcca agagctattt gatgaaatta gaatgaccta catcaaagag   2580
ctaggaaaag ccattgtcaa gagggaagga aactccagcc agaactggca gcggttttat   2640
caactgacaa aactcttgga ttctatgcat gaagtggttg aaaatctcct taactattgc   2700
ttccaaacat tttggataa gaccatgagt attgaattcc ccgagatgtt agctgaaatc   2760
atcaccaatc agataccaaa atattcaaat ggaaatatca aaaaacttct gtttcatcaa   2820
aagtgactgc cttaataaga atggttgcct taaagaaagt cgaattaata gcttttattg   2880
tataaactat cagtttgtcc tgtagaggtt ttgttgtttt atttttttatt gttttcatct   2940
gttgttttgt tttaaatacg cactacatgt ggtttataga gggccaagac ttggcaacag   3000
aagcagttga gtcgtcatca cttttcagtg atgggagagt agatggtgaa atttattagt   3060
taatatatcc cagaaattag aaaccttaat atgtggacgt aatctccaca gtcaaagaag   3120
gatggcacct aaaccaccag tgcccaaagt ctgtgtgatg aactttctct tcatactttt   3180
tttcacagtt ggctggatga aattttctag actttctgtt ggtgtatccc ccccctgtat   3240
agttaggata gcatttttga tttatgcatg gaaacctgaa aaaaagttta caagtgtata   3300
tcagaaaagg gaagttgtgc cttttatagc tattactgtc tggttttaac aatttccttt   3360
atatttagtg aactacgctt gctcattttt tcttacataa tttttttattc aagttattgt   3420
acagctgttt aagatgggca gctagttcgt agctttccca aataaactct aaacattaat   3480
caatcatctg tgtgaaaatg ggttggtgct tctaacctga tggcacttag ctatcagaag   3540
accacaaaaa ttgactcaaa tctccagtat tcttgtcaaa aaaaaaaaaa aaaaagctca   3600
tattttgtat atatctgctt cagtggagaa ttatataggt tgtgcaaatt aacagtccta   3660
actggtatag agcacctagt ccagtgacct gctgggtaaa ctgtggatga tggttgcaaa   3720
agactaattt aaaaaataac taccaagagg ccctgtctgt acctaacgcc ctatttttgc   3780
aatggctata tggcaagaaa gctggtaaac tatttgtctt tcaggacctt ttgaagtagt   3840
ttgtataact tcttaaaagt tgtgattcca gataaccagc tgtaacacag ctgagagact   3900
tttaatcaga caaagtaatt cctctcacta aactttaccc aaaaactaaa tctctaatat   3960
```

-continued ggcaaaaatg gctagacacc cattttcaca ttcccatctg tcaccaattg gttaatcttt 4020
cctgatggta caggaaagct cagctactga tttttgtgat ttagaactgt atgtcagaca 4080
tccatgtttg taaaactaca catccctaat gtgtgccata gagtttaaca caagtcctgt 4140
gaatttcttc actgttgaaa attattttaa acaaaataga agctgtagta gccctttctg 4200
tgtgcacctt accaactttc tgtaaactca aaacttaaca tatttactaa gccacaagaa 4260
atttgatttc tattcaaggt ggccaaatta tttgtgtaat agaaaactga aaatctaata 4320
ttaaaaatat ggaacttcta atatattttt atatttagtt atagtttcag atatatatca 4380
tattggtatt cactaatctg ggaagggaag ggctactgca gctttacatg caatttatta 4440
aaatgattgt aaaatagctt gtatagtgta aaataagaat gatttttaga tgagattgtt 4500
ttatcatgac atgttatata ttttttgtag gggtcaaaga aatgctgatg gataacctat 4560
atgatttata gtttgtacat gcattcatac aggcagcgat ggtctcagaa accaaacagt 4620
ttgctctagg ggaagaggga gatggagact ggtcctgtgt gcagtgaagg ttgctgaggc 4680
tctgacccag tgagattaca gaggaagtta tcctctgcct cccattctga ccacccttct 4740
cattccaaca gtgagtctgt cagcgcaggt ttagtttact caatctcccc ttgcactaaa 4800
gtatgtaaag tatgtaaaca ggagacagga aggtggtgct tacatcctta aaggcaccat 4860
ctaatagcgg gttactttca catacagccc tcccccagca gttgaatgac aacagaagct 4920
tcagaagttt ggcaatagtt tgcatagagg taccagcaat atgtaaatag tgcagaatct 4980
cataggttgc caataataca ctaattcctt tctatcctac aacaagagtt tatttccaaa 5040
taaaatgagg acatgttttt gttttctttg aatgcttttt gaatgttatt tgttattttc 5100
agtattttgg agaaattatt taataaaaaa acaatcattt gcttttttgaa tgctctctaa 5160
aagggaatgt aatattttaa gatggtgtgt aacccggctg gataaatttt tggtgcctaa 5220
gaaaactgct tgaatattct tatcaatgac agtgttaagt ttcaaaaaga gcttctaaaa 5280
cgtagattat cattccttta tagaatgtta tgtggttaaa accagaaagc acatctcaca 5340
cattaatctg attttcatcc caacaatctt ggcgctcaaa aaatagaact caatgagaaa 5400
aagaagatta tgtgcacttc gttgtcaata ataagtcaac tgatgctcat cgacaactat 5460
aggaggcttt tcattaaatg ggaaaagaag ctgtgccctt ttaggatacg tgggggaaaa 5520
gaaagtcatc ttaattatgt ttaattgtgg atttaagtgc tatatggtgg tgctgtttga 5580
aagcagattt atttcctatg tatgtgttat ctggccatcc caacccaaac tgttgaagtt 5640
tgtagtaact tcagtgagag ttggttactc acaacaaatc ctgaaaagta tttttagtgt 5700
ttgtaggtat tctgtgggat actatacaag cagaactgag gcacttagga cataacactt 5760
ttggggtata tatatccaaa tgcctaaaac tatgggagga aaccttggcc accccaaaag 5820
gaaaactaac atgatttgtg tctatgaagt gctggataat tagcatggga tgagctctgg 5880
gcatgccatg aaggaaagcc acgctccctt cagaattcag aggcagggag caattccagt 5940
ttcacctaag tctcataatt ttagttccct tttaaaaacc ctgaaaacta catcaccatg 6000
gaatgaaaaa tattgttata caatacattg atctgtcaaa cttccagaac catggtagcc 6060
ttcagtgaga tttccatctt ggctggtcac tccctgactg tagctgtagg tgaatgtgtt 6120
tttgtgtgtg tgtgtctggt tttagtgtca gaagggaaat aaaagtgtaa ggaggacact 6180
ttaaaccctt tgggtggagt ttcgtaattt cccagactat tttcaagcaa cctggtccac 6240
ccaggattag tgaccaggtt ttcaggaaag gatttgcttc tctctagaaa atgtctgaaa 6300
ggattttatt ttctgatgaa aggctgtatg aaaataccct cctcaaataa cttgcttaac 6360

```
tacatataga ttcaagtgtg tcaatattct attttgtata ttaaatgcta tataatgggg   6420

acaaatctat attatactgt gtatggcatt attaagaagc tttttcatta tttttttatca   6480

cagtaatttt aaaatgtgta aaaattaaaa ccagtgactc ctgtttaaaa ataaaagttg   6540

tagtttttta ttcatgctga ataataatct gtagttaaaa aaaaagtgtc tttttaccta   6600

cgcagtgaaa tgtcagactg taaaaccttg tgtggaaatg tttaactttt atttttttcat   6660

ttaaatttgc tgttctggta ttaccaaacc acacatttgt accgaattgg cagtaaatgt   6720

tagccattta cagcaatgcc aaatatggag aaacatcata ataaaaaaat ctgctttttc   6780

attaaaaaaa aaaaaaaaaa a                                              6801
```

<210> SEQ ID NO 15
<211> LENGTH: 6614
<212> TYPE: DNA
<213> ORGANISM: Homo sapiens

<400> SEQUENCE: 15

```
aggttatgta agggtttgct ttcaccccat tcaaaaggta cctcttcctc ttctcttgct     60

ccctctcgcc ctcattcttg tgcctatgca gacatttgag tagaggcgaa tcactttcac    120

ttctgctggg gaaattgcaa cacgcttctt taaatggcag agagaaggag aaaacttaga    180

tcttctgata ccaaatcact ggaccttaga aggtcagaaa tctttcaagc cctgcaggac    240

cgtaaaatgc gcatgtgtcc aacggaagca ctggggcatg agtggggaag gaatagaaac    300

agaaagaggt tgatattcac tgatggactc caaagaatca ttaactcctg gtagagaaga    360

aaaccccagc agtgtgcttg ctcaggagag gggagatgtg atggacttct ataaaaccct    420

aagaggagga gctactgtga aggtttctgc gtcttcaccc tcactggctg tcgcttctca    480

atcagactcc aagcagcgaa gacttttggt tgattttcca aaaggctcag taagcaatgc    540

gcagcagcca gatctgtcca aagcagtttc actctcaatg ggactgtata tgggagagac    600

agaaacaaaa gtgatgggaa atgacctggg attcccacag cagggccaaa tcagcctttc    660

ctcgggggaa acagacttaa agcttttgga agaaagcatt gcaaacctca ataggtcgac    720

cagtgttcca gagaacccca agagttcagc atccactgct gtgtctgctg cccccacaga    780

gaaggagttt ccaaaaactc actctgatgt atcttcagaa cagcaacatt tgaagggcca    840

gactggcacc aacggtggca atgtgaaatt gtataccaca gaccaaagca cctttgacat    900

tttgcaggat ttggagtttt cttctgggtc cccaggtaaa gagacgaatg agagtccttg    960

gagatcagac ctgttgatag atgaaaactg tttgcttttct cctctggcgg gagaagacga   1020

ttcattcctt ttggaaggaa actcgaatga ggactgcaag cctctcattt taccggacac   1080

taaacccaaa attaaggata atggagatct ggttttgtca agccccagta atgtaacact   1140

gccccaagtg aaaacagaaa aagaagattt catcgaactc tgcacccctg gggtaattaa   1200

gcaagagaaa ctgggcacag tttactgtca ggcaagcttt cctggagcaa atataattgg   1260

taataaaatg tctgccattt ctgttcatgg tgtgagtacc tctggaggac agatgtacca   1320

ctatgacatg aatacagcat ccctttctca acagcaggat cagaagccta tttttaatgt   1380

cattccacca attcccgttg gttccgaaaa ttggaatagg tgccaaggat ctggagatga   1440

caacttgact tctctgggga ctctgaactt ccctggtcga acagtttttt ctaatggcta   1500

ttcaagcccc agcatgagac cagatgtaag ctctcctcca tccagctcct caacagcaac   1560

aacaggacca cctcccaaac tctgcctggt gtgctctgat gaagcttcag gatgtcatta   1620
```

-continued

```
tggagtctta acttgtggaa gctgtaaagt tttcttcaaa agagcagtgg aaggacagca   1680
caattaccta tgtgctggaa ggaatgattg catcatcgat aaaattcgaa gaaaaaactg   1740
cccagcatgc cgctatcgaa aatgtcttca ggctggaatg aacctggaag ctcgaaaaac   1800
aaagaaaaaa ataaaaggaa ttcagcaggc cactacagga gtctcacaag aaacctctga   1860
aaatcctggt aacaaaacaa tagttcctgc aacgttacca caactcaccc ctaccctggt   1920
gtcactgttg gaggttattg aacctgaagt gttatatgca ggatatgata gctctgttcc   1980
agactcaact tggaggatca tgactacgct caacatgtta ggagggcggc aagtgattgc   2040
agcagtgaaa tgggcaaagg caataccagg tttcaggaac ttacacctgg atgaccaaat   2100
gaccctactg cagtactcct ggatgtttct tatggcattt gctctggggt ggagatcata   2160
tagacaatca agtgcaaacc tgctgtgttt tgctcctgat ctgattatta atgagcagag   2220
aatgactcta ccctgcatgt acgaccaatg taaacacatg ctgtatgttt cctctgagtt   2280
acacaggctt caggtatctt atgaagagta tctctgtatg aaaaccttac tgcttctctc   2340
ttcagttcct aaggacggtc tgaagagcca agagctattt gatgaaatta gaatgaccta   2400
catcaaagag ctaggaaaag ccattgtcaa gagggaagga aactccagcc agaactggca   2460
gcggttttat caactgacaa aactcttgga ttctatgcat gaagtggttg aaaatctcct   2520
taactattgc ttccaaacat tttggataa gaccatgagt attgaattcc ccgagatgtt   2580
agctgaaatc atcaccaatc agataccaaa atattcaaat ggaaatatca aaaaacttct   2640
gtttcatcaa aagtgactgc cttaataaga atggttgcct taaagaaagt cgaattaata   2700
gcttttattg tataaactat cagtttgtcc tgtagaggtt ttgttgtttt atttttttatt   2760
gttttcatct gttgttttgt tttaaatacg cactacatgt ggtttataga gggccaagac   2820
ttggcaacag aagcagttga gtcgtcatca cttttcagtg atgggagagt agatggtgaa   2880
atttattagt taatatatcc cagaaattag aaaccttaat atgtggacgt aatctccaca   2940
gtcaaagaag gatggcacct aaaccaccag tgcccaaagt ctgtgtgatg aactttctct   3000
tcatactttt tttcacagtt ggctggatga aattttctag actttctgtt ggtgtatccc   3060
ccccctgtat agttaggata gcatttttga tttatgcatg gaaacctgaa aaaaagttta   3120
caagtgtata tcagaaaagg gaagttgtgc cttttatagc tattactgtc tggttttaac   3180
aatttccttt atatttagtg aactacgctt gctcattttt tcttacataa ttttttattc   3240
aagttattgt acagctgttt aagatgggca gctagttcgt agctttccca aataaactct   3300
aaacattaat caatcatctg tgtgaaaatg ggttggtgct tctaacctga tggcacttag   3360
ctatcagaag accacaaaaa ttgactcaaa tctccagtat tcttgtcaaa aaaaaaaaaa   3420
aaaaagctca tattttgtat atatctgctt cagtggagaa ttatataggt tgtgcaaatt   3480
aacagtccta actggtatag agcacctagt ccagtgacct gctgggtaaa ctgtggatga   3540
tggttgcaaa agactaattt aaaaaataac taccaagagg ccctgtctgt acctaacgcc   3600
ctatttttgc aatggctata tggcaagaaa gctggtaaac tatttgtctt tcaggacctt   3660
ttgaagtagt ttgtataact tcttaaaagt tgtgattcca gataaccagc tgtaacacag   3720
ctgagagact tttaatcaga caaagtaatt cctctcacta aactttaccc aaaaactaaa   3780
tctctaatat ggcaaaaatg gctagacacc cattttcaca ttcccatctg tcaccaattg   3840
gttaatcttt cctgatggta caggaaagct cagctactga tttttgtgat ttagaactgt   3900
atgtcagaca tccatgtttg taaaactaca catccctaat gtgtgccata gagtttaaca   3960
caagtcctgt gaatttcttc actgttgaaa attattttaa acaaaataga agctgtagta   4020
```

```
gccctttctg tgtgcacctt accaactttc tgtaaactca aaacttaaca tatttactaa   4080
gccacaagaa atttgatttc tattcaaggt ggccaaatta tttgtgtaat agaaaactga   4140
aaatctaata ttaaaaatat ggaacttcta atatattttt atatttagtt atagtttcag   4200
atatatatca tattggtatt cactaatctg ggaagggaag ggctactgca gctttacatg   4260
caatttatta aaatgattgt aaaatagctt gtatagtgta aaataagaat gatttttaga   4320
tgagattgtt ttatcatgac atgttatata tttttgtag  gggtcaaaga aatgctgatg   4380
gataacctat atgatttata gtttgtacat gcattcatac aggcagcgat ggtctcagaa   4440
accaaacagt ttgctctagg ggaagaggga gatggagact ggtcctgtgt gcagtgaagg   4500
ttgctgaggc tctgacccag tgagattaca gaggaagtta tcctctgcct cccattctga   4560
ccacccttct cattccaaca gtgagtctgt cagcgcaggt ttagtttact caatctcccc   4620
ttgcactaaa gtatgtaaag tatgtaaaca ggagacagga aggtggtgct tacatcctta   4680
aaggcaccat ctaatagcgg gttactttca catacagccc tcccccagca gttgaatgac   4740
aacagaagct tcagaagttt ggcaatagtt tgcatagagg taccagcaat atgtaaatag   4800
tgcagaatct cataggttgc caataataca ctaattcctt tctatcctac aacaagagtt   4860
tatttccaaa taaaatgagg acatgttttt gttttctttg aatgcttttt gaatgttatt   4920
tgttattttc agtattttgg agaaattatt taataaaaaa acaatcattt gctttttgaa   4980
tgctctctaa aagggaatgt aatattttaa gatggtgtgt aacccggctg gataaatttt   5040
tggtgcctaa gaaaactgct tgaatattct tatcaatgac agtgttaagt ttcaaaaaga   5100
gcttctaaaa cgtagattat cattccttta tagaatgtta tgtggttaaa accagaaagc   5160
acatctcaca cattaatctg attttcatcc caacaatctt ggcgctcaaa aaatagaact   5220
caatgagaaa aagaagatta tgtgcacttc gttgtcaata ataagtcaac tgatgctcat   5280
cgacaactat aggaggcttt tcattaaatg ggaaaagaag ctgtgccctt ttaggatacg   5340
tgggggaaaa gaaagtcatc ttaattatgt ttaattgtgg atttaagtgc tatatggtgg   5400
tgctgtttga aagcagattt atttcctatg tatgtgttat ctggccatcc caacccaaac   5460
tgttgaagtt tgtagtaact tcagtgagag ttggttactc acaacaaatc ctgaaaagta   5520
tttttagtgt ttgtaggtat tctgtgggat actatacaag cagaactgag gcacttagga   5580
cataacactt ttggggtata tatatccaaa tgcctaaaac tatgggagga aaccttggcc   5640
accccaaaag gaaaactaac atgatttgtg tctatgaagt gctggataat tagcatggga   5700
tgagctctgg gcatgccatg aaggaaagcc acgctccctt cagaattcag aggcagggag   5760
caattccagt ttcacctaag tctcataatt ttagttccct tttaaaaacc ctgaaaacta   5820
catcaccatg gaatgaaaaa tattgttata caatacattg atctgtcaaa cttccagaac   5880
catggtagcc ttcagtgaga tttccatctt ggctggtcac tccctgactg tagctgtagg   5940
tgaatgtgtt tttgtgtgtg tgtgtctggt tttagtgtca gaagggaaat aaaagtgtaa   6000
ggaggacact ttaaaccctt tgggtggagt ttcgtaattt cccagactat tttcaagcaa   6060
cctggtccac ccaggattag tgaccaggtt ttcaggaaag gatttgcttc tctctagaaa   6120
atgtctgaaa ggattttatt ttctgatgaa aggctgtatg aaaataccct cctcaaataa   6180
cttgcttaac tacatataga ttcaagtgtg tcaatattct attttgtata ttaaatgcta   6240
tataatgggg acaaatctat attatactgt gtatggcatt attaagaagc tttttcatta   6300
ttttttatca cagtaatttt aaaatgtgta aaaattaaaa ccagtgactc ctgtttaaaa   6360
```

ataaaagttg tagtttttta ttcatgctga ataataatct gtagttaaaa aaaaagtgtc 6420
tttttaccta cgcagtgaaa tgtcagactg taaaaccttg tgtggaaatg tttaactttt 6480
attttttcat ttaaatttgc tgttctggta ttaccaaacc acacatttgt accgaattgg 6540
cagtaaatgt tagccattta cagcaatgcc aaatatggag aaacatcata ataaaaaaat 6600
ctgctttttc atta 6614

<210> SEQ ID NO 16
<211> LENGTH: 6517
<212> TYPE: DNA
<213> ORGANISM: Homo sapiens

<400> SEQUENCE: 16
aggttatgta agggtttgct ttcaccccat tcaaaaggta cctcttcctc ttctcttgct 60
ccctctcgcc ctcattcttg tgcctatgca gacatttgag tagaggcgaa tcactttcac 120
ttctgctggg gaaattgcaa cacgcttctt taaatggcag agagaaggag aaaacttaga 180
tcttctgata ccaaatcact ggaccttaga agttgatatt cactgatgga ctccaaagaa 240
tcattaactc ctggtagaga agaaaacccc agcagtgtgc ttgctcagga gaggggagat 300
gtgatggact tctataaaac cctaagagga ggagctactg tgaaggtttc tgcgtcttca 360
ccctcactgg ctgtcgcttc tcaatcagac tccaagcagc gaagactttt ggttgatttt 420
ccaaaaggct cagtaagcaa tgcgcagcag ccagatctgt ccaaagcagt ttcactctca 480
atgggactgt atatgggaga gacagaaaca aaagtgatgg gaaatgacct gggattccca 540
cagcagggcc aaatcagcct ttcctcgggg gaaacagact taaagctttt ggaagaaagc 600
attgcaaacc tcaataggtc gaccagtgtt ccagagaacc ccaagagttc agcatccact 660
gctgtgtctg ctgcccccac agagaaggag tttccaaaaa ctcactctga tgtatcttca 720
gaacagcaac atttgaaggg ccagactggc accaacggtg gcaatgtgaa attgtatacc 780
acagaccaaa gcacctttga cattttgcag gatttggagt tttcttctgg gtccccaggt 840
aaagagacga atgagagtcc ttggagatca gacctgttga tagatgaaaa ctgtttgctt 900
tctcctctgg cgggagaaga cgattcattc cttttggaag gaaactcgaa tgaggactgc 960
aagcctctca ttttaccgga cactaaaccc aaaattaagg ataatggaga tctggttttg 1020
tcaagcccca gtaatgtaac actgccccaa gtgaaaacag aaaaagaaga tttcatcgaa 1080
ctctgcaccc ctggggtaat taagcaagag aaactgggca cagtttactg tcaggcaagc 1140
tttcctggag caaatataat tggtaataaa atgtctgcca tttctgttca tggtgtgagt 1200
acctctggag gacagatgta ccactatgac atgaatacag catccctttc tcaacagcag 1260
gatcagaagc ctattttaa tgtcattcca ccaattcccg ttggttccga aaattggaat 1320
aggtgccaag gatctggaga tgacaacttg acttctctgg ggactctgaa cttccctggt 1380
cgaacagttt tttctaatgg ctattcaagc cccagcatga gaccagatgt aagctctcct 1440
ccatccagct cctcaacagc aacaacagga ccacctccca aactctgcct ggtgtgctct 1500
gatgaagctt caggatgtca ttatggagtc ttaacttgtg gaagctgtaa agtttcttc 1560 aaaagagcag tggaaggaca gcacaattac ctatgtgctg gaaggaatga ttgcatcatc 1620
gataaaattc gaagaaaaaa ctgcccagca tgccgctatc gaaaatgtct tcaggctgga 1680
atgaacctgg aagctcgaaa aacaaagaaa aaaataaaag gaattcagca ggccactaca 1740
ggagtctcac aagaaacctc tgaaaatcct ggtaacaaaa caatagttcc tgcaacgtta 1800
ccacaactca cccctaccct ggtgtcactg ttggaggtta ttgaacctga agtgttatat 1860

-continued gcaggatatg atagctctgt tccagactca acttggagga tcatgactac gctcaacatg 1920
ttaggagggc ggcaagtgat tgcagcagtg aaatgggcaa aggcaatacc aggtttcagg 1980
aacttacacc tggatgacca aatgacccta ctgcagtact cctggatgtt tcttatggca 2040
tttgctctgg ggtggagatc atatagacaa tcaagtgcaa acctgctgtg ttttgctcct 2100
gatctgatta ttaatgagca gagaatgact ctaccctgca tgtacgacca atgtaaacac 2160
atgctgtatg tttcctctga gttacacagg cttcaggtat cttatgaaga gtatctctgt 2220
atgaaaacct tactgcttct ctcttcagtt cctaaggacg gtctgaagag ccaagagcta 2280
tttgatgaaa ttagaatgac ctacatcaaa gagctaggaa aagccattgt caagagggaa 2340
ggaaactcca gccagaactg gcagcggttt tatcaactga caaaactctt ggattctatg 2400
catgaagtgg ttgaaaatct ccttaactat tgcttccaaa catttttgga taagaccatg 2460
agtattgaat tccccgagat gttagctgaa atcatcacca atcagatacc aaaatattca 2520
aatggaaata tcaaaaaact tctgtttcat caaaagtgac tgccttaata agaatggttg 2580
ccttaaagaa agtcgaatta atagctttta ttgtataaac tatcagtttg tcctgtagag 2640
gttttgttgt tttatttttt attgttttca tctgttgttt tgttttaaat acgcactaca 2700
tgtggtttat agagggccaa gacttggcaa cagaagcagt tgagtcgtca tcacttttca 2760
gtgatgggag agtagatggt gaaatttatt agttaatata tcccagaaat tagaaacctt 2820
aatatgtgga cgtaatctcc acagtcaaag aaggatggca cctaaaccac cagtgcccaa 2880
agtctgtgtg atgaactttc tcttcatact ttttttcaca gttggctgga tgaaattttc 2940
tagactttct gttggtgtat cccccccctg tatagttagg atagcatttt tgatttatgc 3000
atggaaacct gaaaaaaagt ttacaagtgt atatcagaaa agggaagttg tgccttttat 3060
agctattact gtctggtttt aacaatttcc tttatattta gtgaactacg cttgctcatt 3120
ttttcttaca taattttttta ttcaagttat tgtacagctg tttaagatgg gcagctagtt 3180
cgtagctttc ccaaataaac tctaaacatt aatcaatcat ctgtgtgaaa atgggttggt 3240
gcttctaacc tgatggcact tagctatcag aagaccacaa aaattgactc aaatctccag 3300
tattcttgtc aaaaaaaaaa aaaaaaaagc tcatattttg tatatatctg cttcagtgga 3360
gaattatata ggttgtgcaa attaacagtc ctaactggta tagagcacct agtccagtga 3420
cctgctgggt aaactgtgga tgatggttgc aaaagactaa tttaaaaaat aactaccaag 3480
aggccctgtc tgtacctaac gccctatttt tgcaatggct atatggcaag aaagctggta 3540
aactatttgt ctttcaggac cttttgaagt agtttgtata acttcttaaa agttgtgatt 3600
ccagataacc agctgtaaca cagctgagag acttttaatc agacaaagta attcctctca 3660
ctaaacttta cccaaaaact aaatctctaa tatggcaaaa atggctagac acccattttc 3720
acattcccat ctgtcaccaa ttggttaatc tttcctgatg gtacaggaaa gctcagctac 3780
tgatttttgt gatttagaac tgtatgtcag acatccatgt ttgtaaaact acacatccct 3840
aatgtgtgcc atagagttta acacaagtcc tgtgaatttc ttcactgttg aaaattattt 3900
taaacaaaat agaagctgta gtagcccttt ctgtgtgcac cttaccaact ttctgtaaac 3960
tcaaaactta acatatttac taagccacaa gaaatttgat ttctattcaa ggtggccaaa 4020
ttatttgtgt aatagaaaac tgaaaatcta atattaaaaa tatggaactt ctaatatatt 4080
tttatattta gttatagttt cagatatata tcatattggt attcactaat ctgggaaggg 4140
aagggctact gcagctttac atgcaattta ttaaaatgat tgtaaaatag cttgtatagt 4200

-continued

```
gtaaaataag aatgattttt agatgagatt gttttatcat gacatgttat atattttttg   4260
taggggtcaa agaaatgctg atggataacc tatatgattt atagtttgta catgcattca   4320
tacaggcagc gatggtctca gaaaccaaac agtttgctct aggggaagag ggagatggag   4380
actggtcctg tgtgcagtga aggttgctga ggctctgacc cagtgagatt acagaggaag   4440
ttatcctctg cctcccattc tgaccaccct tctcattcca acagtgagtc tgtcagcgca   4500
ggtttagttt actcaatctc cccttgcact aaagtatgta aagtatgtaa acaggagaca   4560
ggaaggtggt gcttacatcc ttaaaggcac catctaatag cgggttactt tcacatacag   4620
ccctccccca gcagttgaat gacaacagaa gcttcagaag tttggcaata gtttgcatag   4680
aggtaccagc aatatgtaaa tagtgcagaa tctcataggt tgccaataat acactaattc   4740
ctttctatcc tacaacaaga gtttatttcc aaataaaatg aggacatgtt tttgttttct   4800
ttgaatgctt tttgaatgtt atttgttatt ttcagtattt tggagaaatt atttaataaa   4860
aaaacaatca tttgcttttt gaatgctctc taaaagggaa tgtaatattt taagatggtg   4920
tgtaacccgg ctggataaat ttttggtgcc taagaaaact gcttgaatat tcttatcaat   4980
gacagtgtta agtttcaaaa agagcttcta aaacgtagat tatcattcct ttatagaatg   5040
ttatgtggtt aaaaccagaa agcacatctc acacattaat ctgattttca tcccaacaat   5100
cttggcgctc aaaaaataga actcaatgag aaaaagaaga ttatgtgcac ttcgttgtca   5160
ataataagtc aactgatgct catcgacaac tataggaggc ttttcattaa atgggaaaag   5220
aagctgtgcc cttttaggat acgtggggga aaagaaagtc atcttaatta tgtttaattg   5280
tggatttaag tgctatatgg tggtgctgtt tgaaagcaga tttatttcct atgtatgtgt   5340
tatctggcca tcccaaccca aactgttgaa gtttgtagta acttcagtga gagttggtta   5400
ctcacaacaa atcctgaaaa gtatttttag tgtttgtagg tattctgtgg gatactatac   5460
aagcagaact gaggcactta ggacataaca cttttggggt atatatatcc aaatgcctaa   5520
aactatggga ggaaaccttg gccaccccaa aaggaaaact aacatgattt gtgtctatga   5580
agtgctggat aattagcatg ggatgagctc tgggcatgcc atgaaggaaa gccacgctcc   5640
cttcagaatt cagaggcagg gagcaattcc agtttcacct aagtctcata attttagttc   5700
ccttttaaaa accctgaaaa ctacatcacc atggaatgaa aaatattgtt atacaataca   5760
ttgatctgtc aaacttccag aaccatggta gccttcagtg agatttccat cttggctggt   5820
cactccctga ctgtagctgt aggtgaatgt gtttttgtgt gtgtgtgtct ggttttagtg   5880
tcagaaggga aataaaagtg taaggaggac actttaaacc ctttgggtgg agtttcgtaa   5940
tttcccagac tattttcaag caacctggtc cacccaggat tagtgaccag gttttcagga   6000
aaggatttgc ttctctctag aaaatgtctg aaaggatttt attttctgat gaaaggctgt   6060
atgaaaatac cctcctcaaa taacttgctt aactacatat agattcaagt gtgtcaatat   6120
tctattttgt atattaaatg ctatataatg gggacaaatc tatattatac tgtgtatggc   6180
attattaaga agctttttca ttattttta tcacagtaat tttaaaatgt gtaaaaatta   6240
aaaccagtga ctcctgttta aaaataaaag ttgtagtttt ttattcatgc tgaataataa   6300
tctgtagtta aaaaaaaagt gtctttttac ctacgcagtg aaatgtcaga ctgtaaaacc   6360
ttgtgtggaa atgtttaact tttattttt catttaaatt tgctgttctg gtattaccaa   6420
accacacatt tgtaccgaat tggcagtaaa tgttagccat ttacagcaat gccaaatatg   6480
gagaaacatc ataataaaaa aatctgcttt ttcatta                            6517
```

<210> SEQ ID NO 17
<211> LENGTH: 6410
<212> TYPE: DNA
<213> ORGANISM: Homo sapiens

<400> SEQUENCE: 17

```
cttctctccc agtgcgagag cgcggcggcg gcagctgaag acccggccgc ccagatgatg     60
cggtggtggg ggacctgccg gcacgcgact ccccccgggc ccaaattgat attcactgat    120
ggactccaaa gaatcattaa ctcctggtag agaagaaaac cccagcagtg tgcttgctca    180
ggagagggga gatgtgatgg acttctataa aaccctaaga ggaggagcta ctgtgaaggt    240
ttctgcgtct tcaccctcac tggctgtcgc ttctcaatca gactccaagc agcgaagact    300
tttggttgat tttccaaaag gctcagtaag caatgcgcag cagccagatc tgtccaaagc    360
agtttcactc tcaatgggac tgtatatggg agagacagaa acaaaagtga tgggaaatga    420
cctgggattc ccacagcagg gccaaatcag cctttcctcg ggggaaacag acttaaagct    480
tttggaagaa agcattgcaa acctcaatag gtcgaccagt gttccagaga accccaagag    540
ttcagcatcc actgctgtgt ctgctgcccc cacagagaag gagtttccaa aaactcactc    600
tgatgtatct tcagaacagc aacatttgaa gggccagact ggcaccaacg gtggcaatgt    660
gaaattgtat accacagacc aaagcacctt tgacattttg caggatttgg agttttcttc    720
tgggtcccca ggtaaagaga cgaatgagag tccttggaga tcagacctgt tgatagatga    780
aaactgtttg ctttctcctc tggcgggaga agacgattca ttccttttgg aaggaaactc    840
gaatgaggac tgcaagcctc tcattttacc ggacactaaa cccaaaatta aggataatgg    900
agatctggtt ttgtcaagcc ccagtaatgt aacactgccc caagtgaaaa cagaaaaaga    960
agatttcatc gaactctgca cccctggggt aattaagcaa gagaaactgg gcacagttta   1020
ctgtcaggca agctttcctg gagcaaatat aattggtaat aaaatgtctg ccatttctgt   1080
tcatggtgtg agtacctctg gaggacagat gtaccactat gacatgaata cagcatccct   1140
ttctcaacag caggatcaga agcctatttt taatgtcatt ccaccaattc ccgttggttc   1200
cgaaaattgg aataggtgcc aaggatctgg agatgacaac ttgacttctc tggggactct   1260
gaacttccct ggtcgaacag tttttctaa tggctattca agccccagca tgagaccaga   1320
tgtaagctct cctccatcca gctcctcaac agcaacaaca ggaccacctc ccaaactctg   1380
cctggtgtgc tctgatgaag cttcaggatg tcattatgga gtcttaactt gtggaagctg   1440
taaagttttc ttcaaaagag cagtggaagg acagcacaat tacctatgtg ctggaaggaa   1500
tgattgcatc atcgataaaa ttcgaagaaa aaactgccca gcatgccgct atcgaaaatg   1560
tcttcaggct ggaatgaacc tggaagctcg aaaaacaaag aaaaaaataa aaggaattca   1620
gcaggccact acaggagtct cacaagaaac ctctgaaaat cctggtaaca aaacaatagt   1680
tcctgcaacg ttaccacaac tcacccctac cctggtgtca ctgttggagg ttattgaacc   1740
tgaagtgtta tatgcaggat atgatagctc tgttccagac tcaacttgga ggatcatgac   1800
tacgctcaac atgttaggag ggcggcaagt gattgcagca gtgaaatggg caaaggcaat   1860
accaggtttc aggaacttac acctggatga ccaaatgacc ctactgcagt actcctggat   1920
gtttcttatg gcatttgctc tggggtggag atcatataga caatcaagtg caaacctgct   1980
gtgttttgct cctgatctga ttattaatga gcagagaatg actctaccct gcatgtacga   2040
ccaatgtaaa cacatgctgt atgtttcctc tgagttacac aggcttcagg tatcttatga   2100
agagtatctc tgtatgaaaa ccttactgct tctctcttca gttcctaagg acggtctgaa   2160
```

```
gagccaagag ctatttgatg aaattagaat gacctacatc aaagagctag gaaaagccat   2220
tgtcaagagg gaaggaaact ccagccagaa ctggcagcgg ttttatcaac tgacaaaact   2280
cttggattct atgcatgaag tggttgaaaa tctccttaac tattgcttcc aaacattttt   2340
ggataagacc atgagtattg aattccccga gatgttagct gaaatcatca ccaatcagat   2400
accaaaatat tcaaatggaa atatcaaaaa acttctgttt catcaaaagt gactgcctta   2460
ataagaatgg ttgccttaaa gaaagtcgaa ttaatagctt ttattgtata aactatcagt   2520
ttgtcctgta gaggttttgt tgttttattt tttattgttt tcatctgttg ttttgtttta   2580
aatacgcact acatgtggtt tatagagggc caagacttgg caacagaagc agttgagtcg   2640
tcatcacttt tcagtgatgg gagagtagat ggtgaaattt attagttaat atatcccaga   2700
aattagaaac cttaatatgt ggacgtaatc tccacagtca aagaaggatg gcacctaaac   2760
caccagtgcc caaagtctgt gtgatgaact ttctcttcat actttttttc acagttggct   2820
ggatgaaatt ttctagactt tctgttggtg tatccccccc ctgtatagtt aggatagcat   2880
ttttgattta tgcatggaaa cctgaaaaaa agtttacaag tgtatatcag aaaagggaag   2940
ttgtgccttt tatagctatt actgtctggt tttaacaatt tcctttatat ttagtgaact   3000
acgcttgctc atttttttctt acataatttt ttattcaagt tattgtacag ctgtttaaga   3060
tgggcagcta gttcgtagct ttcccaaata aactctaaac attaatcaat catctgtgtg   3120
aaaatgggtt ggtgcttcta acctgatggc acttagctat cagaagacca caaaaattga   3180
ctcaaatctc cagtattctt gtcaaaaaaa aaaaaaaaaa agctcatatt ttgtatatat   3240
ctgcttcagt ggagaattat ataggttgtg caaattaaca gtcctaactg gtatagagca   3300
cctagtccag tgacctgctg ggtaaactgt ggatgatggt tgcaaaagac taatttaaaa   3360
aataactacc aagaggccct gtctgtacct aacgccctat ttttgcaatg gctatatggc   3420
aagaaagctg gtaaactatt tgtctttcag gacctttttga agtagtttgt ataacttctt   3480
aaaagttgtg attccagata accagctgta acacagctga gagactttta atcagacaaa   3540
gtaattcctc tcactaaact ttacccaaaa actaaatctc taatatggca aaaatggcta   3600
gacacccatt ttcacattcc catctgtcac caattggtta atctttcctg atggtacagg   3660
aaagctcagc tactgatttt tgtgatttag aactgtatgt cagacatcca tgtttgtaaa   3720
actacacatc cctaatgtgt gccatagagt ttaacacaag tcctgtgaat ttcttcactg   3780
ttgaaaatta ttttaaacaa aatagaagct gtagtagccc tttctgtgtg caccttacca   3840
actttctgta aactcaaaac ttaacatatt tactaagcca caagaaattt gatttctatt   3900
caaggtggcc aaattatttg tgtaatagaa aactgaaaat ctaatattaa aaatatggaa   3960
cttctaatat atttttatat ttagttatag tttcagatat atatcatatt ggtattcact   4020
aatctgggaa gggaagggct actgcagctt tacatgcaat ttattaaaat gattgtaaaa   4080
tagcttgtat agtgtaaaat aagaatgatt tttagatgag attgttttat catgacatgt   4140
tatatatttt ttgtaggggt caaagaaatg ctgatggata acctatatga tttatagttt   4200
gtacatgcat tcatacaggc agcgatggtc tcagaaacca aacagtttgc tctaggggaa   4260
gagggagatg gagactggtc ctgtgtgcag tgaaggttgc tgaggctctg acccagtgag   4320
attacagagg aagttatcct ctgcctccca ttctgaccac ccttctcatt ccaacagtga   4380
gtctgtcagc gcaggtttag tttactcaat ctccccttgc actaaagtat gtaaagtatg   4440
taaacaggag acaggaaggt ggtgcttaca tccttaaagg caccatctaa tagcgggtta   4500
ctttcacata cagccctccc ccagcagttg aatgacaaca gaagcttcag aagtttggca   4560
```

atagtttgca tagaggtacc agcaatatgt aaatagtgca gaatctcata ggttgccaat 4620
aatacactaa ttcctttcta tcctacaaca agagtttatt tccaaataaa atgaggacat 4680
gtttttgttt tctttgaatg ctttttgaat gttatttgtt attttcagta ttttggagaa 4740
attatttaat aaaaaaacaa tcatttgctt tttgaatgct ctctaaaagg gaatgtaata 4800
ttttaagatg gtgtgtaacc cggctggata aatttttggt gcctaagaaa actgcttgaa 4860
tattcttatc aatgacagtg ttaagtttca aaaagagctt ctaaaacgta gattatcatt 4920
cctttataga atgttatgtg gttaaaacca gaaagcacat ctcacacatt aatctgattt 4980
tcatcccaac aatcttggcg ctcaaaaaat agaactcaat gagaaaaaga agattatgtg 5040
cacttcgttg tcaataataa gtcaactgat gctcatcgac aactatagga ggcttttcat 5100
taaatgggaa aagaagctgt gcccttttag gatacgtggg ggaaaagaaa gtcatcttaa 5160
ttatgtttaa ttgtggattt aagtgctata tggtggtgct gtttgaaagc agatttattt 5220
cctatgtatg tgttatctgg ccatcccaac ccaaactgtt gaagtttgta gtaacttcag 5280
tgagagttgg ttactcacaa caaatcctga aaagtatttt tagtgtttgt aggtattctg 5340
tgggatacta tacaagcaga actgaggcac ttaggacata acacttttgg ggtatatata 5400
tccaaatgcc taaaactatg ggaggaaacc ttggccaccc caaaaggaaa actaacatga 5460
tttgtgtcta tgaagtgctg gataattagc atgggatgag ctctgggcat gccatgaagg 5520
aaagccacgc tcccttcaga attcagaggc agggagcaat tccagtttca cctaagtctc 5580
ataattttag ttccctttta aaaaccctga aaactacatc accatggaat gaaaaatatt 5640
gttatacaat acattgatct gtcaaacttc cagaaccatg gtagccttca gtgagatttc 5700
catcttggct ggtcactccc tgactgtagc tgtaggtgaa tgtgtttttg tgtgtgtgtg 5760
tctggtttta gtgtcagaag ggaaataaaa gtgtaaggag gacactttaa accctttggg 5820
tggagtttcg taatttccca gactattttc aagcaacctg gtccacccag gattagtgac 5880
caggttttca ggaaaggatt tgcttctctc tagaaaatgt ctgaaaggat tttattttct 5940
gatgaaaggc tgtatgaaaa taccctcctc aaataacttg cttaactaca tatagattca 6000
agtgtgtcaa tattctattt tgtatattaa atgctatata atggggacaa atctatatta 6060
tactgtgtat ggcattatta agaagctttt tcattatttt ttatcacagt aattttaaaa 6120
tgtgtaaaaa ttaaaaccag tgactcctgt ttaaaaataa aagttgtagt tttttattca 6180
tgctgaataa taatctgtag ttaaaaaaaa agtgtctttt tacctacgca gtgaaatgtc 6240
agactgtaaa accttgtgtg gaaatgttta acttttattt tttcatttaa atttgctgtt 6300
ctggtattac caaaccacac atttgtaccg aattggcagt aaatgttagc catttacagc 6360
aatgccaaat atggagaaac atcataataa aaaaatctgc tttttcatta 6410

<210> SEQ ID NO 18
<211> LENGTH: 7286
<212> TYPE: DNA
<213> ORGANISM: Homo sapiens

<400> SEQUENCE: 18
aggttatgta agggtttgct ttcaccccat tcaaaaggta cctcttcctc ttctcttgct 60
ccctctcgcc ctcattcttg tgcctatgca gacatttgag tagaggcgaa tcactttcac 120
ttctgctggg gaaattgcaa cacgcttctt taaatggcag agagaaggag aaaacttaga 180
tcttctgata ccaaatcact ggaccttaga aggtcagaaa tctttcaagc cctgcaggac 240

-continued

```
cgtaaaatgc gcatgtgtcc aacggaagca ctggggcatg agtggggaag gaatagaaac    300
agaaagaggg taagagaaga aaaaagggaa agtggtgaag gcagggagga aaattgctta    360
gtgtgaatat gcacgcattc atttagtttt caaatccttg ttgagcatga taaaattccc    420
agcatcagac ctcacatgtt ggtttccatt aggatctgcc tgggggaata tctgctgaat    480
cagtggctct gagctgaact aggaaattca ccataattag gagagtcact gtatttctct    540
ccaaaaaaaa aaaagttata cccgagagac aggatcttct gatctgaaat tttcttcact    600
tctgaaattc tctggtttgt gctcatcgtt ggtagctatt tgttcatcaa gagttgtgta    660
gctggcttct tctgaaaaaa ggaatctgcg tcatatctaa gtcagatttc attctggtgc    720
tctcagagca gttagcccag gaaaggggcc agcttctgtg acgactgctg cagaggcagg    780
tgcagtttgt gtgccacaga tattaacttt gataagcact taatgagtgc cttctctgtg    840
cgagaatggg gaggaacaaa atgcagctcc taccctcctc gggctttagt tgtaccttaa    900
taacaggaat tttcatctgc ctggctcctt tcctcaaaga acaaagaaga ctttgcttca    960
ttaaagtgtc tgagaaggaa gttgatattc actgatggac tccaaagaat cattaactcc   1020
tggtagagaa gaaaacccca gcagtgtgct tgctcaggag aggggagatg tgatggactt   1080
ctataaaacc ctaagaggag gagctactgt gaaggtttct gcgtcttcac cctcactggc   1140
tgtcgcttct caatcagact ccaagcagcg aagacttttg gttgattttc caaaaggctc   1200
agtaagcaat gcgcagcagc cagatctgtc caaagcagtt tcactctcaa tgggactgta   1260
tatgggagag acagaaacaa aagtgatggg aaatgacctg ggattcccac agcagggcca   1320
aatcagcctt tcctcggggg aaacagactt aaagcttttg gaagaaagca ttgcaaacct   1380
caataggtcg accagtgttc cagagaaccc caagagttca gcatccactg ctgtgtctgc   1440
tgcccccaca gagaaggagt ttccaaaaac tcactctgat gtatcttcag aacagcaaca   1500
tttgaagggc cagactggca ccaacggtgg caatgtgaaa ttgtatacca cagaccaaag   1560
cacctttgac attttgcagg atttggagtt ttcttctggg tccccaggta aagagacgaa   1620
tgagagtcct tggagatcag acctgttgat agatgaaaac tgtttgcttt ctcctctggc   1680
gggagaagac gattcattcc ttttggaagg aaactcgaat gaggactgca agcctctcat   1740
tttaccggac actaaaccca aaattaagga taatggagat ctggttttgt caagccccag   1800
taatgtaaca ctgccccaag tgaaaacaga aaaagaagat ttcatcgaac tctgcacccc   1860
tggggtaatt aagcaagaga aactgggcac agtttactgt caggcaagct ttcctggagc   1920
aaatataatt ggtaataaaa tgtctgccat ttctgttcat ggtgtgagta cctctggagg   1980
acagatgtac cactatgaca tgaatacagc atccctttct caacagcagg atcagaagcc   2040
tatttttaat gtcattccac caattcccgt tggttccgaa aattggaata ggtgccaagg   2100
atctggagat gacaacttga cttctctggg gactctgaac ttccctggtc gaacagtttt   2160
ttctaatggc tattcaagcc ccagcatgag accagatgta agctctcctc catccagctc   2220
ctcaacagca acaacaggac cacctcccaa actctgcctg gtgtgctctg atgaagcttc   2280
aggatgtcat tatggagtct taacttgtgg aagctgtaaa gttttcttca aaagagcagt   2340
ggaaggacag cacaattacc tatgtgctgg aaggaatgat tgcatcatcg ataaaattcg   2400
aagaaaaaac tgcccagcat gccgctatcg aaaatgtctt caggctggaa tgaacctgga   2460
agctcgaaaa acaaagaaaa aaataaaagg aattcagcag gccactacag gagtctcaca   2520
agaaacctct gaaaatcctg gtaacaaaac aatagttcct gcaacgttac cacaactcac   2580
ccctaccctg gtgtcactgt tggaggttat tgaacctgaa gtgttatatg caggatatga   2640
```

```
tagctctgtt ccagactcaa cttggaggat catgactacg ctcaacatgt taggagggcg   2700
gcaagtgatt gcagcagtga aatgggcaaa ggcaatacca ggtttcagga acttacacct   2760
ggatgaccaa atgaccctac tgcagtactc ctggatgttt cttatggcat ttgctctggg   2820
gtggagatca tatagacaat caagtgcaaa cctgctgtgt tttgctcctg atctgattat   2880
taatgagcag agaatgactc taccctgcat gtacgaccaa tgtaaacaca tgctgtatgt   2940
ttcctctgag ttacacaggc ttcaggtatc ttatgaagag tatctctgta tgaaaacctt   3000
actgcttctc tcttcagttc ctaaggacgg tctgaagagc caagagctat ttgatgaaat   3060
tagaatgacc tacatcaaag agctaggaaa agccattgtc aagagggaag gaaactccag   3120
ccagaactgg cagcggtttt atcaactgac aaaactcttg gattctatgc atgaagtggt   3180
tgaaaatctc cttaactatt gcttccaaac atttttggat aagaccatga gtattgaatt   3240
ccccgagatg ttagctgaaa tcatcaccaa tcagatacca aaatattcaa atggaaatat   3300
caaaaaactt ctgtttcatc aaaagtgact gccttaataa gaatggttgc cttaaagaaa   3360
gtcgaattaa tagcttttat tgtataaact atcagtttgt cctgtagagg ttttgttgtt   3420
ttatttttta ttgttttcat ctgttgtttt gttttaaata cgcactacat gtggtttata   3480
gagggccaag acttggcaac agaagcagtt gagtcgtcat cacttttcag tgatgggaga   3540
gtagatggtg aaatttatta gttaatatat cccagaaatt agaaacctta atatgtggac   3600
gtaatctcca cagtcaaaga aggatggcac ctaaaccacc agtgcccaaa gtctgtgtga   3660
tgaactttct cttcatactt tttttcacag ttggctggat gaaattttct agactttctg   3720
ttggtgtatc ccccccctgt atagttagga tagcattttt gatttatgca tggaaacctg   3780
aaaaaaagtt tacaagtgta tatcagaaaa gggaagttgt gccttttata gctattactg   3840
tctggtttta acaatttcct ttatatttag tgaactacgc ttgctcattt tttcttacat   3900
aattttttat tcaagttatt gtacagctgt ttaagatggg cagctagttc gtagctttcc   3960
caaataaact ctaaacatta atcaatcatc tgtgtgaaaa tgggttggtg cttctaacct   4020
gatggcactt agctatcaga agaccacaaa aattgactca aatctccagt attcttgtca   4080
aaaaaaaaaa aaaaaaagct catattttgt atatatctgc ttcagtggag aattatatag   4140
gttgtgcaaa ttaacagtcc taactggtat agagcaccta gtccagtgac ctgctgggta   4200
aactgtggat gatggttgca aaagactaat ttaaaaaata actaccaaga ggccctgtct   4260
gtacctaacg ccctattttt gcaatggcta tatggcaaga aagctggtaa actatttgtc   4320
tttcaggacc ttttgaagta gtttgtataa cttcttaaaa gttgtgattc cagataacca   4380
gctgtaacac agctgagaga cttttaatca gacaaagtaa ttcctctcac taaactttac   4440
ccaaaaacta aatctctaat atggcaaaaa tggctagaca cccattttca cattcccatc   4500
tgtcaccaat tggttaatct ttcctgatgg tacaggaaag ctcagctact gatttttgtg   4560
atttagaact gtatgtcaga catccatgtt tgtaaaacta cacatcccta atgtgtgcca   4620
tagagtttaa cacaagtcct gtgaatttct tcactgttga aaattatttt aaacaaaata   4680
gaagctgtag tagccctttc tgtgtgcacc ttaccaactt tctgtaaact caaaacttaa   4740
catatttact aagccacaag aaatttgatt tctattcaag gtggccaaat tatttgtgta   4800
atagaaaact gaaaatctaa tattaaaaat atggaacttc taatatattt ttatatttag   4860
ttatagtttc agatatatat catattggta ttcactaatc tgggaaggga agggctactg   4920
cagctttaca tgcaatttat taaaatgatt gtaaaatagc ttgtatagtg taaaataaga   4980
```

-continued

```
atgattttta gatgagattg ttttatcatg acatgttata tattttttgt aggggtcaaa   5040
gaaatgctga tggataacct atatgattta tagtttgtac atgcattcat acaggcagcg   5100
atggtctcag aaaccaaaca gtttgctcta ggggaagagg gagatggaga ctggtcctgt   5160
gtgcagtgaa ggttgctgag gctctgaccc agtgagatta cagaggaagt tatcctctgc   5220
ctcccattct gaccaccctt ctcattccaa cagtgagtct gtcagcgcag gtttagttta   5280
ctcaatctcc ccttgcacta aagtatgtaa agtatgtaaa caggagacag gaaggtggtg   5340
cttacatcct taaaggcacc atctaatagc gggttacttt cacatacagc cctcccccag   5400
cagttgaatg acaacagaag cttcagaagt ttggcaatag tttgcataga ggtaccagca   5460
atatgtaaat agtgcagaat ctcataggtt gccaataata cactaattcc tttctatcct   5520
acaacaagag tttatttcca aataaaatga ggacatgttt ttgttttctt tgaatgcttt   5580
ttgaatgtta tttgttattt tcagtatttt ggagaaatta tttaataaaa aaacaatcat   5640
ttgctttttg aatgctctct aaaagggaat gtaatatttt aagatggtgt gtaacccggc   5700
tggataaatt tttggtgcct aagaaaactg cttgaatatt cttatcaatg acagtgttaa   5760
gtttcaaaaa gagcttctaa aacgtagatt atcattcctt tatagaatgt tatgtggtta   5820
aaaccagaaa gcacatctca cacattaatc tgattttcat cccaacaatc ttggcgctca   5880
aaaaatagaa ctcaatgaga aaaagaagat tatgtgcact tcgttgtcaa taataagtca   5940
actgatgctc atcgacaact ataggaggct tttcattaaa tgggaaaaga agctgtgccc   6000
ttttaggata cgtgggggaa aagaaagtca tcttaattat gtttaattgt ggatttaagt   6060
gctatatggt ggtgctgttt gaaagcagat ttatttccta tgtatgtgtt atctggccat   6120
cccaacccaa actgttgaag tttgtagtaa cttcagtgag agttggttac tcacaacaaa   6180
tcctgaaaag tatttttagt gtttgtaggt attctgtggg atactataca agcagaactg   6240
aggcacttag gacataacac ttttggggta tatatatcca aatgcctaaa actatgggag   6300
gaaaccttgg ccaccccaaa aggaaaacta acatgatttg tgtctatgaa gtgctggata   6360
attagcatgg gatgagctct gggcatgcca tgaaggaaag ccacgctccc ttcagaattc   6420
agaggcaggg agcaattcca gtttcaccta agtctcataa ttttagttcc cttttaaaaa   6480
ccctgaaaac tacatcacca tggaatgaaa aatattgtta tacaatacat tgatctgtca   6540
aacttccaga accatggtag ccttcagtga gatttccatc ttggctggtc actccctgac   6600
tgtagctgta ggtgaatgtg tttttgtgtg tgtgtgtctg gttttagtgt cagaagggaa   6660
ataaaagtgt aaggaggaca ctttaaaccc tttgggtgga gtttcgtaat ttcccagact   6720
attttcaagc aacctggtcc acccaggatt agtgaccagg ttttcaggaa aggatttgct   6780
tctctctaga aaatgtctga aaggatttta ttttctgatg aaaggctgta tgaaaatacc   6840
ctcctcaaat aacttgctta actacatata gattcaagtg tgtcaatatt ctattttgta   6900
tattaaatgc tatataatgg ggacaaatct atattatact gtgtatggca ttattaagaa   6960
gctttttcat tattttttat cacagtaatt ttaaaatgtg taaaaattaa aaccagtgac   7020
tcctgtttaa aaataaaagt tgtagttttt tattcatgct gaataataat ctgtagttaa   7080
aaaaaaagtg tctttttacc tacgcagtga aatgtcagac tgtaaaacct tgtgtggaaa   7140
tgtttaactt ttattttttc atttaaattt gctgttctgg tattaccaaa ccacacattt   7200
gtaccgaatt ggcagtaaat gttagccatt tacagcaatg ccaaatatgg agaaacatca   7260
taataaaaaa atctgctttt tcatta                                        7286
```

<210> SEQ ID NO 19
<211> LENGTH: 4154
<212> TYPE: DNA
<213> ORGANISM: Homo sapiens

<400> SEQUENCE: 19

```
ggcgccgcct ccacccgctc cccgctcggt cccgctcgct cgcccaggcc gggctgccct     60
ttcgcgtgtc cgcgctctct tccctccgcc gccgcctcct ccattttgcg agctcgtgtc    120
tgtgacggga gcccgagtca ccgcctgccc gtcggggacg gattctgtgg gtggaaggag    180
acgccgcagc cggagcggcc gaagcagctg ggaccgggac ggggcacgcg cgcccggaac    240
ctcgacccgc ggagcccggc gcggggcgga gggctggctt gtcagctggg caatgggaga    300
ctttcttaaa taggggctct ccccccaccc atggagaaag gggcggctgt ttacttcctt    360
tttttagaaa aaaaaaatat atttccctcc tgctccttct gcgttcacaa gctaagttgt    420
ttatctcggc tgcggcggga actgcggacg gtggcgggcg agcggctcct ctgccagagt    480
tgatattcac tgatggactc caaagaatca ttaactcctg gtagagaaga aaaccccagc    540
agtgtgcttg ctcaggagag gggagatgtg atggacttct ataaaaccct aagaggagga    600
gctactgtga aggtttctgc gtcttcaccc tcactggctg tcgcttctca atcagactcc    660
aagcagcgaa gacttttggt tgattttcca aaaggctcag taagcaatgc gcagcagcca    720
gatctgtcca aagcagtttc actctcaatg ggactgtata tgggagagac agaaacaaaa    780
gtgatgggaa atgacctggg attcccacag cagggccaaa tcagcctttc ctcgggggaa    840
acagacttaa agcttttgga agaaagcatt gcaaacctca ataggtcgac cagtgttcca    900
gagaacccca agagttcagc atccactgct gtgtctgctg cccccacaga gaaggagttt    960
ccaaaaactc actctgatgt atcttcagaa cagcaacatt tgaagggcca gactggcacc   1020
aacggtggca atgtgaaatt gtataccaca gaccaaagca cctttgacat tttgcaggat   1080
ttggagtttt cttctgggtc cccaggtaaa gagacgaatg agagtccttg gagatcagac   1140
ctgttgatag atgaaaactg tttgctttct cctctggcgg gagaagacga ttcattcctt   1200
ttggaaggaa actcgaatga ggactgcaag cctctcattt taccggacac taaacccaaa   1260
attaaggata atggagatct ggttttgtca agccccagta atgtaacact gccccaagtg   1320
aaaacagaaa aagaagattt catcgaactc tgcacccctg gggtaattaa gcaagagaaa   1380
ctgggcacag tttactgtca ggcaagcttt cctggagcaa atataattgg taataaaatg   1440
tctgccattt ctgttcatgg tgtgagtacc tctggaggac agatgtacca ctatgacatg   1500
aatacagcat ccctttctca acagcaggat cagaagccta tttttaatgt cattccacca   1560
attcccgttg gttccgaaaa ttggaatagg tgccaaggat ctggagatga caacttgact   1620
tctctgggga ctctgaactt ccctggtcga acagtttttt ctaatggcta ttcaagcccc   1680
agcatgagac cagatgtaag ctctcctcca tccagctcct caacagcaac aacaggacca   1740
cctcccaaac tctgcctggt gtgctctgat gaagcttcag gatgtcatta tggagtctta   1800
acttgtggaa gctgtaaagt tttcttcaaa agagcagtgg aaggacagca caattaccta   1860
tgtgctggaa ggaatgattg catcatcgat aaaattcgaa gaaaaaactg cccagcatgc   1920
cgctatcgaa aatgtcttca ggctggaatg aacctggaag ctcgaaaaac aaagaaaaaa   1980
ataaaaggaa ttcagcaggc cactacagga gtctcacaag aaacctctga aaatcctggt   2040
aacaaaacaa tagttcctgc aacgttacca caactcaccc ctaccctggt gtcactgttg   2100
gaggttattg aacctgaagt gttatatgca ggatatgata gctctgttcc agactcaact   2160
```

tggaggatca tgactacgct caacatgtta ggagggcggc aagtgattgc agcagtgaaa 2220
tgggcaaagg caataccagg tttcaggaac ttacacctgg atgaccaaat gaccctactg 2280
cagtactcct ggatgtttct tatggcattt gctctggggt ggagatcata tagacaatca 2340
agtgcaaacc tgctgtgttt tgctcctgat ctgattatta atgagcagag aatgactcta 2400
ccctgcatgt acgaccaatg taaacacatg ctgtatgttt cctctgagtt acacaggctt 2460
caggtatctt atgaagagta tctctgtatg aaaaccttac tgcttctctc ttcagttcct 2520
aaggacggtc tgaagagcca agagctattt gatgaaatta gaatgaccta catcaaagag 2580
ctaggaaaag ccattgtcaa gagggaagga aactccagcc agaactggca gcggttttat 2640
caactgacaa aactcttgga ttctatgcat gaaaatgtta tgtggttaaa accagaaagc 2700
acatctcaca cattaatctg attttcatcc caacaatctt ggcgctcaaa aaatagaact 2760
caatgagaaa aagaagatta tgtgcacttc gttgtcaata ataagtcaac tgatgctcat 2820
cgacaactat aggaggcttt tcattaaatg ggaaaagaag ctgtgccctt ttaggatacg 2880
tgggggaaaa gaaagtcatc ttaattatgt ttaattgtgg atttaagtgc tatatggtgg 2940
tgctgtttga aagcagattt atttcctatg tatgtgttat ctggccatcc caacccaaac 3000
tgttgaagtt tgtagtaact tcagtgagag ttggttactc acaacaaatc ctgaaaagta 3060
tttttagtgt ttgtaggtat tctgtgggat actatacaag cagaactgag gcacttagga 3120
cataacactt ttggggtata tatatccaaa tgcctaaaac tatgggagga aaccttggcc 3180
accccaaaag gaaaactaac atgatttgtg tctatgaagt gctggataat tagcatggga 3240
tgagctctgg gcatgccatg aaggaaagcc acgctccctt cagaattcag aggcagggag 3300
caattccagt ttcacctaag tctcataatt ttagttccct tttaaaaacc ctgaaaacta 3360
catcaccatg gaatgaaaaa tattgttata caatacattg atctgtcaaa cttccagaac 3420
catggtagcc ttcagtgaga tttccatctt ggctggtcac tccctgactg tagctgtagg 3480
tgaatgtgtt tttgtgtgtg tgtgtctggt tttagtgtca gaagggaaat aaaagtgtaa 3540
ggaggacact ttaaaccctt tgggtggagt ttcgtaattt cccagactat tttcaagcaa 3600
cctggtccac ccaggattag tgaccaggtt ttcaggaaag gatttgcttc tctctagaaa 3660
atgtctgaaa ggattttatt ttctgatgaa aggctgtatg aaaataccct cctcaaataa 3720
cttgcttaac tacatataga ttcaagtgtg tcaatattct attttgtata ttaaatgcta 3780
tataatgggg acaaatctat attatactgt gtatggcatt attaagaagc tttttcatta 3840
ttttttatca cagtaatttt aaaatgtgta aaaattaaaa ccagtgactc ctgtttaaaa 3900
ataaaagttg tagtttttta ttcatgctga ataataatct gtagttaaaa aaaaagtgtc 3960
tttttaccta cgcagtgaaa tgtcagactg taaaaccttg tgtggaaatg tttaactttt 4020
attttttcat ttaaatttgc tgttctggta ttaccaaacc acacatttgt accgaattgg 4080
cagtaaatgt tagccattta cagcaatgcc aaatatggag aaacatcata ataaaaaaat 4140
ctgctttttc atta 4154

<210> SEQ ID NO 20
<211> LENGTH: 6787
<212> TYPE: DNA
<213> ORGANISM: Homo sapiens

<400> SEQUENCE: 20
ggcgccgcct ccacccgctc cccgctcggt cccgctcgct cgcccaggcc gggctgccct 60
ttcgcgtgtc cgcgctctct tccctccgcc gccgcctcct ccattttgcg agctcgtgtc 120

```
tgtgacggga gcccgagtca ccgcctgccc gtcggggacg gattctgtgg gtggaaggag    180
acgccgcagc cggagcggcc gaagcagctg ggaccgggac ggggcacgcg cgcccggaac    240
ctcgacccgc ggagcccggc gcggggcgga gggctggctt gtcagctggg caatgggaga    300
ctttcttaaa taggggctct ccccccaccc atggagaaag gggcggctgt ttacttcctt    360
tttttagaaa aaaaaaatat atttccctcc tgctccttct gcgttcacaa gctaagttgt    420
ttatctcggc tgcggcggga actgcggacg gtggcgggcg agcggctcct ctgccagagt    480
tgatattcac tgatggactc caaagaatca ttaactcctg gtagagaaga aaaccccagc    540
agtgtgcttg ctcaggagag gggagatgtg atggacttct ataaaaccct aagaggagga    600
gctactgtga aggtttctgc gtcttcaccc tcactggctg tcgcttctca atcagactcc    660
aagcagcgaa gacttttggt tgattttcca aaaggctcag taagcaatgc gcagcagcca    720
gatctgtcca aagcagtttc actctcaatg ggactgtata tgggagagac agaaacaaaa    780
gtgatgggaa atgacctggg attcccacag cagggccaaa tcagcctttc ctcgggggaa    840
acagacttaa agcttttgga agaaagcatt gcaaacctca ataggtcgac cagtgttcca    900
gagaacccca agagttcagc atccactgct gtgtctgctg cccccacaga gaaggagttt    960
ccaaaaactc actctgatgt atcttcagaa cagcaacatt tgaagggcca gactggcacc   1020
aacggtggca atgtgaaatt gtataccaca gaccaaagca cctttgacat tttgcaggat   1080
ttggagtttt cttctgggtc cccaggtaaa gagacgaatg agagtccttg gagatcagac   1140
ctgttgatag atgaaaactg tttgctttct cctctggcgg gagaagacga ttcattcctt   1200
ttggaaggaa actcgaatga ggactgcaag cctctcattt taccggacac taaacccaaa   1260
attaaggata atggagatct ggttttgtca agccccagta atgtaacact gccccaagtg   1320
aaaacagaaa aagaagattt catcgaactc tgcacccctg gggtaattaa gcaagagaaa   1380
ctgggcacag tttactgtca ggcaagcttt cctggagcaa atataattgg taataaaatg   1440
tctgccattt ctgttcatgg tgtgagtacc tctggaggac agatgtacca ctatgacatg   1500
aatacagcat ccctttctca acagcaggat cagaagccta tttttaatgt cattccacca   1560
attcccgttg gttccgaaaa ttggaatagg tgccaaggat ctggagatga caacttgact   1620
tctctgggga ctctgaactt ccctggtcga acagtttttt ctaatggcta ttcaagcccc   1680
agcatgagac cagatgtaag ctctcctcca tccagctcct caacagcaac aacaggacca   1740
cctcccaaac tctgcctggt gtgctctgat gaagcttcag gatgtcatta tggagtctta   1800
acttgtggaa gctgtaaagt tttcttcaaa agagcagtgg aaggtagaca gcacaattac   1860
ctatgtgctg gaaggaatga ttgcatcatc gataaaattc gaagaaaaaa ctgcccagca   1920
tgccgctatc gaaaatgtct tcaggctgga atgaacctgg aagctcgaaa aacaaagaaa   1980
aaaataaaag gaattcagca ggccactaca ggagtctcac aagaaacctc tgaaaatcct   2040
ggtaacaaaa caatagttcc tgcaacgtta ccacaactca cccctaccct ggtgtcactg   2100
ttggaggtta ttgaacctga agtgttatat gcaggatatg atagctctgt tccagactca   2160
acttggagga tcatgactac gctcaacatg ttaggagggc ggcaagtgat tgcagcagtg   2220
aaatgggcaa aggcaatacc aggtttcagg aacttacacc tggatgacca aatgacccta   2280
ctgcagtact cctggatgtt tcttatggca tttgctctgg ggtggagatc atatagacaa   2340
tcaagtgcaa acctgctgtg ttttgctcct gatctgatta ttaatgagca gagaatgact   2400
ctaccctgca tgtacgacca atgtaaacac atgctgtatg tttcctctga gttacacagg   2460
```

-continued

```
cttcaggtat cttatgaaga gtatctctgt atgaaaacct tactgcttct ctcttcagtt   2520
cctaaggacg gtctgaagag ccaagagcta tttgatgaaa ttagaatgac ctacatcaaa   2580
gagctaggaa aagccattgt caagagggaa ggaaactcca gccagaactg gcagcggttt   2640
tatcaactga caaaactctt ggattctatg catgaagtgg ttgaaaatct ccttaactat   2700
tgcttccaaa catttttgga taagaccatg agtattgaat tccccgagat gttagctgaa   2760
atcatcacca atcagatacc aaaatattca aatggaaata tcaaaaaact tctgtttcat   2820
caaaagtgac tgccttaata agaatggttg ccttaaagaa agtcgaatta atagctttta   2880
ttgtataaac tatcagtttg tcctgtagag gttttgttgt tttatttttt attgttttca   2940
tctgttgttt tgttttaaat acgcactaca tgtggtttat agagggccaa gacttggcaa   3000
cagaagcagt tgagtcgtca tcacttttca gtgatgggag agtagatggt gaaatttatt   3060
agttaatata tcccagaaat tagaaacctt aatatgtgga cgtaatctcc acagtcaaag   3120
aaggatggca cctaaaccac cagtgcccaa agtctgtgtg atgaactttc tcttcatact   3180
tttttcaca gttggctgga tgaaattttc tagactttct gttggtgtat cccccccctg   3240
tatagttagg atagcatttt tgatttatgc atggaaacct gaaaaaaagt ttacaagtgt   3300
atatcagaaa agggaagttg tgccttttat agctattact gtctggtttt aacaatttcc   3360
tttatattta gtgaactacg cttgctcatt ttttcttaca taattttta ttcaagttat   3420
tgtacagctg tttaagatgg gcagctagtt cgtagctttc ccaaataaac tctaaacatt   3480
aatcaatcat ctgtgtgaaa atgggttggt gcttctaacc tgatggcact tagctatcag   3540
aagaccacaa aaattgactc aaatctccag tattcttgtc aaaaaaaaaa aaaaaaaagc   3600
tcatattttg tatatatctg cttcagtgga gaattatata ggttgtgcaa attaacagtc   3660
ctaactggta tagagcacct agtccagtga cctgctgggt aaactgtgga tgatggttgc   3720
aaaagactaa tttaaaaaat aactaccaag aggccctgtc tgtacctaac gccctatttt   3780
tgcaatggct atatggcaag aaagctggta aactatttgt ctttcaggac cttttgaagt   3840
agtttgtata acttcttaaa agttgtgatt ccagataacc agctgtaaca cagctgagag   3900
acttttaatc agacaaagta attcctctca ctaaacttta cccaaaaact aaatctctaa   3960
tatggcaaaa atggctagac acccattttc acattcccat ctgtcaccaa ttggttaatc   4020
tttcctgatg gtacaggaaa gctcagctac tgatttttgt gatttagaac tgtatgtcag   4080
acatccatgt ttgtaaaact acacatccct aatgtgtgcc atagagttta acacaagtcc   4140
tgtgaatttc ttcactgttg aaaattattt taaacaaaat agaagctgta gtagcccttt   4200
ctgtgtgcac cttaccaact ttctgtaaac tcaaaactta acatatttac taagccacaa   4260
gaaatttgat ttctattcaa ggtggccaaa ttatttgtgt aatagaaaac tgaaaatcta   4320
atattaaaaa tatggaactt ctaatatatt tttatattta gttatagttt cagatatata   4380
tcatattggt attcactaat ctgggaaggg aagggctact gcagctttac atgcaattta   4440
ttaaaatgat tgtaaaatag cttgtatagt gtaaaataag aatgattttt agatgagatt   4500
gttttatcat gacatgttat atattttttg taggggtcaa agaaatgctg atggataacc   4560
tatatgattt atagtttgta catgcattca tacaggcagc gatggtctca gaaaccaaac   4620
agtttgctct aggggaagag ggagatggag actggtcctg tgtgcagtga aggttgctga   4680
ggctctgacc cagtgagatt acagaggaag ttatcctctg cctcccattc tgaccaccct   4740
tctcattcca acagtgagtc tgtcagcgca ggtttagttt actcaatctc cccttgcact   4800
aaagtatgta aagtatgtaa acaggagaca ggaaggtggt gcttacatcc ttaaaggcac   4860
```

catctaatag cgggttactt tcacatacag ccctccccca gcagttgaat gacaacagaa 4920
gcttcagaag tttggcaata gtttgcatag aggtaccagc aatatgtaaa tagtgcagaa 4980
tctcataggt tgccaataat acactaattc ctttctatcc tacaacaaga gtttatttcc 5040
aaataaaatg aggacatgtt tttgttttct ttgaatgctt tttgaatgtt atttgttatt 5100
ttcagtattt tggagaaatt atttaataaa aaaacaatca tttgcttttt gaatgctctc 5160
taaaagggaa tgtaatattt taagatggtg tgtaacccgg ctggataaat ttttggtgcc 5220
taagaaaact gcttgaatat tcttatcaat gacagtgtta agtttcaaaa agagcttcta 5280
aaacgtagat tatcattcct ttatagaatg ttatgtggtt aaaaccagaa agcacatctc 5340
acacattaat ctgattttca tcccaacaat cttggcgctc aaaaaataga actcaatgag 5400
aaaaagaaga ttatgtgcac ttcgttgtca ataataagtc aactgatgct catcgacaac 5460
tataggaggc ttttcattaa atgggaaaag aagctgtgcc cttttaggat acgtggggga 5520
aaagaaagtc atcttaatta tgtttaattg tggatttaag tgctatatgg tggtgctgtt 5580
tgaaagcaga tttatttcct atgtatgtgt tatctggcca tcccaaccca aactgttgaa 5640
gtttgtagta acttcagtga gagttggtta ctcacaacaa atcctgaaaa gtatttttag 5700
tgtttgtagg tattctgtgg gatactatac aagcagaact gaggcactta ggacataaca 5760
cttttggggt atatatatcc aaatgcctaa aactatggga ggaaaccttg gccaccccaa 5820
aaggaaaact aacatgattt gtgtctatga agtgctggat aattagcatg ggatgagctc 5880
tgggcatgcc atgaaggaaa gccacgctcc cttcagaatt cagaggcagg gagcaattcc 5940
agtttcacct aagtctcata attttagttc ccttttaaaa accctgaaaa ctacatcacc 6000
atggaatgaa aaatattgtt atacaataca ttgatctgtc aaacttccag aaccatggta 6060
gccttcagtg agatttccat cttggctggt cactccctga ctgtagctgt aggtgaatgt 6120
gtttttgtgt gtgtgtgtct ggttttagtg tcagaaggga aataaaagtg taaggaggac 6180
actttaaacc ctttgggtgg agtttcgtaa tttcccagac tattttcaag caacctggtc 6240
cacccaggat tagtgaccag gttttcagga aaggatttgc ttctctctag aaaatgtctg 6300
aaaggatttt attttctgat gaaaggctgt atgaaaatac cctcctcaaa taacttgctt 6360
aactacatat agattcaagt gtgtcaatat tctattttgt atattaaatg ctatataatg 6420
gggacaaatc tatattatac tgtgtatggc attattaaga agctttttca ttattttta 6480 tcacagtaat tttaaaatgt gtaaaaatta aaaccagtga ctcctgttta aaaataaaag 6540
ttgtagtttt ttattcatgc tgaataataa tctgtagtta aaaaaaaagt gtctttttac 6600
ctacgcagtg aaatgtcaga ctgtaaaacc ttgtgtggaa atgtttaact tttattttt 6660 catttaaatt tgctgttctg gtattaccaa accacacatt tgtaccgaat tggcagtaaa 6720
tgttagccat ttacagcaat gccaaatatg gagaaacatc ataataaaaa aatctgcttt 6780
ttcatta 6787

<210> SEQ ID NO 21
<211> LENGTH: 4104
<212> TYPE: DNA
<213> ORGANISM: Homo sapiens

<400> SEQUENCE: 21
ggcgccgcct ccacccgctc cccgctcggt cccgctcgct cgcccaggcc gggctgccct 60
ttcgcgtgtc cgcgctctct tccctccgcc gccgcctcct ccattttgcg agctcgtgtc 120

-continued

```
tgtgacggga gcccgagtca ccgcctgccc gtcggggacg gattctgtgg gtggaaggag    180
acgccgcagc cggagcggcc gaagcagctg ggaccgggac ggggcacgcg cgcccggaac    240
ctcgacccgc ggagcccggc gcggggcgga gggctggctt gtcagctggg caatgggaga    300
ctttcttaaa taggggctct ccccccaccc atggagaaag gggcggctgt ttacttcctt    360
tttttagaaa aaaaaaatat atttccctcc tgctccttct gcgttcacaa gctaagttgt    420
ttatctcggc tgcggcggga actgcggacg gtggcgggcg agcggctcct ctgccagagt    480
tgatattcac tgatggactc caaagaatca ttaactcctg gtagagaaga aaaccccagc    540
agtgtgcttg ctcaggagag gggagatgtg atggacttct ataaaaccct aagaggagga    600
gctactgtga aggtttctgc gtcttcaccc tcactggctg tcgcttctca atcagactcc    660
aagcagcgaa gacttttggt tgattttcca aaaggctcag taagcaatgc gcagcagcca    720
gatctgtcca aagcagtttc actctcaatg ggactgtata tgggagagac agaaacaaaa    780
gtgatgggaa atgacctggg attcccacag cagggccaaa tcagcctttc ctcgggggaa    840
acagacttaa agcttttgga agaaagcatt gcaaacctca ataggtcgac cagtgttcca    900
gagaacccca agagttcagc atccactgct gtgtctgctg cccccacaga gaaggagttt    960
ccaaaaactc actctgatgt atcttcagaa cagcaacatt tgaagggcca gactggcacc   1020
aacggtggca atgtgaaatt gtataccaca gaccaaagca cctttgacat tttgcaggat   1080
ttggagtttt cttctgggtc cccaggtaaa gagacgaatg agagtccttg gagatcagac   1140
ctgttgatag atgaaaactg tttgctttct cctctggcgg gagaagacga ttcattcctt   1200
ttggaaggaa actcgaatga ggactgcaag cctctcattt taccggacac taaacccaaa   1260
attaaggata atggagatct ggttttgtca agccccagta atgtaacact gccccaagtg   1320
aaaacagaaa aagaagattt catcgaactc tgcacccctg gggtaattaa gcaagagaaa   1380
ctgggcacag tttactgtca ggcaagcttt cctggagcaa atataattgg taataaaatg   1440
tctgccattt ctgttcatgg tgtgagtacc tctggaggac agatgtacca ctatgacatg   1500
aatacagcat ccctttctca acagcaggat cagaagccta tttttaatgt cattccacca   1560
attcccgttg gttccgaaaa ttggaatagg tgccaaggat ctggagatga caacttgact   1620
tctctgggga ctctgaactt ccctggtcga acagtttttt ctaatggcta ttcaagcccc   1680
agcatgagac cagatgtaag ctctcctcca tccagctcct caacagcaac aacaggacca   1740
cctcccaaac tctgcctggt gtgctctgat gaagcttcag gatgtcatta tggagtctta   1800
acttgtggaa gctgtaaagt tttcttcaaa agagcagtgg aaggacagca caattaccta   1860
tgtgctggaa ggaatgattg catcatcgat aaaattcgaa gaaaaaactg cccagcatgc   1920
cgctatcgaa aatgtcttca ggctggaatg aacctggaag ctcgaaaaac aaagaaaaaa   1980
ataaaaggaa ttcagcaggc cactacagga gtctcacaag aaacctctga aaatcctggt   2040
aacaaaacaa tagttcctgc aacgttacca caactcaccc ctaccctggt gtcactgttg   2100
gaggttattg aacctgaagt gttatatgca ggatatgata gctctgttcc agactcaact   2160
tggaggatca tgactacgct caacatgtta ggagggcggc aagtgattgc agcagtgaaa   2220
tgggcaaagg caataccagg tttcaggaac ttacacctgg atgaccaaat gaccctactg   2280
cagtactcct ggatgtttct tatggcattt gctctggggt ggagatcata tagacaatca   2340
agtgcaaacc tgctgtgttt tgctcctgat ctgattatta atgagcagag aatgactcta   2400
ccctgcatgt acgaccaatg taaacacatg ctgtatgttt cctctgagtt acacaggctt   2460
caggtatctt atgaagagta tctctgtatg aaaaccttac tgcttctctc ttcaggttgg   2520
```

tagaacacct tttcacctta tgtcaaaagc atgaaatatg aaggcctaga aacaaaggtt 2580
aatttatata catagtacta ataattatac caagtctact attatttcct actagtcaga 2640
tgatttttat gaatgtaaaa tattagaaag gcacagtaag tgacaccaag attaataaga 2700
caaataggta tggcagaaac agagaggtat atgagctgca tagggatctc tgttgataag 2760
aatctgtgta gactttttc tccttccttc ctttgatctt tgatcatggg aagacatgga 2820
aaaagaaagc taactacagt gattttgtcc actacactgt tatttggtta aaaattttag 2880
tttcctaatg agtattagca tgtatgagaa attatgggag aaaaaggcgc atcctagaaa 2940
aggtgtgctt aattactatt ggggattggt taacatagca tgggagctgg attgtcagag 3000
attcattatc tagaaaatgg caacaagagt ttataaaacg aacttctgtg agattacttt 3060
ttagctagca aagacaaaga tgtccttcag taggtgaagt gataaactat gatacatcca 3120
gatgatggaa tactattgag gactaaaaag aaataagctg tcaagccatg aaaacacatg 3180
gagggacgtt aaatgcatat tactaagtga aaaaagctaa tctgaaaggg ctacatactg 3240
tgtgattcta actatataac attccataaa aggcaaaact gtgaagacag caaaaaaaaa 3300
tcagcggttg ccagggttta gaaggaaggg agggataaat gtgcagagca cagaggattt 3360
ttagggcagt gaaaatactt cgtatgatac tacaatggtg gaaacatgtc attatacatt 3420
tatccaaacc caaagaatgt ccaccaccaa gagtgaaccc tcaactatgg actttgggtg 3480
atgatgtgtg ggacaggagg tatatgaaaa atctctgtac cttcctccca attttgctgt 3540
gaacttaaaa ctgctctaaa aaaagtcttt tttaaaaaaa gctctatgaa ctagttggta 3600
ttataaacct taggccattt caagtaaaaa ttacatatca atgtttatta aatactgagt 3660
taatagctga atacctcttt catatacaaa taagtacatt tgcaattttt taaaaagtct 3720
taattccatt agtaactgtg gtttcatagt tgccaaataa ctgtaagcta tggatgttgc 3780
acaagactgt gattttattt aatcatttca tatctattta aacatttcca aagcgcacat 3840
tcatcttaat gttttcacac tatttttgct caacaaaaag ttattttatg ttaatggata 3900
taagaagtat taataatatt tcagtcaagg caagagaacc cgataaagat cattgctaga 3960
gacgtttaat gttacctgta gcggtacact tgttaaagaa gtgattaagc agttacataa 4020
aattctgatc atagctttga ttgataccat gaaggtataa ttcagtgcct ggatactaac 4080
aactttactt gtttaaaaaa aaaa 4104

<210> SEQ ID NO 22
<211> LENGTH: 431
<212> TYPE: PRT
<213> ORGANISM: Homo sapiens

<400> SEQUENCE: 22

Met Thr Val Lys Thr Glu Ala Ala Lys Gly Thr Leu Thr Tyr Ser Arg
1               5                   10                  15

Met Arg Gly Met Val Ala Ile Leu Ile Ala Phe Met Lys Gln Arg Arg
            20                  25                  30

Met Gly Leu Asn Asp Phe Ile Gln Lys Ile Ala Asn Asn Ser Tyr Ala
        35                  40                  45

Cys Lys His Pro Glu Val Gln Ser Ile Leu Lys Ile Ser Gln Pro Gln
    50                  55                  60

Glu Pro Glu Leu Met Asn Ala Asn Pro Ser Pro Pro Pro Ser Pro Ser
65                  70                  75                  80

Gln Gln Ile Asn Leu Gly Pro Ser Ser Asn Pro His Ala Lys Pro Ser

```
                85                  90                  95

Asp Phe His Phe Leu Lys Val Ile Gly Lys Gly Ser Phe Gly Lys Val
            100                 105                 110

Leu Leu Ala Arg His Lys Ala Glu Glu Val Phe Tyr Ala Val Lys Val
        115                 120                 125

Leu Gln Lys Lys Ala Ile Leu Lys Lys Lys Glu Glu Lys His Ile Met
    130                 135                 140

Ser Glu Arg Asn Val Leu Leu Lys Asn Val Lys His Pro Phe Leu Val
145                 150                 155                 160

Gly Leu His Phe Ser Phe Gln Thr Ala Asp Lys Leu Tyr Phe Val Leu
                165                 170                 175

Asp Tyr Ile Asn Gly Gly Glu Leu Phe Tyr His Leu Gln Arg Glu Arg
            180                 185                 190

Cys Phe Leu Glu Pro Arg Ala Arg Phe Tyr Ala Ala Glu Ile Ala Ser
        195                 200                 205

Ala Leu Gly Tyr Leu His Ser Leu Asn Ile Val Tyr Arg Asp Leu Lys
    210                 215                 220

Pro Glu Asn Ile Leu Leu Asp Ser Gln Gly His Ile Val Leu Thr Asp
225                 230                 235                 240

Phe Gly Leu Cys Lys Glu Asn Ile Glu His Asn Ser Thr Thr Ser Thr
                245                 250                 255

Phe Cys Gly Thr Pro Glu Tyr Leu Ala Pro Glu Val Leu His Lys Gln
            260                 265                 270

Pro Tyr Asp Arg Thr Val Asp Trp Trp Cys Leu Gly Ala Val Leu Tyr
        275                 280                 285

Glu Met Leu Tyr Gly Leu Pro Pro Phe Tyr Ser Arg Asn Thr Ala Glu
    290                 295                 300

Met Tyr Asp Asn Ile Leu Asn Lys Pro Leu Gln Leu Lys Pro Asn Ile
305                 310                 315                 320

Thr Asn Ser Ala Arg His Leu Leu Glu Gly Leu Leu Gln Lys Asp Arg
                325                 330                 335

Thr Lys Arg Leu Gly Ala Lys Asp Asp Phe Met Glu Ile Lys Ser His
            340                 345                 350

Val Phe Phe Ser Leu Ile Asn Trp Asp Asp Leu Ile Asn Lys Lys Ile
        355                 360                 365

Thr Pro Pro Phe Asn Pro Asn Val Ser Gly Pro Asn Asp Leu Arg His
    370                 375                 380

Phe Asp Pro Glu Phe Thr Glu Glu Pro Val Pro Asn Ser Ile Gly Lys
385                 390                 395                 400

Ser Pro Asp Ser Val Leu Val Thr Ala Ser Val Lys Glu Ala Ala Glu
                405                 410                 415

Ala Phe Leu Gly Phe Ser Tyr Ala Pro Pro Thr Asp Ser Phe Leu
            420                 425                 430


<210> SEQ ID NO 23
<211> LENGTH: 526
<212> TYPE: PRT
<213> ORGANISM: Homo sapiens

<400> SEQUENCE: 23

Met Val Asn Lys Asp Met Asn Gly Phe Pro Val Lys Lys Cys Ser Ala
1               5                   10                  15

Phe Gln Phe Phe Lys Lys Arg Val Arg Arg Trp Ile Lys Ser Pro Met
            20                  25                  30
```

```
Val Ser Val Asp Lys His Gln Ser Pro Ser Leu Lys Tyr Thr Gly Ser
        35                  40                  45

Ser Met Val His Ile Pro Pro Gly Glu Pro Asp Phe Glu Ser Ser Leu
    50                  55                  60

Cys Gln Thr Cys Leu Gly Glu His Ala Phe Gln Arg Gly Val Leu Pro
65                  70                  75                  80

Gln Glu Asn Glu Ser Cys Ser Trp Glu Thr Gln Ser Gly Cys Glu Val
                85                  90                  95

Arg Glu Pro Cys Asn His Ala Asn Ile Leu Thr Lys Pro Asp Pro Arg
            100                 105                 110

Thr Phe Trp Thr Asn Asp Asp Pro Ala Phe Met Lys Gln Arg Arg Met
        115                 120                 125

Gly Leu Asn Asp Phe Ile Gln Lys Ile Ala Asn Asn Ser Tyr Ala Cys
    130                 135                 140

Lys His Pro Glu Val Gln Ser Ile Leu Lys Ile Ser Gln Pro Gln Glu
145                 150                 155                 160

Pro Glu Leu Met Asn Ala Asn Pro Ser Pro Pro Pro Ser Pro Ser Gln
                165                 170                 175

Gln Ile Asn Leu Gly Pro Ser Ser Asn Pro His Ala Lys Pro Ser Asp
            180                 185                 190

Phe His Phe Leu Lys Val Ile Gly Lys Gly Ser Phe Gly Lys Val Leu
        195                 200                 205

Leu Ala Arg His Lys Ala Glu Glu Val Phe Tyr Ala Val Lys Val Leu
    210                 215                 220

Gln Lys Lys Ala Ile Leu Lys Lys Lys Glu Glu Lys His Ile Met Ser
225                 230                 235                 240

Glu Arg Asn Val Leu Leu Lys Asn Val Lys His Pro Phe Leu Val Gly
                245                 250                 255

Leu His Phe Ser Phe Gln Thr Ala Asp Lys Leu Tyr Phe Val Leu Asp
            260                 265                 270

Tyr Ile Asn Gly Gly Glu Leu Phe Tyr His Leu Gln Arg Glu Arg Cys
        275                 280                 285

Phe Leu Glu Pro Arg Ala Arg Phe Tyr Ala Ala Glu Ile Ala Ser Ala
    290                 295                 300

Leu Gly Tyr Leu His Ser Leu Asn Ile Val Tyr Arg Asp Leu Lys Pro
305                 310                 315                 320

Glu Asn Ile Leu Leu Asp Ser Gln Gly His Ile Val Leu Thr Asp Phe
                325                 330                 335

Gly Leu Cys Lys Glu Asn Ile Glu His Asn Ser Thr Thr Ser Thr Phe
            340                 345                 350

Cys Gly Thr Pro Glu Tyr Leu Ala Pro Glu Val Leu His Lys Gln Pro
        355                 360                 365

Tyr Asp Arg Thr Val Asp Trp Trp Cys Leu Gly Ala Val Leu Tyr Glu
    370                 375                 380

Met Leu Tyr Gly Leu Pro Pro Phe Tyr Ser Arg Asn Thr Ala Glu Met
385                 390                 395                 400

Tyr Asp Asn Ile Leu Asn Lys Pro Leu Gln Leu Lys Pro Asn Ile Thr
                405                 410                 415

Asn Ser Ala Arg His Leu Leu Glu Gly Leu Leu Gln Lys Asp Arg Thr
            420                 425                 430

Lys Arg Leu Gly Ala Lys Asp Asp Phe Met Glu Ile Lys Ser His Val
        435                 440                 445

Phe Phe Ser Leu Ile Asn Trp Asp Asp Leu Ile Asn Lys Lys Ile Thr
```

450 455 460

Pro Pro Phe Asn Pro Asn Val Ser Gly Pro Asn Asp Leu Arg His Phe
465 470 475 480

Asp Pro Glu Phe Thr Glu Glu Pro Val Pro Asn Ser Ile Gly Lys Ser
485 490 495

Pro Asp Ser Val Leu Val Thr Ala Ser Val Lys Glu Ala Ala Glu Ala
500 505 510

Phe Leu Gly Phe Ser Tyr Ala Pro Pro Thr Asp Ser Phe Leu
515 520 525

<210> SEQ ID NO 24
<211> LENGTH: 459
<212> TYPE: PRT
<213> ORGANISM: Homo sapiens

<400> SEQUENCE: 24

Met Ser Ser Gln Ser Ser Ser Leu Ser Glu Ala Cys Ser Arg Glu Ala
1 5 10 15

Tyr Ser Ser His Asn Trp Ala Leu Pro Pro Ala Ser Arg Ser Asn Pro
20 25 30

Gln Pro Ala Tyr Pro Trp Ala Thr Arg Arg Met Lys Glu Glu Ala Ile
35 40 45

Lys Pro Pro Leu Lys Ala Phe Met Lys Gln Arg Arg Met Gly Leu Asn
50 55 60

Asp Phe Ile Gln Lys Ile Ala Asn Asn Ser Tyr Ala Cys Lys His Pro
65 70 75 80

Glu Val Gln Ser Ile Leu Lys Ile Ser Gln Pro Gln Glu Pro Glu Leu
85 90 95

Met Asn Ala Asn Pro Ser Pro Pro Pro Ser Pro Ser Gln Gln Ile Asn
100 105 110

Leu Gly Pro Ser Ser Asn Pro His Ala Lys Pro Ser Asp Phe His Phe
115 120 125

Leu Lys Val Ile Gly Lys Gly Ser Phe Gly Lys Val Leu Leu Ala Arg
130 135 140

His Lys Ala Glu Glu Val Phe Tyr Ala Val Lys Val Leu Gln Lys Lys
145 150 155 160

Ala Ile Leu Lys Lys Lys Glu Glu Lys His Ile Met Ser Glu Arg Asn
165 170 175

Val Leu Leu Lys Asn Val Lys His Pro Phe Leu Val Gly Leu His Phe
180 185 190

Ser Phe Gln Thr Ala Asp Lys Leu Tyr Phe Val Leu Asp Tyr Ile Asn
195 200 205

Gly Gly Glu Leu Phe Tyr His Leu Gln Arg Glu Arg Cys Phe Leu Glu
210 215 220

Pro Arg Ala Arg Phe Tyr Ala Ala Glu Ile Ala Ser Ala Leu Gly Tyr
225 230 235 240

Leu His Ser Leu Asn Ile Val Tyr Arg Asp Leu Lys Pro Glu Asn Ile
245 250 255

Leu Leu Asp Ser Gln Gly His Ile Val Leu Thr Asp Phe Gly Leu Cys
260 265 270

Lys Glu Asn Ile Glu His Asn Ser Thr Thr Ser Thr Phe Cys Gly Thr
275 280 285

Pro Glu Tyr Leu Ala Pro Glu Val Leu His Lys Gln Pro Tyr Asp Arg
290 295 300

```
Thr Val Asp Trp Trp Cys Leu Gly Ala Val Leu Tyr Glu Met Leu Tyr
305                 310                 315                 320

Gly Leu Pro Pro Phe Tyr Ser Arg Asn Thr Ala Glu Met Tyr Asp Asn
                325                 330                 335

Ile Leu Asn Lys Pro Leu Gln Leu Lys Pro Asn Ile Thr Asn Ser Ala
            340                 345                 350

Arg His Leu Leu Glu Gly Leu Leu Gln Lys Asp Arg Thr Lys Arg Leu
        355                 360                 365

Gly Ala Lys Asp Asp Phe Met Glu Ile Lys Ser His Val Phe Phe Ser
    370                 375                 380

Leu Ile Asn Trp Asp Asp Leu Ile Asn Lys Lys Ile Thr Pro Pro Phe
385                 390                 395                 400

Asn Pro Asn Val Ser Gly Pro Asn Asp Leu Arg His Phe Asp Pro Glu
                405                 410                 415

Phe Thr Glu Glu Pro Val Pro Asn Ser Ile Gly Lys Ser Pro Asp Ser
            420                 425                 430

Val Leu Val Thr Ala Ser Val Lys Glu Ala Ala Glu Ala Phe Leu Gly
        435                 440                 445

Phe Ser Tyr Ala Pro Pro Thr Asp Ser Phe Leu
    450                 455


<210> SEQ ID NO 25
<211> LENGTH: 445
<212> TYPE: PRT
<213> ORGANISM: Homo sapiens

<400> SEQUENCE: 25

Met Gly Glu Met Gln Gly Ala Leu Ala Arg Ala Arg Leu Glu Ser Leu
1               5                   10                  15

Leu Arg Pro Arg His Lys Lys Arg Ala Glu Ala Gln Lys Arg Ser Glu
            20                  25                  30

Ser Phe Leu Leu Ser Gly Leu Ala Phe Met Lys Gln Arg Arg Met Gly
        35                  40                  45

Leu Asn Asp Phe Ile Gln Lys Ile Ala Asn Asn Ser Tyr Ala Cys Lys
    50                  55                  60

His Pro Glu Val Gln Ser Ile Leu Lys Ile Ser Gln Pro Gln Glu Pro
65                  70                  75                  80

Glu Leu Met Asn Ala Asn Pro Ser Pro Pro Pro Ser Pro Ser Gln Gln
                85                  90                  95

Ile Asn Leu Gly Pro Ser Ser Asn Pro His Ala Lys Pro Ser Asp Phe
            100                 105                 110

His Phe Leu Lys Val Ile Gly Lys Gly Ser Phe Gly Lys Val Leu Leu
        115                 120                 125

Ala Arg His Lys Ala Glu Glu Val Phe Tyr Ala Val Lys Val Leu Gln
    130                 135                 140

Lys Lys Ala Ile Leu Lys Lys Lys Glu Glu Lys His Ile Met Ser Glu
145                 150                 155                 160

Arg Asn Val Leu Leu Lys Asn Val Lys His Pro Phe Leu Val Gly Leu
                165                 170                 175

His Phe Ser Phe Gln Thr Ala Asp Lys Leu Tyr Phe Val Leu Asp Tyr
            180                 185                 190

Ile Asn Gly Gly Glu Leu Phe Tyr His Leu Gln Arg Glu Arg Cys Phe
        195                 200                 205

Leu Glu Pro Arg Ala Arg Phe Tyr Ala Ala Glu Ile Ala Ser Ala Leu
    210                 215                 220
```

```
Gly Tyr Leu His Ser Leu Asn Ile Val Tyr Arg Asp Leu Lys Pro Glu
225                 230                 235                 240

Asn Ile Leu Leu Asp Ser Gln Gly His Ile Val Leu Thr Asp Phe Gly
                245                 250                 255

Leu Cys Lys Glu Asn Ile Glu His Asn Ser Thr Thr Ser Thr Phe Cys
            260                 265                 270

Gly Thr Pro Glu Tyr Leu Ala Pro Glu Val Leu His Lys Gln Pro Tyr
        275                 280                 285

Asp Arg Thr Val Asp Trp Trp Cys Leu Gly Ala Val Leu Tyr Glu Met
    290                 295                 300

Leu Tyr Gly Leu Pro Pro Phe Tyr Ser Arg Asn Thr Ala Glu Met Tyr
305                 310                 315                 320

Asp Asn Ile Leu Asn Lys Pro Leu Gln Leu Lys Pro Asn Ile Thr Asn
                325                 330                 335

Ser Ala Arg His Leu Leu Glu Gly Leu Leu Gln Lys Asp Arg Thr Lys
            340                 345                 350

Arg Leu Gly Ala Lys Asp Asp Phe Met Glu Ile Lys Ser His Val Phe
        355                 360                 365

Phe Ser Leu Ile Asn Trp Asp Asp Leu Ile Asn Lys Lys Ile Thr Pro
    370                 375                 380

Pro Phe Asn Pro Asn Val Ser Gly Pro Asn Asp Leu Arg His Phe Asp
385                 390                 395                 400

Pro Glu Phe Thr Glu Glu Pro Val Pro Asn Ser Ile Gly Lys Ser Pro
                405                 410                 415

Asp Ser Val Leu Val Thr Ala Ser Val Lys Glu Ala Ala Glu Ala Phe
            420                 425                 430

Leu Gly Phe Ser Tyr Ala Pro Pro Thr Asp Ser Phe Leu
        435                 440                 445
```

<210> SEQ ID NO 26
<211> LENGTH: 2414
<212> TYPE: DNA
<213> ORGANISM: Homo sapiens

<400> SEQUENCE: 26

```
tttttataa ggccgagcgc gcggcctggc gcagcatacg ccgagccggt ctttgagcgc      60

taacgtcttt ctgtctcccc gcggtggtga tgacggtgaa aactgaggct gctaagggca     120

ccctcactta ctccaggatg aggggcatgg tggcaattct catcgctttc atgaagcaga     180

ggaggatggg tctgaacgac tttattcaga agattgccaa taactcctat gcatgcaaac     240

accctgaagt tcagtccatc ttgaagatct cccaacctca ggagcctgag cttatgaatg     300

ccaacccttc tcctccacca agtccttctc agcaaatcaa ccttggcccg tcgtccaatc     360

ctcatgctaa accatctgac tttcacttct tgaaagtgat cggaaagggc agttttggaa     420

aggttcttct agcaagacac aaggcagaag aagtgttcta tgcagtcaaa gttttacaga     480

agaaagcaat cctgaaaaag aaagaggaga agcatattat gtcggagcgg aatgttctgt     540

tgaagaatgt gaagcaccct ttcctggtgg gccttcactt ctctttccag actgctgaca     600

aattgtactt tgtcctagac tacattaatg gtggagagtt gttctaccat ctccagaggg     660

aacgctgctt cctggaacca cgggctcgtt tctatgctgc tgaaatagcc agtgccttgg     720

gctacctgca ttcactgaac atcgtttata gagacttaaa accagagaat attttgctag     780

attcacaggg acacattgtc cttactgact tcggactctg caaggagaac attgaacaca     840
```

```
acagcacaac atccaccttc tgtggcacgc cggagtatct cgcacctgag gtgcttcata    900

agcagcctta tgacaggact gtggactggt ggtgcctggg agctgtcttg tatgagatgc    960

tgtatggcct gccgcctttt tatagccgaa acacagctga aatgtacgac aacattctga   1020

acaagcctct ccagctgaaa ccaaatatta caaattccgc aagacacctc ctggagggcc   1080

tcctgcagaa ggacaggaca aagcggctcg gggccaagga tgacttcatg gagattaaga   1140

gtcatgtctt cttctcctta attaactggg atgatctcat taataagaag attactcccc   1200

cttttaaccc aaatgtgagt gggcccaacg acctacggca ctttgacccc gagtttaccg   1260

aagagcctgt ccccaactcc attggcaagt cccctgacag cgtcctcgtc acagccagcg   1320

tcaaggaagc tgccgaggct ttcctaggct tttcctatgc gcctcccacg gactctttcc   1380

tctgaaccct gttagggctt ggttttaaag gattttatgt gtgtttccga atgttttagt   1440

tagccttttg gtggagccgc cagctgacag gacatcttac aagagaattt gcacatctct   1500

ggaagcttag caatcttatt gcacactgtt cgctggaagc tttttgaaga gcacattctc   1560

ctcagtgagc tcatgaggtt ttcattttta ttcttccttc caacgtggtg ctatctctga   1620

aacgagcgtt agagtgccgc cttagacgga ggcaggagtt tcgttagaaa gcggacgctg   1680

ttctaaaaaa ggtctcctgc agatctgtct gggctgtgat gacgaatatt atgaaatgtg   1740

ccttttctga agagattgtg ttagctccaa agcttttcct atcgcagtgt ttcagttctt   1800

tattttccct tgtggatatg ctgtgtgaac cgtcgtgtga gtgtggtatg cctgatcaca   1860

gatggatttt gttataagca tcaatgtgac acttgcagga cactacaacg tgggacattg   1920

tttgtttctt ccatatttgg aagataaatt tatgtgtaga ctttttgta agatacggtt   1980

aataactaaa atttattgaa atggtcttgc aatgactcgt attcagatgc ttaaagaaag   2040

cattgctgct acaaatattt ctatttttag aaagggtttt tatggaccaa tgccccagtt   2100

gtcagtcaga gccgttggtg tttttcattg tttaaaatgt cacctgtaaa atgggcatta   2160

tttatgtttt ttttttgca ttcctgataa ttgtatgtat tgtataaaga acgtctgtac   2220

attgggttat aacactagta tatttaaact tacaggctta tttgtaatgt aaaccaccat   2280

tttaatgtac tgtaattaac atggttataa tacgtacaat ccttccctca tcccatcaca   2340

caactttttt tgtgtgtgat aaactgattt tggtttgcaa taaaaccttg aaaaatattt   2400

acatataaaa aaaa                                                     2414
```

```
<210> SEQ ID NO 27
<211> LENGTH: 3208
<212> TYPE: DNA
<213> ORGANISM: Homo sapiens

<400> SEQUENCE: 27

agatattcat gaaccgttgc ttcttccagc ctcgccttct cgctccctct gcctttctgg     60

cgctgttctc cctccctccc tctggcttct gctctttctt actccttctc tcagctgctt    120

aactacagct cccactggaa cttgcacaat caaaaacaac tctcctctct caagccgcct    180

ccaggagcgc atcacctgga gaagagcgac tcgctccccg cgccggccgc ggaagagcag    240

ccaggtagct gggggcgggg aggcgtaccc ttctcccgct cggtaagagc cacagcatct    300

ccccggagat tggccgtatc ccaccgtccg gcccccaggg tcctgcagcg gtgatgcata    360

tgtttcggag caatgatgga aggagaaaag ccgctgtcgg tggcaactga aagtggggag    420

aggttgctgc agtagctggt gctgcagaat gcgcgagtga agaactgagc cccgctagat    480

tctccatccc gctcagtctt cattaactgt ctgcaggagg taaaccgggg aaacagatat    540
```

```
gcactaacca ggcgggtgcc aacctggatc tataactgtg aattccccac ggtggaaaat    600
ggtaaacaaa gacatgaatg gattcccagt caagaaatgc tcagccttcc aatttttttaa    660
gaagcgggta cgaaggtgga tcaagagccc aatggtcagt gtggacaagc atcagagtcc    720
cagcctgaag tacaccggct cctccatggt gcacatccct ccaggggagc cagacttcga    780
gtcttccttg tgtcaaacat gcctgggtga acatgctttc caaagagggg ttctccctca    840
ggagaacgag tcatgttcat gggaaactca atctgggtgt gaagtgagag agccatgtaa    900
tcatgccaac atcctgacca agcccgatcc aagaaccttc tggactaatg atgatccagc    960
tttcatgaag cagaggagga tgggtctgaa cgactttatt cagaagattg ccaataactc   1020
ctatgcatgc aaacaccctg aagttcagtc catcttgaag atctcccaac ctcaggagcc   1080
tgagcttatg aatgccaacc cttctcctcc accaagtcct tctcagcaaa tcaaccttgg   1140
cccgtcgtcc aatcctcatg ctaaaccatc tgactttcac ttcttgaaag tgatcggaaa   1200
gggcagtttt ggaaaggttc ttctagcaag acacaaggca gaagaagtgt tctatgcagt   1260
caaagtttta cagaagaaag caatcctgaa aaagaaagag gagaagcata ttatgtcgga   1320
gcggaatgtt ctgttgaaga atgtgaagca ccctttcctg gtgggccttc acttctcttt   1380
ccagactgct gacaaattgt actttgtcct agactacatt aatggtggag agttgttcta   1440
ccatctccag agggaacgct gcttcctgga accacgggct cgtttctatg ctgctgaaat   1500
agccagtgcc ttgggctacc tgcattcact gaacatcgtt tatagagact taaaaccaga   1560
gaatattttg ctagattcac agggacacat tgtccttact gacttcggac tctgcaagga   1620
gaacattgaa cacaacagca caacatccac cttctgtggc acgccggagt atctcgcacc   1680
tgaggtgctt cataagcagc cttatgacag gactgtggac tggtggtgcc tgggagctgt   1740
cttgtatgag atgctgtatg gcctgccgcc tttttatagc cgaaacacag ctgaaatgta   1800
cgacaacatt ctgaacaagc ctctccagct gaaaccaaat attacaaatt ccgcaagaca   1860
cctcctggag ggcctcctgc agaaggacag gacaaagcgg ctcggggcca aggatgactt   1920
catggagatt aagagtcatg tcttcttctc cttaattaac tgggatgatc tcattaataa   1980
gaagattact ccccctttta acccaaatgt gagtgggccc aacgacctac ggcactttga   2040
ccccgagttt accgaagagc ctgtccccaa ctccattggc aagtcccctg acagcgtcct   2100
cgtcacagcc agcgtcaagg aagctgccga ggctttccta ggcttttcct atgcgcctcc   2160
cacggactct ttcctctgaa ccctgttagg gcttggtttt aaaggatttt atgtgtgttt   2220
ccgaatgttt tagttagcct tttggtggag ccgccagctg acaggacatc ttacaagaga   2280
atttgcacat ctctggaagc ttagcaatct tattgcacac tgttcgctgg aagctttttg   2340
aagagcacat tctcctcagt gagctcatga ggttttcatt tttattcttc cttccaacgt   2400
ggtgctatct ctgaaacgag cgttagagtg ccgccttaga cggaggcagg agtttcgtta   2460
gaaagcggac gctgttctaa aaaaggtctc ctgcagatct gtctgggctg tgatgacgaa   2520
tattatgaaa tgtgcctttt ctgaagagat tgtgttagct ccaaagcttt tcctatcgca   2580
gtgtttcagt tctttatttt cccttgtgga tatgctgtgt gaaccgtcgt gtgagtgtgg   2640
tatgcctgat cacagatgga ttttgttata agcatcaatg tgacacttgc aggacactac   2700
aacgtgggac attgtttgtt tcttccatat ttggaagata aatttatgtg tagacttttt   2760
tgtaagatac ggttaataac taaaatttat tgaaatggtc ttgcaatgac tcgtattcag   2820
atgcttaaag aaagcattgc tgctacaaat atttctattt ttagaaaggg tttttatgga   2880
```

-continued

```
ccaatgcccc agttgtcagt cagagccgtt ggtgtttttc attgtttaaa atgtcacctg   2940
taaaatgggc attatttatg ttttttttt tgcattcctg ataattgtat gtattgtata   3000
aagaacgtct gtacattggg ttataacact agtatattta aacttacagg cttatttgta   3060
atgtaaacca ccattttaat gtactgtaat taacatggtt ataatacgta caatccttcc   3120
ctcatcccat cacacaactt tttttgtgtg tgataaactg attttggttt gcaataaaac   3180
cttgaaaaat atttacatat aaaaaaaa                                       3208
```

<210> SEQ ID NO 28
<211> LENGTH: 2459
<212> TYPE: DNA
<213> ORGANISM: Homo sapiens

<400> SEQUENCE: 28

```
aagtggggtt cataacagaa cagggatagc cgtctctggc tcgtgctctc atgtcatctc     60
agagttccag cttatcagag gcatgtagca gggaggctta ttccagccat aactgggctc    120
tacctccagc ctccagaagt aatccccaac ctgcatatcc ttgggcaacc cgaagaatga    180
aagaagaagc tataaaaccc cctttgaaag ctttcatgaa gcagaggagg atgggtctga    240
acgactttat tcagaagatt gccaataact cctatgcatg caaacaccct gaagttcagt    300
ccatcttgaa gatctcccaa cctcaggagc ctgagcttat gaatgccaac ccttctcctc    360
caccaagtcc ttctcagcaa atcaaccttg gcccgtcgtc caatcctcat gctaaaccat    420
ctgactttca cttcttgaaa gtgatcggaa agggcagttt tggaaaggtt cttctagcaa    480
gacacaaggc agaagaagtg ttctatgcag tcaaagtttt acagaagaaa gcaatcctga    540
aaaagaaaga ggagaagcat attatgtcgg agcggaatgt tctgttgaag aatgtgaagc    600
accctttcct ggtgggcctt cacttctctt tccagactgc tgacaaattg tactttgtcc    660
tagactacat taatggtgga gagttgttct accatctcca gagggaacgc tgcttcctgg    720
aaccacgggc tcgtttctat gctgctgaaa tagccagtgc cttgggctac ctgcattcac    780
tgaacatcgt ttatagagac ttaaaaccag agaatatttt gctagattca cagggacaca    840
ttgtccttac tgacttcgga ctctgcaagg agaacattga acacaacagc acaacatcca    900
ccttctgtgg cacgccggag tatctcgcac ctgaggtgct tcataagcag ccttatgaca    960
ggactgtgga ctggtggtgc ctgggagctg tcttgtatga gatgctgtat ggcctgccgc   1020
ctttttatag ccgaaacaca gctgaaatgt acgacaacat tctgaacaag cctctccagc   1080
tgaaaccaaa tattacaaat tccgcaagac acctcctgga gggcctcctg cagaaggaca   1140
ggacaaagcg gctcggggcc aaggatgact tcatggagat taagagtcat gtcttcttct   1200
ccttaattaa ctgggatgat ctcattaata agaagattac tcccccttt aacccaaatg   1260
tgagtgggcc caacgaccta cggcactttg accccgagtt taccgaagag cctgtcccca   1320
actccattgg caagtcccct gacagcgtcc tcgtcacagc cagcgtcaag gaagctgccg   1380
aggctttcct aggcttttcc tatgcgcctc ccacggactc tttcctctga accctgttag   1440
ggcttggttt taaaggattt tatgtgtgtt tccgaatgtt ttagttagcc ttttggtgga   1500
gccgccagct gacaggacat cttacaagag aatttgcaca tctctggaag cttagcaatc   1560
ttattgcaca ctgttcgctg gaagcttttt gaagagcaca ttctcctcag tgagctcatg   1620
aggttttcat ttttattctt ccttccaacg tggtgctatc tctgaaacga gcgttagagt   1680
gccgccttag acggaggcag gagtttcgtt agaaagcgga cgctgttcta aaaaaggtct   1740
cctgcagatc tgtctgggct gtgatgacga atattatgaa atgtgccttt tctgaagaga   1800
```

ttgtgttagc tccaaagctt ttcctatcgc agtgtttcag ttctttattt tcccttgtgg 1860
atatgctgtg tgaaccgtcg tgtgagtgtg gtatgcctga tcacagatgg attttgttat 1920
aagcatcaat gtgacacttg caggacacta caacgtggga cattgtttgt ttcttccata 1980
tttggaagat aaatttatgt gtagactttt ttgtaagata cggttaataa ctaaaattta 2040
ttgaaatggt cttgcaatga ctcgtattca gatgcttaaa gaaagcattg ctgctacaaa 2100
tatttctatt tttagaaagg gtttttatgg accaatgccc cagttgtcag tcagagccgt 2160
tggtgttttt cattgtttaa aatgtcacct gtaaaatggg cattatttat gttttttttt 2220
ttgcattcct gataattgta tgtattgtat aaagaacgtc tgtacattgg gttataacac 2280
tagtatattt aaacttacag gcttatttgt aatgtaaacc accattttaa tgtactgtaa 2340
ttaacatggt tataatacgt acaatccttc cctcatccca tcacacaact ttttttgtgt 2400
gtgataaact gattttggtt tgcaataaaa ccttgaaaaa tatttacata taaaaaaaa 2459

<210> SEQ ID NO 29
<211> LENGTH: 2638
<212> TYPE: DNA
<213> ORGANISM: Homo sapiens

<400> SEQUENCE: 29
acattcctga cctctccctc cccctttcc ctctttcttt ccttccttcc tcctcttcca 60
agttctggga tttttcagcc ttgcttggtt ttggccaaaa gcacaaaaaa ggcgttttcg 120
gaagcgaccc gaccgtgcac aagggccatt tgtttgtttt gggactcggg gcaggaaatc 180
ttgcccggcc tgagtcacgg cggctccttc aaggaaacgt cagtgctcgc cggtcgctct 240
cgtctgccgc gcgccccgcc gcccgctgcc catgggggag atgcagggcg cgctggccag 300
agcccggctc gagtccctgc tgcggccccg ccacaaaaag agggccgagg cgcagaaaag 360
gagcgagtcc ttcctgctga gcggactggc tttcatgaag cagaggagga tgggtctgaa 420
cgactttatt cagaagattg ccaataactc ctatgcatgc aaacaccctg aagttcagtc 480
catcttgaag atctcccaac ctcaggagcc tgagcttatg aatgccaacc cttctcctcc 540
accaagtcct tctcagcaaa tcaaccttgg cccgtcgtcc aatcctcatg ctaaaccatc 600
tgactttcac ttcttgaaag tgatcggaaa gggcagtttt ggaaaggttc ttctagcaag 660
acacaaggca gaagaagtgt tctatgcagt caaagtttta cagaagaaag caatcctgaa 720
aaagaaagag gagaagcata ttatgtcgga gcggaatgtt ctgttgaaga atgtgaagca 780
ccctttcctg gtgggccttc acttctcttt ccagactgct gacaaattgt actttgtcct 840
agactacatt aatggtggag agttgttcta ccatctccag agggaacgct gcttcctgga 900
accacgggct cgtttctatg ctgctgaaat agccagtgcc ttgggctacc tgcattcact 960
gaacatcgtt tatagagact taaaaccaga gaatattttg ctagattcac agggacacat 1020
tgtccttact gacttcggac tctgcaagga gaacattgaa cacaacagca caacatccac 1080
cttctgtggc acgccggagt atctcgcacc tgaggtgctt cataagcagc cttatgacag 1140
gactgtggac tggtggtgcc tgggagctgt cttgtatgag atgctgtatg gcctgccgcc 1200
tttttatagc cgaaacacag ctgaaatgta cgacaacatt ctgaacaagc ctctccagct 1260
gaaaccaaat attacaaatt ccgcaagaca cctcctggag ggcctcctgc agaaggacag 1320
gacaaagcgg ctcggggcca aggatgactt catggagatt aagagtcatg tcttcttctc 1380
cttaattaac tgggatgatc tcattaataa gaagattact ccccctttta acccaaatgt 1440

-continued gagtgggccc aacgacctac ggcactttga ccccgagttt accgaagagc ctgtccccaa 1500
ctccattggc aagtcccctg acagcgtcct cgtcacagcc agcgtcaagg aagctgccga 1560
ggctttccta ggcttttcct atgcgcctcc cacggactct ttcctctgaa ccctgttagg 1620
gcttggtttt aaaggatttt atgtgtgttt ccgaatgttt tagttagcct tttggtggag 1680
ccgccagctg acaggacatc ttacaagaga atttgcacat ctctggaagc ttagcaatct 1740
tattgcacac tgttcgctgg aagctttttg aagagcacat tctcctcagt gagctcatga 1800
ggttttcatt tttattcttc cttccaacgt ggtgctatct ctgaaacgag cgttagagtg 1860
ccgccttaga cggaggcagg agtttcgtta gaaagcggac gctgttctaa aaaaggtctc 1920
ctgcagatct gtctgggctg tgatgacgaa tattatgaaa tgtgcctttt ctgaagagat 1980
tgtgttagct ccaaagcttt tcctatcgca gtgtttcagt tctttatttt cccttgtgga 2040
tatgctgtgt gaaccgtcgt gtgagtgtgg tatgcctgat cacagatgga ttttgttata 2100
agcatcaatg tgacacttgc aggacactac aacgtgggac attgtttgtt tcttccatat 2160
ttggaagata aatttatgtg tagacttttt tgtaagatac ggttaataac taaaatttat 2220
tgaaatggtc ttgcaatgac tcgtattcag atgcttaaag aaagcattgc tgctacaaat 2280
atttctattt ttagaaaggg tttttatgga ccaatgcccc agttgtcagt cagagccgtt 2340
ggtgtttttc attgtttaaa atgtcacctg taaaatgggc attatttatg ttttttttt 2400 tgcattcctg ataattgtat gtattgtata aagaacgtct gtacattggg ttataacact 2460
agtatattta aacttacagg cttatttgta atgtaaacca ccattttaat gtactgtaat 2520
taacatggtt ataatacgta caatccttcc ctcatcccat cacacaactt tttttgtgtg 2580
tgataaactg attttggttt gcaataaaac cttgaaaaat atttacatat aaaaaaaa 2638

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
cttcccaccc acttgtgctt 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
gaaaggtgcc agaggagacc 20

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
ccccctattt taatcggagt ac 22

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
ttttgaagag cacagaacac cct 23

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
atgttcacat tagtacacct tgcc 24

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
tctcagatcc aggcttgctt actgtc 26

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
atggccccag atatgttcca 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
cccaaggtct cagagccagt 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38
cgtctgggga gtaggcaaat 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
cccgagggag gatgtgaaac 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
accagactga atgtgcaagc 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
agggtttttg atggcactga 20

<210> SEQ ID NO 42
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
gggataatgg tgattgagat ggctcgagcc atctcaatca ccattatcct tttt 54

<210> SEQ ID NO 43
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
ccggcacagg cttcaggtat cttatctcga gataagatac ctgaagcctg tgtttttg 58

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
ccatcttgtc gtcaatgtta tgaagc 26

<210> SEQ ID NO 45

<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
agcttctggg ttgtctcctc agtgg 25

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
cagatctcca tgtgccagaa 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
cttgcccatt gctttattgg 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
tgcaccacca actgcttagc 20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
ggcatggact gtggtcatga g 21

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
gtctgcggcg gtgttctg 18

<210> SEQ ID NO 51
<211> LENGTH: 18

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

tgccgaccca gcaagatc                                                  18
```